United States Patent
Fisher et al.

(12) 
(10) Patent No.: US 6,448,269 B1
(45) Date of Patent: Sep. 10, 2002

(54) GLYCOPROTEIN IIB/IIIA ANTAGONISTS

(75) Inventors: Matthew J. Fisher, Carmel; Anne Marie Happ, Indianapolis; Joseph A. Jakubowski, Indianapolis; Michael Dean Kinnick, Indianapolis; Allen D. Kline, Bargersville; Michael John Martinelli, Indianapolis; John Michael Morin, Jr., Brownsburg, all of IN (US); Michael Paal; Gerd Rühter, both of Hamburg (DE); Kenneth James Ruterbories, Indianapolis, IN (US); Daniel J. Sall, Greenwood, IN (US); Theo Schotten, Vierhoefen (DE); Marshall A. Skelton, Indianapolis, IN (US); Wolfgang Stenzel, Reinbek (DE); Robert Theodore Vasileff, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/883,639

(22) Filed: Jun. 18, 2001

Related U.S. Application Data

(63) Continuation of application No. 09/412,142, filed on Oct. 5, 1999, now abandoned, which is a continuation of application No. 09/047,285, filed on Mar. 24, 1998, now Pat. No. 6,020,362, which is a continuation of application No. 08/376,191, filed on Jan. 19, 1995, now Pat. No. 5,731,324, which is a continuation-in-part of application No. 08/255,821, filed on Jul. 8, 1994, now Pat. No. 5,618,843, which is a continuation-in-part of application No. 08/096,220, filed on Jul. 22, 1993, now abandoned.

(51) Int. Cl.$^7$ ...................... C07D 401/12; A61K 31/47
(52) U.S. Cl. ...................... 514/320; 514/456; 546/205; 549/398
(58) Field of Search .......................... 549/398; 514/456, 514/320; 546/205

(56) References Cited

U.S. PATENT DOCUMENTS

| 5,039,805 A | 8/1991 | Alig et al. ................ 546/224 |
| 5,041,453 A | 8/1991 | Huang et al. .............. 514/314 |
| 5,059,609 A | * 10/1991 | Eggler et al. ............. 514/314 |
| 5,064,814 A | 11/1991 | Klein et al. ................ 514/18 |

FOREIGN PATENT DOCUMENTS

| EP | 0 169 443 | 1/1986 |
| EP | 0 315 399 | 11/1988 |
| EP | 0 430 459 | 11/1990 |
| EP | 0 435 235 | 7/1991 |
| EP | 0 456 835 | 11/1991 |
| EP | 0 531 883 | 3/1992 |
| EP | 0 478 328 | 4/1992 |
| EP | 0 540 051 | 5/1993 |
| EP | 0 635 492 A1 | 1/1995 |
| EP | 0 655 439 A2 | 5/1995 |
| GB | 2 276 384 | 9/1994 |
| WO | WO 89/04303 | 1/1989 |
| WO | WO 89/04304 | 1/1989 |
| WO | WO 92/20705 | 11/1992 |
| WO | WO 93/00095 | 1/1993 |
| WO | WO 93/08174 | 4/1993 |
| WO | WO 93/12074 | 6/1993 |
| WO | WO 94/29273 | 12/1994 |

OTHER PUBLICATIONS

Chemical Abstracts; vol. 84. No. 13. Abstract 90500a dated Mar. 29, 1976, pp. 556; Barxzai–Beke, et al.

Journal American Chemical Society; 1994 vol. 116. No. 116, pp. 5077–5083; McDowell, et al.

Chemical Abstracts; vol. 75. No. 10. Abstract 7439ly dated Sep. 6, 1971, pp. 278; Satoh, et al.

Journal American Chemical Society; 1993 vol. 115, pp. 8861–8862; Ku, et al.

Annual Reports In Medicinal Chemistry; 1993 vol. 28, pp. 79–86; Blackburn, et al.

Chemical Abstracts; vol. 100, No. 17. pp. 638, Abstract 138973n dated Apr. 23, 1984; Otsuka Pharmaceutical Co.

* cited by examiner

*Primary Examiner*—Zinna Northington Davis
(74) *Attorney, Agent, or Firm*—Knobbe, Martens, Olson & Bear LLP

(57) ABSTRACT

This invention relates to certain bicyclic compounds having a nucleus formed of two fused six membered rings, for example, benzopyran, isoquinoline, isoquinolone, tetrahydronaphthalene, dihydronaphthalene, or tetralone, substituted with both basic and acidic functionality, which are useful in inhibition of platelet aggregation.

18 Claims, No Drawings

GLYCOPROTEIN IIB/IIIA ANTAGONISTS

CROSS-REFERENCE TO RELATED APPLICATIONS

This application is a continuation of patent application Ser. No. 09/412,142, filed Oct. 5, 1999, now abandoned which is a continuation of Ser. No. 09/047,285, filed Mar. 24, 1998, now U.S. Pat. No. 6,020,362 which is a continuation of Ser. No. 08/376,191, filed Jan. 19, 1995, now U.S. Pat. No. 5,731,324, which is continuation-in-part of Ser. No. 08/255,821, filed Jul. 8, 1994, now U.S. Pat. No. 5,618,843, which is a continuation-in-part of Ser. No. 08/096,220, filed Jul. 22, 1993, abandoned.

FIELD OF THE INVENTION

This invention relates to bicyclic compounds useful as glycoprotein IIb/IIIa antagonists for the prevention of thrombosis.

BACKGROUND OF THE INVENTION

The most prevalent vascular disease states are related to platelet dependent narrowing of the blood supply such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis or abrupt closure following angioplasty, carotid endarterectomy, anastomosis of vascular grafts, and etc. These conditions represent a variety of disorders thought to be initiated by platelet activation on vessel walls. Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin the GPIIb/IIIa binding site becomes available to fibrinogen, eventually resulting in platelet aggregation and clot formation.

Heretofore it has been proposed to block these thrombus formation sites by the use of various therapeutic agents.

U.S. Pat. No. 5,064,814 teaches N-amidino-piperidine carboxyl cyclic amino acid derivatives as anti-thrombotic agents.

U.S. Pat. 5,039,805 teaches various benzoic acid and phenylacetic acid derivatives for the inhibition of the binding of fibrinogen to the fibrinogen receptor, glycoprotein IIb/IIIa.

Seven membered ring containing bicyclic compounds are taught to be fibrinogen antagonists in PCT International patent application WO 93/00095.

EP 456835 describes bicyclic compounds having fused six membered rings (quinazoline-3-alkanoic acid derivates) which are reported to have an inhibitory effect on platelet aggregation.

PCT International patent application WO 93/08174 describes nonpeptidyl integrin inhibitors which are bicyclic 6 and 7 membered fused ring systems which have therapeutic applications in diseases for which blocking platelet aggregation is indicated.

Patent Application WO94/12478 describes the preparation of 6,5-bicyclic compounds stated to be effective for inhibiting platelet aggregation.

Patent Application WO94/08962 describes the preparation of 6,5-bicyclic compounds stated to be effective for inhibiting platelet aggregation.

British Patent application GB 2276384 describes novel oxoquinazolin derivatives stated to have fibrinogen receptor antagonistic activity.

The article, "From Peptide to Non-Peptide. 1. The Elucidation of a Bioactive Conformation of the arginine-glycine-aspartic Acid Recognition Sequence", by Robert S. McDowell, et. al., J. Am. Chem. Soc. 1994, 116, pp. 5069–5076, describes design of non-peptidal inhibitors of fibrinogen-glycoprotein IIb/IIIa binding.

The publication, "Chapter 9. Glycoprotein IIbIIIa Antagonists" by Brent K. Blackburn and Thomas R. Gadek, Annual Reports in Medicinal Chemistry—28, Section II—Cardiovascular and Pulmonary Agents, pp 79–88, 1993, publ. by Academic Pres, Inc., describes non-peptides as antagonists of GPIIbIIIa/fibrinogen interaction.

The article, "From Peptide to Non-Peptide. 2. The de Novo Design of Potent, Non-Peptidal Inhibitors of Platelet Aggregation Based on a Benzodiazepinedione Scaffold", by Robert S. McDowell, et. al., J. Am. Chem. Soc. 1994, 116, pp 5077–5083, describes benzodiazepinedione which are inhibitors of platelet aggregation.

Quinoline compounds have been recited in the patent literature for a variety of medicinal uses. For example, European Patent Application 0 315 399; U.S. Pat. No. 5,041,453; PCT Patent Application WO 89/04303, and PCT Patent Application WO 89/04304 describe quinoline derivatives useful as lipoxygenase inhibitors and/or leukotriene antagonists possessing anti-inflammatory and anti-allergic. properties. These compounds must contain three aromatic rings, each interrupted with oxygen, or sulfur, and possibly other groups.

There is a need in the area of cardiovascular and cerebrovascular therapeutics for alternative agents which can be used in the prevention and treatment of thrombi.

It is a discovery of this invention that certain novel bicyclic compounds block the GPIIb/IIIa fibrinogen receptor, thereby inhibiting platelet aggregation and subsequent thrombus formation. Pharmaceutical formulations containing the bicyclic compounds of this invention inhibit aggregation and are useful for the prophylaxis and treatment of thrombogenic diseases, such as myocardial infarction, angina, stroke, peripheral arterial disease, disseminated intravascular coagulation and venous thrombosis.

SUMMARY OF THE INVENTION

The present invention is a novel bicyclic compound having a nucleus formed from two fused six membered rings, A and B, represented by the formula (I), as hereinafter defined, and all pharmaceutically acceptable salts, solvates and prodrug derivatives thereof:

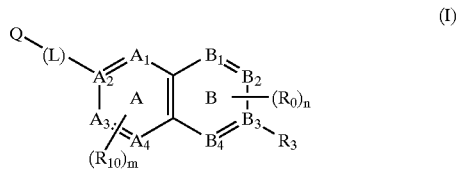

(I)

Another aspect of the invention is a pharmaceutical formulation containing the novel bicyclic compounds of the invention.

Another aspect of the invention is a method of inhibiting platelet aggregation, inhibiting fibrinogen binding, or preventing thrombosis by administering to a mammal the bicyclic compounds of the invention.

Another aspect of this invention is a method of treating a human to alleviate the pathological effects of atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts; wherein the method comprises administering to said human the novel bicyclic compound of this invention.

DETAILED DESCRIPTION OF THE INVENTION

The term "alkyl" used herein refers to a monovalent straight or branched chain radical of from one to ten carbon atoms, including, but not limited to methyl, ethyl, n-propyl, isopropyl, n-butyl, isobutyl, tert-butyl, n-hexyl, and the like.

The term, "halosubstituted alkyl" as used herein refers to an alkyl group as just defined, substituted by one, two or three halogen atoms selected from fluorine, chlorine, bromine, and iodine. Examples of such groups include chloromethyl, bromoethyl, trifluoromethyl, and the like.

The term, "aryl", when used alone means a homocyclic aromatic radical whether or not fused. Preferred aryl groups include phenyl, napthyl, biphenyl, phenanthrenyl, naphthacenyl, and the like.

The term, "substituted aryl", denotes an aryl group substituted with one, two, or three substituents chosen from halogen, hydroxy, protected hydroxy, cyano, nitro, $C_1$–$C_{10}$ alkyl, $C_1$–$C_{10}$ alkoxy, trifluoromethyl, amino, aminomethyl, and the like. Examples of such groups are 4-chlorophenyl, 2-methylphenyl, 3-methyl-4-hydroxyphenyl, and 3-ethoxyphenyl.

The term, "arylalkyl", means one, two or three aryl groups having the number of carbon atoms designated, appended to an alkyl radical having the number of carbon atoms designated. A typical arylalkyl group is the benzyl group.

The term "alkenyl" as used herein refers to a monovalent straight or branched chain radical of from two to six carbon atoms containing a carbon double bond including, but not limited to, 1-propenyl, 2-propenyl, 2-methyl-l-propenyl, 1-butenyl, 2-butenyl and the like.

The term, "alkylene" as used herein refers to a divalent straight or branched chain group of from one to ten carbon atoms, including but not limited to, —CH$_2$—, —(CH$_2$)$_2$—, —(CH$_2$)$_3$—, —CH(CH$_3$)—, —CH(C$_2$H$_5$)—, —CH(CH$_3$)CH$_2$—, and the like.

The term "alkenylene" as used herein refers to a divalent straight or branched chain group of from two to ten carbon atoms containing a carbon-carbon double bond, including but not limited to, —CH=CH—, —C(CH$_3$)=CH—, CH=CH—CH$_2$—, —CH=C(CH$_3$)—CH$_2$—, —CH$_2$CH (CH=CH$_2$)CH$_2$, and the like.

The term, "alkynylene" as used herein refers to a divalent straight or branched chain group of from two to ten carbon atoms containing a carbon-carbon triple bond, including but not limited to,

—C≡C—, —C≡C—C—
           |
           CH$_3$ and the like.

The term, "amidino" refers to the radical having the structural formula;

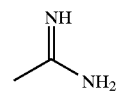

The term, "basic radical" refers to an organic radical which is a proton acceptor. Illustrative basic radicals are amidino, piperidyl, guanidino, and amino.

The term, "basic group" refers to an organic group containing one or more basic radicals. A basic group may comprise only an basic radical.

The term, "non-interfering organic radical" is any organic substituent present on the bicyclic compound of formula (I) which is not deleterious to its efficacy as a Glycoprotein IIb/IIIa antagonist.

The term, "acid radical" refers to an organic radical which is a proton donor. Illustrative acid radicals include;

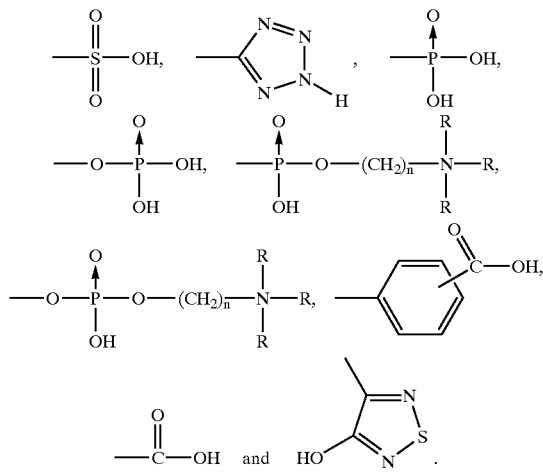

The term, "acidic group" is an organic group containing one or more acid radicals. An acidic group may comprise only an acid radical.

Compounds of the Invention

Compounds of this invention have the general formula (I) shown below:

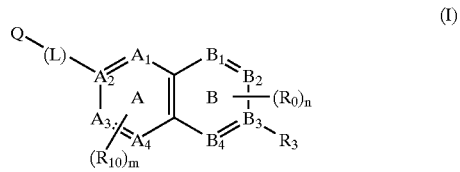

(I)

and all pharmaceutically acceptable salts, solvates and prodrug derivatives thereof.

The bicyclic nucleus of (I) is formed from the fusion of two six membered rings "A" and "B" having carbon bridging atoms. The dashed lines in the structural formula (I) signify the optional presence of an additional bond, that is, unsaturation that will lend aromatic character to the ring structure. It will be understood that the bridging carbon atoms will either be unsubstituted or substituted (with hydrogen) depending on the degree of unsaturation in the bicyclic ring system. The A ring atoms $A_1$, $A_2$, $A_3$, and $A_4$ and the B ring atoms $B_1$, $B_2$, $B_3$, $B_4$ of formula (I) are independently selected from carbon, oxygen, sulfur, and nitrogen, with the proviso that at least two of $B_1$, $B_2$, $B_3$, $B_4$ are carbon. More precisely, $A_1$, $A_3$, and $A_4$ are independently selected from carbon, oxygen, sulfur, and nitrogen and $A_2$ is independently selected from carbon or nitrogen, provided that $A_2$ have an unsatisfied bond if $A_2$ is N and provided that at least two of $A_1$, $A_2$, $A_3$, and $A_4$ are carbon. Correspondingly, $B_1$, $B_2$, and $B_4$ are independently selected from carbon, oxygen, sulfur, and nitrogen and $B_3$ is independently selected from carbon or nitrogen and provided that $B_3$ have an unsatisfied bond if $B_3$ is N and provided that at least two of $B_1$, $B_2$, $B_3$ and $B_4$ are carbon.

The bicyclic nuclei of the compounds of the invention may be formed from ring systems inclusive of, but not limited to, any of the nuclei (1 through 16) depicted below:

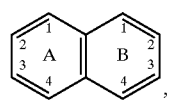
(1)

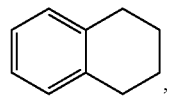
(2)

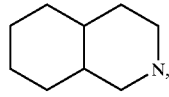
(3)

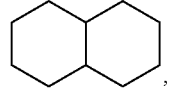
(4)

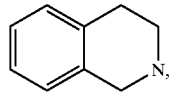
(5)

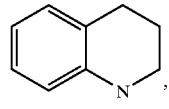
(6)

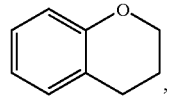
(7)

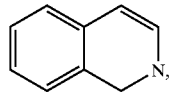
(8)

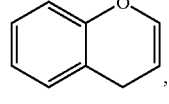
(9)

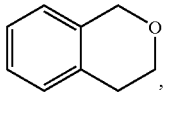
(10)

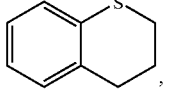
(11)

-continued

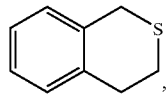
(12)

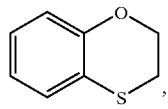
(13)

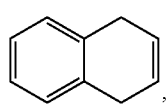
(14)

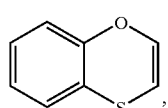
(15)

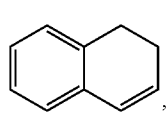
(16)

The nuclei depicted by formulae (1) to (16) supra., and (17) to (30) infra., have the A and B ring atom numberings and corresponding substituent placements as shown in (1) above. For example, the nuclei (Imm) and (Ipp).

(Imm)           (Ipp)

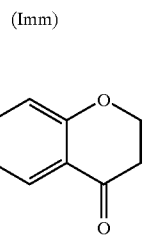 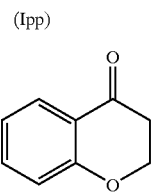

would yield different products within the scope of formula (I).

Compounds of the invention corresponding to formula (I) with nuclei (1) to (19) are represented by the formulae (Ia) to (Ie) below:

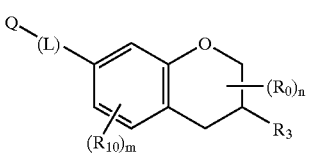
(Ia)

(Ib)
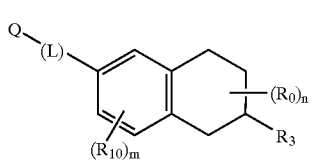

(Ic)
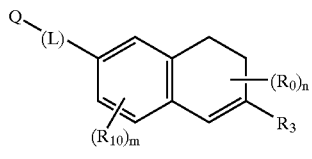

(Id)
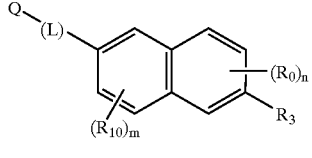

(Ie)
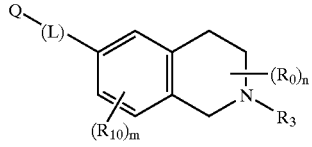

(If)
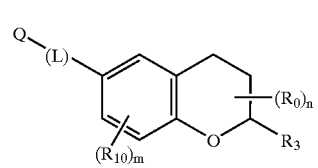

(Ig)
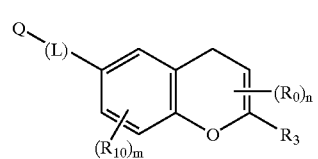

(Ih)
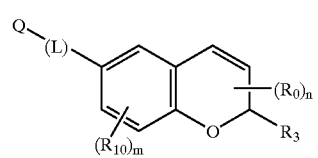

(Ii)
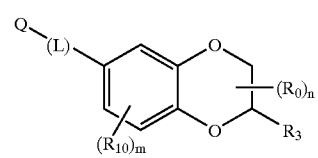

(Ij)
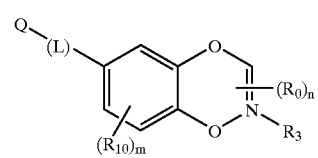

(Ijj)

Other bicyclic nuclei suitable for forming the compounds of formula (I) are represented by the formulae (17) through (21a) below:

(17)
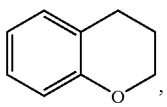

(18)
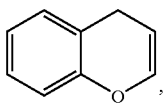

(19)
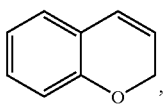

(20)
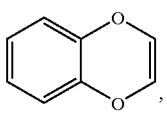

(21)
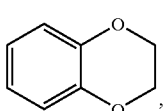

(21a)
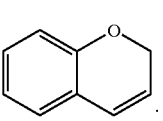

Compounds of the invention corresponding to formula (I) with nuclei (17) to (21a) are represented by the formulae (If) through (Ijj) below:

Bicyclic nuclei ring substituted with =O suitable for forming the compounds of formula (I) are represented by the formulae (22) through (27) below:

(22)
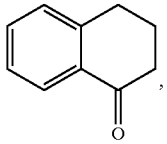

(23)
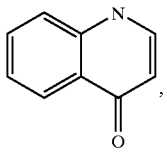

(24)
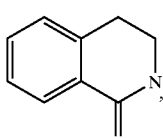

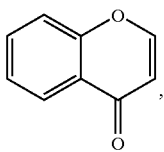 (25),

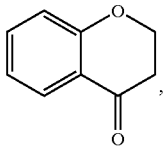 (26),

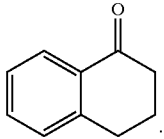 (27).

Compounds of the invention corresponding to formula (I) with oxo substituted nuclei (22) to (27) are represented by the formulae (Ik) to (Im) below:

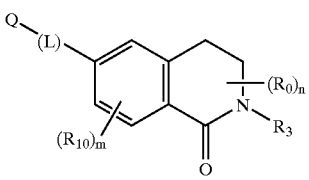 (Ik)

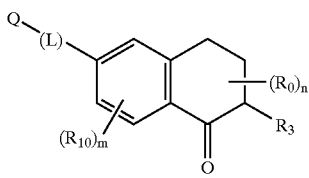 (Il)

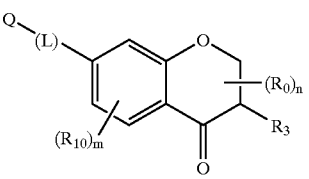 (Im)

Other bicyclic nuclei ring substituted with =O suitable for forming the compounds of formula (I) are represented by the formulae (28) through (30) below:

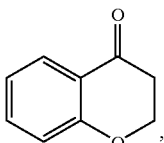 (28),

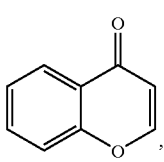 (29),

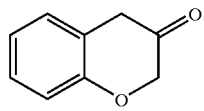 (30).

Compounds of the invention corresponding to formula (I) with nuclei (28) to (30) are represented by the formulae (In) to (Ip) below:

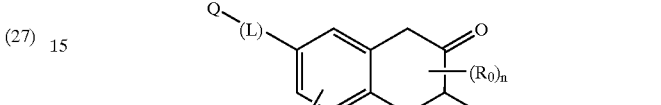 (In)

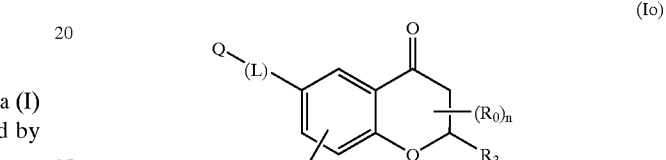 (Io)

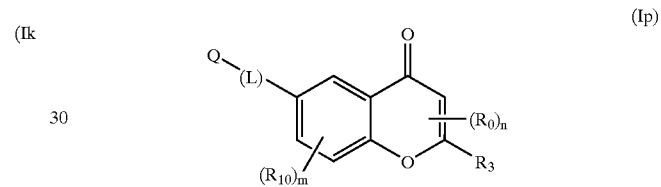 (Ip)

The most preferred nuclei for the compounds of this invention are isoquinoline, isoquinolone, naphthalene, tetrahydronapthalene, tetralone, dihydronaphthalene, and benzopyran.

The substituent $R_3$ is an acidic group or a pharmaceutically acceptable salt or solvate thereof, (or a prodrug derivative of said acidic group) and preferably is an acidic group containing carboxyl functionality. The $R_3$ group may be the sole substituent of ring atom $B_3$. Alternatively, when the $B_3$ atom can accept two bonds, these bonds may be satisfied by a double bond on the $R_3$ group (with the $R_3$ double bond attached directly to the B ring of formula I), or a second $R_3$ group, or a second group selected from hydrogen, $C_1$–$C_{10}$ alkyl, $C_1$–$C_{10}$ halosubstituted alkyl, $C_2$–$C_{10}$ alkenyl, $C_2$–$C_{10}$ alkynyl, $C_3$–$C_{10}$ cycloalkyl, aryl, $C_7$–$C_{12}$ aralkyl, hydroxy, $C_1$–$C_{10}$ alkoxy, $C_1$–$C_{10}$ aralkoxy, carboxy, acyl, cyano, halo, nitro, and sulfo.

$R_3$, the acidic group, is preferably selected from the group having members represented by the following formulae:

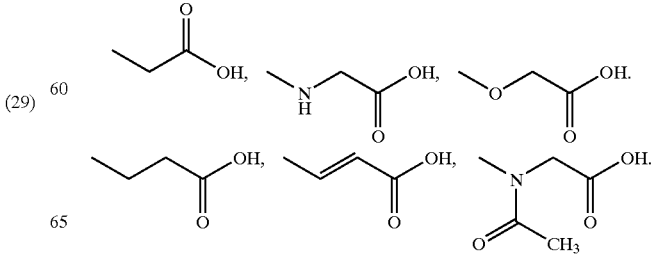

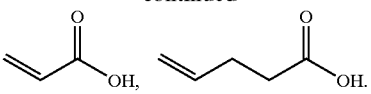

The substituents $R_0$ are non-interfering organic radicals and are the same or different on each atom $B_1$, $B_2$, and $B_4$ and the same or different between atoms $B_1$, $B_2$, and $B_4$ and are independently selected from hydrogen, $C_1$–$C_{10}$ alkyl, $C_1$–$C_{10}$ halosubstituted alkyl, $C_2$–$C_{10}$ alkenyl, $C_2$–$C_{10}$ alkynyl, $C_3$–$C_{10}$ cycloalkyl, aryl, $C_6$–$C_{12}$ arylalkyl, hydroxy, $C_1$–$C_{10}$ alkoxy, $C_6$–$C_{12}$ arylalkoxy, amino, substituted amino, carbamoyl, carboxy, acyl, cyano, halo, nitro, sulfo; with the proviso that only one of $B_1$, $B_2$, and $B_4$ may also be substituted with =O or =S.

The number, n, of $R_0$ substituents attached to the atoms $B_1$, $B_2$, and $B_4$ of the B ring is an integer from 0 to 6 and depends on the sum of the number of unsatisfied bonds present in the individual atoms $B_1$, $B_2$, and $B_4$. Typically, n will be from 2 to 6 for most of the compounds of the invention. Thus, for example, where the B ring is saturated, $B_2$ is oxygen, and $B_1$ and $B_4$ are carbon, then no $R_0$ substituent will be present on atom $B_2$ as shown in structural formula (Iq) below:

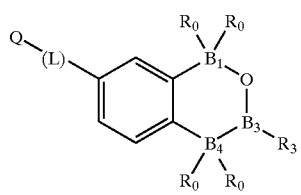

For B rings having unsaturation, the number of unsatisfied bonds present in the individual atoms $B_1$, $B_2$, and $B_4$ is decreased and the number of $R_0$ substituents required is correspondingly less. Thus, for example, where the B ring is unsaturated, $B_2$ is nitrogen, and $B_1$ and $B_4$ are carbon, then no $R_0$ substituent will be present on $B_2$ as shown in structural formula (Ir) below:

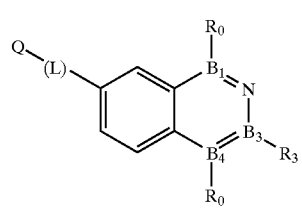

The A ring atoms $A_1$, $A_2$, $A_3$, and $A_4$ are independently selected from carbon, oxygen, sulfur, and nitrogen, with the proviso that at least two of $A_1$, $A_2$, $A_3$, and $A_4$ are carbon.

The substituents $R_{10}$ are the same or different on each atom $A_1$, $A_3$, and $A_4$ and the same or different between atoms $A_1$, $A_3$ and $A_4$, and are independently selected from hydrogen, $C_1$–$C_{10}$ alkyl, $C_1$–$C_{10}$ halosubstituted alkyl, $C_2$–$C_{10}$ alkenyl, $C_2$–$C_{10}$ alkynyl, $C_3$–$C_{10}$ cycloalkyl, aryl, $C_6$–$C_{12}$ arylalkyl, hydroxy, alkoxy, $C_6$–$C_{12}$ arylalkoxy, carboxy, acyl, cyano, halo, nitro, and sulfo; with the proviso that only one of $A_1$, $A_3$, and $A_4$ may also be substituted with =O or =S when two sites are available for substitution on a single atom (viz., when one or more of the dashed lines in the A ring of Formula I are absent and an A atom is carbon).

The number, m, of $R_{10}$ substituents attached to the atoms $A_1$, $A_3$, and $A_4$ of the A ring is an integer from 0 to 6 and depends on the sum of the number of unsatisfied bonds present in the individual atoms $A_1$, $A_3$, and A4 in a manner analogous to the substitution of $R_0$ groups on the B ring as describe d above. Typically, n will be from 2 to 6 for most of the compounds of the invention. The atom, $A_2$, of the A ring is substituted by linking group —(L)— alone when $A_2$ has only one unsatisfied bond, however, when $A_2$ has two unsatisfied bonds the second bond may be satisfied by a group selected from hydrogen, alkyl, halosubstituted $C_1$–$C_{10}$ alkyl, $C_2$–$C_{10}$ alkenyl, $C_2$–$C_{10}$ alkynyl, $C_3$–$C_{10}$ cycloalkyl, aryl, $C_7$–$C_{12}$ arylalkyl, hydroxy, $C_1$–$C_{10}$ alkoxy, $C_7$–$C_{12}$ arylalkoxy, acyl, cyano, halo, nitro, sulfo, and a basic group.

The linking group —(L)— attached to the $A_2$ atom of the A ring and is (i) a bond, or (ii) a divalent substituted or unsubstituted chain of from 1 to 10 atoms (viz., there are 1 to 10 atoms in the chain between the linking divalent bonds, with all other atoms pendent from these chain atoms). For example, when —(L)— is a bond the compound of the invention may have the structural formula Is as follows:

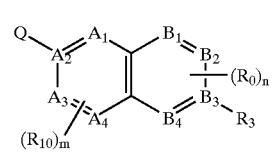

Alternatively, when —(L)— is the linking group

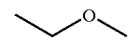

the compound of the invention may have the structural formula (It) as follows:

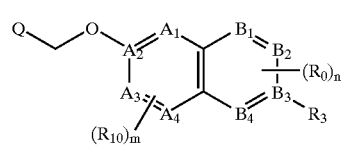

Alkylene, alkenylene and alkynylene groups are suitable as linking groups. Preferred linking groups have 1 to 4 chain atoms and correspond to the general formulae:

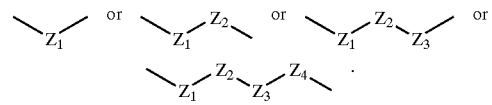

where $Z_1$, $Z_2$, $Z_3$, and $Z_4$ are atoms selected from the group consisting of carbon, nitrogen, sulfur, and oxygen. Linking groups containing three chain atoms such as,

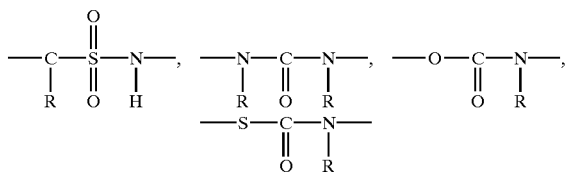

where R is hydrogen or alkyl, may be used.

Particularly preferred are linking groups containing two chain atoms such as;

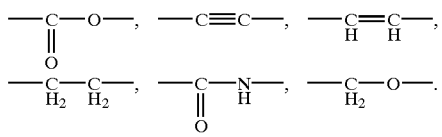

The linking group;

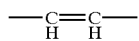

has cis and trans forms and both such forms and their mixtures in all proportions are within this invention.

Asymmetric linkers, for example, the linkers

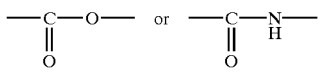

may be reversed in their point of attachment between the nucleus A ring and the basic group Q, as depicted in formulae (Iu) and (Iv) below:

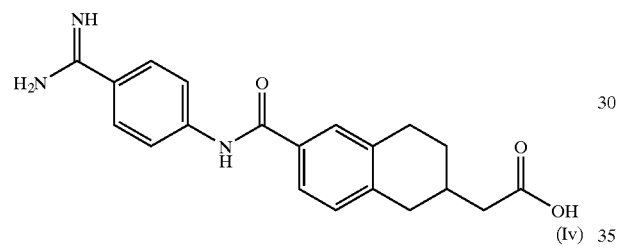

(Iu)

(Iv)

The substituent Q of formula (I) is a basic group. A basic group contains one or more basic radicals, $Q_1$. Suitable basic radicals contain one or more nitrogen atoms and include amino, imino, amidino, N-alkylamidines, N,N'-dialkyamidines, N-arylamidines, aminomethyleneamino, iminomethylamino, guanidino, aminoguanidino, alkylamino, dialkylamino, trialkylamino, alkylideneamino, pyrrolyl, imidazolyl, pyrazolyl, pyridyl, pyrazinyl, pyrimidinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, amide, thioamide, benzamidino, pteridinyl, 4aH-carbozolyl, carbozolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, or any of the preceding substituted with amino, imino, amidino, aminomethyleneamino, iminomethylamino, guanidino, alkylamino, dialkylamino, trialkylamino, tetrahydroisoquinoline, dihydrosioindole, alkylideneamino groups or a group represented by the formula;

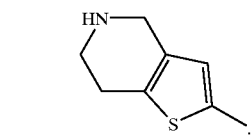

Preferred basic radicals are selected from amino, piperidyl, guanidino, and amidino. The most preferred basic radicals are amidino and piperidyl represented by the formulae;

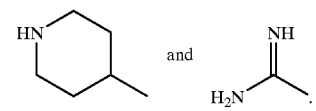

The basic group Q may have the form of a basic radical (such as $Q_1$ on formula Iw, infra.) pendant on a cyclic ring. Thus, Q, the basic group, may comprise two parts, namely, (i) one or more basic radicals, $Q_1$ and (ii) a cyclic group, "D", having from 5 to 8 ring atoms. The D ring attached to the $A_2$ atom of the A ring of the bicyclic nucleus throuth the linking group —(L)— as shown in formula (I), supra. The D ring may also have substituents $R_{20}$ which are selected from chlorine, fluorine or non-interfering organic radicals. The $R_{20}$ substituents may be t in number, where t is an integer from zero to the number of unsatisfied bonds in the D ring. The basic radical $Q_1$ attaches to the D ring in the manner shown in formula (Iw) below:

(Iw)

$(Q_1)_w$ — D — $(R_{20})_t$ (attaches to Atom $A_2$ through linking group.

Suitable D rings are formed from a nucleus selected from the group consisting of; benzene, cycloheptadiene, cycloheptatriene, cycloheptane, cyclohexane, cyclohexene, cyclohexadiene, cycloheptene, cyclooctadiene, cyclooctane, cyclooctatetraene, cyclooctene, cyclopentane, cyclopentene, imidazole, isooxazole, morpholine, oxazole, piperazine, piperidine, pyrazine, pyrazole, pyridine, pyrimidine, pyrrole, pyrrolidine, pyrroline, tetrahydropyridine, tetrahydropyrimidine, 1H-tetrazole, thiazolidine, thiazole, thiopyran, 1,3,5-triazine, 1,2,3-triazole, 1,2,4-triazole, dihydrofuran, dihydropyran, dioxane, dioxepin, dioxolane, furan, oxocane, tetrahydrofuran, tetrahydropyran, thiophene, and tetrahydrothiophene.

General formula (Ix) for the preferred compounds of the invention having a basic radical attached to a cyclic ring of 5 to 8 atoms is shown below:

(Ix)

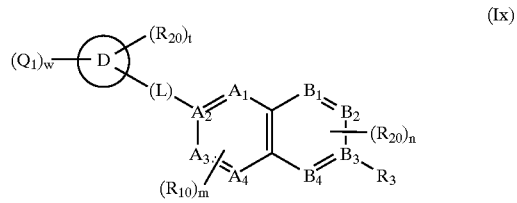

wherein;

$A_1$, $A_3$, $A_4$ are independently selected from carbon, oxygen, sulfur, and nitrogen;

$A_2$ is independently selected from carbon or nitrogen, provided that $A_2$ have an unsatisfied bond if $A_2$ is N and provided that at least two of $A_1$, $A_2$, $A_3$, and $A_4$ are carbon;

$B_1$, $B_2$, $B_4$ are independently selected from carbon, oxygen, sulfur, and nitrogen;

$B_3$ is independently selected from carbon or nitrogen, provided that $B_3$ have an unsatisfied bond if $B_3$ is N and provided that at least two of $B_1$, $B_2$, $B_3$, $B_4$ are carbon;

$R_3$ is an acidic group containing one or more acid radicals;

n is a number from 0 to 6;

$R_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamoyl, carboxy, acyl, cyano, halo, nitro, sulfo, =O, or =S; with the proviso that if $R_0$ is =O or =S, then only one of $B_1$, $B_2$, $B_3$, and $B_4$ may be nitrogen;

m is a number from 0 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, =O, and =S; with the proviso that only one $R_{10}$ may be =O or =S;

t is a number from 0 to 3;

$R_{20}$ is the same or different and is independently selected from hydrogen, halogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo;

linking group —(L)— is a bond or a divalent substituted or unsubstituted chain of from 1 to 10 atoms selected from the group consisting of carbon, nitrogen, sulfur, and oxygen; and;

D is a ring formed from 5 to 8 ring atoms and said ring atoms are independently selected from carbon, nitrogen, oxygen, or sulfur, with the proviso that at least two D ring atoms are carbon;

w is an integer from 1 to 3;

$Q_1$ is a basic radical.

Compounds of the invention having A, B, and D rings are represented by the following formulae (Iy) to (Iah) below:

(Iy)

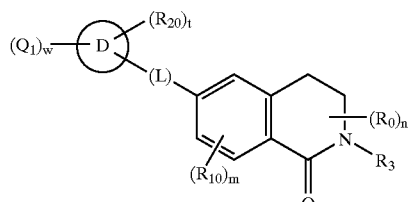

(Iz)

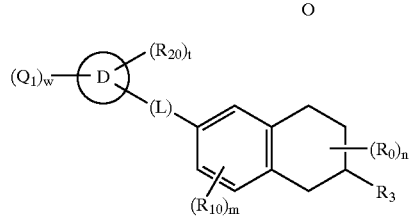

(Iaa)

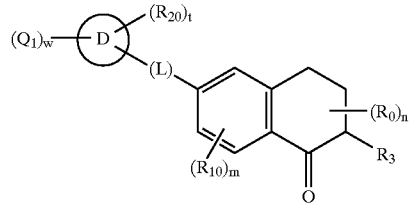

(Iab)

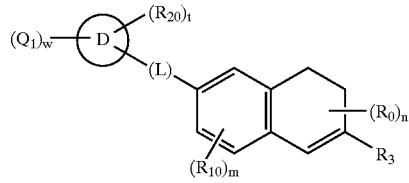

(Iac)

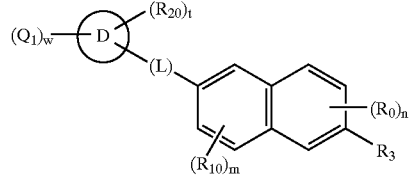

(Iad)

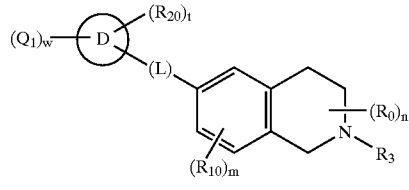

(Iae)

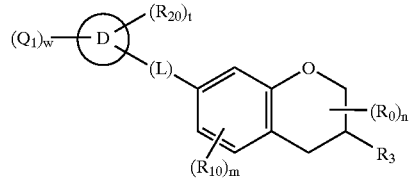

(Iaf)

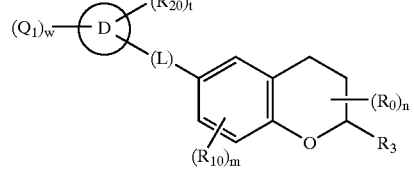

(Iag)

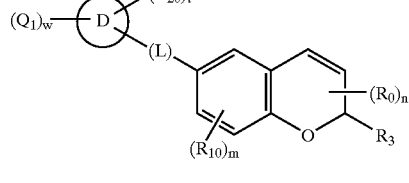

(Iah)

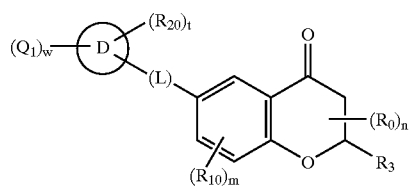

A preferred basic group Q has a six membered D ring as represented by formula (Iai) below;

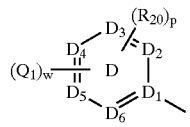
(Iai)

where p is an integer from 0 to 8, as for example, the specific Q groups:

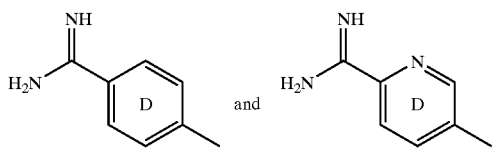

A preferred embodiment of the compound of the invention is represented by formula II, below:

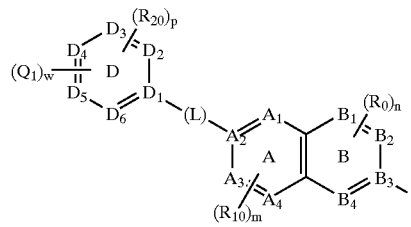
(II)

In formula II the basic group on atom $A_2$ of the nucleus has two parts, namely, (i) a six membered ring, D, which attaches to linking group —(L)—, and (ii) basic radical(s), $Q_1$, (where w is an integer from 1 to 3) attached to the D ring. The basic radicals are as previously defined.

Atoms $D_2$, $D_3$, $D_4$, $D_5$ and $D_6$ are independently selected from carbon, nitrogen, oxygen, or sulfur and atom $D_1$ is selected from carbon or nitrogen; with the proviso that at least two of $D_1$, $D_2$, $D_3$, $D_4$, $D_5$ and $D_6$ are carbon. $Q_1$ is a basic radical as previously defined. Preferred ring structures having pendant $Q_1$ are those where atoms $D_1$, $D_2$, $D_3$, $D_4$, $D_5$ and $D_6$ form a cyclic ring selected from the group consisting of benzene, pyridine, piperidine, 1,2-piperazine, 1,3-piperazine, 1,4-piperazine, pyran, thiopyran, thiabenzene, cyclohexene, and cyclohexane, with benzene being the most preferred.

A preferred basic radical $Q_1$ is an amidino radical.

The substituents $R_{20}$ are the same or different on each atom $D_2$, $D_3$, $D_5$, and $D_6$ and the same or different between atoms $D_2$, $D_3$, $D_5$, and $D_6$ and are non-interfering organic radicals independently selected from hydrogen, alkyl, halosubstituted alkyl, alkenyl, alkynyl, cycloalkyl, aryl, arylalkyl, hydroxy, alkoxy, aralkoxy, amino, substituted amino, carbamoyl, carboxy, acyl, cyano, halo, nitro, and sulfo. The number, p, of substituents $R_{20}$ is an integer from 0 to 8 depending on the sum of the number of unsatisfied bonds present in the individual atoms $D_2$, $D_3$, $D_5$, and $D_6$.

Preferred compounds of this invention are based on benzamidine substituted isoquinoline, isoquinolone, naphthalene, tetrahydronaphthalene, dihydronaphthalene, benzopyran, and tetralone nuclei, as partially illustrated in formulae (III) through (IIIe) below:

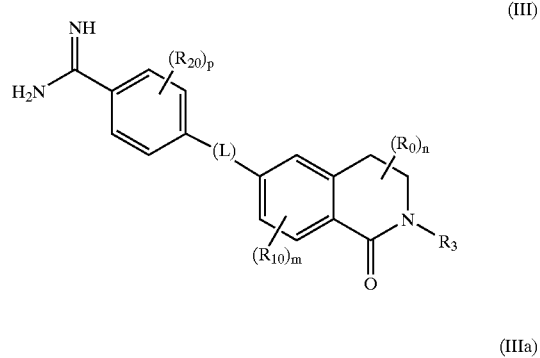
(III)

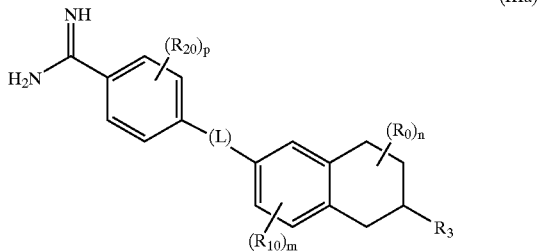
(IIIa)

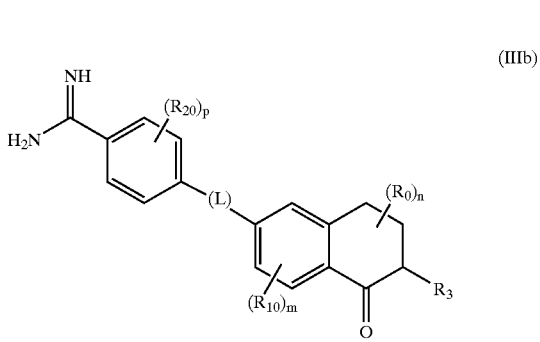
(IIIb)

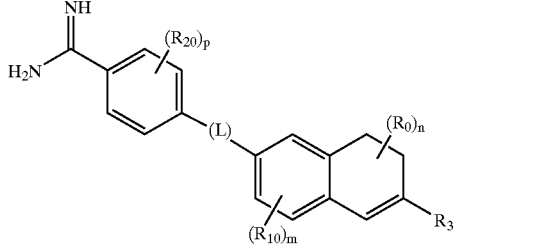
(IIIc)

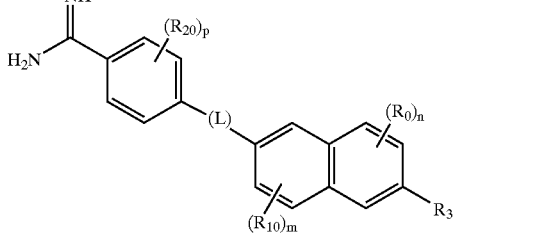
(IIId)

-continued

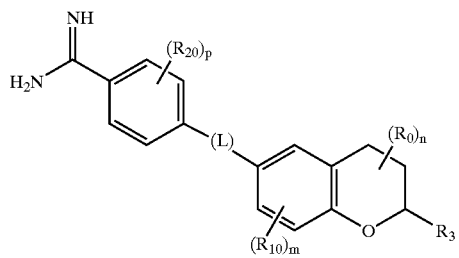
(IIIe)

where —(L)—, n, m, p, $R_0$, $R_3$, $R_{10}$ and $R_{20}$ are as previously defined. Most preferred are compounds where $R_{10}$ and $R_{20}$ are hydrogen and —(L)— has 2 carbon atoms.

Another preferred aspect of the invention is where the D ring is contains one or more (preferably 1 or 2) substituents independently selected from chlorine or fluorine. The chlorine and fluorine substituents may be added to any 5 to 8 membered D ring described above. Illustrative compounds of the invention with substitution of six membered D rings are shown in formulae (IV) to (IVb) below:

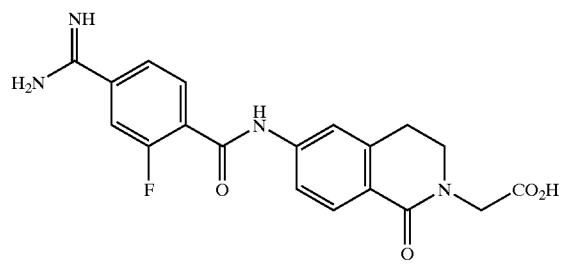
(IV)

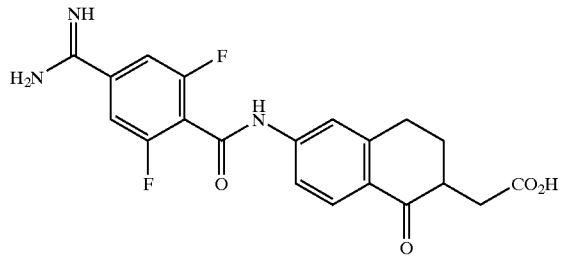
(IVa)

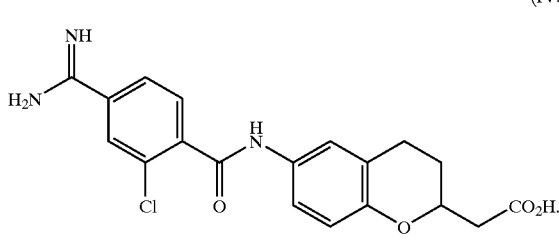
(IVb)

Without being bound by any theory of operation it is believed that the electron withdrawing groups such as fluorine reduce the basicity of the basic group and enhance the oral bioavailability of the compounds of the invention.

Specific compounds of the invention of the isoquinoline type which are highly preferred are represented by the following structural formulae (V) to (Vv) or a pharmaceutically acceptable salt, solvate or prodrug derivative thereof:

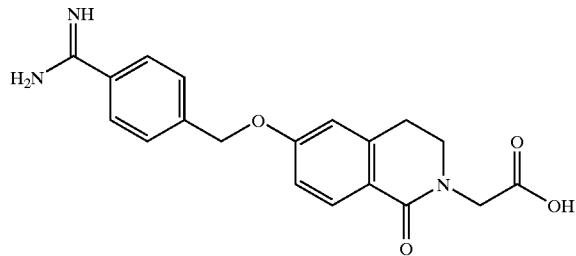
(V)

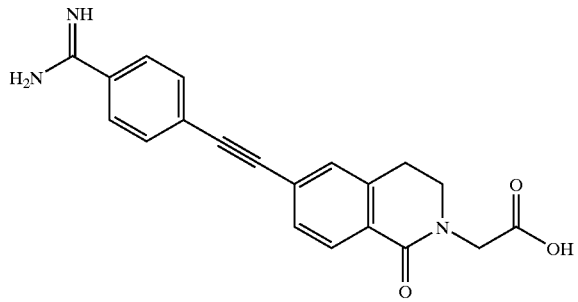
(Va)

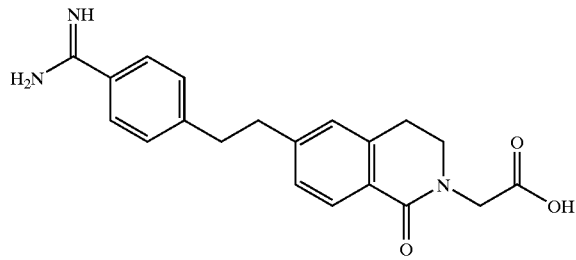
(Vb)

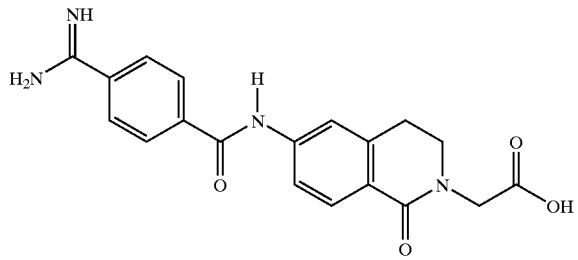
(Vc)

-continued
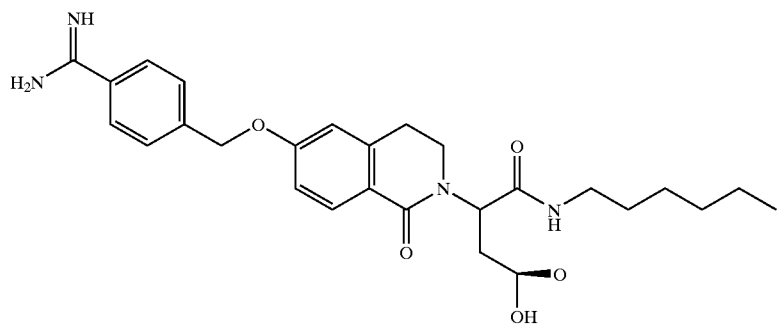
(Vd)
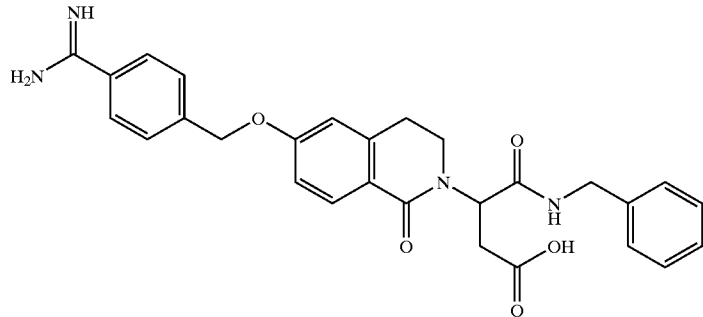
(Ve)
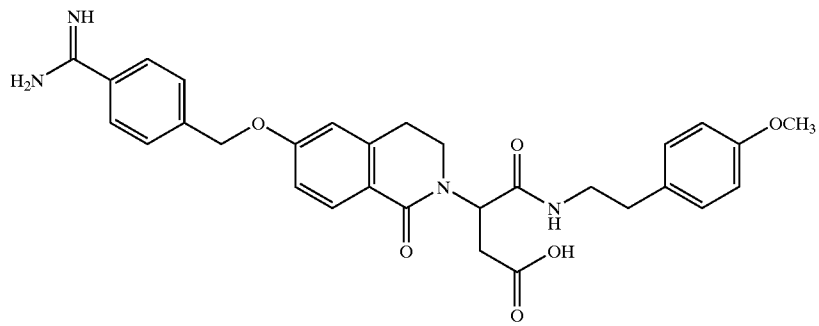
(Vf)
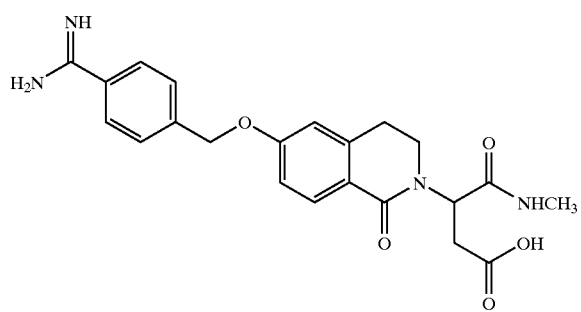
(Vg)
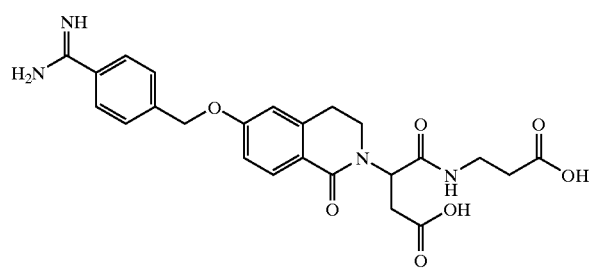
(Vh)
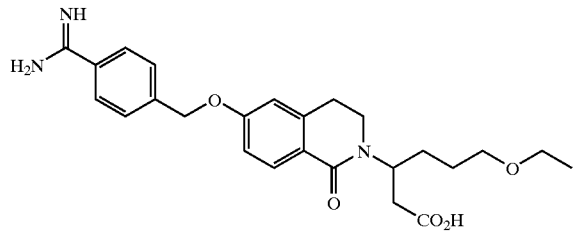
(Vi)
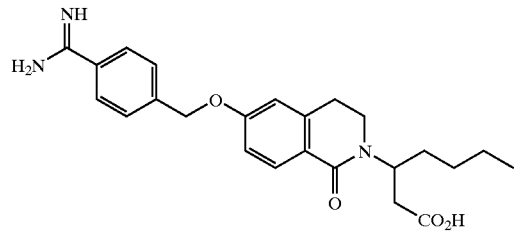
(Vj)

-continued
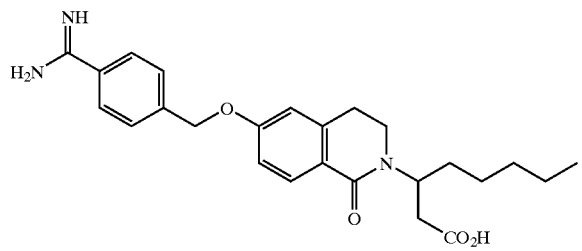
(Vk)
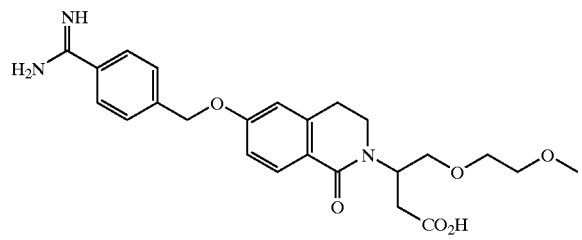
(Vl)
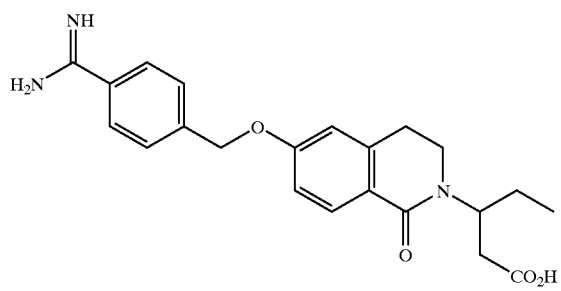
(Vm)
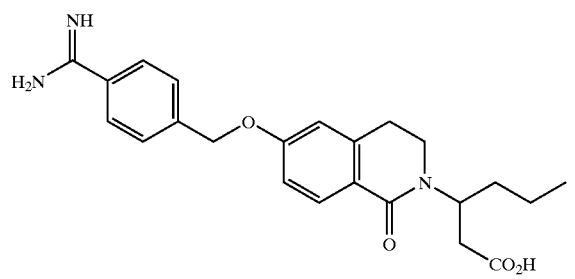
(Vn)
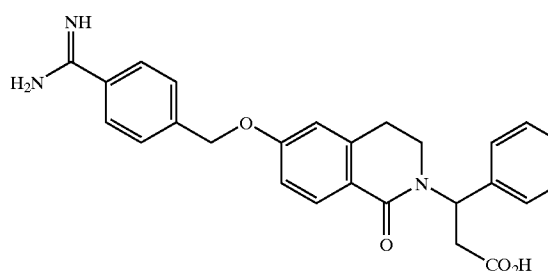
(Vo)
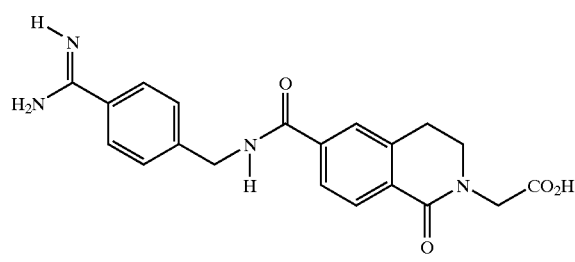
(Vp)
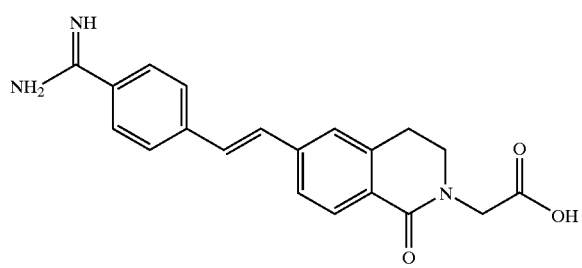
(Vq)
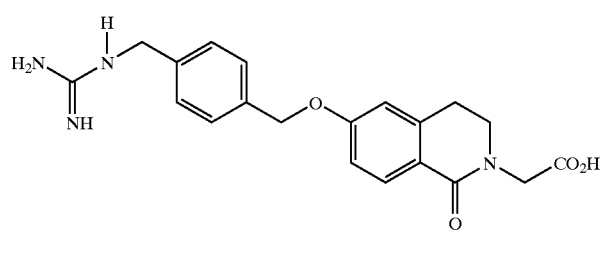
(Vr)
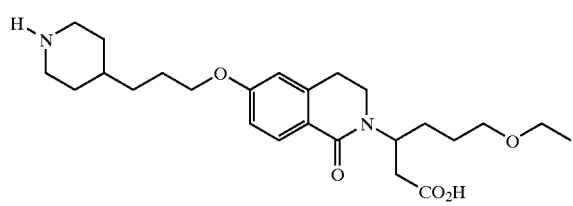
(Vs)
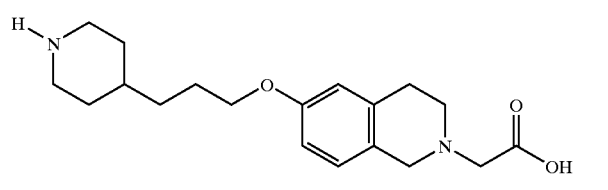
(Vt)
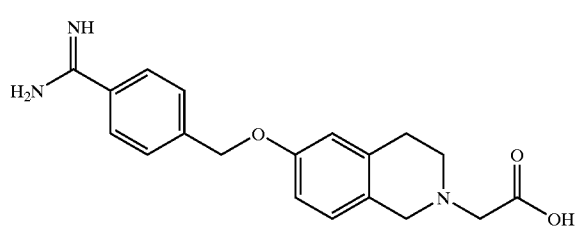
(Vu)
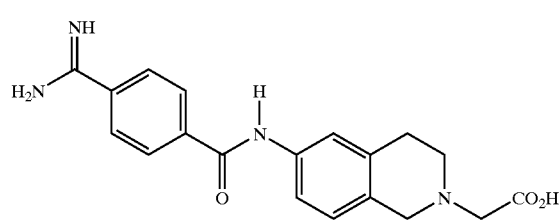
(Vv)

and mixtures of compounds (V) to (Vv).
Other specific compounds of the invention of the naphthalene/tetralin-type which are highly preferred are represented by the following structural formulae (VI) to (VIp) or pharmaceutically acceptable salts, solvates or pro-drug derivatives thereof:
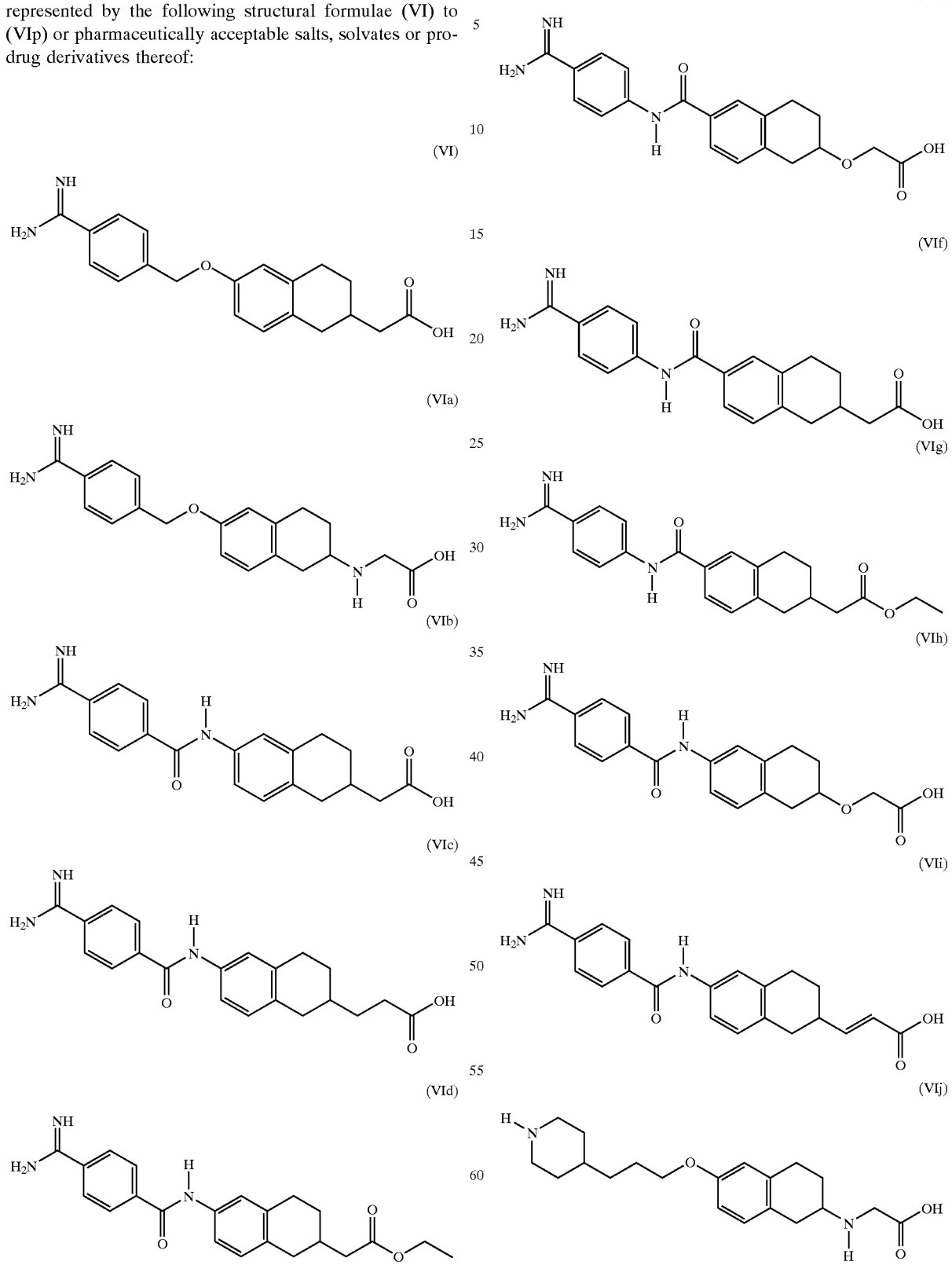

-continued
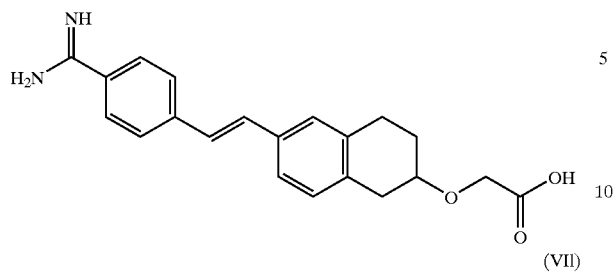
(VIk)
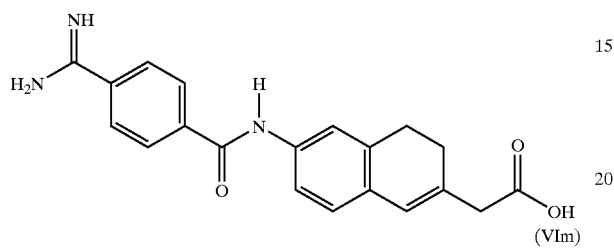
(VIl)
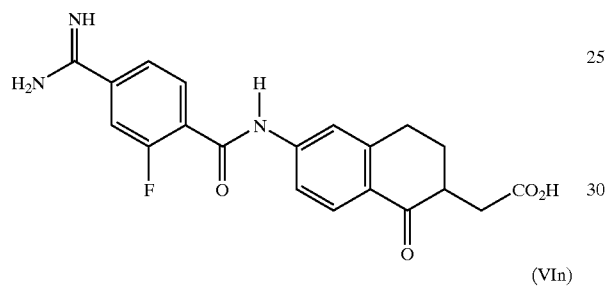
(VIm)
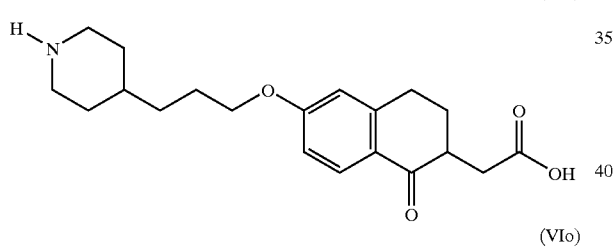
(VIn)
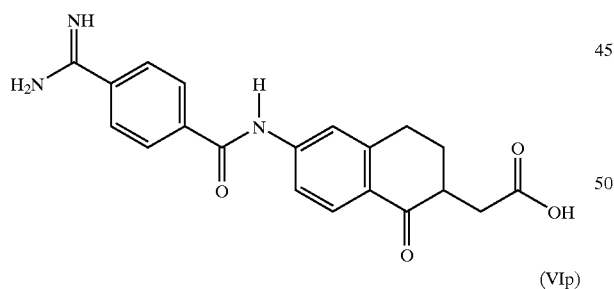
(VIo)
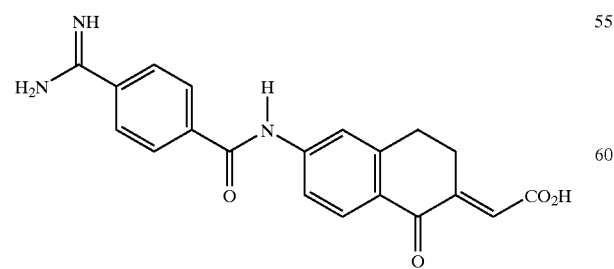
(VIp)
and mixtures of compounds (VI) through (VIp).
Other preferred specific compounds of the invention are represented by the following structural formulae (L) to LXIII) and all pharmaceutically acceptable salts, solvates and prodrug derivatives thereof:
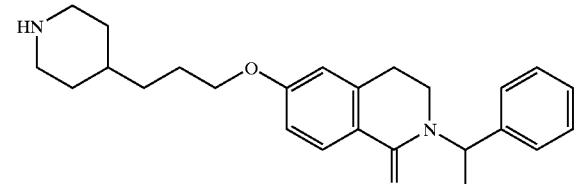
(L)
(LI)
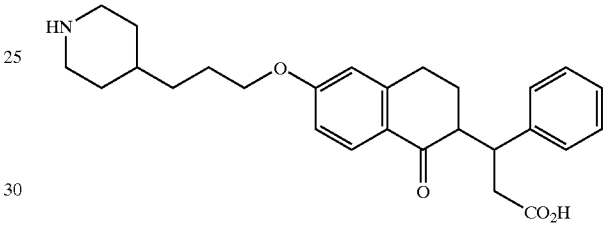
(LII)
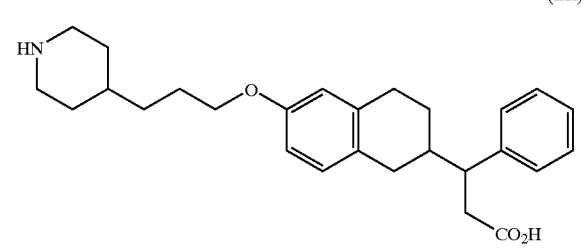
(LIII)
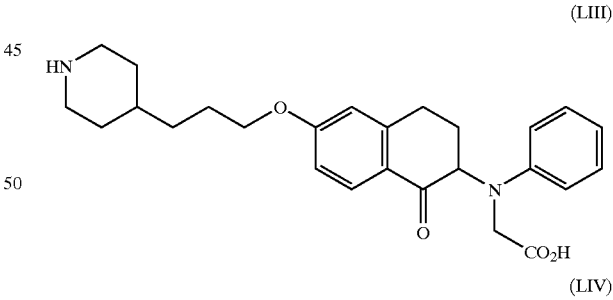
(LIV)
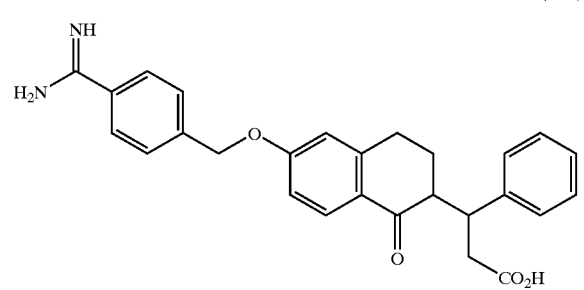

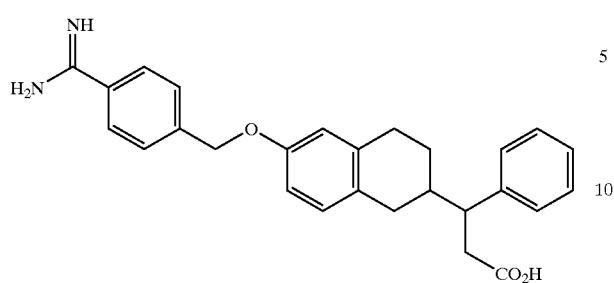
(LV)
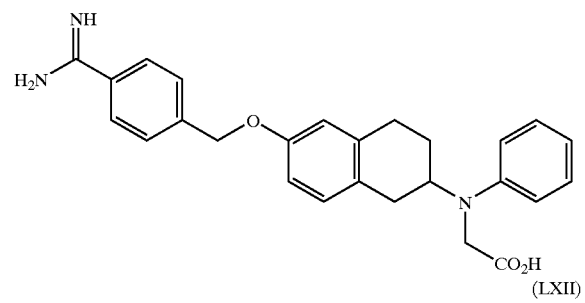
(LXI)
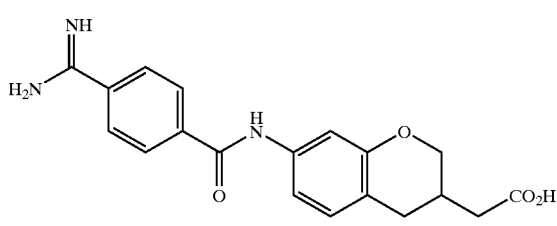
(LVI)
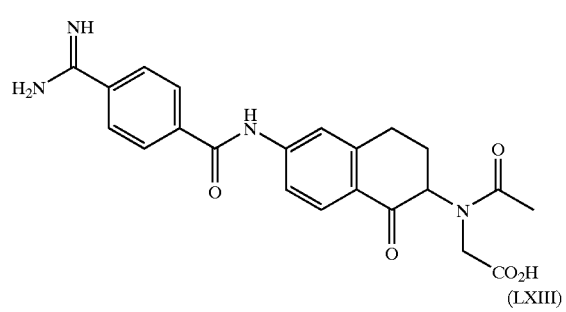
(LXII)
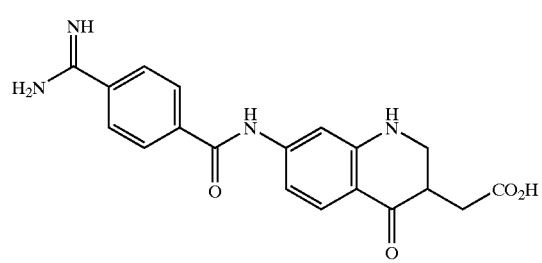
(LXIII)
(LVII)
(LVIII)
(LIX)
(LX)
and mixtures of any of (L) to (LXIII)
Other specific compounds of the invention of the benzopyran-type which are highly preferred are represented by the following structural formulae (VIII) to (VIIIi) or a pharmaceutically acceptable salt, solvate or prodrug derivatives thereof:
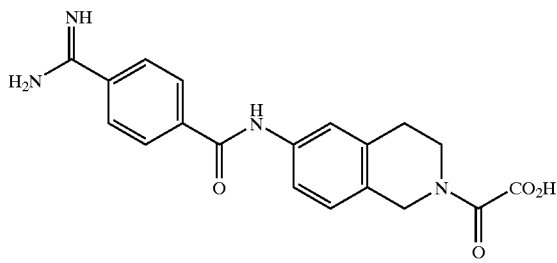
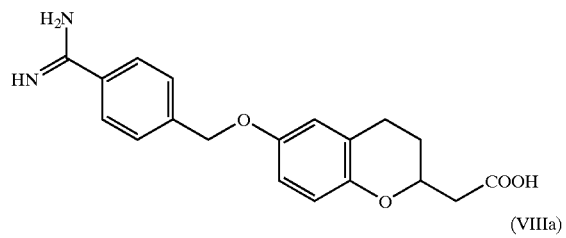
(VIII)
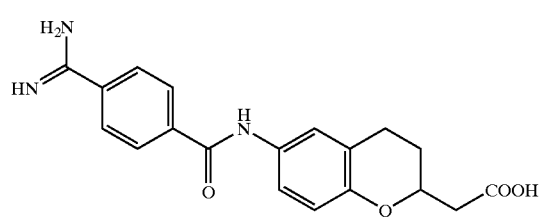
(VIIIa)

(VIIIb)
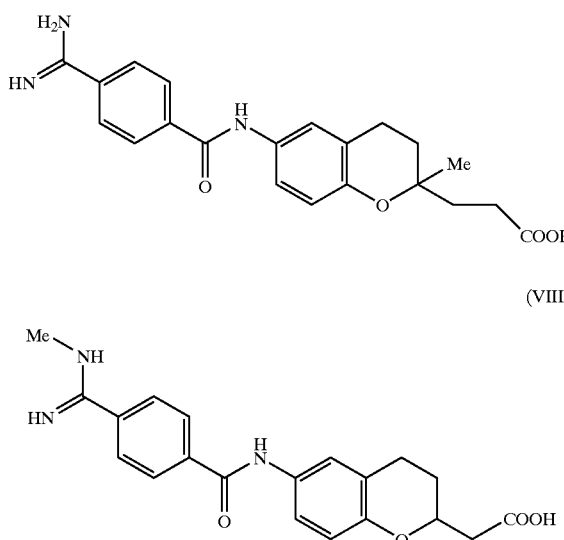
(VIIIc)
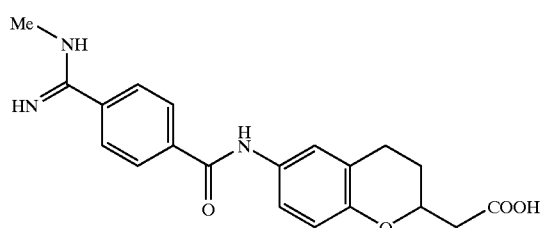
(VIIId)
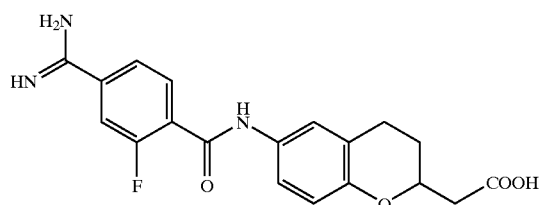
(VIIIe)
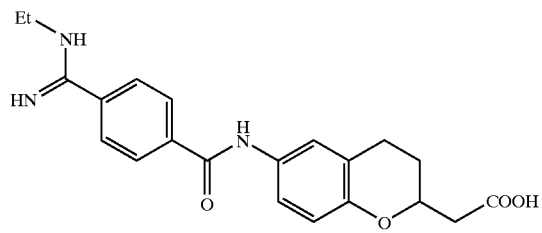
(VIIIf)
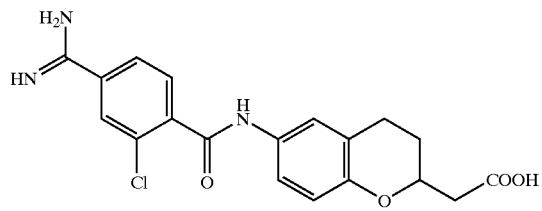
(VIIIg)
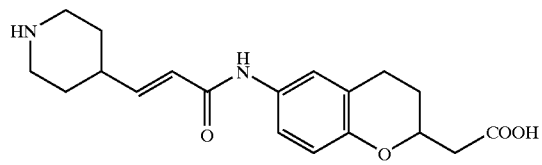
(VIIIh)
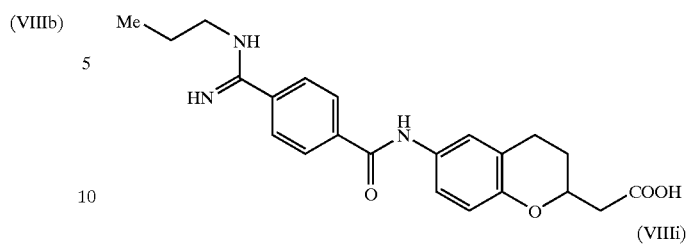
(VIIIi)
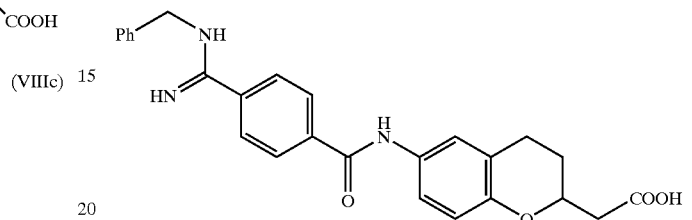
Other compounds of the invention having a bicyclic nucleus with an A ring oxygen atom are represented for the following formulae (IX) to (IX1) below:
(IX)
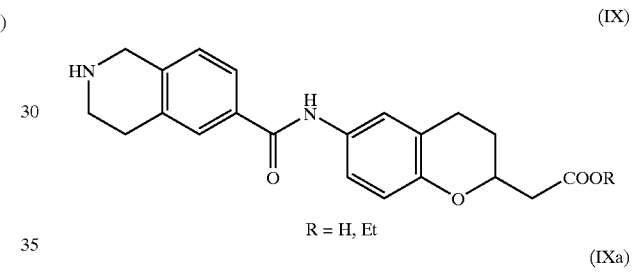
R = H, Et
(IXa)
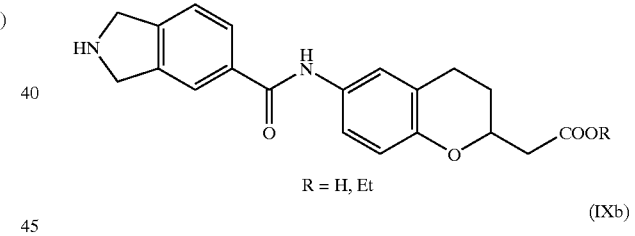
R = H, Et
(IXb)
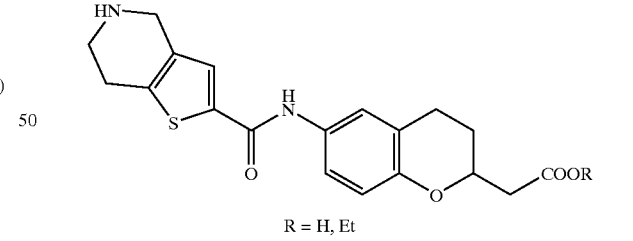
R = H, Et
(IXc)
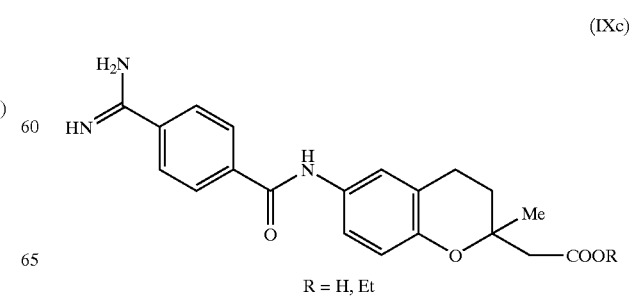
R = H, Et

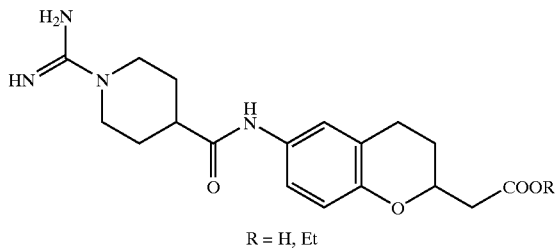

(IXd)

R = H, Et

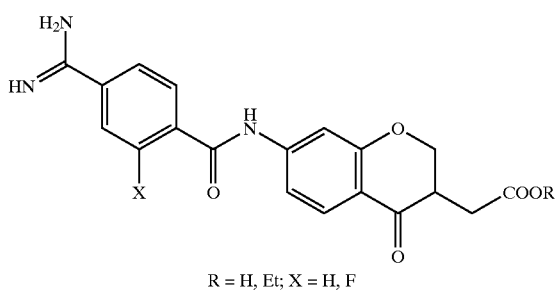

(IXe)

R = H, Et; X = H, F

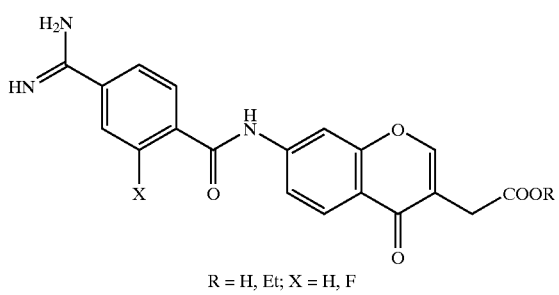

(IXf)

R = H, Et; X = H, F

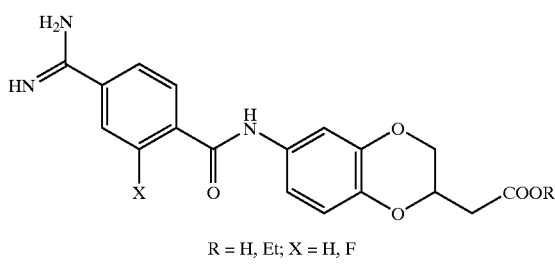

(IXg)

R = H, Et; X = H, F

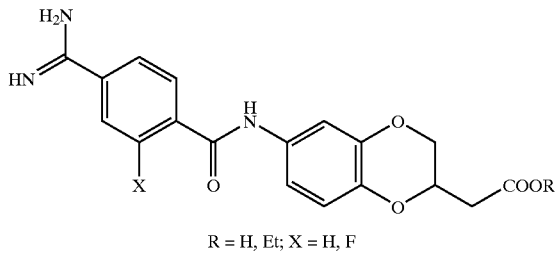

(IXh)

R = H, Et; X = H, F

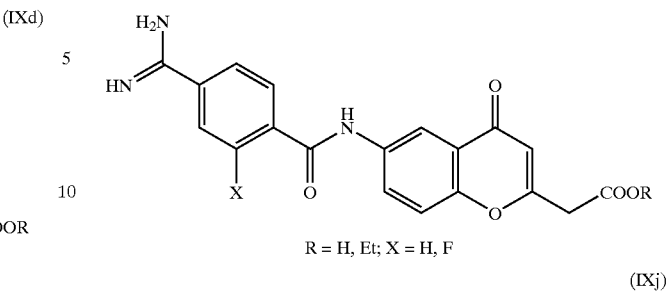

(IXi)

R = H, Et; X = H, F

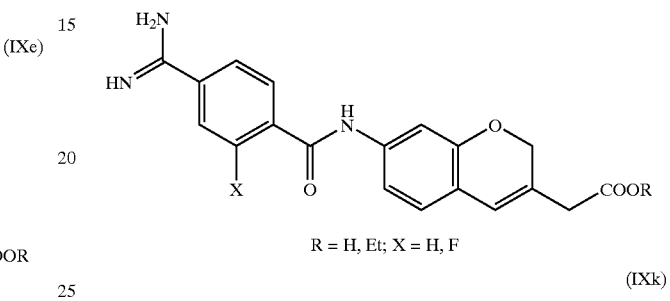

(IXj)

R = H, Et; X = H, F

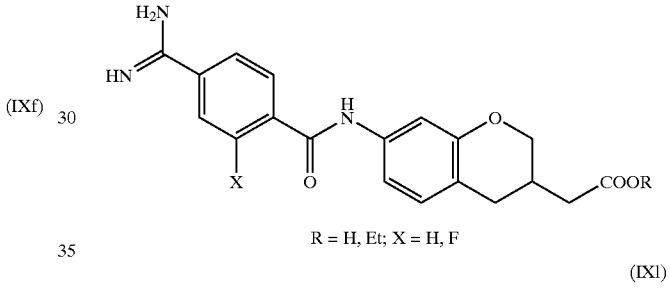

(IXk)

R = H, Et; X = H, F

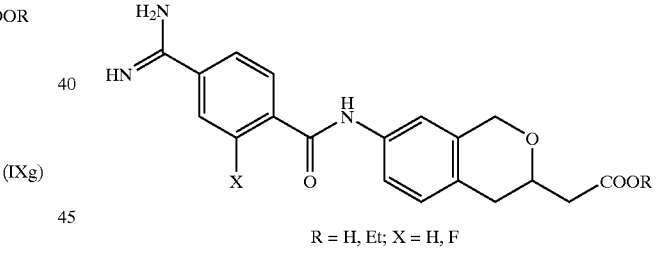

(IXl)

R = H, Et; X = H, F

The compounds of the invention possess at least one acidic functional substituent (viz., $R_3$ of Formula I) and, as such, are capable of forming salts. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an anion exchange resin on the salt cycle.

Included within the definition of pharmaceutically acceptable salts are the relatively non-toxic, inorganic and organic base addition salts of compounds of the present invention, for example, ammonium, quaternary ammonium, and amine actions, derived from nitrogenous bases of sufficient basicity to form salts with the compounds of this invention (see, for example, S. M. Berge, et. al., "Pharmaceutical Salts," J. Phar. Sci., 66: 1–19 (1977)).

The basic portion of the compounds of the invention (viz., group Q of formula I and group $Q_1$ of formula II) may be reacted with suitable organic or inorganic acids to form salts of the invention. Representative salts include those selected from the group comprising; acetate, benzenesulfonate, benzoate, bicarbonate, bisulfate, bitartrate, borate, camsylate, carbonate, chloride, clavulanate, dihydrochloride, edetate, edisylate, estolate, esylate, fumarate, gluceptate, gluconate, glutamate, glycollylarsanllate, hexylresorcinate, hydrabamine, hydrobromide, hydrochloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

The compounds of the formula (I) can also be in the form of zwitterions, since they contain both acidic and basic functionality and are capable of self-protonation.

Certain compounds of the invention possess one or more chiral centers and may thus exist in optically active forms. Likewise, when the compounds contain an alkenyl or alkenylene group there exists the possibility of cis- and trans-isomeric forms of the compounds. The R- and S- isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrug Derivatives of Compounds of the Invention

Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendant on the compounds of this invention are preferred prodrugs. In some cases it is desirable to prepare double ester type prodrugs such as (acyloxy) alkyl esters or ((alkoxycarbonyl)oxy)alkyl esters.

Preferred are the $C_1$–$C_8$ alkyl, $C_2$–$C_8$ alkenyl, aryl, $C_7$–$C_{12}$ substituted aryl, and $C_7$–$C_{12}$ arylalkyl esters of the compounds of the invention (per formula I). Particularly preferred are the $C_1$–$C_4$ alkyl esters, for example, where the $R_3$ acidic group has been esterified to form a group represented by one of the following formulae:

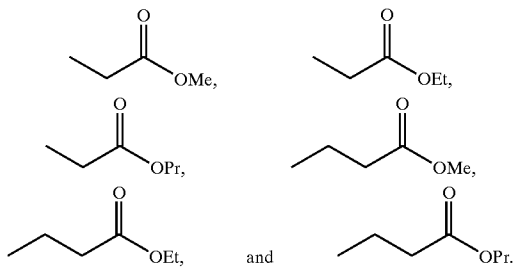

Other specific prodrug derivatives which are compounds of the invention are represented by the formulae (Xa) and (Xb) shown below:

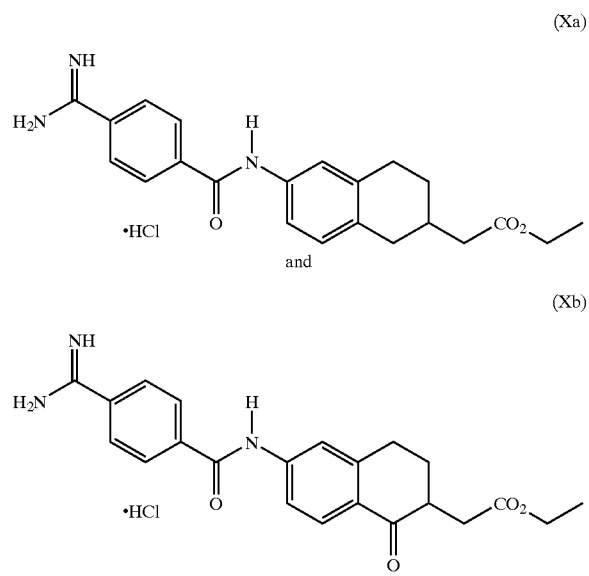

Acylated basic radicals which are part of basic group on the compounds of the invention have been found to significantly enhance bioavailability. Without being bound by any theory of operation, it is believed that lowering the basicity of basic group (Q) makes the compounds of this invention less subject to "food effect", that is, they have good availability in therapeutic administration to an animal without fasting.

Compounds of this invention may beneficially be dual prodrug derivatives. For example, the acidic group ($R_3$) may be reacted to form an ester and the basic group Q (or basic radical $Q_1$) may additionally be reacted to form an acylated basic derivative. Moreover, the prodrug derivatives of the compounds of this invention may be combined with other features herein taught to enhance bioavailability, for example, substitution of fluorine atoms on the D ring of the compounds of formula (II). These combined features result in a compound such as represented by the formula (Xc):

(Xc)

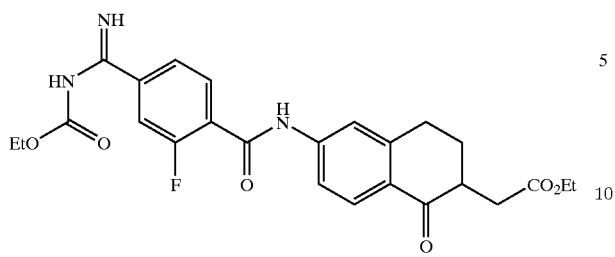

Another highly preferred class of prodrugs of the invention are those formed by acylating the basic radicals (e.g., $Q_1$) present on the compounds of the invention. The acyl portion of the acylated basic radical has the general formula:

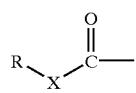

where R is $C_1$–$C_8$ alkyl, $C_2$–$C_8$ alkenyl, aryl, $C_7$–$C_{12}$ substituted aryl, and $C_7$–$C_{12}$ arylalkyl; and X is a bond, C, O, S, or N. Preferably R is $C_1$–$C_4$ alkyl and X is oxygen. For example, acylated basic radical prodrugs of the invention are prepared and illustrated in A, B, C, and D below:

A) acylation of amidine results in a prodrug derivative group:

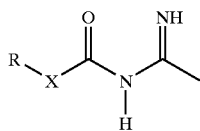

B) acylation of a cyclic amine such as piperidine results in a prodrug derivative group:

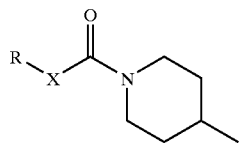

C) acylation of guanidine results in a prodrug derivative group:

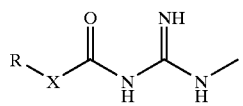

D) acylation of a primary amine results in a prodrug derivative group:

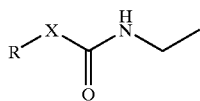

where, for A, B, C, and D above, R is as defined above for the acylated portion of the basic group.

The therapeutic compounds of this invention include prodrug derivatives of bicyclic compounds having a nucleus formed from two fused six membered rings, A and B, represented by the formula (Xd):

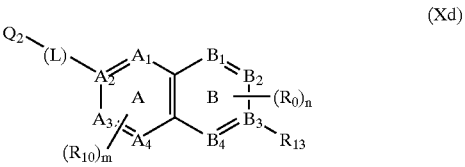

(Xd)

wherein;

$A_1$, $A_3$, $A_4$ are independently selected from carbon, oxygen, sulfur, and nitrogen;

$A_2$ is independently selected from carbon or nitrogen, provided that $A_2$ have an unsatisfied bond if $A_2$ is N and provided that at least two of $A_1$, $A_2$, $A_3$, and $A_4$ are carbon;

$B_1$, $B_2$, $B_4$ are independently selected from carbon, oxygen, sulfur, and nitrogen;

$B_3$ is independently selected from carbon or nitrogen, provided that $B_3$ have an unsatisfied bond if $B_3$ is N and provided that at least two of $B_1$, $B_2$, $B_3$, $B_4$ are carbon;

n is a number from 2 to 6;

$R_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamoyl, carboxy, acyl, cyano, halo, nitro, sulfo, $=O$, or $=S$; with the proviso that if $R_0$ is $=O$ or $=S$, then only one of $B_1$, $B_2$, $B_3$, and $B_4$ may be nitrogen;

m is a number from 2 to 6;

$R_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, $=O$, and $=S$; with the proviso that only one $R_{10}$ may be $=O$ or $=S$;

linking group —(L)— is a bond or a divalent substituted or unsubstituted chain of from 1 to 10 atoms selected from the group consisting of carbon, nitrogen, sulfur, and oxygen; and;

$Q_2$ is selected from (i) a basic group, or (ii) a basic group containing an acylated basic radical;

$R_{13}$ is selected from (i) an acidic group containing an acid radical, or (ii) an acidic group containing an ester derivative of an acid radical;

provided that at $Q_2$ is a basic group containing an acylated basic radical or $R_{13}$ is an acidic group containing an ester derivative of an acid radical.

A preferred form of prodrug derivative is a compound of formula (Xd) having dual prodrug functionality, that is, where $Q_2$ is a basic group containing an acylated basic radical and $R_{13}$ is an acidic group containing an ester derivative of an acid radical.

Another preferred form of prodrug is a compound of formula (Xd) wherein the acylated portion of the acylated basic radical has the general formula:

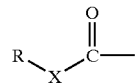

where R is $C_1$–$C_8$ alkyl, $C_2$–$C_8$ alkenyl, aryl, $C_7$–$C_{12}$ substituted aryl, and $C_7$–$C_{12}$ arylalkyl; and X is a bond, C, O, S, or N. Preferably R is $C_1$–$C_4$ alkyl and X is oxygen.

The group $Q_2$ may comprise two parts, namely, (i) one or more radicals selected from basic radicals or acylated basic radicals each designated, "$Q_3$", and (ii) a cyclic group D (as previously defined form formula Iw). zzz A general formula for the prodrug derivatives of this invention is a bicyclic compound having a nucleus formed from two fused six membered rings, A and B, represented by the formula (Xe), or a pharmaceutically acceptable salt, solvate or prodrug derivative thereof:

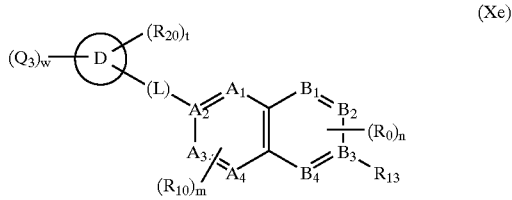

(Xe)

wherein;
$A_1$, $A_3$, $A_4$ are independently selected from carbon, oxygen, sulfur, and nitrogen;
$A_2$ is independently selected from carbon or nitrogen, provided that $A_2$ have an unsatisfied bond if $A_2$ is N and provided that at least two of $A_1$, $A_2$, $A_3$, and $A_4$ are carbon;
$B_1$, $B_2$, $B_4$ are independently selected from carbon, oxygen, sulfur, and nitrogen;
$B_3$ is independently selected from carbon or nitrogen, provided that $B_3$ have an unsatisfied bond if $B_3$ is N and provided that at least two of $B_1$, $B_2$, $B_3$, $B_4$ are carbon;
n is a number from 0 to 6;
$R_0$ is the same or different and is independently selected from hydrogen, alkyl, halosubstituted alkyl, alkenyl, alkynyl, cycloalkyl, aryl, arylalkyl, hydroxy, alkoxy, aralkoxy, amino, substituted amino, carbamoyl, carboxy, acyl, cyano, halo, nitro, sulfo, =O, or =S; with the proviso that if $R_0$ is =O or =S, then only one of $B_1$, $B_2$, $B_3$, and $B_4$ may be nitrogen;
m is a number from 0 to 6;
$R_{10}$ is the same or different and is independently selected from hydrogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo, =O, and =S; with the proviso that only one $R_{10}$ may be =O or =S;
t is a number from 0 to 3;
$R_{20}$ is the same or different and is independently selected from hydrogen, halogen, alkyl, halosubstituted alkyl, alkenyl, alkynyl, cycloalkyl, aryl, arylalkyl, hydroxy, alkoxy, aralkoxy, carboxy, acyl, cyano, halo, nitro, sulfo;
linking group —(L)— is a bond or a divalent substituted or unsubstituted chain of from 1 to 10 atoms selected from the group consisting of carbon, nitrogen, sulfur, and oxygen; and;
D is a ring formed from 5 to 8 ring atoms and said ring atoms are independently selected from carbon, nitrogen, oxygen, or sulfur, with the proviso that at least two D ring atoms are carbon;
w is an integer from 1 to 3;
$Q_3$ is selected from (i) a basic radical, or (ii) an acylated basic radical;
$R_{13}$ is selected from (i) an acidic group containing an acid radical, or (ii) an acidic group containing an ester derivative of an acid radical;
provided that $Q_3$ is an acylated basic radical or $R_{13}$ is an acidic group containing an ester derivative of an acid radical;

The integer w is preferably 1.

It is preferred in formula (Xe) that $R_{20}$ be chlorine and/or fluorine and t equal 1 or 2. Also preferred are compounds of formula (Xe) wherein $Q_3$ is an acylated basic radical and $R_{13}$ is an acidic group containing an ester derivative of an acid radical.

The most preferred acylated basic groups are carbamic acid esters of amidine, piperidine, or guanidine basic radicals. Carbamate acid $C_1$ to $C_4$ alkyl esters of amidine radicals are most highly preferred.

Carbamate ester prodrug derivatives of the invention may be prepared by a method such as shown in Scheme 27.

Preferred prodrug derivatives of the compounds of the invention having various features discused in this section are represented by the formulae (Xf) to (Xr) below:

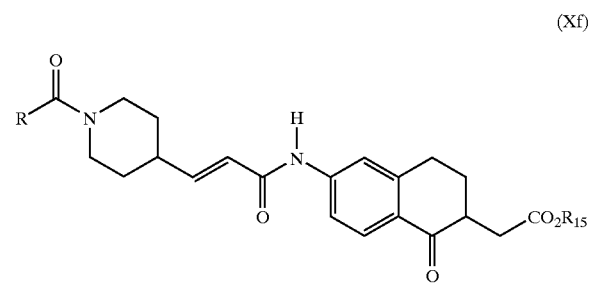

(Xf)

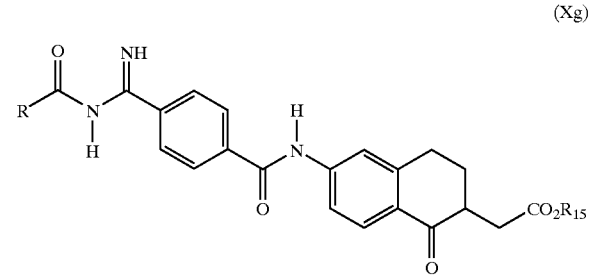

(Xg)

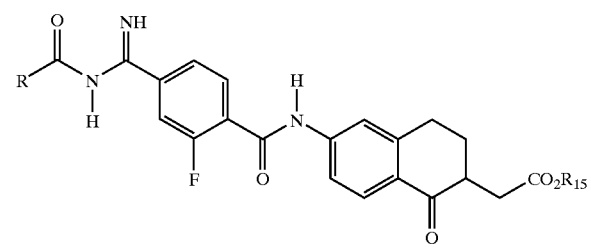

(Xh)

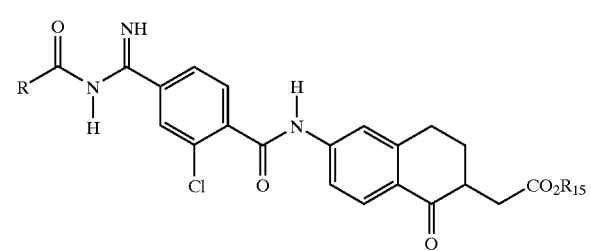

(Xi)

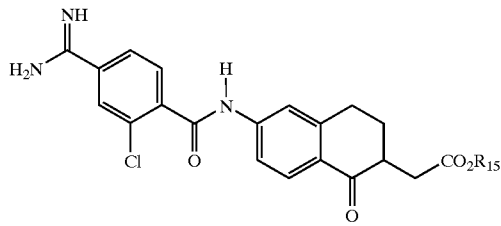 (Xj)

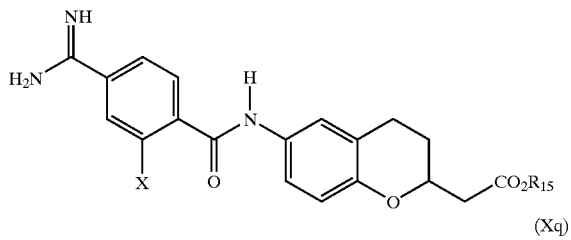 (Xp)

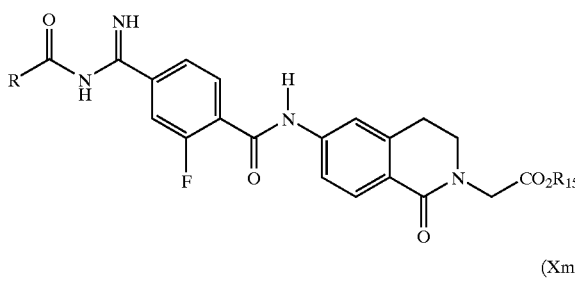 (Xk)

(Xq)

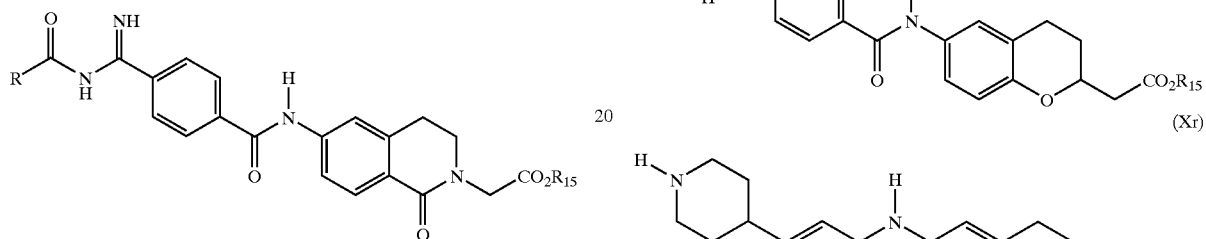

(Xr)

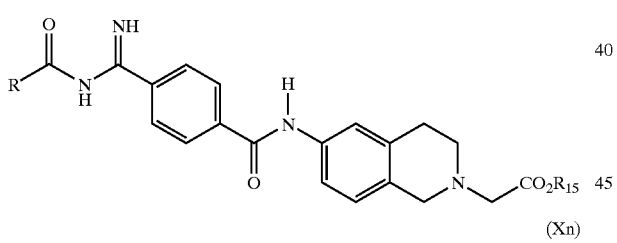 (Xl)

where, R=—H, —OMe, —OEt, —OPr
X=—Cl, —F, —H,
$R_{15}$=Me, Et, Pr.

Method of Making Compounds of the Invention

General synthesis schemes 1 through 33, infra., are used to prepare the compounds of the invention.

The following abbreviations are used throughout the synthesis Schemes and Examples:

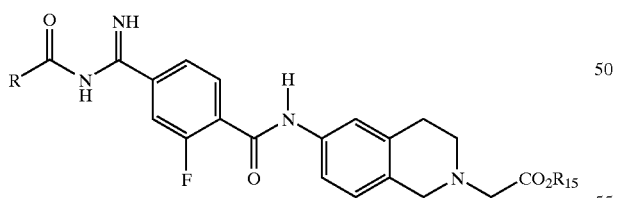 (Xm)

| | |
|---|---|
| TBAF | tetra-butyl ammonium fluoride |
| Tf | (triflate)-trifluoromethane sulfonate |
| Boc | tertiary-butoxy carbonyl |
| Bn | benzyl |
| Bu$^t$ | tertiary butyl |
| DMF | dimethyl formamide |
| TFA | trifluoroacetic acid |
| Cbz | benzyloxycarbonyl |
| EDCI | 1-(3-dimethylaminopropyl)-3-ethyl carbodiimide |
| DMAP | dimethylaminopyridine |
| LHMDS | lithium hexamethyl disilazane |
| THF | tetrahydrofuran |
| DIBAH | diisobutyl aluminum hydride |
| Boc$_2$O | di-tert-butyl dicarbonate |
| HMDS | hexamethyl disilazane |
| TSOH | p-toluene sulfonic acid |
| MCPBA | meta-chloro-peroxy benzoic acid |
| NMO | 4-methylmorpholine-N-oxide |
| TFAA | Trifluoroacetic anhydride |
| TBSCL | tert-butyl dimethyl silyl chloride |
| TMEDA | N,N,N',N'-tetramethylethylenediamine |
| LDA | lithium diisopropylamide |

(Xn)

where, R = -H, -OMe, -OEt, -Opr, Cl-C4 alkyl; R15 = Me, Et, Pr; and (Xo)

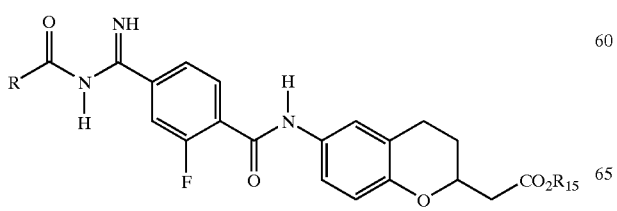

General Comments

The reactions described in the reaction schemes are carried out using standard chemical methodologies described and referenced in standard textbooks. Starting materials are commercially available reagents and reactions are carried out in standard laboratory glassware under reaction conditions of standard temperature and pressure, except where otherwise indicated.

Scheme 1

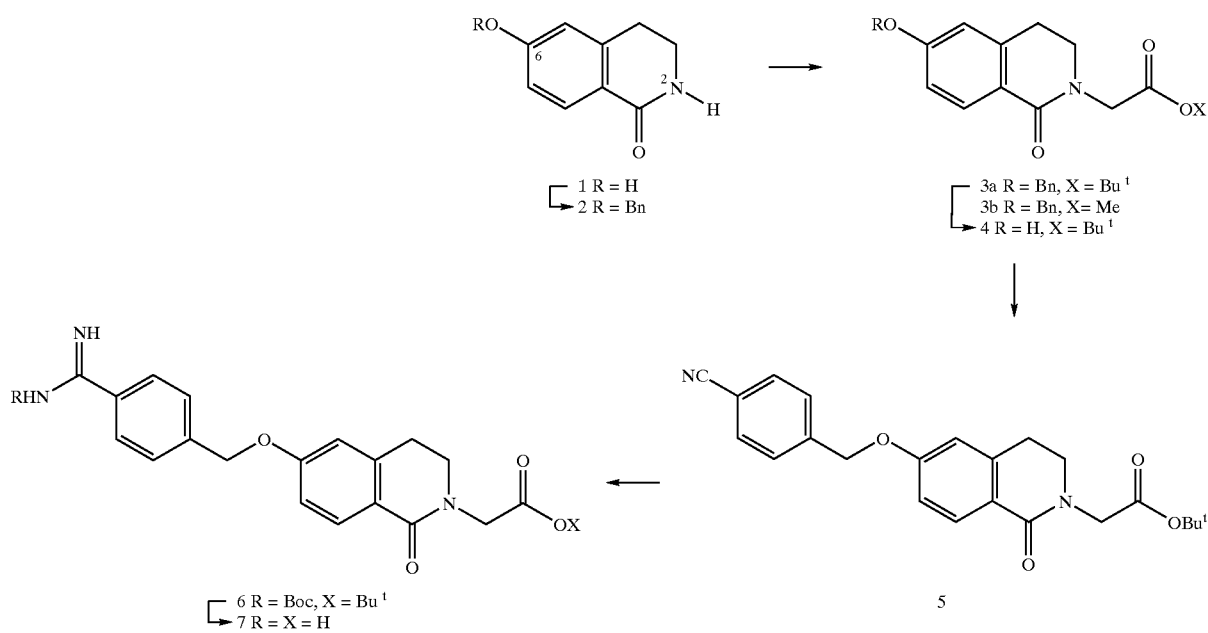

Scheme 1 teaches a method of preparing 2,6-disubstituted isoquinolones having an ether linked arginine isostere at $C_6$ and an acetic acid residue at position 2. In the first step of Scheme 1, isoquinolone (1) reacts with benzyl bromide in the presence of potassium carbonate in refluxing acetone to give a benzyl protected phenol (2). This compound reacts with sodium hydride and is then alkylated on nitrogen with either alpha-bromo tert-butyl acetate or alpha-bromo methyl acetate to give a 2-substituted isoquinolone (3a) (6-benzyloxy-3,4-dihydro-1-oxo-2(1H)isoquinolone acetic acid-1, -dimethylethyl ester) or (3b). The $C_6$ benzyl group is subsequently removed with hydrogen and palladium and subsequent alkylation of the 6-hydroxy group is accomplished with $K_2CO_3$ and alkyl bromide to give the di-substituted isoquinolone (5). Compound (5) is then transformed into the Boc protected amidine (6) using a series of reactions, namely; (i) reacting the nitrile with $H_2S$, (ii) alkylating the intermediate thioamide with methyl iodide, (iii) reacting the intermediate thioimidate with ammonium acetate, and (iv) thereafter Boc protecting the formed amidine to give compound (6). Compound (6) is deprotected with neat TFA giving (7) as the TFA salt.

Scheme 2

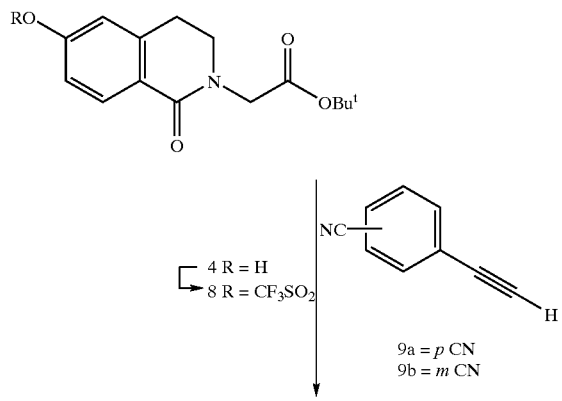

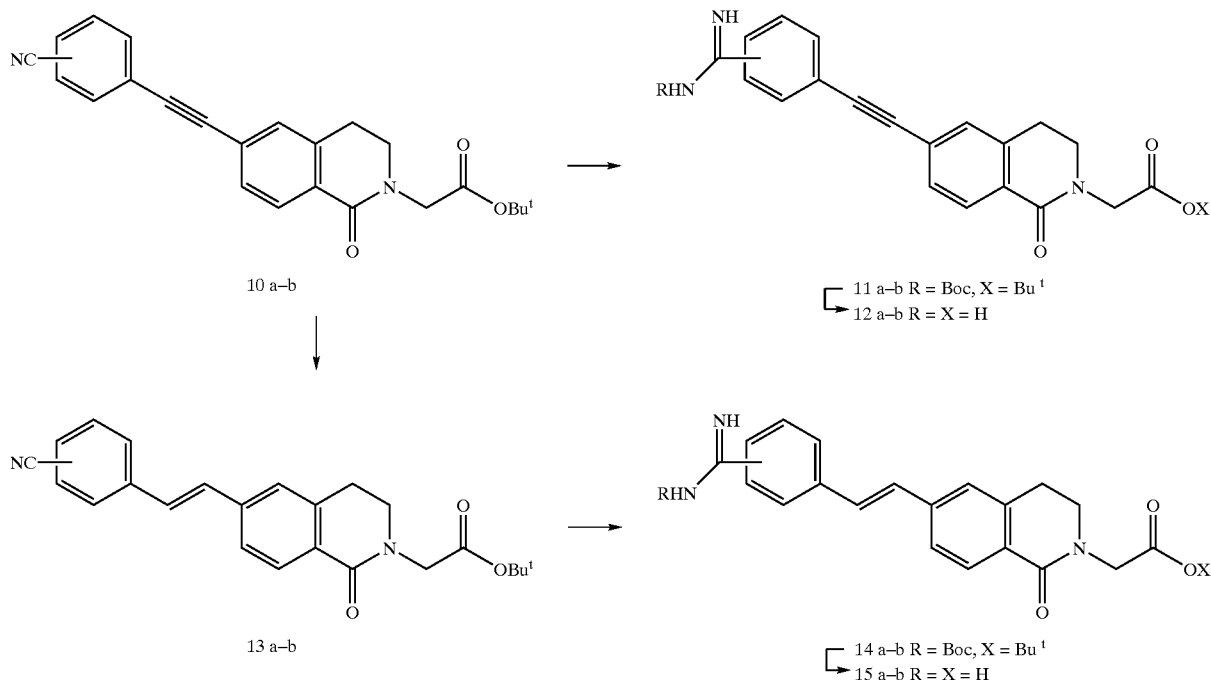

Scheme 2 describes a synthesis method suitable to give carbon substitution at position $C_6$ of the bicyclic nucleus. In this scheme compound (4) (6-hydroxy-3,4-dihydro-1-oxo-2(1H)isoquinolone acetic acid-1,1-dimethylethyl ester) from Scheme 1 is transformed into the triflate (8) using triflic anhydride and pyridine. The compound is thereafter reacted with the acetylenic compound (9a) or (9b) in the presence of palladium to give acetylene linked benzonitrile (10a) or (10b). Compound (10a) or (10b) is transformed again with the same set of procedures used to transform compound (5) (6-[(4 cyanophenyl) methoxy]-3,4-dihydro-1-oxo-2(1H)isoquinolone acetic acid, -1,1-dimethyl ethyl ester) to compound (6) (6-[[4-(1,1 dimethyl ethoxy carbonyl aminoiminomethyl)phenyl]methoxy]-3,4-dihydro-1-oxo-2(1H)isoquinolone acetic acid-1,1-dimethyl ethyl ester) to yield the amidine product (11a) or (11b). Compounds (11a) or (11b) may also be deprotected again with TFA to give compound (12a) or (12b). Alternatively, intermediate (10a) or (10b) can be either partially or fully hydrogenated as shown in the scheme giving the alkylene or alkenylene linked compound (13a) or (13b). Compound (13a) or (13b) is again transformed using the nitrile to amidine conversion previously described (Scheme 1, steps 5>6), giving compound (14a) or (14b) which is subsequently deprotected with TFA to give compound (15a) or (15b).

Scheme 3

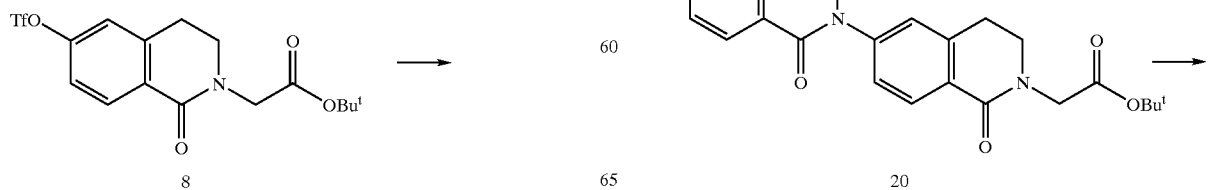

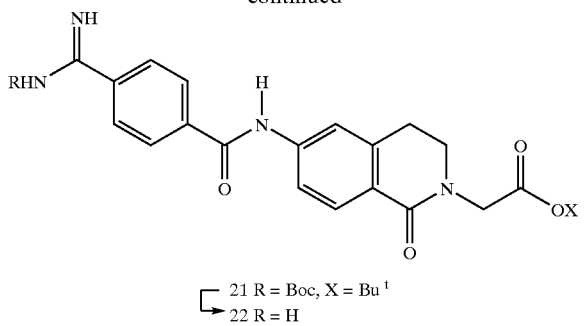

21 R = Boc, X = Bu$^t$
22 R = H

Scheme 3 describes the preparation of isoquinolones containing nitrogen substitution at $C_6$. This scheme starts with triflate (8) whose preparation was previously described in Scheme 2. The triflate is transformed to aryl ester (16) via the use of palladium, carbon monoxide and methanol. The ester (16) is then saponified with lithium hydroxide in aqueous THF. The free acid (7) is then subjected to a Curtius rearrangement (viz., formation of an isocyanate by thermal decomposition of acyl azides). The required acyl azide is formed with a triphenyl phosphoryl azide and then pyrolized in situ to give an isocyanate which is then trapped with benzyl alcohol giving Cbz protected aniline (18).

CBz-Aniline (18) is then transformed into free amine (19) with catalytic hydrogenation. Amine (19) is then acylated with paracyanobenzoic acid in the presence of EDCI and DMAP giving the amide-linked compound (20). Compound (20) is then transformed into the Boc protected amidine (21) again using the conditions of Scheme 1 and that compound is then deprotected with TFA to give compound (22).

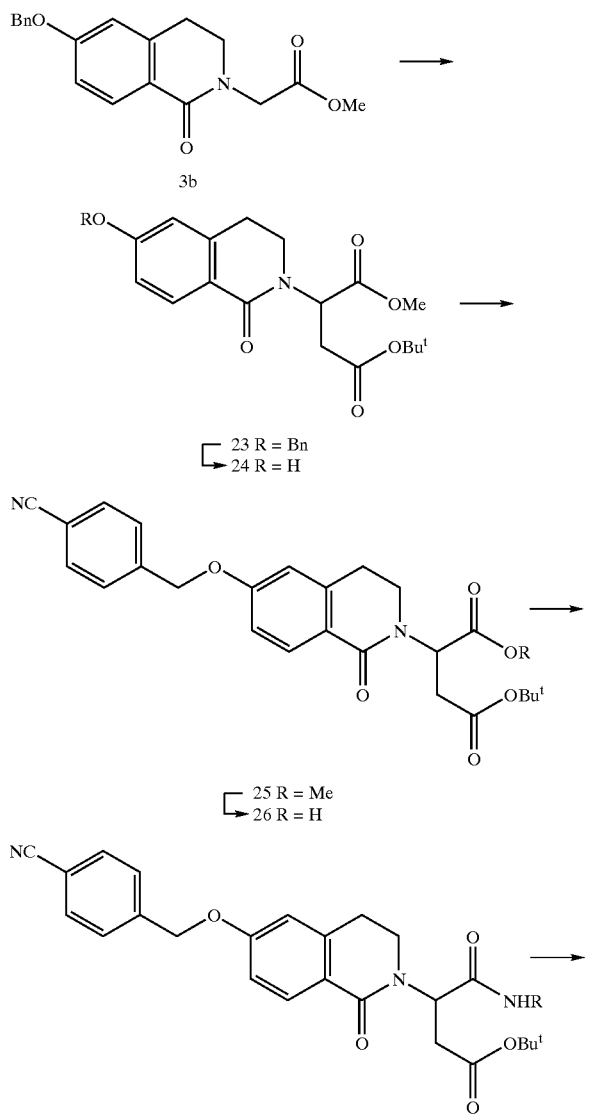

Scheme 4

3b

23 R = Bn
24 R = H

25 R = Me
26 R = H 27 a–e

-continued

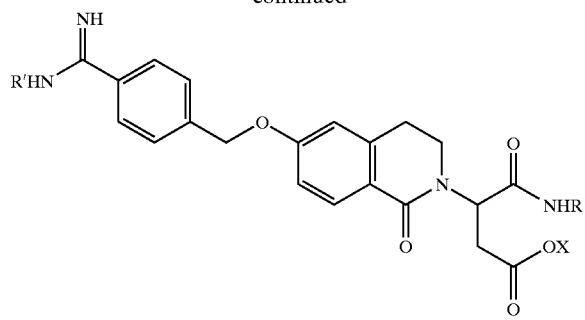

28 a–e R' = Boc, X = Bu^t
29 a–e R' = X = H

Amines (a) to (e):

(a) - hexyl amine
(b) - benzyl amine
(c) - p-methoxy phenethyl amine
(d) - methyl amine
(e) - beta-amino-butylalanine Scheme 4 describes how to make 2,6-disubstituted isoquinilones in which the 2-position is substituted with an aspartic acid moiety. Scheme 4 starts with compound (3b) whose preparation is described in Scheme 1. Compound (3b) is deprotonated with LHMDS and the resulting anion is quenched with alpha-bromo-t-butyl acetate to give compound (23). The 6-benzyl group of compound (23) is removed with palladium and hydrogen to give the free phenol (24). Compound (24) is then alkylated as described for the preparation of compound (5) in Scheme 1. The methyl ester (25) is then saponified with lithium hydroxide in THF to give the free carboxylate (26). The free carboxylate is then coupled with a variety of amines in the presence of EDCI and DMAP to give the half amide esters (27a) thru (27e). The half amide esters (27a) thru (27e) are then transformed again using the same protocol as previously described in Scheme 1 (steps 5–6) to give the Boc protected amidines (28a) thru (28e). The Boc protected amidine is then deprotected with TFA to give compounds (29a) thru (29e).

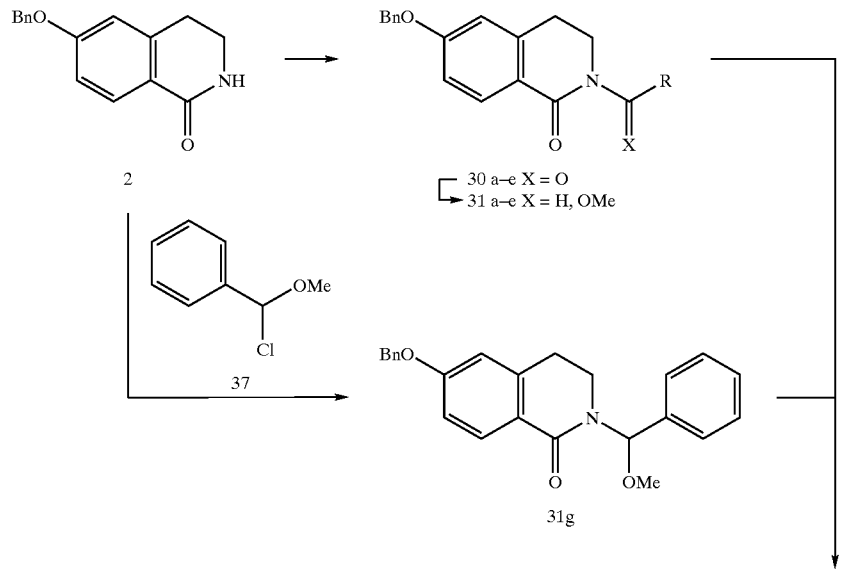

Scheme 5

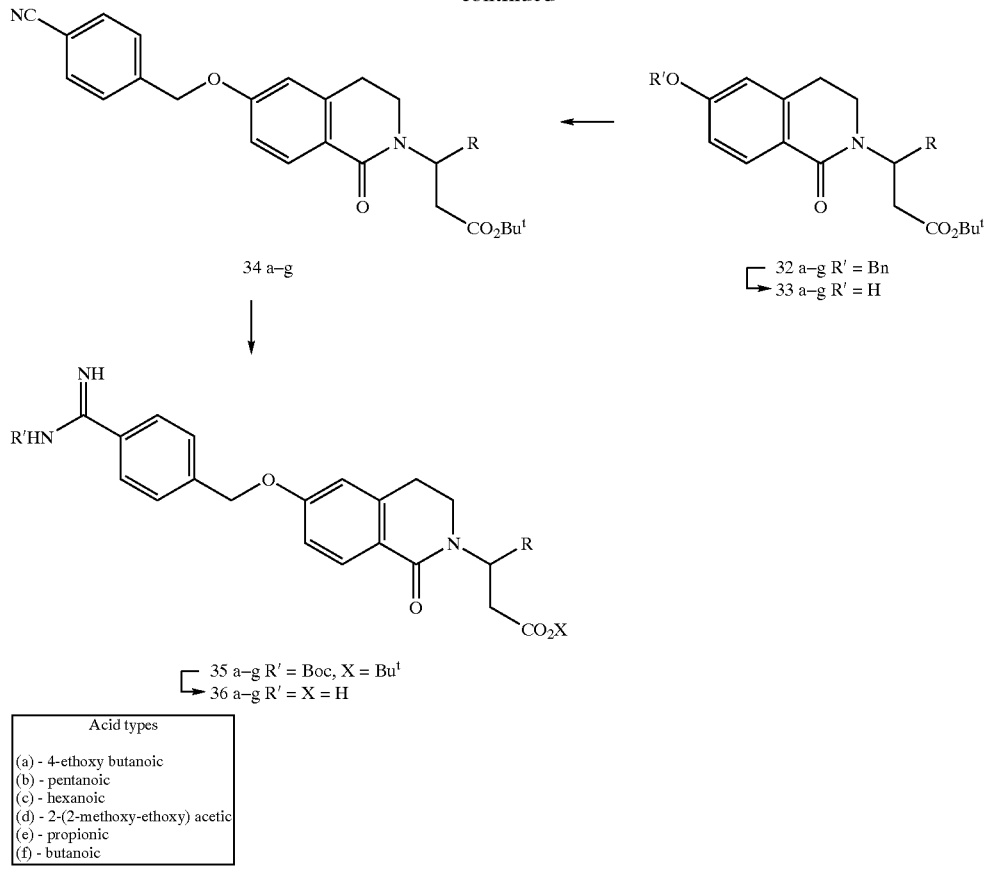

34 a–g 32 a–g R' = Bn
33 a–g R' = H 35 a–g R' = Boc, X = Bu$^t$
36 a–g R' = X = H

Acid types (a) - 4-ethoxy butanoic
(b) - pentanoic
(c) - hexanoic
(d) - 2-(2-methoxy-ethoxy) acetic
(e) - propionic
(f) - butanoic Scheme 5 describes the preparation of 2,6-di-substituted isoquinilones in which the 2-position is substituted by an aspartate isostere. Scheme 5 compounds differ from the compounds prepared in Scheme 4 in that the R group of the Scheme 5 compound (36) does not contain an amide linkage like the Scheme 4 compounds (29a) thru (29e). Compound (2), the starting material, is prepared by the method of Scheme 1, then acylated with a variety of activated acids (acid halides or anhydrides) to give the corresponding imides (30a) thru (30e). Thereafter the imide is selectively reduced at its exocyclic carbonyl with DIBAH and then entrapped with acidic methanol to give alpha-methoxy amides (31a) thru (31e). Alternatively, alpha-methoxy amides (31) can be prepared by reacting the sodium salt of (2) with an appropriate alpha chloro ether (37). All of the alpha-methoxy amides (31a) thru (31g) are reacted with boron trifluoride etherate in the presence of a ketene acetal to give the beta,beta-di-substituted propionates (32a) through (32g). Thereafter, the benzyl group is removed from the 6 position by catalytic hydrogenation and phenols can be alkylated again in the same manner as shown in Scheme 1 (steps 4>5) to give the ether linked nitrites (34a) to (34g). That nitrile can then be converted to the Boc protected amidine (35a) to (35g) as shown in Scheme 1 (steps 5>6), Thereafter, deprotection gives the final compounds (36a) to (36g).

Scheme 6

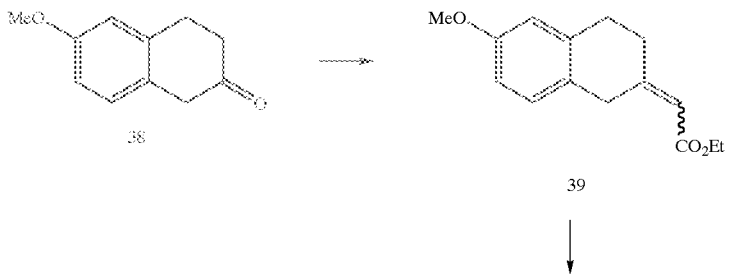

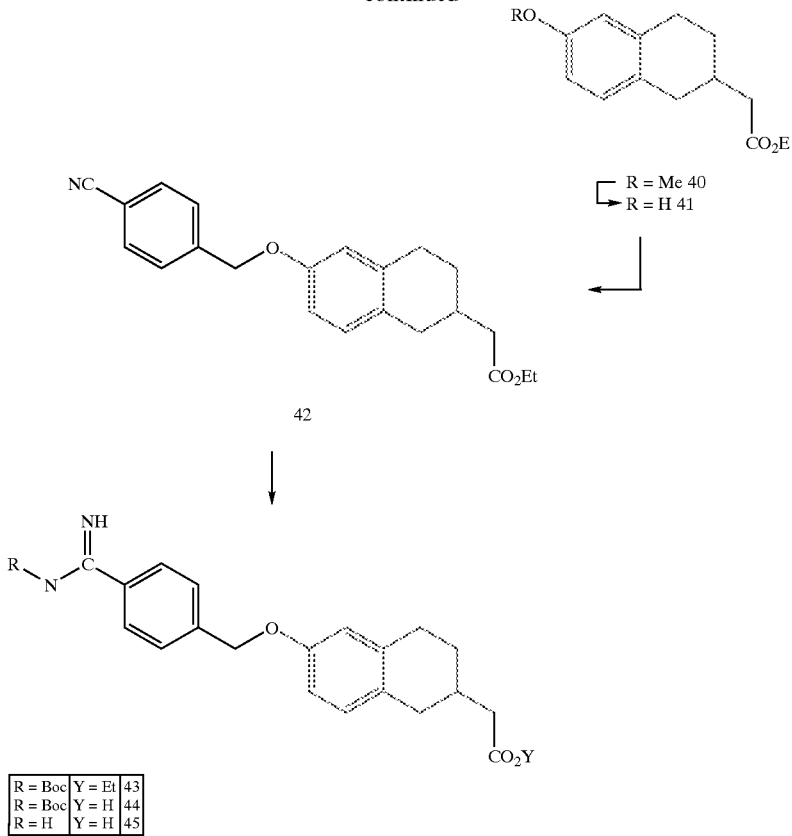

Scheme 6 describes the preparation of compounds of the invention having a tetralin nucleus. 6-methoxy-2-tetralone (38) is reacted with tert-butyl diethylphosphono acetate to give unsaturated ester (39). Subsequent hydrogenation removes the unsaturation to give compound (40). Compound (40) is treated with boron tribromide and the crude product is reesterified with HCl and ethanol to give (41). The phenol (41) is then alkylated in the same manner as shown in Scheme 1 (step 4–5) giving (42). The nitrile can then be converted to the Boc protected amidine (43) as shown in Scheme 1 (step 5–6). The amidino ester (43) is then saponified with sodium hydroxide to give compound (44), which then is later deprotected with TFA and anisole to give the final product (45).

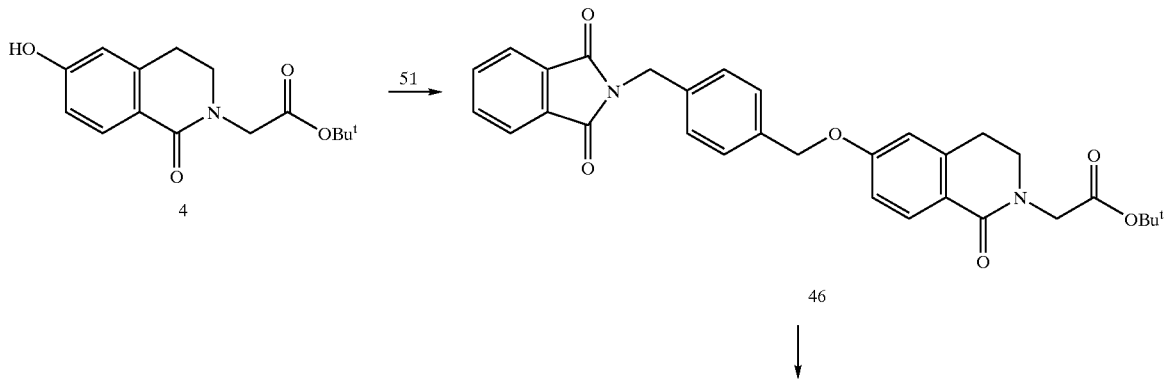

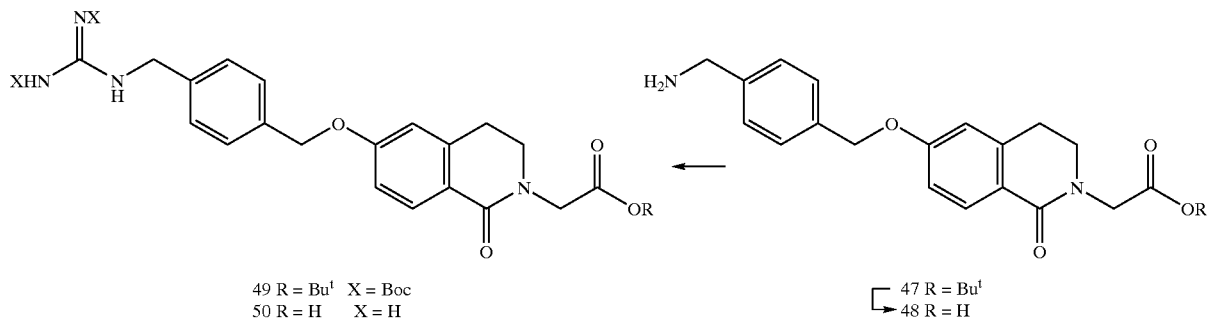

49 R = Bu$^t$  X = Boc
50 R = H  X = H

47 R = Bu$^t$
48 R = H

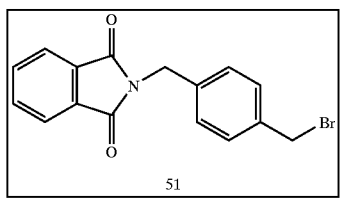
51

Scheme 7 describes the preparation of compounds of the invention having a guanidine group as the basic functionality. Phenol (4), prepared in scheme 1, is alkylated with bromide (51) (prepared from the dibromide and potassium pthalimide) giving adduct (46). This compound is deprotected with aqueous hydrazine giving amine (47). Compound (47) is transformed into protected guanidine (49) with N,N'-bis(tert-butoxy carbonyl)-S-methyl-isothiourea. Compound (49) is deprotected with TFA giving product (50) as the trifluoroacetate salt.

Scheme 8

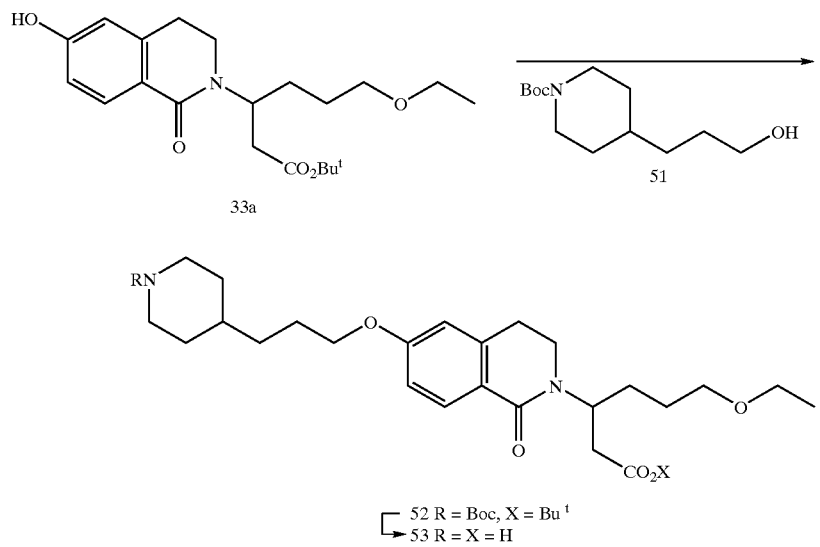

52 R = Boc, X = Bu$^t$
53 R = X = H

Scheme 8 describes the preparation of compounds of the invention having an amine group as the basic functionality.

Compound (33a), prepared in scheme 5, is coupled with alcohol (51) (prepared from 3-(4-pyridyl)-propanol using standard protocols) using triphenyl phosphene and diethyl azodicarboxylate giving compound (52). Compound (52) is deprotected with neat TFA giving product (53) as the TFA salt.

an ether linked benzamidine or an ether linked 4-alkylpiperidine moiety. The scheme begins with 6-methoxy-2-tetralone (60) which is sequentially treated with $NaBH_4$ and then with DIBAH giving dihydoxy compound 62. The phenolic hydroxyl can be selectively alkylated with either α-bromo-p-tolunitrile or the appropriate 4-alkylpiperidine giving compounds 63 and 67 respectively. Both compounds are then alkylated with tert-butyl bromoacetate under phase transfer conditions providing 64 and 68. Nitrile 64 is converted to the Boc protected amidine 65 and

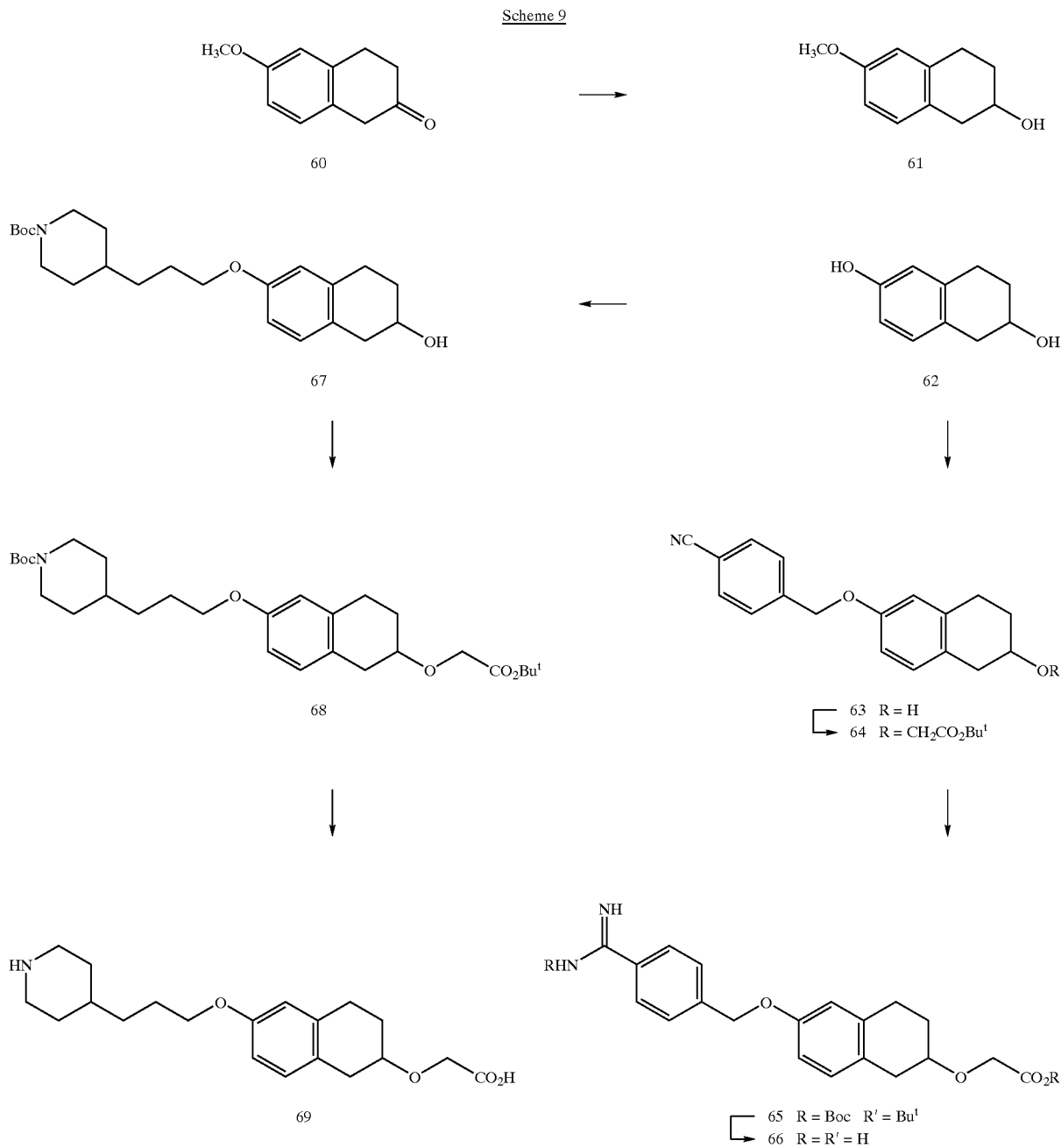

Scheme 9

Scheme 9 describes the preparation of 2-6 disubstituted tetralins in which the 2 position is occupied by an a-alkoxyacetic acid residue and the 6 position retains either then to product 66 using the same sequence of reactions described in Scheme 1. Compound 68 is converted to the fully deprotected 69 by treatment with TFA.

Scheme 10

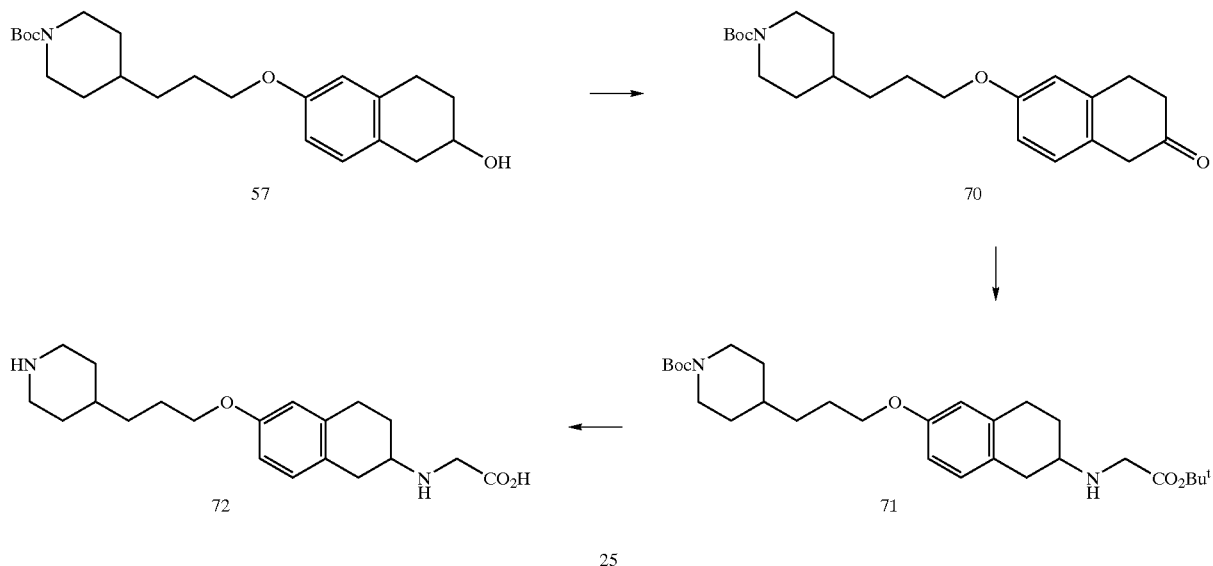

Scheme 10 outlines the preparation of 2,6-disubstituted tetralins in which an α-aminoacetic acid moiety resides at position 2 and an ether linked 4-alkylpiperidiene emanates from position 6. Alchohol 67, prepared in Scheme 9, is oxidized with DMSO and TFAA using the conditions of Swern giving ketone 70 which is reductively aminated with glycine tert-butyl ester giving 71. This material is then deprotected with TFA giving 72.

Scheme 11

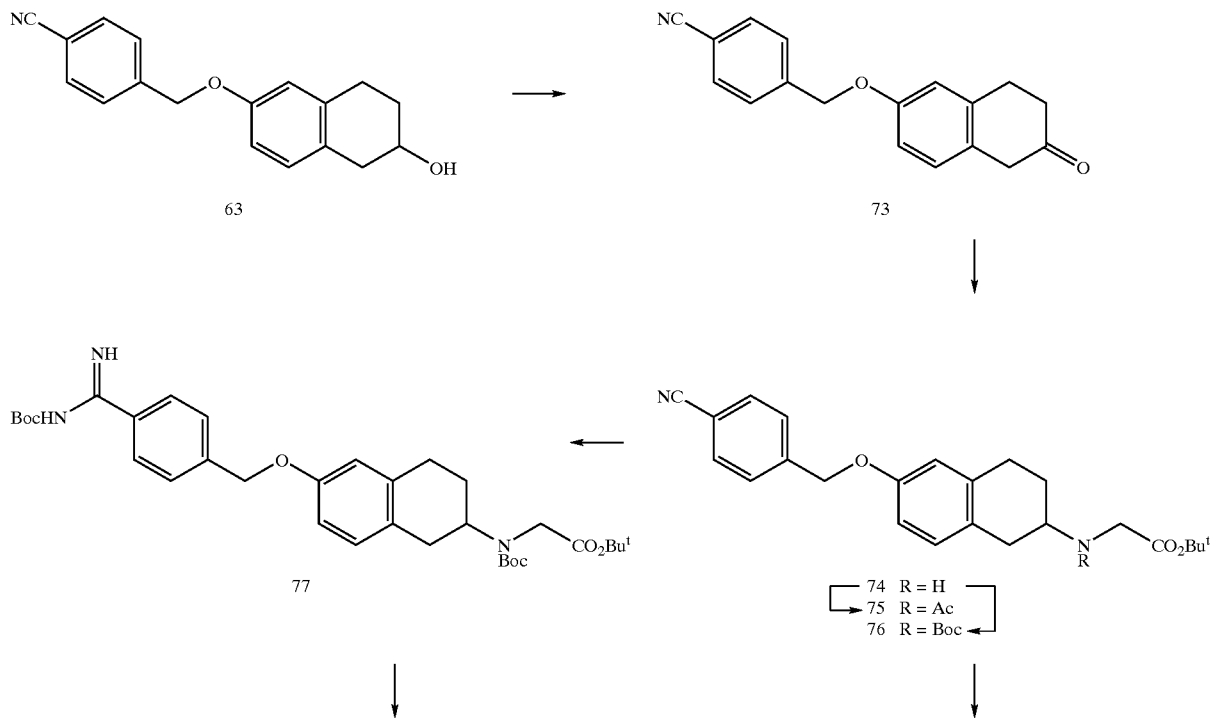

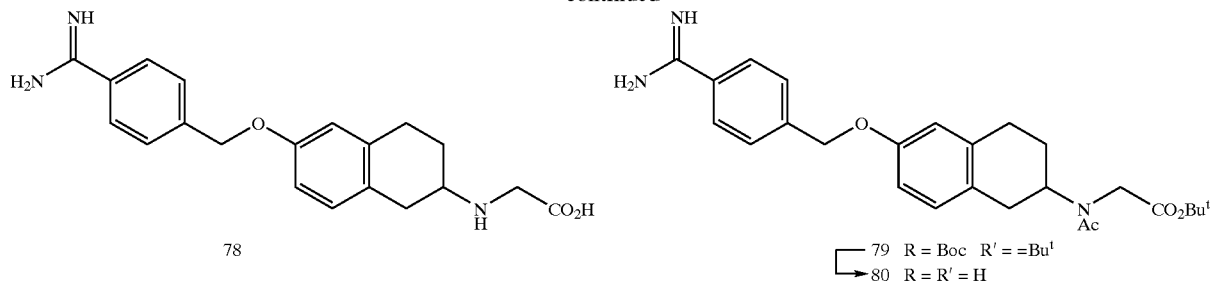

Scheme 11 outlines the preparation of 2,6-disubstituted tetralins in which the 2 position retains an α-aminoacetic acid residue and the 6 position is occupied by an ether linked benzamidine. The synthesis starts with alcohol 63 (Scheme 9) which is oxidized with TFAA and DMSO (method of Swern) giving ketone 73. This material is then reductively aminated with glycine tert-butyl ester giving 74. The secondary nitrogen is then either Boc protected (76) or acylated (75). The Boc derivative is then transformed into protected amidine 77 using the same sequence of reactions outlined in Scheme 1. The material is then fully deprotected with TFA giving 78. In a like manner, the acetyl derivative 75 is transformed into 80.

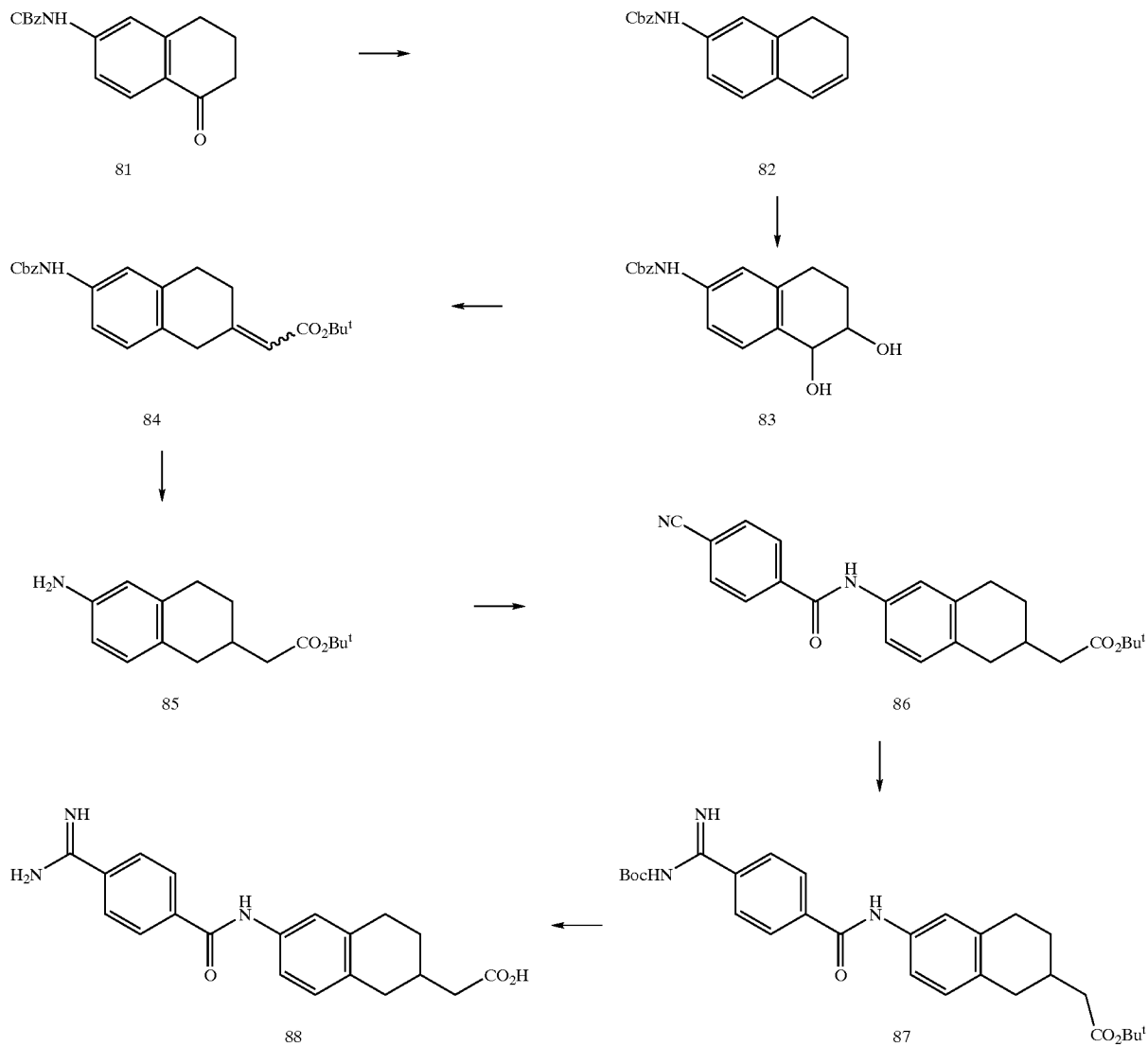

Scheme 12 outlines the preparation of tetralins having an acetic acid residue at $C_2$ and an amide linked benzamidine at $C_6$. In the first step, tetralone 81 is reduced with $NaBH_4$ and the resultant unstable alcohol is dehydrated with TsOH in benzene giving dihydronapthalene 82. Osymylation of 82 affords diol 83 which is then subjected to the action of TsOH in refluxing benzene. The unstable 2-tetralone thus formed is not isolated but rather allowed to react with the sodium salt of tert-butyl diethylphosphonoacetate giving unsaturated ester 84 as a mixture of olefin isomers. This material is subjected to hydrogenation over palladium which effects saturation of the olefin and removal of the CBz group providing aniline 85. Acylation of 85 with 4-cyanobenzoic acid is accomplished with the aid of EDCI and the resulting amide 86 is transformed into the Boc protected amidine 87 using conditions previously described in Scheme 1. Removal of the Boc moiety and cleavage of the tert-butyl ester is accomplished with TFA giving 88.

Scheme 13 describes the preparation of tetralin derivatives in which position 2 is substituted with an a-alkoxyacetic acid moiety and position 6 is substituted by an amide linked benzamidine. In this scheme, compound 82 from Scheme 12 is allowed to react with NaH and benzylbromide giving tertiary carbamate 88. This material is then subjected to osmylation and dehydration in the same manner as described for compound 83 in Scheme 12. The formed unstable 2-tetralone is immediately reduced to alcohol 90 with $NaBH_4$. This material is alkylated with tert-butyl bromoacetate under phase transfer conditions resulting in ether 91. Catalytic hydrogenation liberates the 6-amino moiety (92) which is acylated with 4-cyanobenzoic acid in the presence of EDCI giving 93. Nitrile 93 is transformed into Boc protected amidine 94 using the series of transformations described in Scheme 1. Simultaneous deprotection of the amidine and acid moieties is accomplished with TFA giving final product 95.

Scheme 13

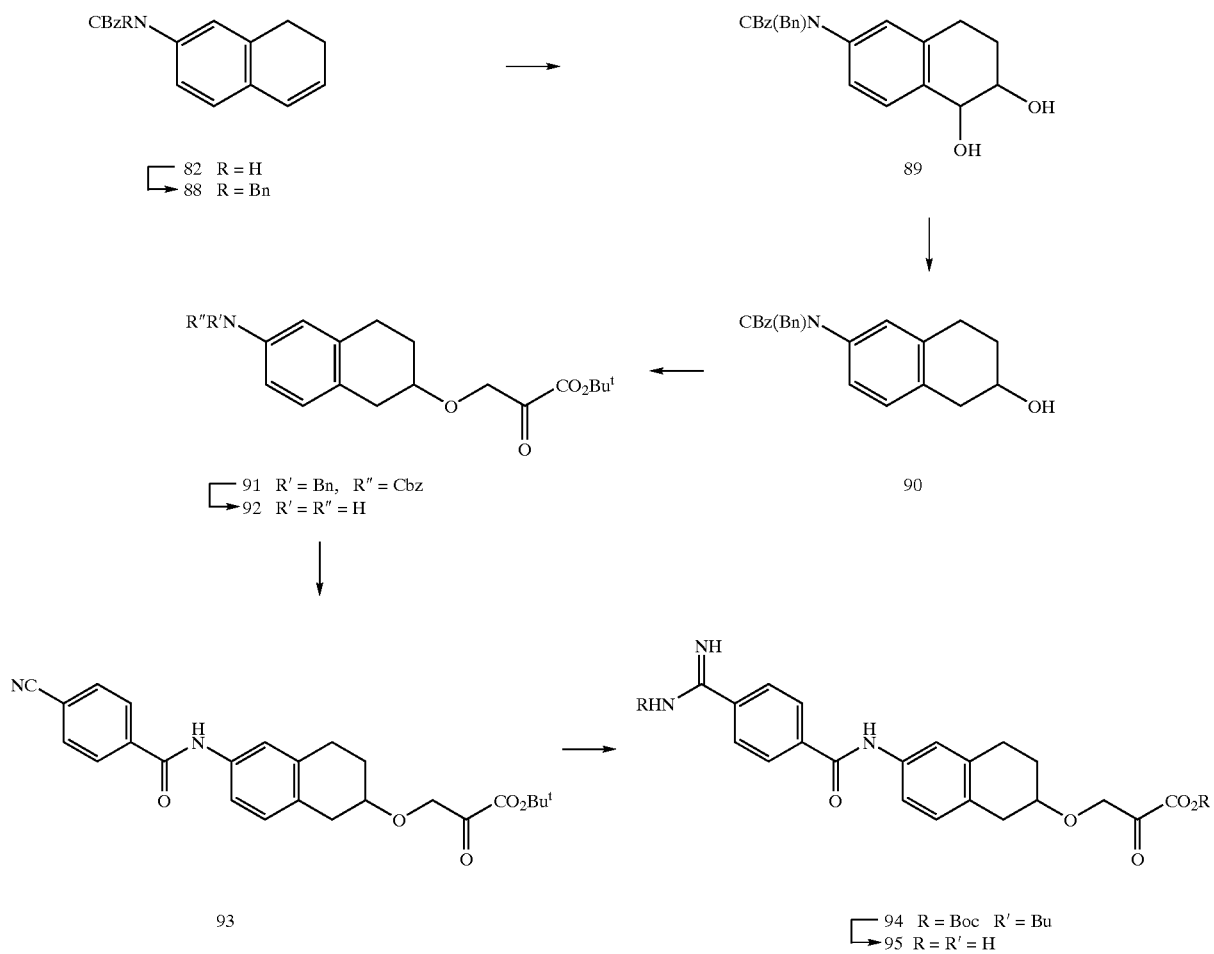

Scheme 14

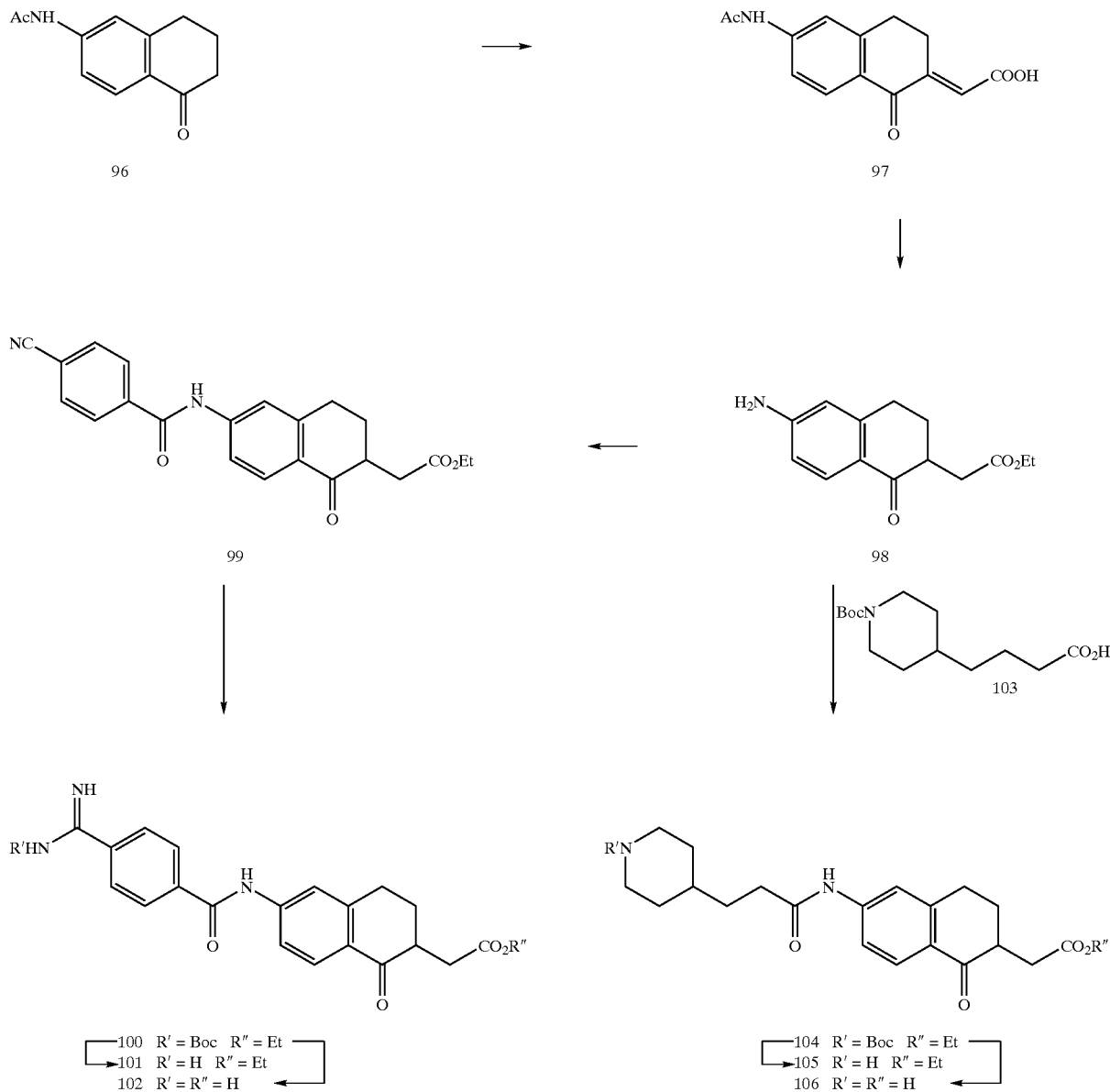

Scheme 14 outlines the synthesis of tetralones bearing an acetic acid moiety at position 2 and either an amide linked benzamidine or amide linked 4-alkylpiperidine at position 6. The scheme starts with tetralone 96 which is allowed to react with glyoxylic acid in the presence of NaOH yielding condensation product 97. The unsaturated ester 97 is reduced with Zn in HOAC and the resulting compound is transformed into aniline 98 by first removing the acetate with 6N HCl and then esterifying the acid moiety with ethanolic HCl. This material is then acylated with 4-cyanobenzoic acid via the agency of EDCI giving 99. The nitrile moiety of 99 is converted to Boc protected amidine 100 using the series of reactions described in Scheme 1. Saponification of the ester moiety with NaOH followed by treatment with TFA gives 102.

Compounds containing an amide linked 4-alkylpiperdine can be prepared by acylating aniline 98 with 103 giving analog 104. Saponification of ester 104 followed by TFA deprotection of the piperidine gives 106.

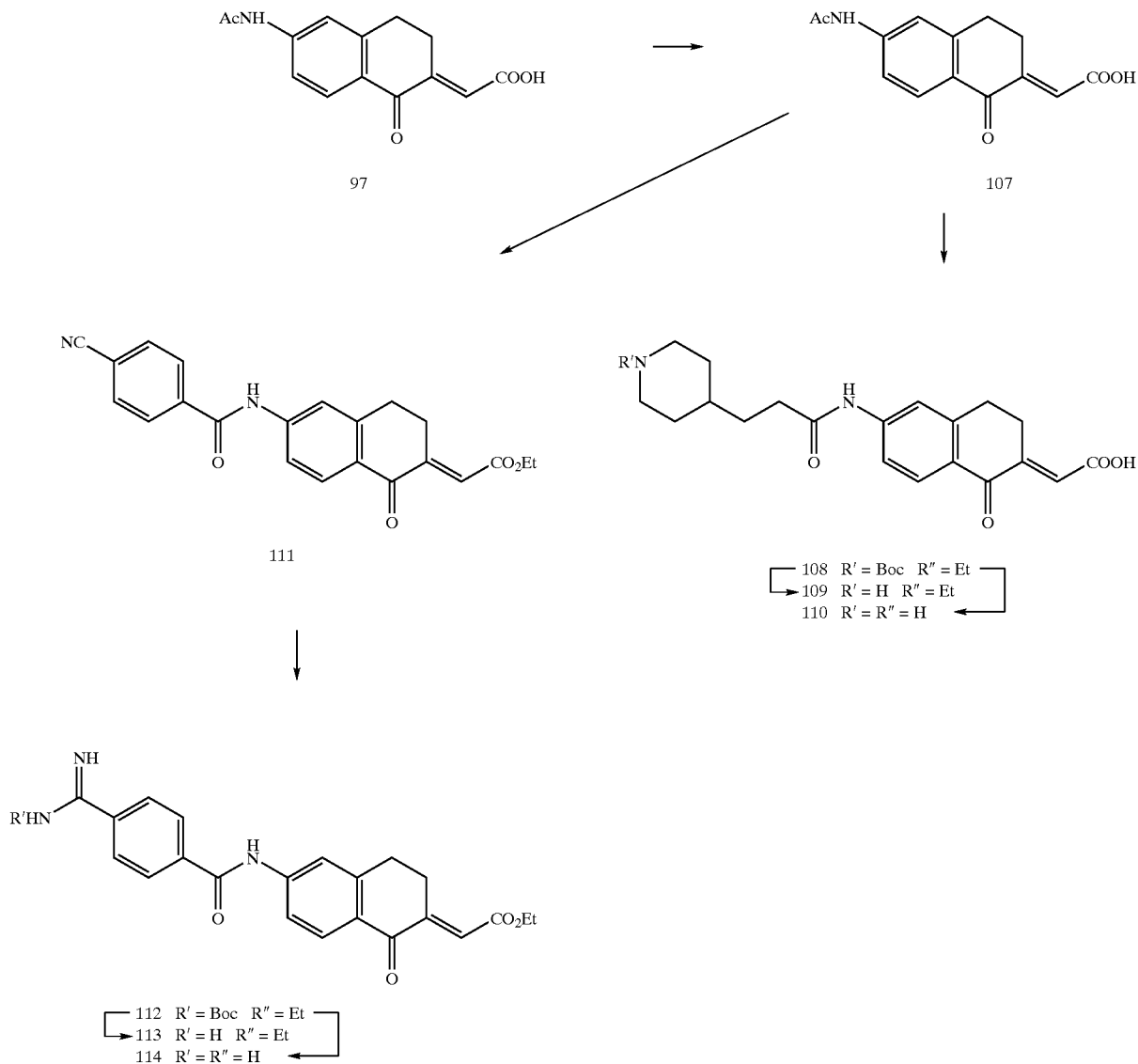

Scheme 15

Scheme 15 teaches a method of preparing tetralone derivatives in which position 2 is occupied by an unsaturated acid and position 6 is substituted by either an amide linked benzamidine or a 4-akylpiperidine. In the first step, compound 97 (scheme 14) can be is converted to aniline 107 by removing the acetate with 6N HCl and subsequent esterification with ethanolic HCl. This material can then be acylated with either 4-cyanobenzoic acid or the appropriate 4-alkylpiperidine (103). In the former case, the nitrile 111 can be transformed into amidine 112 using the same sequence of reactions described in Scheme 1. Saponification of 112 followed by treatment with TFA should yield 114. Piperidine adduct 108 can be subjected to saponification and TFA deprotection providing 110 in a similar manner.

Scheme 16

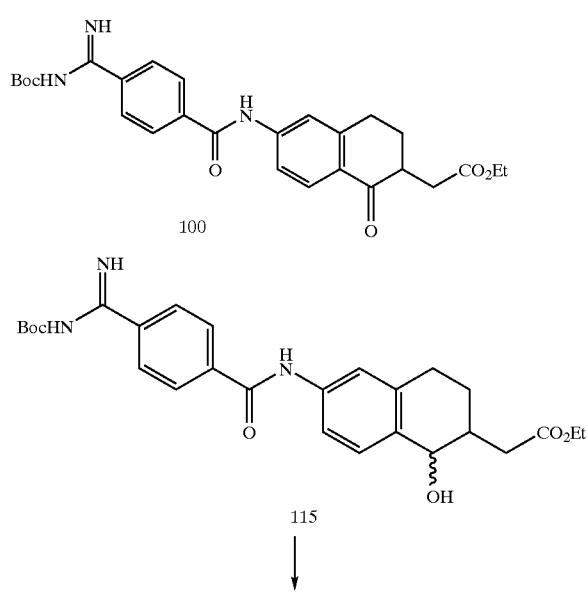
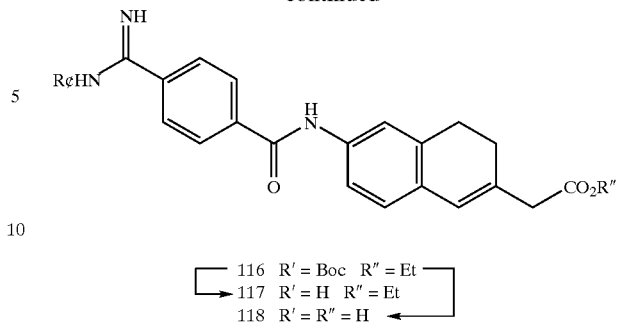

Scheme 16 describes the preparation of dihydronapthalene derivatives containing an acetic acid moiety at position 2 and an amide linked benzamidine at position 6. Tetralone 100 (Scheme 14) is allowed to react with $NaBH_4$ in ethanol giving unstable alcohol 115. This material is treated with TsOH in THF giving dehydrated product 116. Ester saponification followed by deblocking the amidine with TFA gives the desired product 118.

Scheme 17

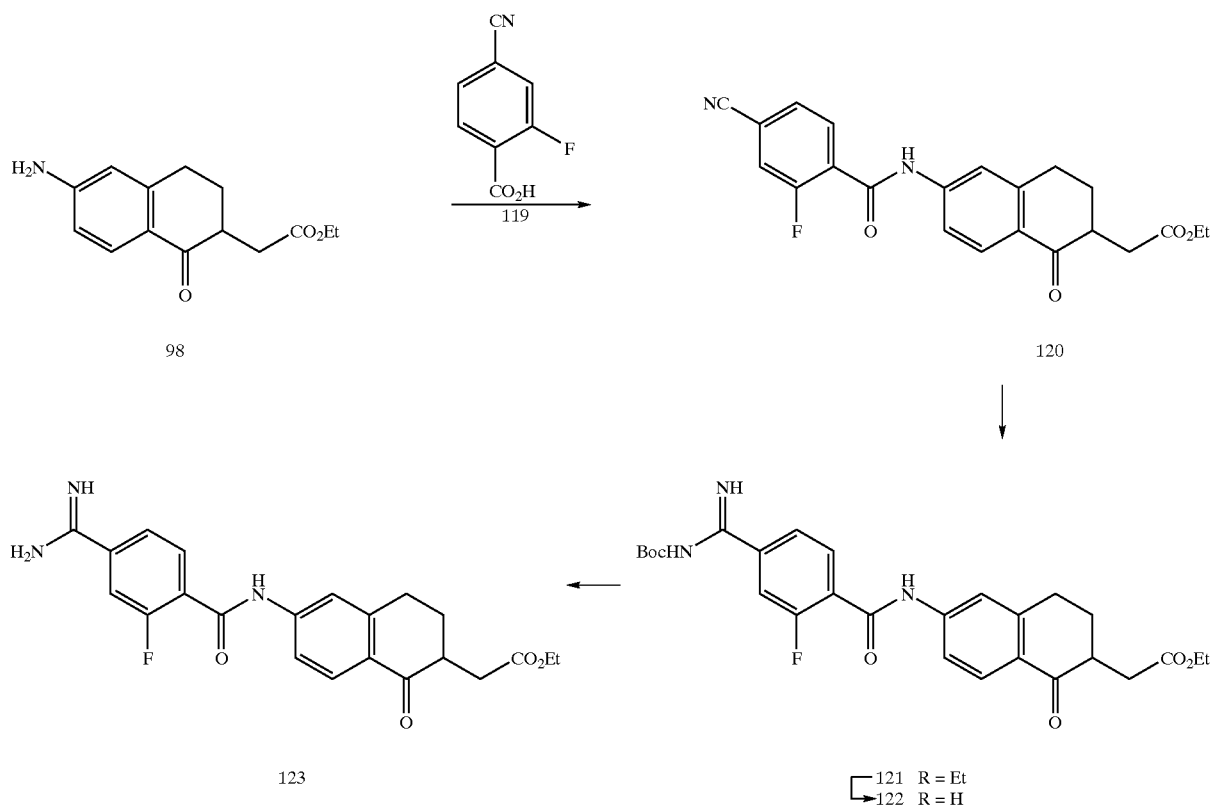

Scheme 17 outlines the general preparation of 2,6-disubstituted tetralones in which the 2 position is substituted with an acetic acid residue and the 6 position contains an amide-linked halogen-substituted benzamidine. Aniline 98 (prepared in Scheme 14) is allowed to react with benzoic acid 119 (prepared from 4-amino-2-fluoro-toluene using standard methods) in the presence of EDCI and DMAP. The resulting amide (120) is transformed into Boc protected amidine 121 using the same procedures outlined in Scheme 1. The ester moiety is then hydrolyzed giving acid 122 and then treatment with TFA provides compound 123.

position 2 and an ether linked arginine isostere at position 6. In the first step of Scheme 18, bromonapthalene 124 is subjected to transmetalation with t-BuLi and the resulting anion is quenched with ethyl oxalate. The resulting adduct 125 is then reduced with $NaBH_4$ and the formed alcohol is acylated with acetic anhydride. Catalytic hydrogenation removes the benzilic acetate and liberates the 6-hydroxy moiety giving compound 126. The free phenol is then alkylated with α-bromo-p-tolunitrile in the presence of $K_2CO_3$ giving disubstituted naphthalene 127. The nitrile moiety is then transformed into the Boc protected amidine 128 using the same sequence of reactions previously described in Scheme 1.

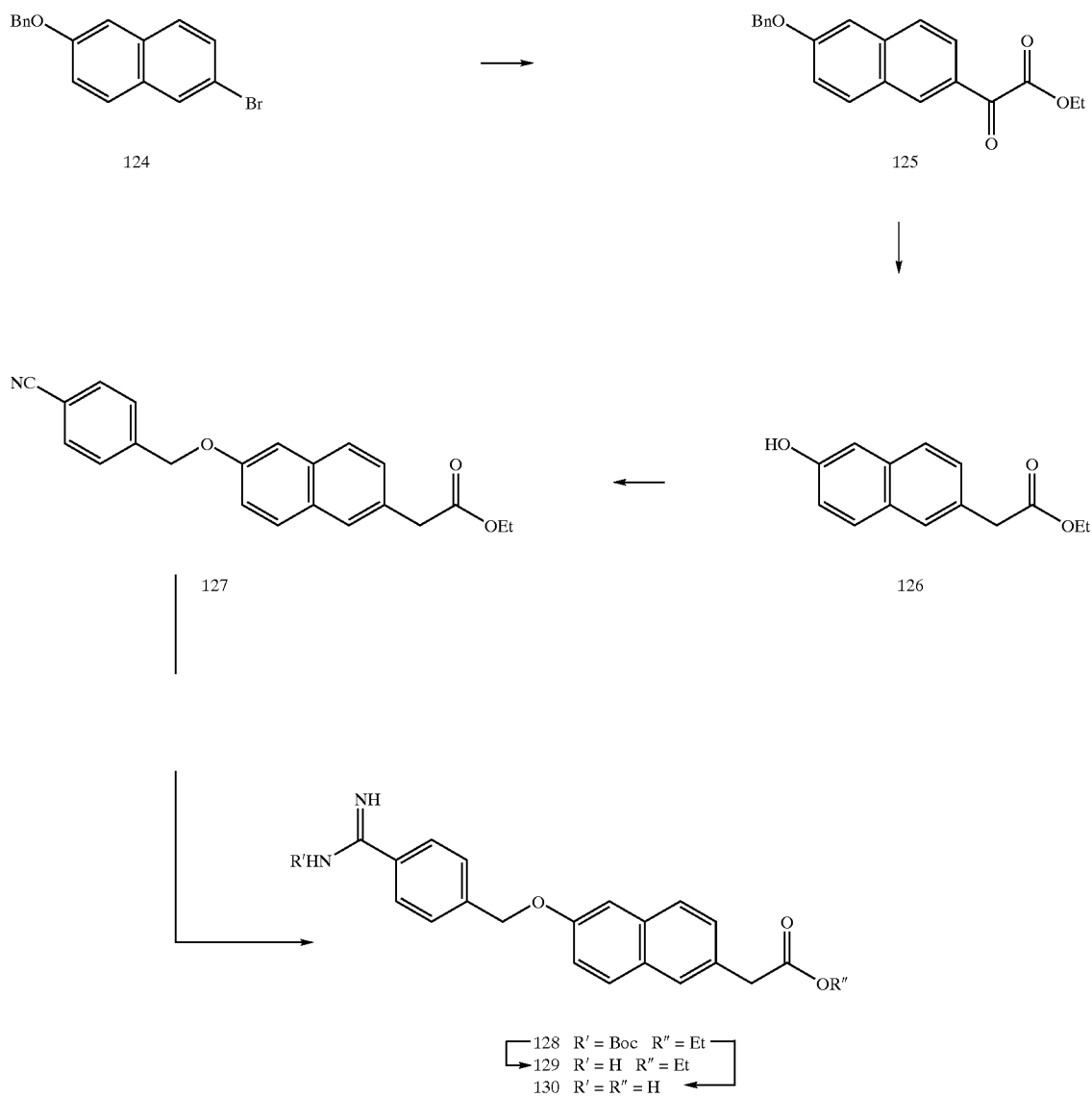

Scheme 18

Scheme 18 teaches a method of preparing 2,6-disubstituted napthalenes having an acetic acid residue at Saponification of the ester in 128 followed by removal of the Boc group with TFA gives final compound 130.

Scheme 19

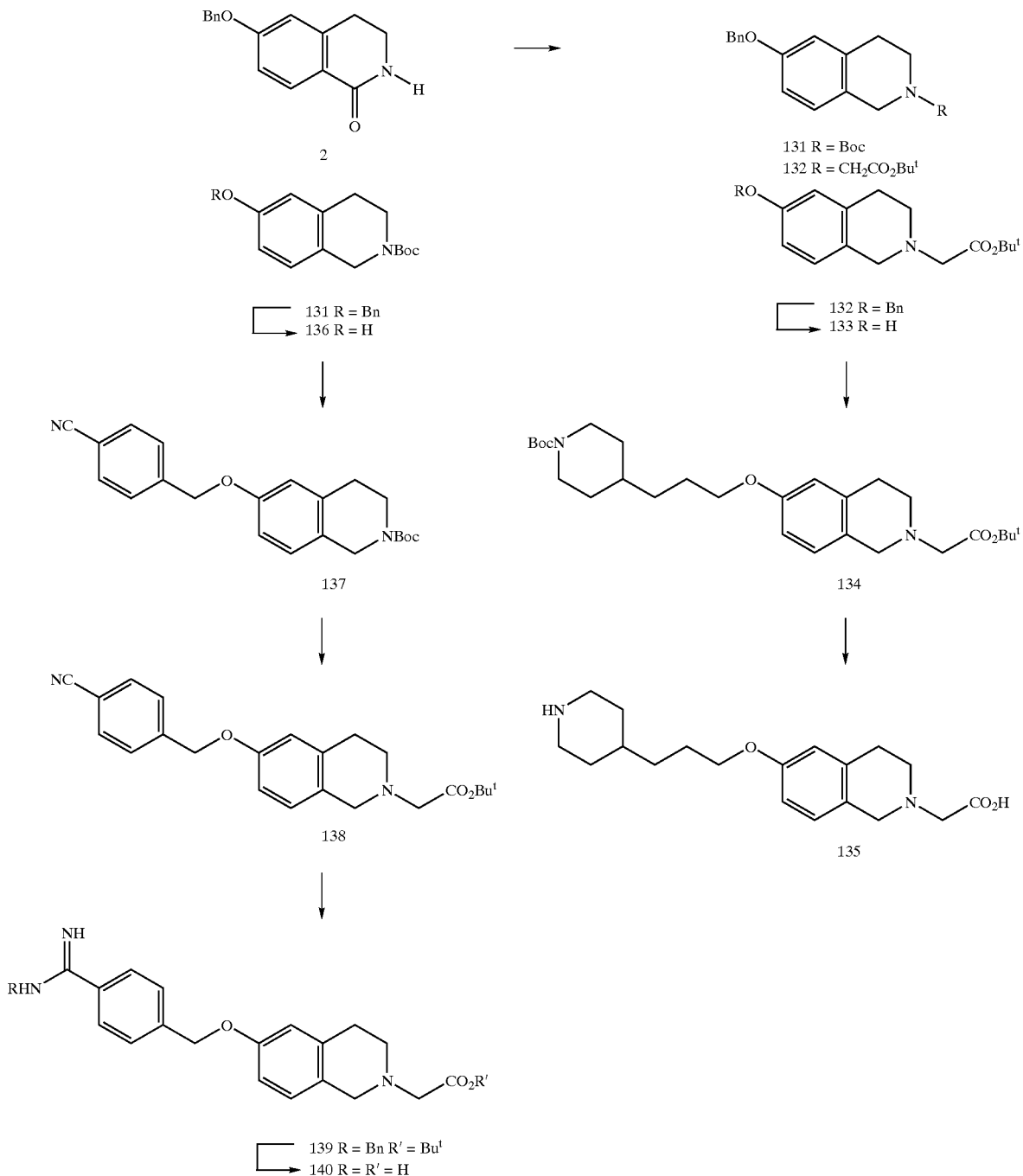

Scheme 19 describes the preparation of disubstituted tetrahydroisoquinoline derivatives bearing an acetic acid moiety at position 2 and either an ether linked benzamidine or 4-alkyl piperidine moiety at position 6. The initial isoquinoline nucleus is prepared by LiAlH$_4$ reduction of benzyl protected isoquinolone 2 (Scheme 1). This material was processed by either Boc protection giving compound 131 or alkylated with tert-butyl bromoacetate resulting in the formation of 132. The Boc protected material was subjected to hydrogenation which liberated the C$_6$ phenol which was then alkylated with α-bromotolunitrile giving adduct 137. The Boc group of this compound was cleaved with TFA and the resulting amine was then alkylated with tert-butyl bromoacetate giving compound 138. This compound was transformed into the Boc protected amidine 139 and then to the deprotected variant 140 using the procedures outlined in Scheme 1. The N-alkylated compound 132 was similarly subjected to hydrogenation and the resulting phenol was alkylated with the appropriate 4-alkylpiperidine giving 134. This material was deprotected with TFA giving 135.

Scheme 20

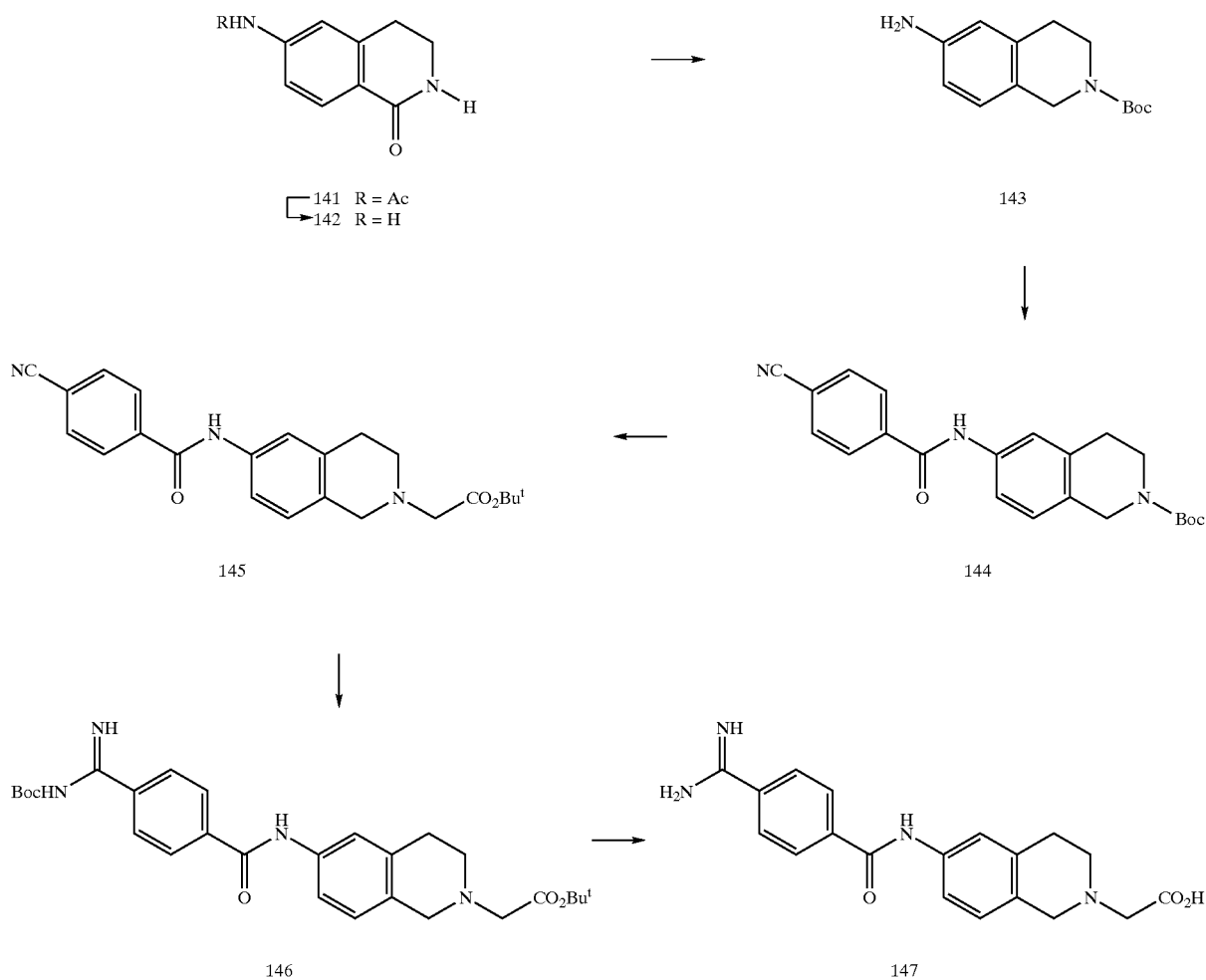

Scheme 20 teaches how to prepare 2,6-disubstituted tetrahydroisoquinoline derivatives bearing an acetic acid residue at position 2 and an amide linked benzamidine at position 6. The synthesis begins with acidic hydrolysis of the 6-acetamido group of isoquinolone 141 giving aniline 142. The crude material is then subjected to the action of benzyl bromide and $K_2CO_3$ in $CH_3CN$ giving a mixture of mono and di-benzyl protected isoquinolones. This mixture is subjected to $LiAlH_4$ reduction forming the tetrahydroisoquinoline which is immediately treated with di-tert-butyl dicarbonate. The formed Boc protected material is then hydrogenated over palladium providing aniline 143. This material is acylated with p-cyanobenzoic acid giving 144. Treatment of this material with TFA gives the secondary amine which is alkylated with tert-butyl bromoacetate providing 145. Conversion of 145 to the Boc protected amidine 146 and then to its deprotected congener 147 is accomplished using the same procedures as outlined in Scheme 1.

Scheme 21

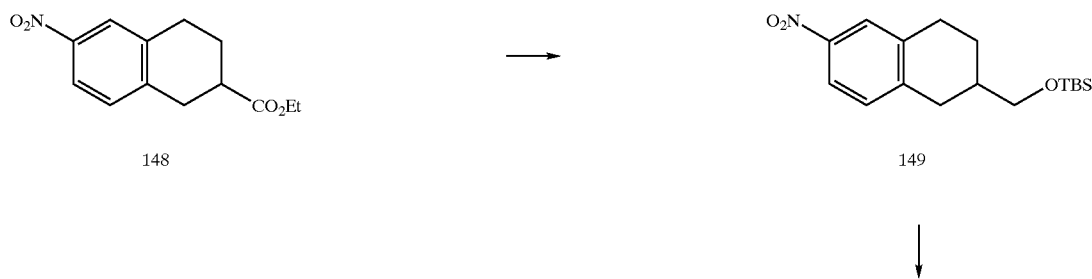

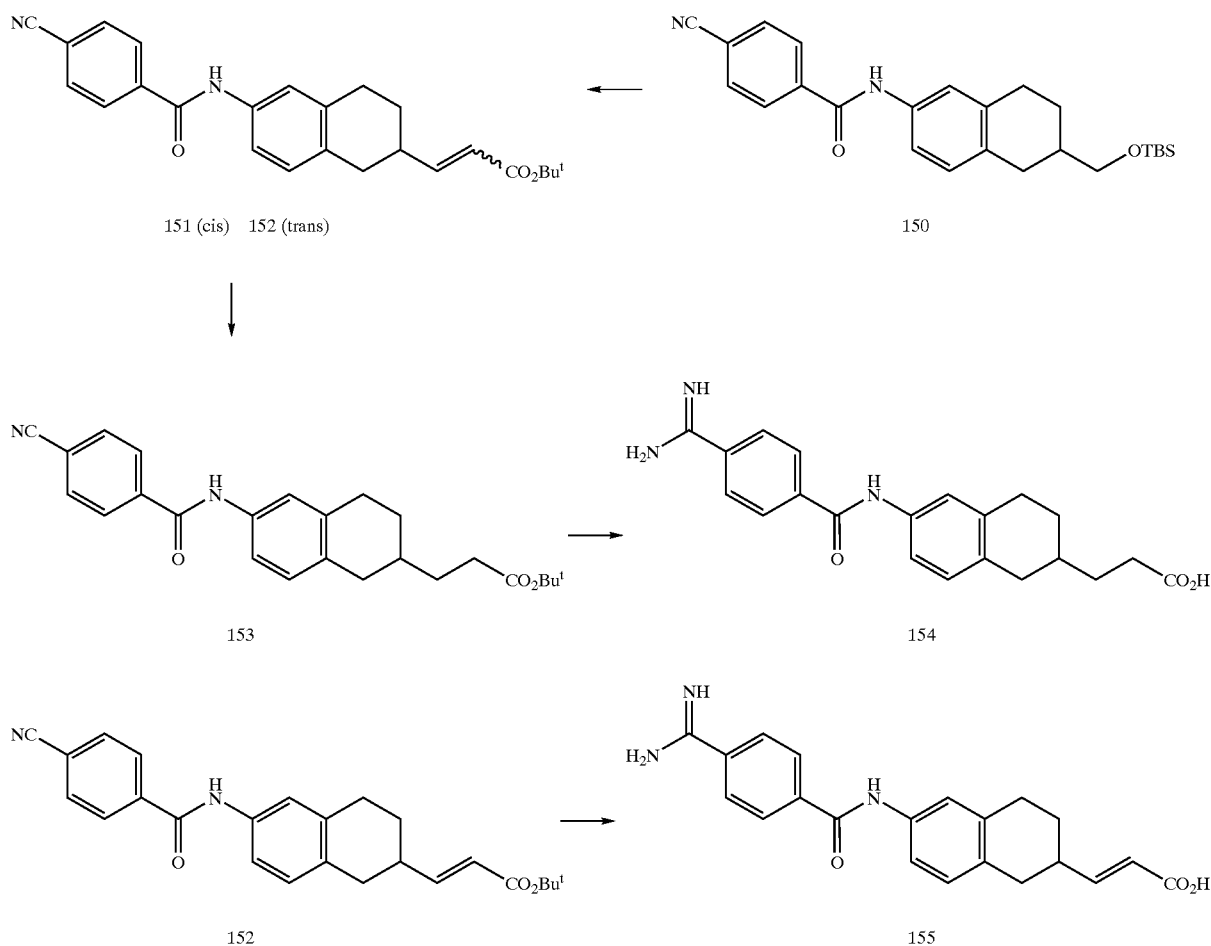

Scheme 21 describes a synthesis method suitable for the formation of 2,6-disubstituted tetralins containing a propionate or propenoate moiety at position 2 and an amide linked benzamidine at position 6. In the first step, nitro ester 148 is reduced with LiBH$_4$ and the resultant alcohol is protected as its TBS ether. Compound 149 is then subjected to hydrogenation and the formed aniline is immediately treated with EDCI and p-cyanobenzoic acid giving amide 150. The silyl group of 150 is removed and the derived alcohol is subjected to oxidation with DMSO and oxalyl chloride (method of Swern). The aldehyde thus formed is not purified, rather it is allowed to react with the sodium salt of t-butyl diethylphosphonoacetate which yields a separable mixture of 151 (cis) and 152 (trans) olefin isomers. The trans isomer 152 is converted to the Boc protected amidine and then to deprotected compound 155 using the sequence described in Scheme 1. The cis isomer is subjected to hydrogenation over palladium to give saturated analog 153. This material is also converted to the Boc protected amidine and then to its deprotected congener 154 as described in Scheme 1.

Scheme 22

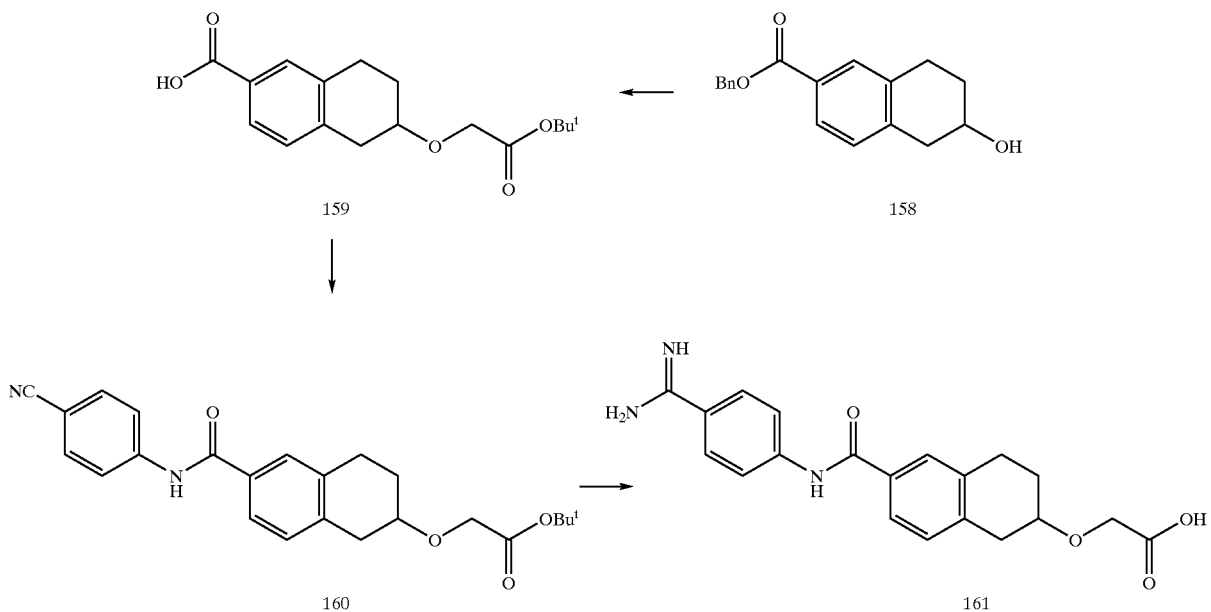

Scheme 22 describes a synthesis method for disubstituted tetralins bearing an α-alkoxyacetic acid residue at $C_2$ and a $C_6$ carboxyl linked benzamidine. This scheme begins with 6-bromo-2-tetralone (156) which is reduced with $NaBH_4$ and the resultant alcohol protected as its tert-butyldimethylsilyl (TBS) ether giving 157. Treatment of this compound with t-BuLi effects halogen metal exchange and the formed anion is quenched with $CO_2$. The resulting carboxylate is immediately transformed into the benzyl ester with benzyl alcohol and EDCI. The TBS group is removed during workup with TBAF affording alcohol 158. The free secondary hydroxyl is alkylated with tert-butyl bromoacetate using phase transfer conditions and the 6-carboxylate is liberated via catalytic hydrogenation affording 159. Amide 160 is the result of allowing 159 to react with 4-cyanoaniline in the presence of EDCI and DMAP. Nitrile 160 is converted to the BOC protected amidine and thereafter to the fully deprotected 161 using conditions outlined in Scheme 1.

Scheme 23

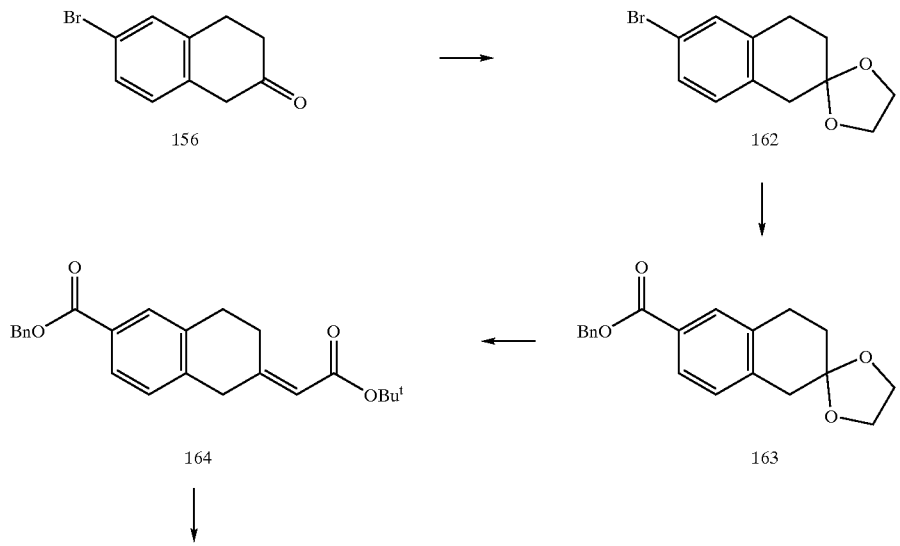

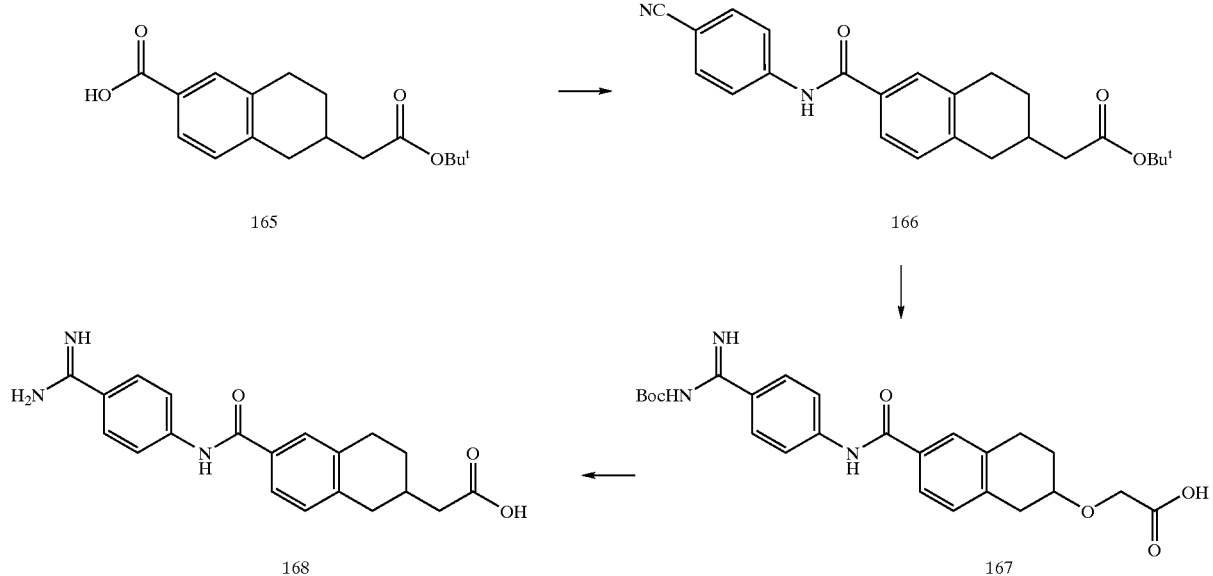

Scheme 23 outlines the preparation of tetralins having an acetic acid residue at $C_2$ and a $C_6$ carboxyl linked benzamidine. In the first step, bromotetralone 156 is treated with ethylene glycol and TsOH under dehydrating conditions giving ketal 162. This material is treated with tBuLi and the resulting anion is quenched with $CO_2$. The formed acid is immediately esterified with benzyl alcohol and EDCI giving 163. The spiro ketal contained in 163 is cleaved with aqueous HCl in acetone and the formed ketone is allowed to react with the sodium salt of tert butyl diethylphosphonoacetate giving 164 as a mixture of olefin isomers. Catalytic hydrogenation over Pd removes the unsaturation and liberates the $C_6$ carboxylate giving acid 165. Condensation of this compound with 4-aminobenzonitrile gives amide 166. Conversion of 166 to Boc protected amidine 167 and then to final compound 168 is accomplished using the same sequence outlined in Scheme 1.

Scheme 24

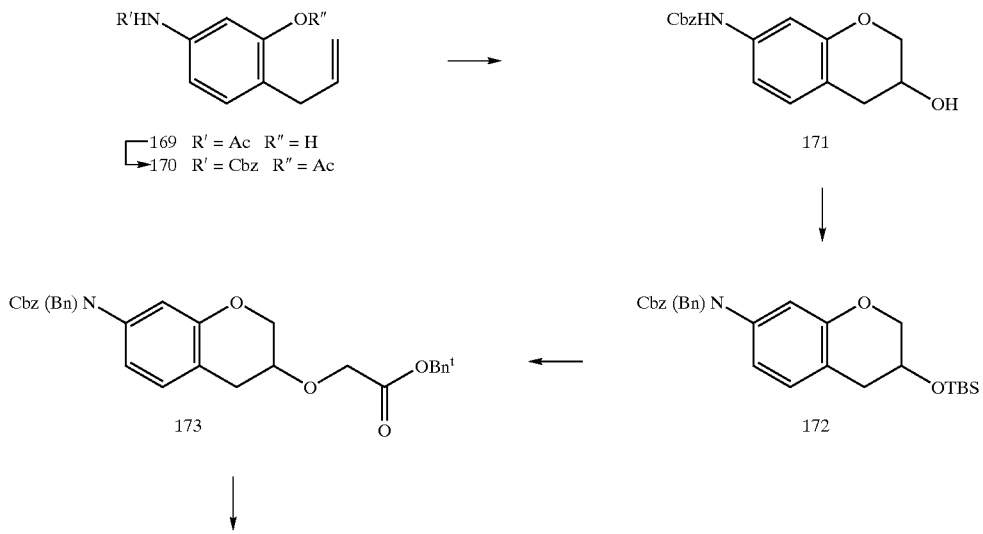

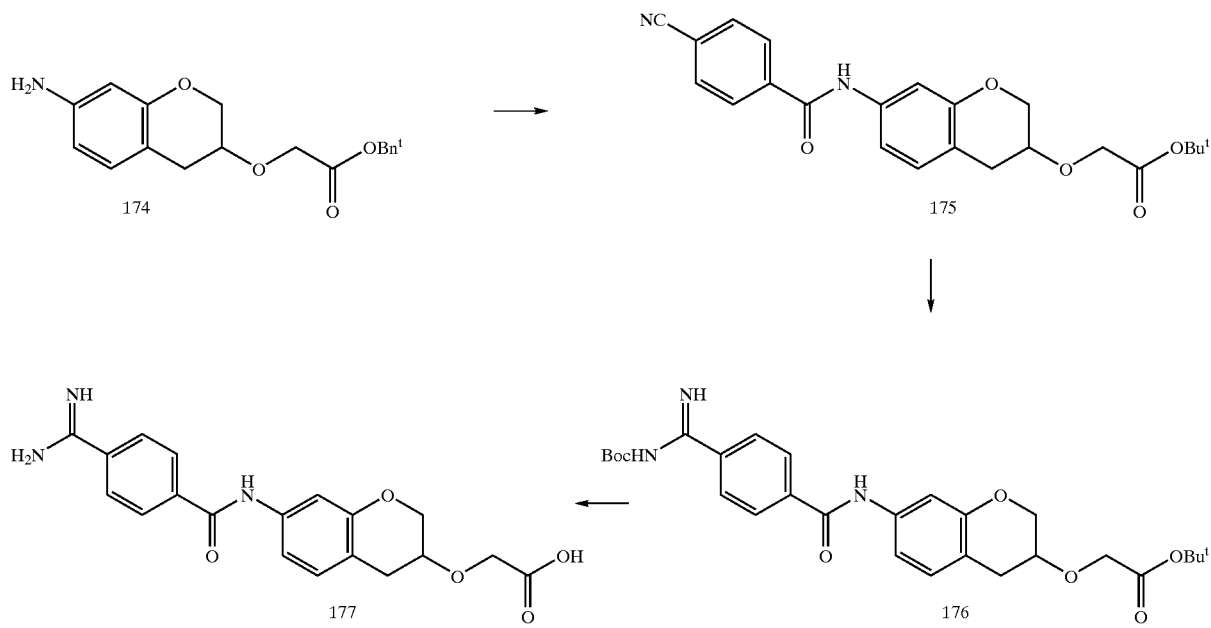

Scheme 24 describes the preparation of 3,7-disubstituted benzopyrans in which the 3-position is substituted with an α-alkoxyacetic acid moiety and the 7 position is substituted with an amide linked benzamidine. The synthesis begins with the allyl substituted aromatic 169. Acetamide hydrolysis is effected with NaOH in EtOH (Claisens alkali) and the resulting aniline is re-protected as its CBz counterpart. The free phenol is then acylated with acetic anhydride giving 170. The olefin is reacted with MCPBA giving the corresponding epoxide which is rearranged in the presence of NaI giving a mixture of 3-hydroxy and 3-acetoxy benzopyrans. This mixture is treated with LiOH giving alcohol 171. The alcohol moiety of 171 is then converted to its TBS ether and the resulting compound is alkylated on nitrogen to give fully protected 172. Liberation of the $C_3$ hydroxy with TBAF followed by alkylation with tert-butyl bromoacetate under phase transfer condition gives 173. Catalytic hydrogenation provides aniline 174 which is acylated with 4-cyanobenzoic acid, providing amide 175. This material is first converted to the corresponding protected benzamidine 176 and then to its deblocked congener 177 using the same sequence of events outlined in Scheme 1.

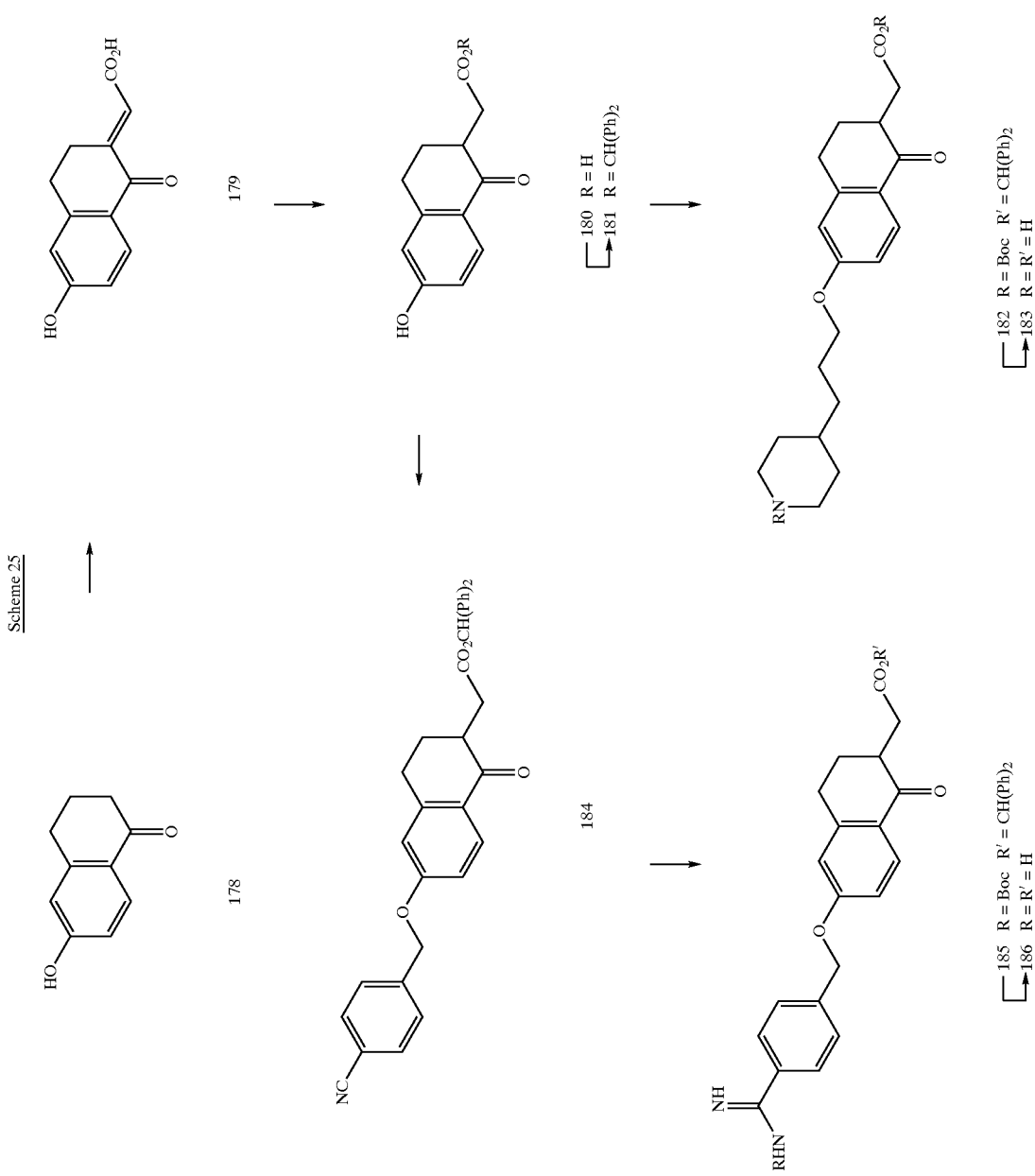

Scheme 25 outlines the preparation of 2,6-disubstituted tetralones in which the 2 position is substituted by an acetic acid moiety and the 6 position is substituted by either an alkoxy-linked benzamidine or alkoxy-linked 4-alkylpiperidine. In the first step, tetralone 178 is treated with NaOH and glyoxylic acid giving adduct 179. This material is reduced with Zn in acetic acid and the resulting acid (180) is reacted with diphenyldiazomethane giving benzhydryl ester 181. The free phenol can then be alkylated with α-bromo-p-tolunitrile to give 184 or with the appropriate 4-alkylpiperdine giving 182. Nitrile 184 is then converted to the corresponding Boc protected amidine 185 and then to the fully deprotected compound 186 using the same sequence of reaction outlined in Scheme 1. Compound 182 is deprotected with TFA giving compound 183.

Scheme 26 teaches a method to prepare tetrahydroisoquinolins in which the 2-position is substituted by an oxamic acid residue and the 6-position contains an ether linked benzamidine. In the first step, isoquinolone 2 is treated with LiAlH$_4$ and the resulting product of reduction is acylated with methyl oxalylchloride giving compound 187. This material is subjected to hydrogenation and the resulting phenol is alkylated with either α-bromotolunitrile or the appropriate 4-alkylpiperidine giving compounds 191 and 189 respectively. The nitrile moiety of 191 is transformed into Boc protected amidine 192 using the same procedures described in scheme 1. This material is then saponified with NaOH and the resulting acid is treated with TFA giving 193. Compound 190 is prepared using a similar saponification deprotection sequence.

Scheme 26

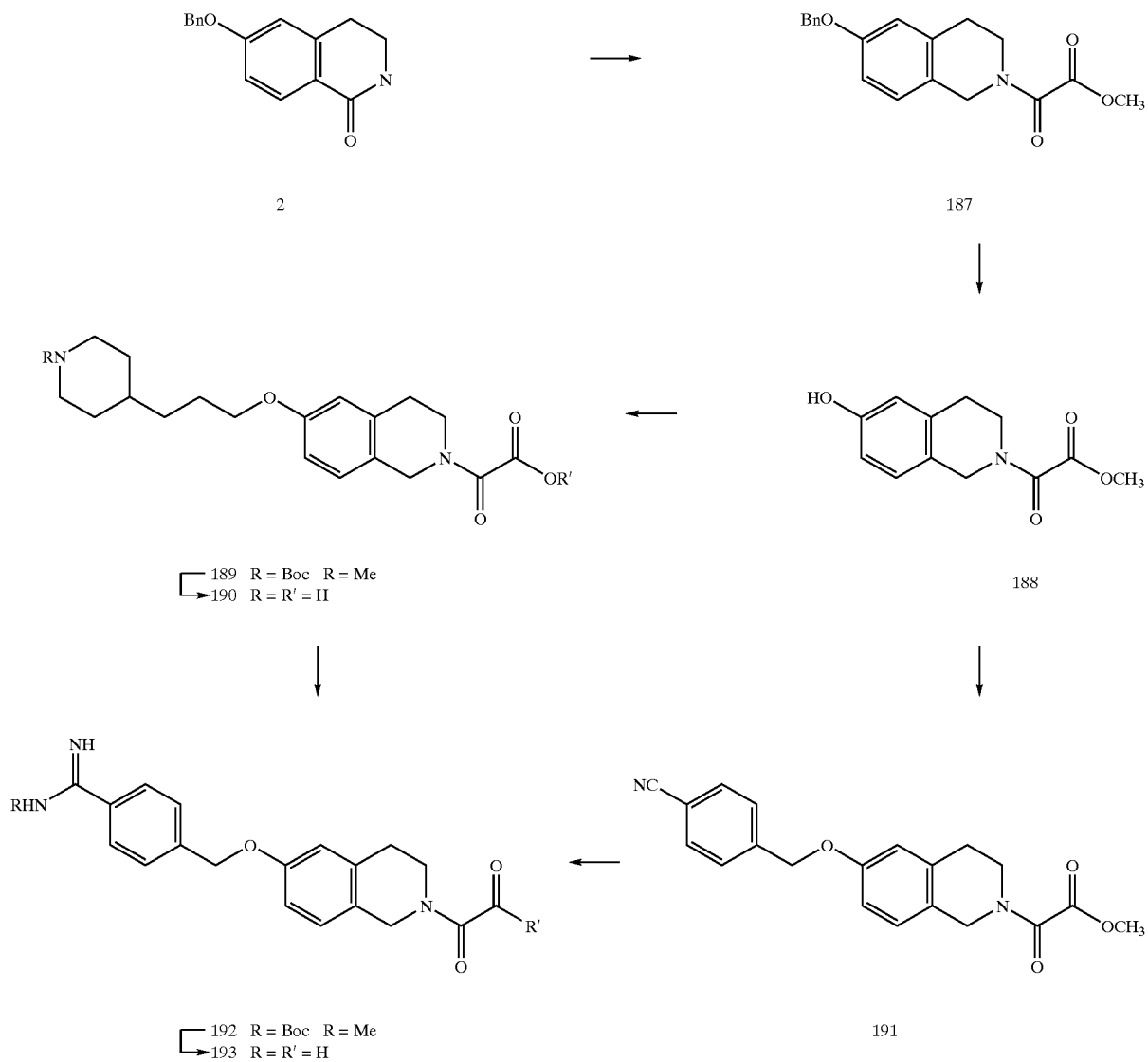

Scheme 27

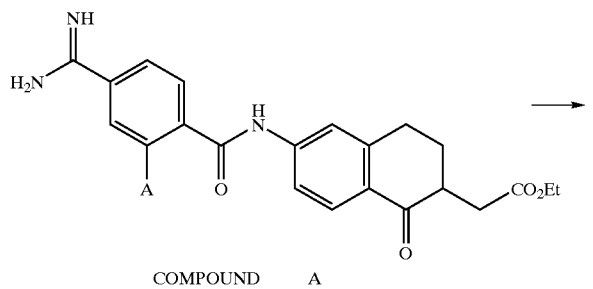

| COMPOUND | A |
|---|---|
| 365 | H |
| 366 | F |

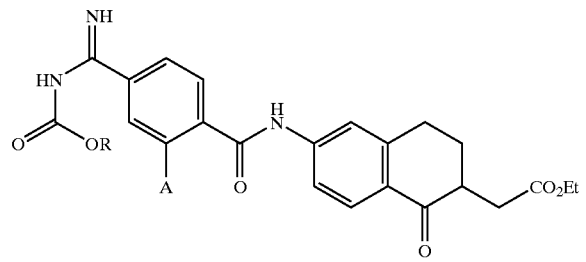

| COMPOUND | A | R |
|---|---|---|
| 367 | H | Ethyl |
| 368 | H | Propyl |
| 369 | F | Ethyl |
| 370 | F | Propyl |

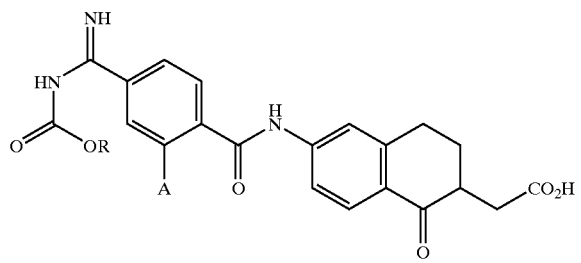

| COMPOUND | A | R |
|---|---|---|
| 371 | H | Propyl |

Scheme 27 describes the acylation of the amidine moiety contained in 2,6-disubstituted tetralones 365 and 366 which are prepared from compounds 102 and 123 (Scheme 14 and 17 respectively) by esterification with ethanol. The acylation is accomplished by reacting the benzamidine containing compound with an alkyl chloroformate in the presence of aqueous base, thus forming the derivatives 367 to 370. These materials can then be subjected to saponification with ethanolic NaOH yielding the free acid (see 371 in Scheme 27).

Scheme 28

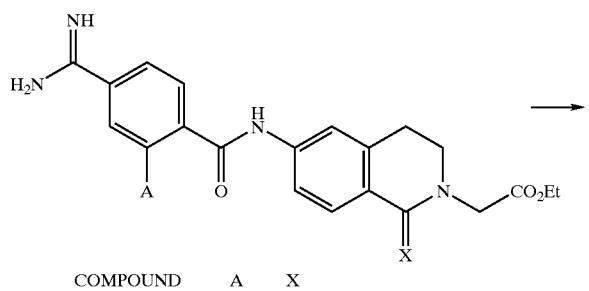

| COMPOUND | A | X |
|---|---|---|
| 372 | H | H, H |
| 373 | F | H, H |
| 374 | H | O |
| 375 | F | O |

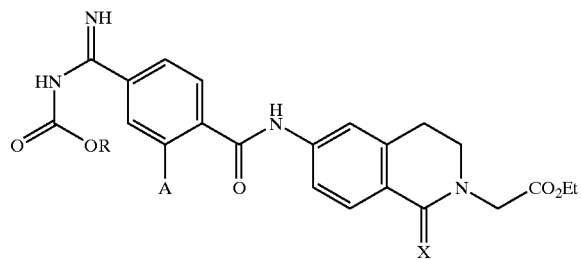

| COMPOUND | A | X | R |
|---|---|---|---|
| 376 | H | H, H | Ethyl |
| 377 | H | H, H | Propyl |
| 378 | F | H, H | Ethyl |
| 379 | F | H, H | Propyl |
| 380 | H | O | Ethyl |
| 381 | H | O | Propyl |
| 382 | F | O | Ethyl |
| 383 | F | O | Propyl |

The procedure of Scheme 27 is general and has also been applied to compounds containing an isoquinolone nucleus as shown in Scheme 28. In a like manner, one can also prepare N-acylated derivatives of benzamidine containing tetrahydroisoquinolins or benzopyrans.

Scheme 29

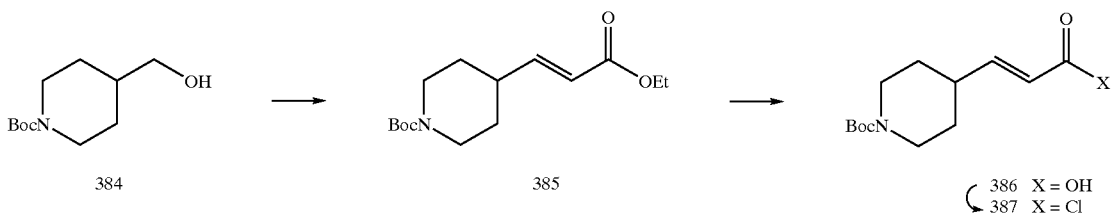

384    385    386 X = OH
              387 X = Cl

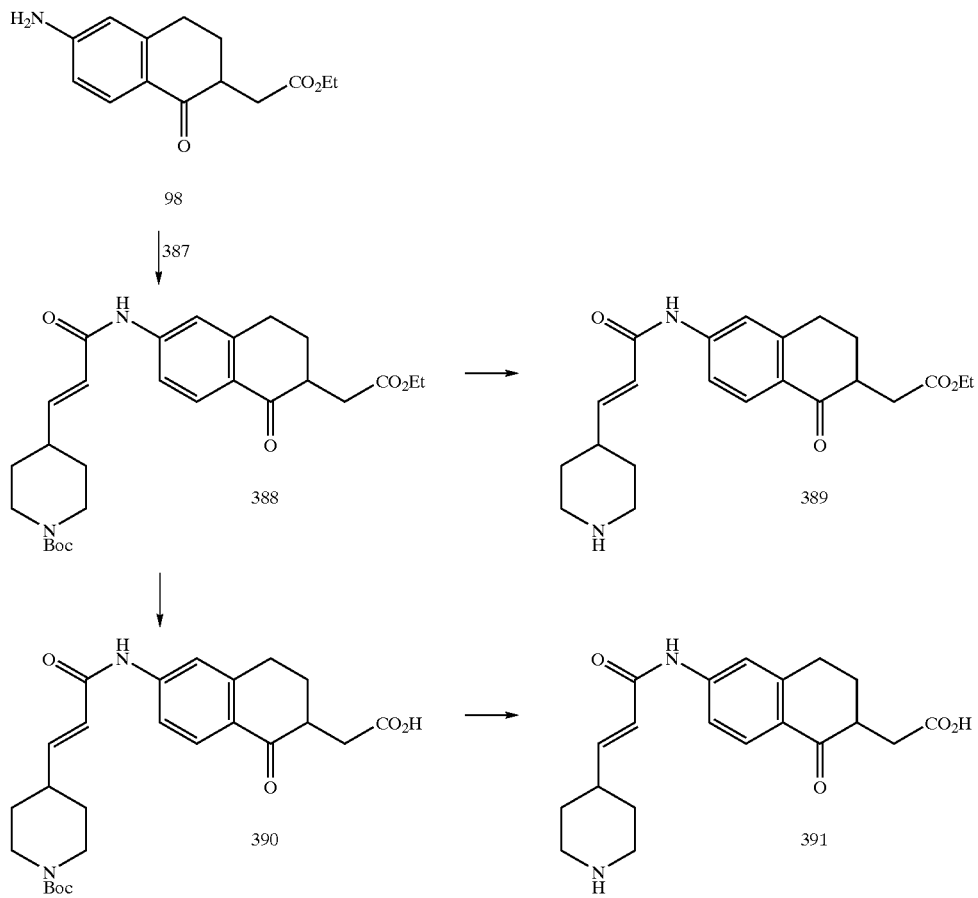

Scheme 29 describes the preparation of 2,6-disubstituted tetralones in which the 2-position is occupied by an acetic acid residue and the 6-position maintains an amide linked 4-propenoyl piperidine moiety. In the first step, alcohol 384 (prepared form 4-pyridylcarbinol by hydrogenation and protection) is oxidized with oxalyl chloride and DMSO giving the corresponding aldehyde. This material is not characterized but rather, reacted crude with the sodium salt of triethyl phosphonoacetate which gives the desired unsaturated ester 385. This material is saponified with LiOH and the resulting acid 386 is activated with oxalyl chloride giving 387. Aniline 98 reacts with acid chloride 387 giving adduct 388. This compound is N-deprotected with TFA giving ester 389 after salt exchange with HCl. Alternatively, saponification with LiOH first gives the free acid 390 which can then be N-deprotected with TFA providing 391.

Scheme 30

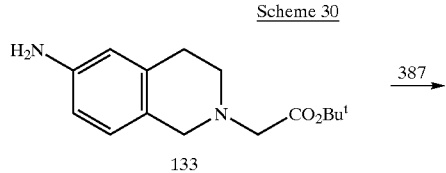

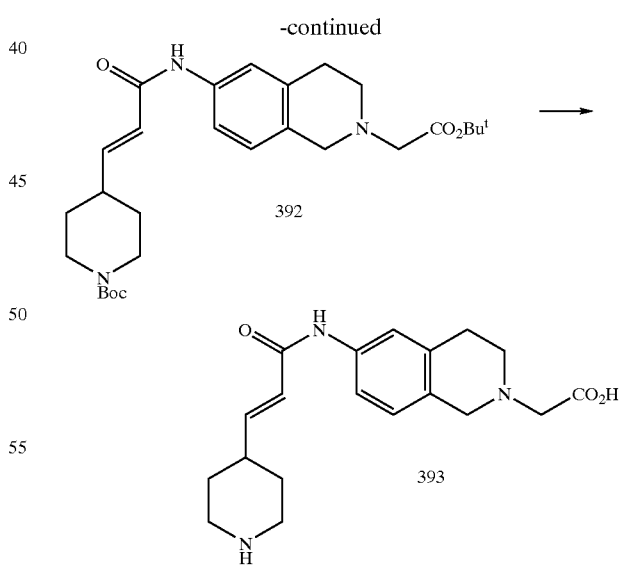

Scheme 30 teaches the preparation of 2,6 disubstituted tetrahydroisoquinolines bearing an acetic acid residue at position 2 and an amide linked 4-propenoyl piperidine at position 6. In the first step, the 6-amino moiety of 133 is acylated with acid chloride 387 (Scheme 29) giving adduct 392. This material can be fully deprotected with TFA providing 393.

Scheme 31

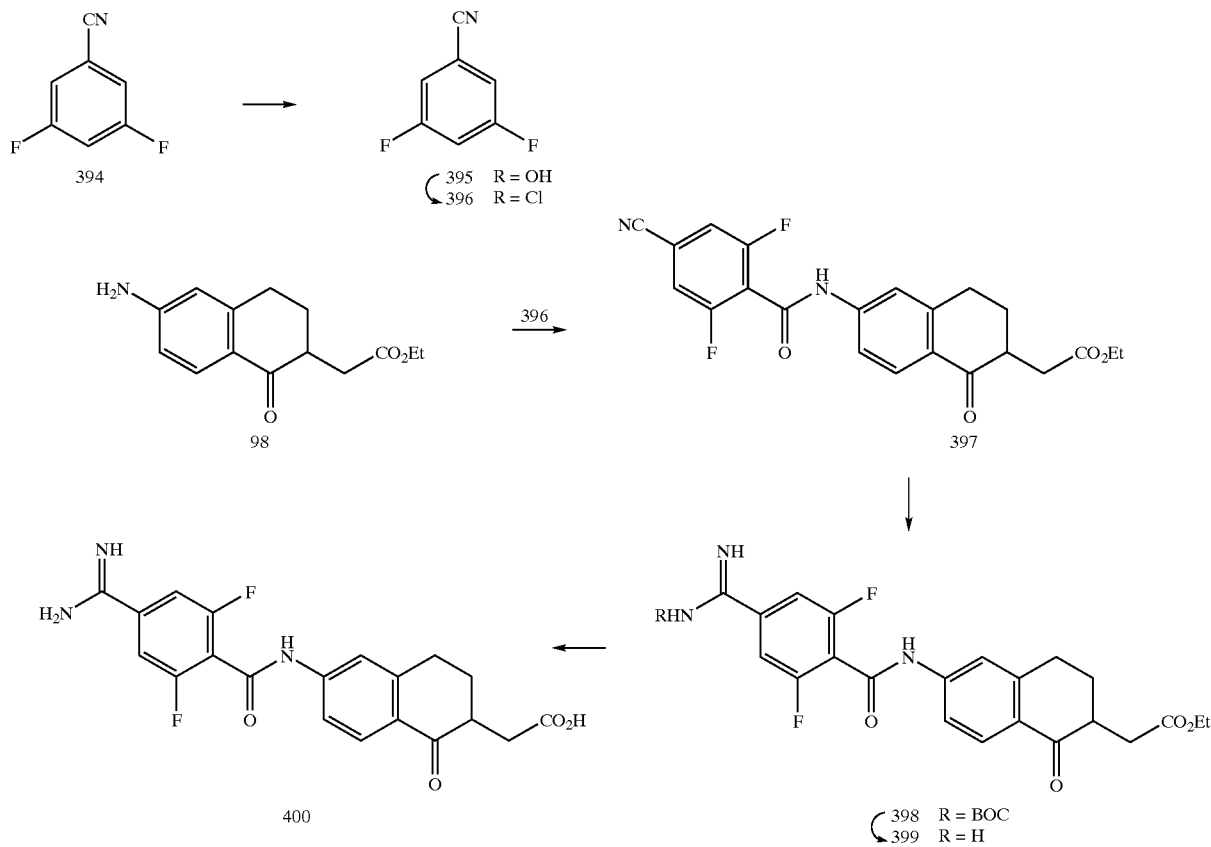

Scheme 31 outlines the preparation of 2,6-disubstituted tetralones in which the 2 position is occupied by an acetic acid moiety and the 6 position supports an amide-linked difluoro benzamidine. In the first step, difluoro benzonitrile 394 is lithiated with n-butyl lithium and the resulting anion is quenched with $CO_2$ giving acid 395. This compound is then treated with oxalyl chloride and the resulting acid chloride 396 is reacted with aniline 98 giving adduct 397. The nitrile moiety in 397 is transformed into Boc protected amidine 398 using the same sequence of reactions employed for conversion of 5 to 6 as described in Scheme 1. Compound 398 can be deprotected with TFA providing 399. Alternatively, 398 can be fully deprotected by first cleaving the ester moiety with NaOH and then deprotecting the amidine with TFA yielding 400.

Scheme 32

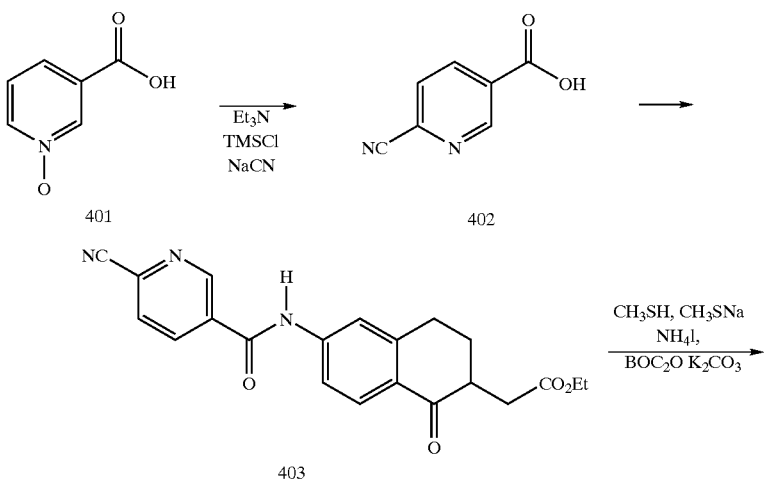

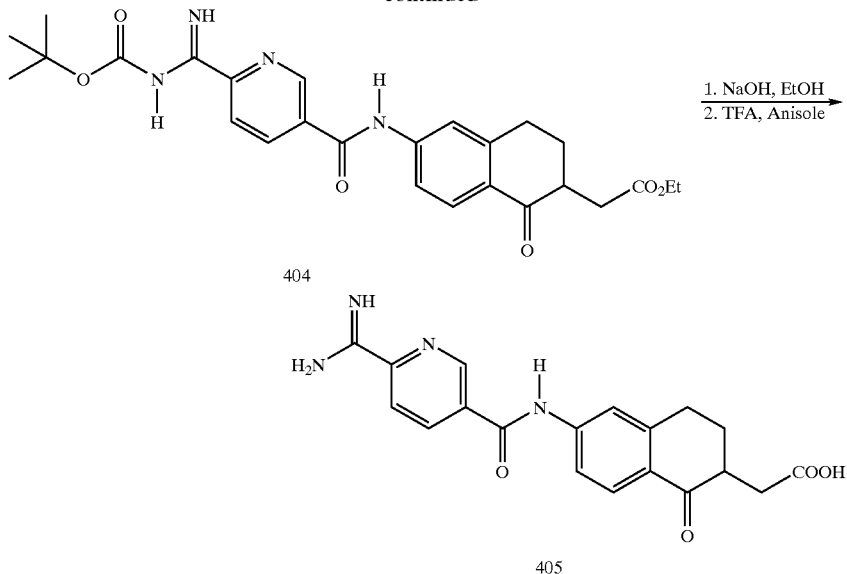

Scheme 32 describes the preparation of 2,6-disubstituted tetralones bearing an acetic acid moiety at position 2 and an amide-linked amidino pyridine at position 6. In the first step, pyridine 401 is reacted with $Et_3N$, TMSCl, and NaCN giving acid 402. This material is coupled with aniline 98 giving adduct 403. The nitrile in 403 is then reacted with the sodium salt of methane thiol giving the methylthioimidate. This intermediate is reacted with ammonium iodide providing an amidine which is BOC protected giving 404. Compound 404 is first reacted with ethanolic NaOH to cleave the ester and then with TFA to deprotect the amidine providing the fully deprotected congener 405.

Scheme 33 describes the preparation of 2,6-disubstituted tetralones in which the amide-linked amidine contains a thiophene nucleus. In the first step, thiophene 406 is metalated with LDA and the resulting anion is quenched with $CO_2$ giving acid 407. This acid is reacted with compound 98 in the presence of EDCI giving amide 408. The nitrile moiety in 408 is converted to a Boc protected amidine 409 using the same sequence of reactions used for the formation of compound 6 in Scheme 1. The resulting compound is first saponified with ethanolic NaOH and then N-deprotected with TFA giving compound 410 as the TFA salt.

Scheme 33

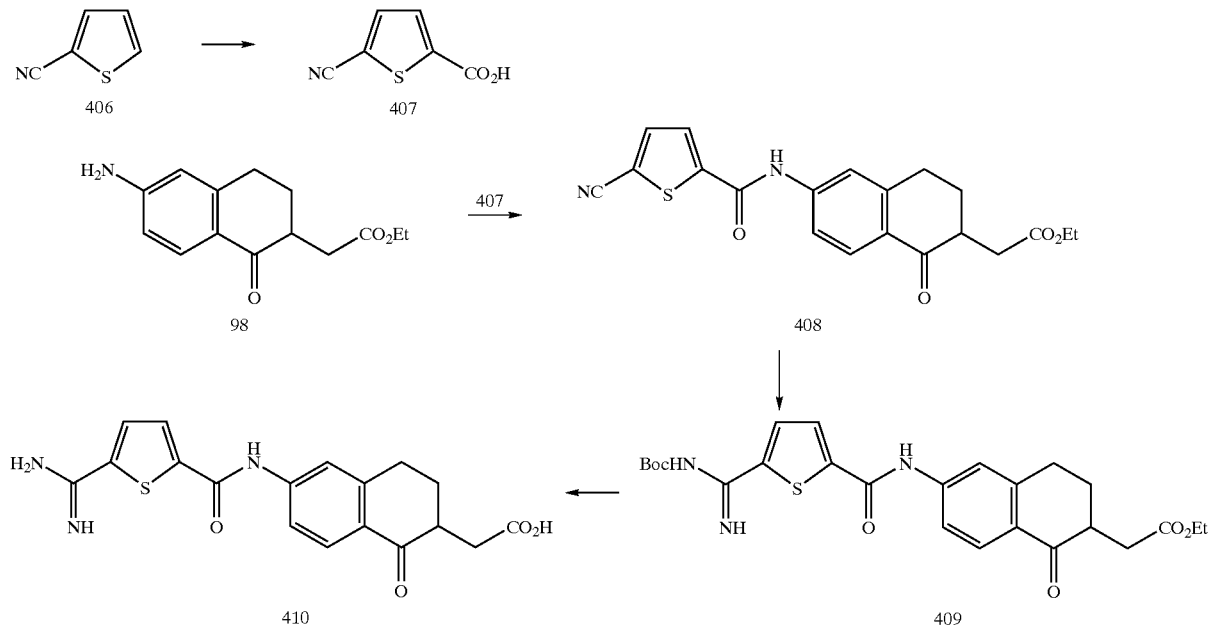

Scheme 34

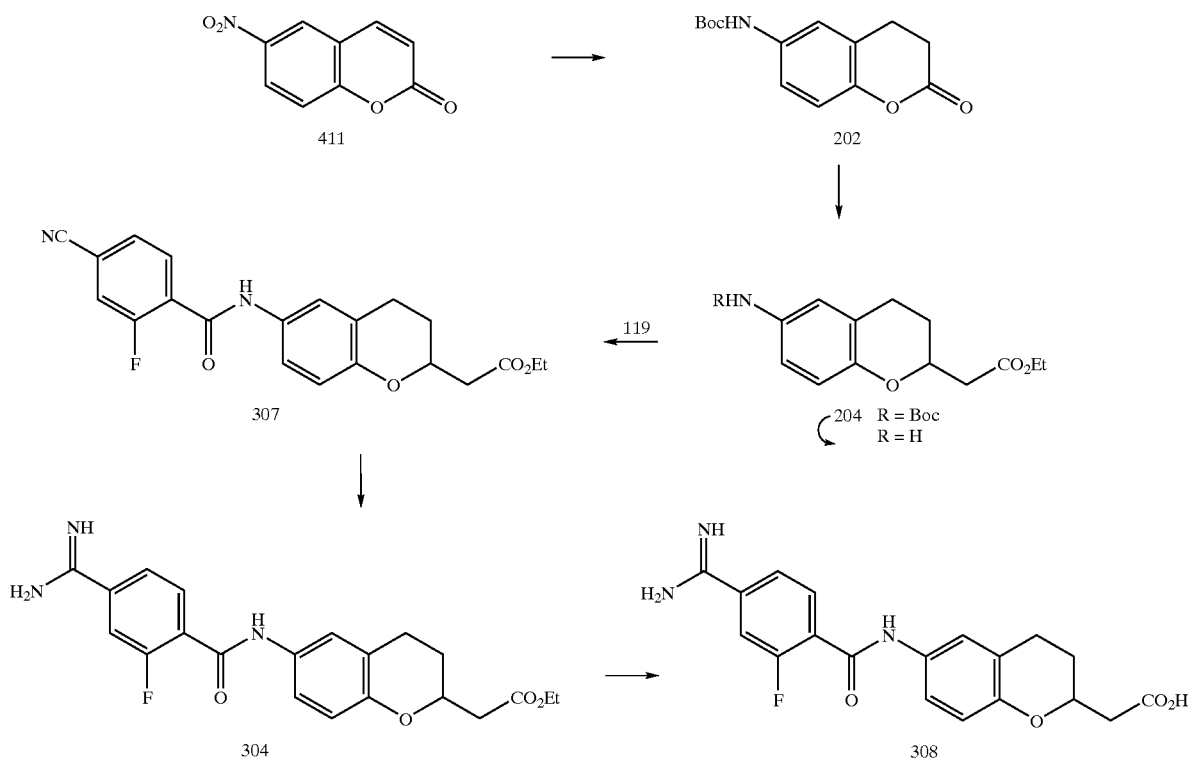

Scheme 34 teaches the preparation of 2,6 disubstituted benzopyrans in which the 2 position retains an acetic acid moiety and the 6 position contains an amide-linked fluoro-substituted benzamidine. In the first transformation, the nitro group is reduced with ammonium formate and palladium and the resulting aniline is Boc protected. The B ring unsaturation is then removed with Pd/C giving lactone 202. This material is reduced with DIBAH giving an intermediate lactol which is reacted with ethoxycarbonylmethylene triphenylphosphorane giving benzopyran 204. This material is then N-deprotected with TFA and the resulting aniline reacted with the acid chloride derived from fluoro-acid 119 giving adduct 307. This material was then subjected to the action of HCl in ethanol giving the intermediate imino-ether which was not characterized but instead reacted with ammonia resulting in the formation of 304. This material was then hydrolyzed with NaOH in ethanol giving the desired free acid 308 after neutralization.

The following examples describe the preparation of compounds of the invention (unless otherwise indicated).

EXAMPLES

The following examples are provided to enable one skilled in the art to practice the present invention. These examples, however, are not to be read as limiting the scope of the invention as it is defined by the appended claims.

The reference numbers used in the following Examples refer to the corresponding compound shown in the preceding reaction Schemes 1 through 26:

Example 1

Preparation of 6-[[4-(Aminoiminomethyl)phenyl]methoxy]-3,4-dihydro-1-oxo-2(1H)-isoquinoline Acetic Acid Trifluoroacetate, a Compound Represented by the Formula (7)

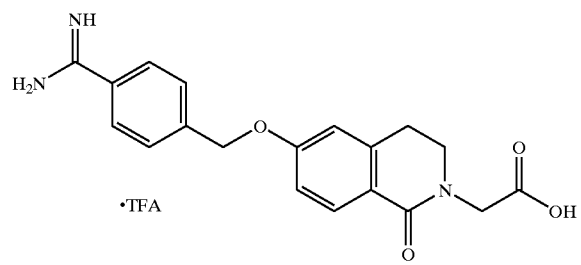

7

Part A:
A mixture of phenol (1) (6-hydroxy-3,4-dihydro-1-oxo-2 (1H)isoquinoline (1.0 g, 6.14 mmol), benzyl bromide (1.0 g, 6.14 mmol) $K_2CO_3$ (0.93 g, 6.74 mmol), and acetone (15 mL) was maintained at reflux for 12 hours and then allowed to cool to room temperature. The mixture was then diluted with EtOAc and washed with $H_2O$. The organic material was dried ($MgSO_4$) and concentrated. The crude residue was recrystallized from EtOAc/Hexanes giving 1.53 g (98%) of (2) (6-benzyloxy-3,4-dihydro-1-oxo-2(1H)isoguinoline) as a white solid.
Part B:
To a solution of lactam (2) (0.1 g, 0.39 mmol) in THF (4 mL) was added sodium hydride (0.017 g of a 60% dispersion in mineral oil, 0.43 mmol). The resulting mixture was maintained at reflux for 1 hour and then allowed to cool to room temperature. The mixture was then treated with tert-butyl bromoacetate (0.07 g, 0.43 mmol). After one hour the reaction was quenched by the addition of H₂O (10 mL) and the resulting mixture was extracted with EtOAc. The combined extracts were dried (using MgSO₄) and concentrated. The crude material was purified by chromatography (silica gel, 2:1 Hexane:EtOAc) to give 0.14 g (99%) of (3a) as a white solid.

Part C:

A mixture of (3a) (0.13 g, 0.37 mmol), Pd/C (0.14 g, 10% on carbon), and EtOAc (5 mL) was stirred under an atmosphere of hydrogen (balloon) for 1.5 hours and then filtered. The filtrate was concentrated giving 0.13 g (100%) of (4) as an essentially pure white solid.

Part D:

A mixture of (4) (1.00 g, 3.60 mmol), α-bromo-p-tolunitrile (0.71 g, 3.60 mmol), K₂CO₃ (0.50 g, 3.60 mmol), and acetone (35 mL) was maintained at reflux for 4 hours and then allowed to cool to room temperature. The resulting mixture was concentrated and the residue chromatographed on silica (1:1 hexane-EtOAc) giving 1.38 g (98%) of (5) as a clear oil.

Part E:

A mixture of (5) (0.385 g, 0.982 mmol), pyridine (5.5 mL), and Et₃N (0.55 mL) was saturated with H₂S and allowed to stand for 2 days. This solution was then diluted with H₂O and the resulting mixture was extracted with EtOAc and the extracts concentrated. The crude isolate was taken up in a mixture of acetone (5 mL) and CH₃I (2.5 mL) and maintained at reflux for 1 hour. This mixture was allowed to cool to room temperature and then concentrated. The crude isolate was taken up in MeOH (5 mL) and treated with NH₄OAc. The resulting solution was maintained at 60° C. for 2 hours and then concentrated. The crude isolate was then taken up in a solution of THF/H₂O (1:1 6 mL) and treated with K₂CO₃ (0.179 g, 1.30 mmol) and Boc₂O (0.202 g, 0.95 mmol) and the resulting mixture was stirred at room temperature for 2 hours. The reaction mixture was then diluted with EtOAc and washed with water. The organic material was then concentrated and the crude isolate was purified by chromatography (silica gel 200–400 mesh, 30:1 CHCl₃-MeOH) giving 0.311 g (62%), of (6) as a clear oil.

Part F:

A mixture of (6) (0.311 g, 0.612 mmol) and TFA (5 mL) was maintained at room temperature for 1 hour and then concentrated. The residue was taken up in H₂O and the mixture was washed with Et₂O. The remaining aqueous material was lyopholized giving 0.31 g of (7) a white solid.

¹HNMR (300 MHz, CD₃OD) 3.03 (t, J=6.5 Hz, 2H), 3.68 (t, J=6.5 Hz, 2H), 4.29 (s, 2H), 5.30 (s, 2H), 6.94 (d, J=1.9 Hz, 1H), 7.0 (dd, J=1.9, 8.6 Hz, 2H), 7.69 (d, J=8.5 Hz, 2H), 7.84 (d, J=8.5 Hz, 2H), 7.87 (d, J=8.6 Hz, 1H), IR (CHCl₃) 2928, 1695, 1435, 1286 cm⁻¹; MS (FAB) m/e 354.1451 (354.1454 calc'd for C₁₉H₂₀N₃O₄).

Example 2

Preparation of 6-[[4-(Aminoiminomethyl)phenyl]ethynyl]-3,4-dihydro-1-oxo-2(1H)-isoquinoline Acetic Acid Trifluoroacetate, a Compound Represented by the Formula (12a)

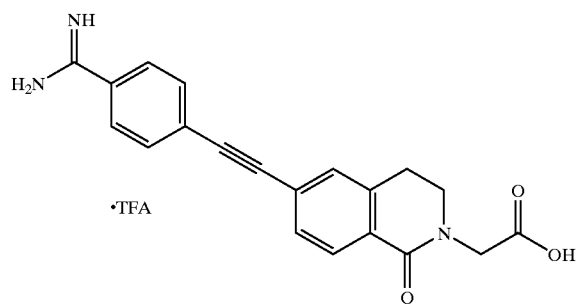

12a

Part A:

To a solution of (4) (9.5 g, 34.2 mmol) and freshly distilled pyridine (250 mL) was added trifluoromethanesulfonic anhydride (5.8 mL, 34.2 mmol) at 0° C. The resulting solution was allowed to warm to room temperature and then quenched by the addition of H₂O (125 mL). The mixture was extracted with EtOAc and the extract dried (MgSO₄) and concentrated. The crude material was purified by chromatography (silica gel, 4:1 hexane:ethyl acetate) to give 11.54 g (82.4%) of (8) (6-[[(trifluoromethyl)sufonyl]oxy]-3,4-dikydro-1-oxo-2(1H)isoquinoline acetic acid-1,1-dimethyl ester) as a white solid.

Part B:

A mixture of (8) (0.325 g, 0.79 mmol), (9a) (0.141 g, 1.11 mmol), bis (triphenylphosphine)-palladium (II) chloride (0.014 g, 0.02 mmol), anhydrous DMF (2.5 mL), and freshly distilled Et₃N (0.5 mL) was stirred at 90° C. for 1 hour. At this time, H₂O (25 mL) was added and the mixture was extracted with EtOAc (2×75 mL). The extracts were dried over MgSO₄ and concentrated. The crude material was purified by column chromatography (silica gel, 5:2 hexane:EtOAc) to give 0.173 g (57%) of (10a) as an orange solid.

Part C:

Following the general procedure used for the preparation of (6), (Example 1, part E) compound (11a) was prepared in 53% yield starting from 0.13 g of (10a).

Part D:

Following the general procedure employed for the preparation of (7), Example 1, part F compound (12a) (6-[[4-(aminoiminomethyl)phenyl]ethynyl]-3,4-dihydro-1-oxo-2 (1H)-isoquinolineacetic acid trifluoroacetate) was prepared in 76% yield starting from 0.089 g of (11a).

¹HNMR (300 MHz, CD₃OD) 3.11 (t, J=6.6 Hz, 2H), 3.73 (t, J=6.5 Hz, 2H), 4.34 (s, 2H), 7.51 (s, 1H), 7.55 (d, J=7.8 Hz, 1H), 7.78 (d, J=8.7 Hz, 2H), 7.83 (d, J=7.4 Hz, 2H), 7.97 (d, J=8.0 Hz, 1H); IR (KBr) 3355, 3085, 1709, 1610, 1183 cm⁻¹; MS(FAB) m/e 348.1332 (348.1348 calc'd for C₂₀H₁₈N₃O₃).

Example 3

Preparation of 6-[2-[4-(Aminoiminomethyl)phenyl]ethyl]-3,4-dihydro-1-oxo-2(1H)-isoquinoline Acetic Acid Trifluoroacetate, a Compound Represented by the Formula (15a)

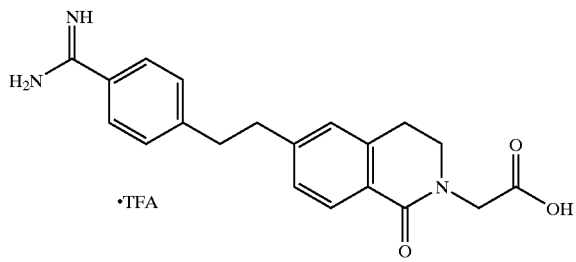

15a

Part A:

A mixture of (10a) (0.10 g, 0.26 mmol), Pd/C (0.10 g of 10% on carbon), and EtOAc (15 mL) was stirred under an atmosphere of hydrogen (balloon) for 1.5 hours and then filtered and concentrated to give 0.10 g, (100%) of (13a) as an off white solid.

Part B:

Following the general procedure employed in the preparation of (6), (Example 1, part E) compound (14a) was prepared in 78% yield starting from 0.095 g of (13a).

Part C:

Following the general procedure employed for the preparation of (7) (Example 1, part F), compound (15a) was prepared in 60% yield starting from 0.09 g of (14a).

$^1$HNMR (300 MHz, CD$_3$OD) 3.01 (m, 6H), 3.64 (t, J=6.6 Hz, 2H), 4.28 (s, 2H), 7.10 (m, 3H), 7.39 (d, J=8.2 Hz, 2H), 7.67 (d, 8.2 Hz, 2H), 7.77 (d, J=8.4 Hz, 1H); IR (KBr) 3337, 3112, 1641, 1210, 1188 cm$^{-1}$. MS(FAB) m/e 352.1655 (352.1661 calc'd for C$_{20}$H$_{22}$N$_3$O$_3$).

Example 4

Preparation of 6-[[(4-(Aminoiminomethyl)benzoyl]amino]-3,4-dihydro-1-oxo-2(1H)-isoquinoline Acetic Acid Trifluoroacetate, a Compound Represented by the Formula (22)

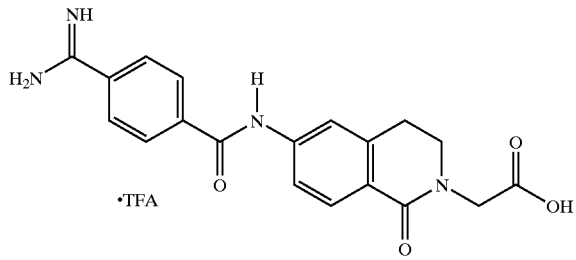

22

Part A:

A solution of (8) (Example 2, part A) (5.0 g, 12.2 mmol), DMF(25 mL), palladium (II) acetate (0.082 g, 0.37 mmol), triphenylphosphine (0.19 g, 0.73 mmol), freshly distilled Et$_3$N (3.4 mL, 24.4 mmol), and anhydrous MeOH (9.9 mL 244 mmol) was stirred under an atmosphere of CO (balloon) at 65° C. for 15 hours. The reaction mixture was then allowed to cool and diluted with H$_2$O. The resulting mixture was extracted with EtOAc (2×100 mL). The combined extracts were dried (MgSO$_4$) and concentrated. The crude material was purified by column chromatography (silica gel; 3:1 Hexane:EtOAc) to afford 2.80 g (72%) of (16) (6-(methoxy carbonyl)-3,4-dihydro-1-oxo-2(1H)isoquinolone acetic acid-1,1-dimethyl ester) as an off-white solid.

Part B:

A solution of (16) (2.8 g, 8.7 mmol) and THF (87 mL) was treated with aqueous LiOH (87 mL of a 0.1 N solution, 8.7 mmol) and the resulting solution was maintained at room temperature for 1 hour. The reaction mixture was then concentrated to ½ volume and extracted with EtOAc. A portion of the aqueous material was then acidified (pH=5) with 1N HCl and this mixture was then extracted with EtOAc. The combined extracts were then dried (MgSO$_4$) and concentrated affording 0.37 g of (17) as a viscous oil. The remaining aqueous material was lyopholized providing 2.06 g of (17) as the lithium salt.

Part C:

A solution of (17) (0.200 g, 0.66 mmol) and anhydrous toluene (50 mL) was treated with diphenyl-phosphorylazide (282.3 ml, 1.31 mmol) and freshly distilled Et$_3$N (0.18 mL, 1.31 mmol) and the resulting solution was maintained at 85° C. for 2 hours. The reaction was then allowed to cool to room temperature where it was treated with benzyl alcohol (0.14 mL, 1.31 mmol) and stirred for an additional hour. The reaction mixture was then concentrated and the crude isolate was purified by column chromatography (silica gel, 1:1 hexane:EtOAc) to yield 0.21 g (79%) of (18) (6-[(benzyloxy carbonyl)amino]-3,4-dihydro-1-oxo-2(1H) isoquinolone acetic acid-1,1-dimethyl ester) as a white solid.

Part D:

A mixture of (18) (0.20 g, 0.49 mmol), EtOH (20 mL), EtOAc (20 mL), and Pd/C (0.2 g of 10% on C) was stirred under an atmosphere of hydrogen (balloon) for 1 hour and then filtered and concentrated giving 0.138 g (100%) of (19) (6-amino-3,4-dihydro-1-oxo-2(1H)isoquinoline acetate acid-1,1-dimethyl ethyl ester) as a white solid.

Part E:

A solution of the (19) (0.125 g, 0.45 mmol), anhydrous dichloromethane (2.5 mL), para-cyanobenzoic acid (0.066 g, 0.45 mmol), 1-(3-dimethylaminopropyl)-3-ethyl-carbodiimide hydrochloride (EDCI) (0.095 g, 0.50 mmol) and 4-dimethylaminopyridine (DMAP) (10.0 mg) was maintained at room temperature for 2 hours and then concentrated. The crude isolate was purified by column chromatography (silica gel; 2:1 EtOAc:hexane) to give 0.176 g (96%) of a (20) as a white solid.

Part F:

Following general procedure employed for the synthesis of (6) (Example 1, part E), compound (21) was prepared in 36% yield starting from 0.17 g of (20).

Part G:

Following the general procedure employed for the synthesis of (7) (Example 1, part F), compound (22) was prepared in 76% yield starting from 0.07 g of (21). $^1$HNMR (300 MHz, CD$_3$OD) 3.09 (t, J=6.6 Hz, 2H), 3.72 (t, J=6.6 Hz, 2H), 4.32 (s, 2H), 7.67 (d, 1H), 7.80 (br s, 1H), 7.94 (d, J=8.3 Hz, 3H), 8.16 (d, J=8.2 Hz, 2H); IR (CHCl$_3$) 3354, 3007, 1634, 1538, 1196 cm$^{-1}$; MS (FD) m/e 367. Anal. Calc'd for C$_{21}$H$_{19}$F$_3$N$_4$O$_6$: C, 52.50; H, 3.99; N, 11.66. Found: C, 52.62; H, 4.21: N, 11.41.

Example 5

Preparation of (+−)-6-[[4-(Aminoiminomethyl)phenyl]methoxy]-3,4-dihydro-1-oxo-beta[hexylamino Carbonyl]-2(1H)-isoquinolone Propanoic Acid Trifluoroacetate, a Compound Represented by the Formula (29a)

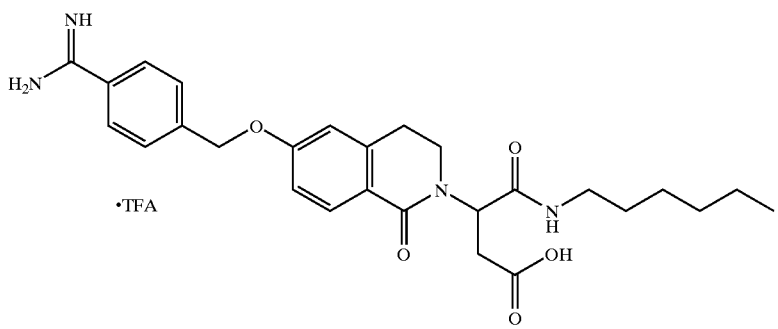

Part A:
Following the procedure outlined for the preparation of (3a) (Example 1, part B), (3b) was prepared in 60% yield starting from lactam (2) and methyl bromoacetate.

Part B:
A solution of (3b) (1.95 g, 6.0 mmol) and THF (10 mL) was added to a solution of LHMDS (prepared from n-BuLi and HMDS according to standard protocols, 6.6 mmol) and THF (10 mL) at −78° C. After 1 hour, the solution was treated with tert-butyl bromoacetate (1.1 mL, 6.6 mmol) and allowed to warm to room temperature. The mixture was diluted with EtOAc (100 mL) and washed with $H_2O$. The organic material was dried ($MgSO_4$) and concentrated. Chromatography (silica gel, 200–400 mesh, 2:1 hexanes/EtOAc) gave 2.17 g (82%) of (23) as a clear oil.

Part C:
Following the procedure employed for the preparation of (4), (Example 1, part C) compound (24) was prepared in 94% yield starting from 2.17 g of (23).

Part D:
A mixture of (24) (1.79 g, 5.12 mmol), alpha-bromo-p-tolunitrile (1.11 g, 5.64 mmol), $K_2CO_3$ (0.78 g, 5.64 mmol), $Bu_4NI$ (cat.) and DMF (10 mL) was stirred at 80° C. for 3 hours and then allowed to cool to room temperature. The mixture was then diluted with EtOAc (100 mL) and washed with $H_2O$. The organic material was concentrated and the crude isolate was purified by chromatography (silica gel, 200–400 mesh, 1.5:1 Hexanes/EtOAc) giving 2.32 g (98%) of (25) as a clear oil.

Part E:
A mixture of (25) (0.46 g, 1.0 mmol), aqueous LiOH (11 mL of a 0.1N solution, 1.1 mmol) and THF (11 mL) was stirred at room temperature for 3 hours and then concentrated to ½ volume. The remaining aqueous material was washed once with $Et_2O$ and then acidified to pH 3 with 1N HCl. This mixture was extracted with EtOAc and the combined extracts were concentrated. The crude residue was taken up in $CH_2Cl_2$ (5 mL) and treated with hexylamine (0.15 mL, 1.1 mmol), EDCI (0.28 g, 1.5 mmol), and DMAP (cat). The resulting mixture was maintained at room temperature for 4 hours and then diluted with EtOAc and washed with $H_2O$. The organic material was concentrated and the crude residue was purified by chromatography (silica gel, 200–400 mesh, 1:1 hexanes/EtOAc) giving 0.52 g (92%) of (27a) as a clear oil.

Part F:
Following the procedure employed for the preparation of (6) (Example 1, part E), (28a) was prepared in 75% yield starting from 0.52 g of (27a).

Part G:
Following the procedure for the preparation of (7) (Example 1, part F), (29a) was prepared in 82% yield starting from 0.47 g of (28a).

$^1$H NMR (300 MHz, $CD_3OD$) 0.83 (m, 3H), 1.27 (m, 6H), 1.45 (m, 2H), 2.71 (dd, J=8.0, 15.9 Hz, 1H), 3.1 (m, 5H), 3.59 (m, 2H), 5.28 (s, 2H), 5.48 (t, J=7.7 Hz, 1H), 6.90 (d, J=2.0 Hz, 1H), 6.98 (dd, J=2.0, 8.7 Hz, 1H), 7.70 (d, J=8.2 Hz, 2H), 7.83 (d, J=8.2 Hz, 2H), 7.90 (d, J=8.7 Hz, 1H); IR (KBr) 3331, 1668, 1605, 1278, 1188 cm$^{-1}$; MS (FAB) m/e 495.2612 (495.2607 calc'd for $C_{27}H_{35}N_4O_5$).

Example 6

Preparation of (+−)-6-[[4-(Aminoiminomethyl)phenyl]methoxy]-3,4-dihydro-1-oxo-beta-[[(phenylmethyl)amino]carbonyl]-2(1H)-isoquinoline Propanoic Acid Trifluoroacetate, a Compound Represented by the Formula (29b)

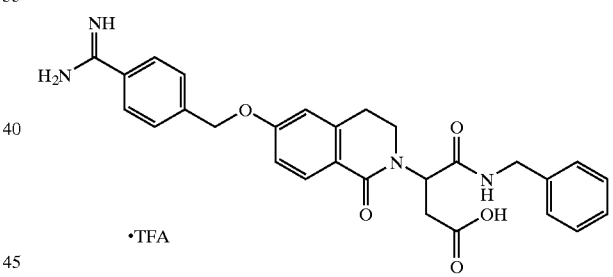

Part A:
Following the procedure employed for the preparation of (27a) (Example 5, part E), (27b) was prepared in 84% yield starting from 0.46 g of (26) (Example 5, part E) and 0.12 g of benzyl amine.

Part B:
Following the procedure employed for the preparation of (6) (Example 1, part E), 28b was prepared in 76% yield starting from 0.45 g of (27b).

Part C:
Following the procedure employed for the preparation of (7) (Example 1, part F), (29b) was prepared in 72% yield starting from 0.41 g of (28b).

$^1$H NMR (300 MHz, $CD_3OD$) 2.70 (dd, J=7.2, 16.1 Hz, 1H), 2.90, (br t, J=6.4 Hz, 2H), 3.08 (dd, J=7.9, 15.8 Hz, 1H), 3.60 (m, 2H), 4.30 (dd, J=5.7, 14.9 Hz, 1H), 4.43 (dd, J=6.3, 14.9 Hz, 1H), 5.28 (s, 2H), 5.50 (t, J=7.5 Hz, 1H), 6.87 (m, 1H), 6.97 (dd, J=2.0, 8.6 Hz, 1H), 7.25 (m, 5H), 7.71 (d, J=8.3 Hz, 2H), 7.87 (d, J=8.3 Hz, 2H), 7.90 (d, J=8.5 Hz, 1H); IR (KBr) 3333, 3092, 1668, 1604, 1278, 1185 cm$^{-1}$; MS (FAB) m/e 501.2151 (501.2138 calc'd for $C_{28}H_{29}N_4O_5$).

Example 7

Preparation of (+−)-6-[[4-(Aminoiminomethyl)
phenyl]methoxy]-3,4-dihydro-1-oxo-beta-[[(4-
methoxyphenyl Ethyl)amino]carbonyl]-2(1H)-
isoquinoline Propanoic Acid Trifluoroacetate, a
Compound Represented by the Formula (29c)

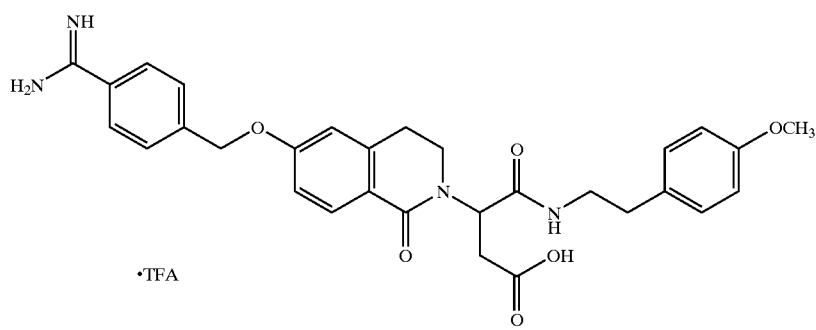

29c

Part A:
Following the general procedure employed for the preparation of (27a) (Example 5, part E), (27c) was prepared in 76% yield starting from 0.46 g of (26) and 0.17 g of p-methoxy phenethylamine.
Part B:
Following the procedure employed for the preparation of (6) (Example 1, part E), (28c) was prepared in 85% yield starting from 0.44 g of (27c).
Part C:
Following the procedure employed for the preparation of (7) (Example 1, part f), (29c) was prepared in 80% yield starting from 0.45 g of (28c).
$^1$H NMR (300 MHz, CD$_3$OD) 2.75 (m, 5H), 3.05 (dd, J=7.4, 15.8 Hz, 1H), 3.30 (m, 2H), 3.50 (m, 2H), 3.66 (s, 3H), 5.30 (s, 2H), 5.47 (t, J=7.7 Hz, 1H), 6.65 (d, J=8.4 Hz, 2H), 6.90 (m, 1H), 6.98 (dd, J=2.2, 8.5 Hz, 1H), 7.05 (d, J=8.4 Hz, 1H), 7.71 (d, J=8.4 Hz, 2H), 7.81 (d, J=8.4 Hz, 2H), 7.90 (d, J=8.5 Hz, 1H).

Example 8

Preparation of (+−)-6-[[4-(Aminoiminomethyl)
phenyl]methoxy]-3,4-dihydro-beta-[(methylamino)
carbonyl]-1-oxo-2(1H)-isoquinoline Propanoic Acid
Trifluoroacetate, a Compound Represented by the
Formula (29d)

29d

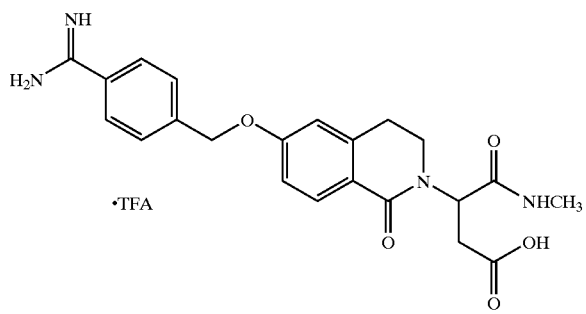

Part A:
Following the general procedure employed for the preparation of (27a), (27d) was prepared in 80% yield starting from 0.46 g of (26), 0.07 g of methylamine hydrochloride, and 0.15 mL of Et$_3$N.
Part B:
Following the procedure employed for the preparation of (6) (Example 1, part E), (28d) was prepared in 63% yield starting from 0.37 g of (27d).
Part C:
Following the procedure employed for the preparation of (7) (Example 1, part F), (29d) was prepared in 76% yield starting from 0.30 g of (28d).
$^1$H NMR (300 MHz, CD$_3$OD) 2.75 (m, 4H), 3.0 (m, 2H), 3.10 (dd, J=7.4, 15.9 Hz, 1H), 3.60 (m, 2H), 5.29 (s, 2H), 5.44 (t, J=7.6 Hz, 1H), 6.90 (d, J=2.2 Hz, 1H), 6.98 (dd J=2.2, 8.4 Hz, 1H), 7.69 (d, J=8.2 Hz, 2H), 7.82 (d, J=8.2 Hz, 2H), 7.89 (d, J=8.4 Hz, 1H); IR (KBr) 3335, 3105, 1668, 1605, 1480, 1278, 1185 cm$^{-1}$; MS (FAB) m/e 425.1819 (425.1825 calc'd for C$_{22}$H$_{25}$N$_4$O$_5$).

Example 9

Preparation of (+−)-6-[[4-(Aminoiminomethyl)
phenyl]methoxy]-beta-[[(2-carboxyethyl)amino]
carbonyl-3,4-dihydro-1-oxo-2(1H)-isoquinoline
Propanoic Acid Trifluoroacetate, a Compound
Represented by the Formula (29e)

29e

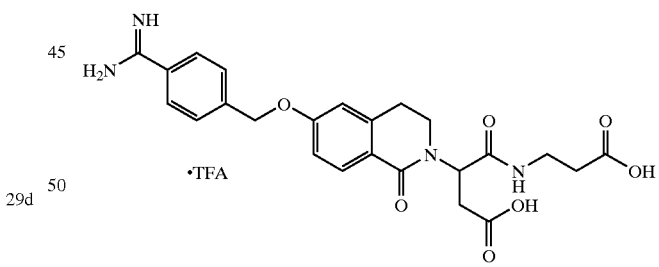

Part A:
Following the general procedure employed for the preparation of (27a) (Example 5, part E), (27e) was prepared in 74% yield starting from 0.46 g of (26), 0.2 g of beta-amino-t-butylalanine hydrochloride, and 0.15 mL of Et$_3$N.
Part B:
Following the procedure employed for the preparation of (6) (Example 1, part E), (28e) was prepared in 65% yield starting from 0.42 g of (27e).
Part C:
Following the procedure employed for the preparation of (7) (Example 1, part F), (29e) was prepared in 89% yield starting from 0.45 g of (28e).

$^1$H NMR (300 MHz, CD$_3$OD) 2.48 (t, J=6.2 Hz, 2H), 2.65 (dd, J=8.2, 15.8 Hz, 1H), 3.05 (m, 3H), 3.35 (m, 2H), 3.50 (m, 2H), 5.28 (s, 2H), 5.49 (t, J=7.7 Hz, 1H), 6.89 (m, 1H), 6.95 (dd, J=2.2, 8.4 Hz, 1H), 7.68 (d, J=8.5 Hz, 2H), 7.84 (d, J=8.5 Hz, 2H), 7.90 (d, J=8.4 Hz, 1H); IR (KBr) 3338, 3108, 1669, 1604, 1278, 1187 cm$^{-1}$; MS (FAB) m/e 483. Anal. Calc'd for C$_{26}$H$_{27}$N$_4$O$_9$F$_3$: C, 52.35; H, 4.56; N, 9.39. Found: C, 52.43; H, 4.82; N, 9.13.

Example 10

Preparation of (+−)-6-[[4-(Aminoiminomethyl) phenyl]methoxy]-b-(3-ethoxypropyl)-3,4-dihydro-1-oxo-2(1H)-isoquinoline Propanoic Acid Trifluoroacetate, a Compound Represented by the Formula (36a)

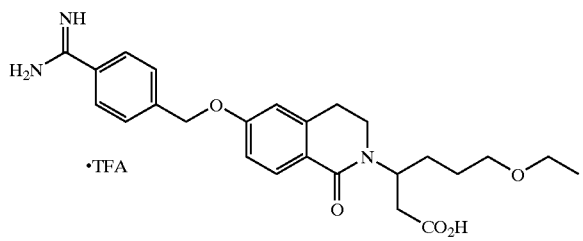

36a

Part A:

A solution of (2) (Example 1, part A), (6.53 g, 25.8 mmol), and THF (100 mL) was treated with NaH (1.13 g of a 60% dispersion in oil, 28.3 mmol) and the resulting mixture was maintained at reflux for 1 hour. The mixture was allowed to cool to room temperature and then was treated with 4-ethoxy-butanoyl chloride (28.4 mmol, prepared from the acid using standard protocols) and DMAP (cat). The resulting mixture was stirred at room temperature for 16 hours and then diluted with EtOAc. The organic mixture was washed with H$_2$O and concentrated. The crude material was purified by chromatography (silica gel, 200–400 mesh, hexanes-EtOAc, 4:1) to give 6.12 g (65%) of (30a) as a clear oil.

Part B:

A solution of (30a) (6.12 g, 16.7 mmol) in THF (10 mL) was treated with DIBAH (3.9 mL, 21.68 mmol) at −78° C. After 1 hour, the reaction was quenched by the addition of methanolic HCl (79 mL of a 1.1M solution). The mixture was then diluted with EtOAc and washed with H$_2$O and saturated aqueous NaHCO$_3$. The organic material was concentrated and the crude residue was purified by chromatography (silica gel, 200–400 mesh, hexanes/EtOAc/Et$_3$N, 3:1:.01) giving 4.09 g (64%) of (31a) as a clear oil.

Part C:

A mixture of (31a) (3.25 g, 8.48 mmol), dimethyl-t-butylsiloxy-1-t-butoxy-ethene (9.24 g, 42.4 mmol), and CH$_2$Cl$_2$ (30 mL) was treated with BF$_3$.eEt$_2$O (1.1 mL, 8.48 mmol) at −78° C. The resulting solution was allowed to warm to room temperature over 2 hours and then was quenched by the addition of saturated aqueous NaHCO$_3$ (20 mL). The resulting mixture was extracted with EtOAc and the extracts were concentrated. The crude product was purified by chromatography (silica gel, 200–400 mesh, hexanes/EtOAc 4:1) giving 3.1 g (78%) of (32a) as a clear oil.

Part D:

Following the procedure employed for the preparation of (4) (Example 1, part C), (33a) was prepared in 88% yield starting from 3.1 g of (32a).

Part E:

Following the procedure employed for the preparation of (25) (Example 5, part D), (34a) was prepared in 95% yield starting from 0.53 g of (33a).

Part F:

Following the procedure employed for the preparation of (6) (Example 1, part E), Compound (35a) was prepared in 40% yield starting from 0.71 g of (34a).

Part G:

Following the procedure employed for the preparation of (7) (Example 1, part F), (36a) was prepared in 85% yield starting from 0.32 g of (35a).

$^1$H NMR (300 MHz, CD$_3$OD) 1.15 (t, J=6.9 Hz, 3H), 1.40–1.80 (m, 4H), 2.60 (m, 2H), 2.95 (m, 2H), 3.49 (m, 6H), 5.10 (m, 1H), 5.29 (s, 2H), 6.94 (d, J=2.3 Hz, 1H), 6.97 (dd, J=2.2, 8.7 Hz, 1H), 7.70 (d, J=8.3 Hz, 2H), 7.82 (d, J=8.5 Hz, 2H), 7.85 (d, J=8.8 Hz); IR (KBr) 3334, 3105, 1668, 1604, 1134 cm$^{-1}$; MS (FAB) m/e 454.2380 (454.2342 calc'd for C$_{25}$H$_{32}$N$_3$O$_5$).

Example 11

Preparation of (+−)-6-[[4-(Aminoiminomethyl) phenyl]methoxy]-b-butyl-3,4-dihydro-1-oxo-2(1H)-isoquinoline Propanoic Acid Trifluoroacetate, a Compound Represented by the Formula (36b)

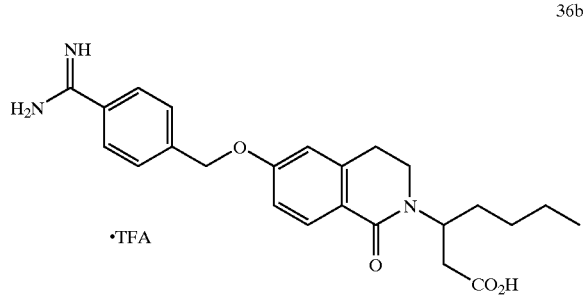

36b

Part A:

Following the procedure employed for the preparation of (30a) (Example 10, part A), (30b) was prepared in 90% yield starting from (2) (0.3 g) and pentanoic anhydride (0.24 g).

Part B:

Following the procedure employed for the preparation of (31a) (Example 10, part B), (31b) was prepared in 83% yield starting from 0.39 g of (30b).

Part C:

Following the procedure employed for the preparation of (32a) (Example 10, part C), (32b) was prepared in 52% yield starting from 0.33 g of (31a).

Part D:

Following the procedure employed for the preparation of (4) (Example 1, part C), (33b) was prepared in 98% yield starting from 0.22 g of (32b).

Part E:

Following the procedure employed for the preparation of (25) (Example 5, part D), (34b) was prepared in 95% yield starting from 0.17 g of (33b).

Part F:

Following the procedure employed for the preparation of (6) (Example 1, part E), (35b) was prepared in 56% yield starting from 0.23 g of (34b).

Part G:

Following the procedure employed for the preparation of (7) (Example 1, part F), (36b) was prepared in 89% yield starting from 0.14 g of (35b)

¹H NMR (300 MHz, CD₃OD) 0.89 (t, J=7.15 Hz, 3H), 1.35 (m, 4H), 1.65 (m, 2H), 2.60 (m, 2H), 2.95 (m, 2H), 3.50 (m, 2H), 5.05 (m, 1H), 5.29 (s, 2H), 6.95 (m, 2H), 7.70 (d, J=8.4 Hz, 2H), 7.84 (app t, J=8.2 Hz, 3H); IR (KBr) 3333, 3107, 1667, 1604, 1138 cm⁻¹; MS (FAB) m/e 424. Anal. Calc'd for $C_{26}H_{30}N_3O_6$: C, 58.10; H, 5.12; N, 7.82. Found: C, 57.85; H, 5.56; N, 7.56.

Example 12

Preparation of (+−)-6-[[4-(Aminoiminomethyl)phenyl]methoxyl]-3,4-dihydro-1-oxo-b-pentyl-2(1H)-isoquinolinepropanoic Acid Trifluoroacetate, a Compound Represented by the Formula (36c)

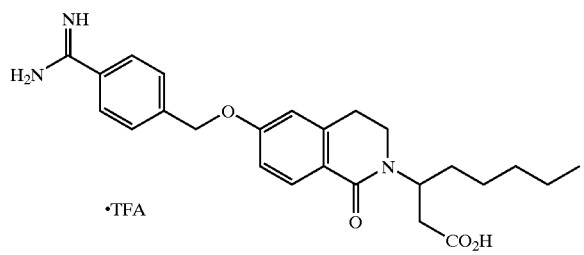

36c

Part A:

Following the procedure employed for the preparation of (30a) (Example 10, part A), (30c) was prepared in 95% yield starting from (2) (0.75 g) and hexanoyl chloride (0.43 g).

Part B:

Following the procedure employed for the preparation of (31a) (Example 10, part B), (31c) was prepared in 64% yield starting from 1.1 g of (30c).

Part C:

Following the procedure employed for the preparation of (32a) (Example 10, part C), (32c) was prepared in 70% yield starting from 0.80 g of (31c).

Part D:

Following the procedure employed for the preparation of (4) (Example 1, part C), (33c) was prepared in 87% yield starting from 0.69 g of (32c).

Part E:

Following the procedure employed for the preparation of (25) (Example 5, part D), (34c) was prepared in 88% yield starting from 0.13 g of (33c).

Part F:

Following the procedure employed for the preparation of (6) (Example 1, part E), (35c) was prepared in 65% yield starting from 0.18 g of (34c).

Part G:

Following the procedure employed for the preparation of (7) (Example 1, part F), (36c) was prepared in 80% yield starting from (35b).

¹H NMR (300 MHz, CD₃OD) 0.90 (m, 3H), 1.30 (m, 6H), 1.60 (m, 2H), 1.26 (m, 2H), 2.97 (m, 2H), 3.45 (m, 2H), 5.05 (m, 1H), 5.30 (2, 2H), 6.88 (m, 1H), 6.94 (m, 1H), 7.70 (d, J=8.3 Hz, 2H); 7.83 (d, J=8.4 Hz, 2H), 7.85 (d, J=9 Hz, 1H), IR (KBr) 3335, 3115, 1668, 1481, 1188 cm⁻¹; MS (FAB) m/e 438.2366 (438.2393 calc'd for $C_{25}H_{32}N_3O_4$).

Example 13

Preparation of (+−)-6-[[4-(Aminoiminomethyl)phenyl]methoxy]-3,4-dihydro-1-oxo-beta-(1,4-dioxyhexyl)-2(1H)-isoquinoline Propionoic Acid Trifluoroacetate, a Compound Represented by the Formula (36d)

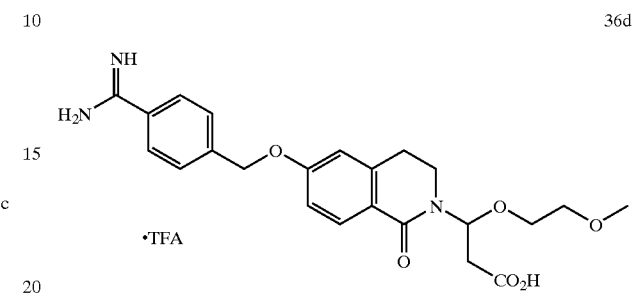

36d

Part A:

Following the procedure employed for the preparation of (30a) (Example 10, part A), (30d) was prepared in 81% yield starting from (2) (2.0 g) and 2-methoxyethoxy acetyl chloride (2.35 g).

Part B:

Following the procedure employed for the preparation of (31a) (Example 10, part B), (31d) was prepared in 52% yield starting from 2.35 g of (30d).

Part C:

Following the procedure employed for the preparation of (32a) (Example 10, part C), (32d) was prepared in 42% yield starting with 0.57 g of (31d).

Part D:

Following the procedure employed for the preparation of (4) (Example 1, part C), (33d) was prepared in 96% yield starting from 0.30 g of (32d).

Part E:

Following the procedure employed for the preparation of (25) (Example 5, part D), (34d) was prepared in 91% yield starting from 0.23 g of (33d).

Part F:

Following the procedure employed for the preparation of (6) (Example 1, part E), (35d) was prepared in 15% yield starting from 0.27 g of (34d).

Part G:

Following the procedure employed for the preparation of (7) (Example 1, part F), (36d) was prepared in 98% yield starting from 0.05 g of (35d).

¹H NMR (300 MHz, CD₃OD): 2.70 (t, J=6.2 Hz, 2H), 2.93 (t, J=6.2 Hz, 2H), 3.30 (s, 3H), 3.47–3.78 (m, 8H), 5.09 (br s, 1H), 5.29 (s, 2H), 6.88 (d, J=2.2 Hz, 1H), 6.95 (dd, J=2.2, 8.7 Hz, 1H), 7.82 (d, J=8.0 Hz, 2H), 7.84–7.86 (m, 3H). IR (KBr) 3350, 3114, 1669, 1604, 1482, 1385, 1279, 1186, 1029, 842 cm⁻¹; MS (FAB) m/e=456.3. Anal. Calc'd for $C_{26}H_{30}F_3N_3O_8$: C, 54.84; H, 5.31; N, 7.38. Found: C, 54.61; H 5.26; N, 7.37.

Example 14

Preparation of (+−)-6-[[4-(Aminoiminomethyl)phenyl]methoxy]b-ethyl-3,4-dihydro-1-oxo-2(1H)-isoquinoline Propanoic Acid Trifluoroacetate, a Compound Represented by the Formula (36e)

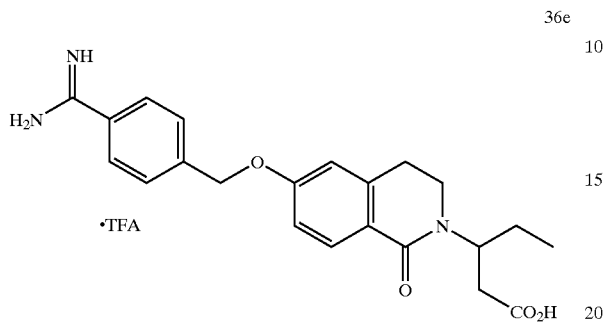

Part A:

Following the procedure employed for the preparation of (30a) (Example 10, part A), (30e) was prepared in 69% yield starting from (2) (1.5 g) and propanoyl chloride (1.26 g).

Part B:

Following the procedure employed for the preparation of (31a) (Example 10, part B), (31e) was prepared in 73% yield starting from 1.2 g of (30e).

Part C:

Following the procedure employed for the preparation of (32a) (Example 10, part C), (32e) was prepared in 49% yield starting from 0.92 g of (32e).

Part D:

Following the procedure employed for the preparation of (4) (Example 1, part C), (33e) was prepared in 89% yield starting from 0.55 g of (32e).

Part E:

Following the procedure employed for the preparation of (25) (Example 5, part D), (34e) was prepared in 86% yield starting from 0.36 g of (33e).

Part F:

Following the procedure employed for the preparation of (6) (Example 1, part E), (35e) was prepared in 36% yield starting from 0.38 g of (34e).

Part G:

Following the procedure employed for the preparation of (7) (Example 1, part F), (36e) was prepared in 92% yield starting from 0.22 g of (35e).

$^1$H NMR (300 MHz, CD$_3$OD): 0.91 (t, J=7.3 Hz, 3H), 1.62–1.69 (m, 2H), 2.55–2.62 (m, 2H), 2.92–2.97 (m, 2H), 3.42–3.53 (m, 2H), 4.94 (m, 1H), 5.29 (s, 2H), 6.89 (d, J=2.5 Hz, 1H), 6.95 (dd, J=2.5, 8.6 Hz, 1H), 7.70 (d, J=8.4 Hz, 2H), 7.84–7.87 (m, 3H). IR(KBr) 3330, 3109, 2973, 1670, 1604, 1481, 1344, 1256, 1041, 835 cm$^{-1}$; MS(FAB) m/e 396.1923, (396.1923 calc'd for C$_{22}$H$_{26}$N$_3$O$_4$).

Example 15

Preparation of (+−)-6-[[4-(Aminoiminomethyl)phenyl]methoxy]-3,4-dihydro-1-oxo-b-propyl-2(1H)-isoquinoline Propanoic Acid Trifluoroacetate, a Compound Represented by the Formula (36f)

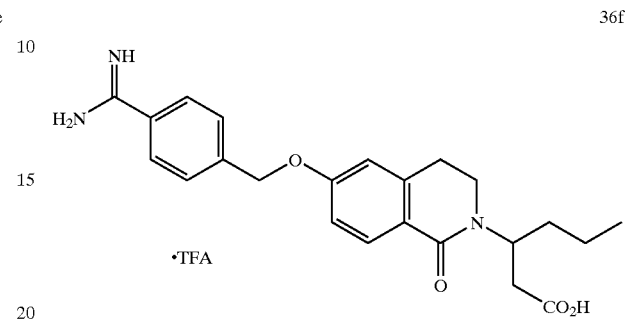

Part A:

Following the procedure employed for the preparation of (30a) (Example 10, part A), (30f) was prepared in 77% yield starting from (2) (Example 1, part A) (1.0 g) and butanoyl chloride (0.98 g).

Part B:

Following the procedure employed for the preparation of (31a) (Example 10, part B), (31f) was prepared in 73% yield starting from 0.6 g of (30f).

Part C:

Following the procedure employed for the preparation of (32a) (Example 10, part C), (32f) was prepared in 46% yield starting from 0.44 g of (31f).

Part D:

Following the procedure employed for the preparation of (4) (Example 1, part C), (33f) was prepared in 90% yield starting from 0.24 g of (32f).

Part E:

Following the procedure employed for the preparation of (25) (Example 5, part D), (34f) was prepared in 88% yield starting from 0.16 g of (33f).

Part F:

Following the procedure employed for the preparation of (6) (Example 1, part E), (35f) was prepared in 44% yield starting from 0.19 g of (34f).

Part G:

Following the procedure employed for the preparation of (7) (Example 1, part F), (36f) was prepared in 66% yield starting from 0.085 g of (35f).

$^1$H NMR (300 MHz, CD$_3$OD): 0.95 (t, J=7.3 Hz, 3H), 1.29–1.36 (m, 2H), 1.54–1.71 (m, 2H), 2.56–2.62 (m, 2H), 2.91–2.96 (m, 2H), 3.43–3.53 (m, 2H), 5.09 (br s, 1H), 5.29 (S, 2H), 6.88 (d, J=2.1 Hz, 1H), 6.96 (dd, J=2.1, 8.5 Hz, 1H), 7.70 (d, J=8.2 Hz, 2H), 7.82 (d, J=8.2 Hz, 2H), 7.85 (d, J=8.5 Hz, 1H); IR (KBr) 3327, 3106, 2963, 2874, 1670, 1628, 1604, 1480, 1278, 1136 cm$^{-1}$; MS (FAB) m/e 410.2077 (410.2079 calc'd for C$_{23}$H$_{28}$N$_3$O$_4$).

Example 16

Preparation of (+−)-6-[[4-(Aminoiminomethyl)phenyl]methoxy]-3,4-dihydro-1-oxo-b-phenyl-(1H)-isoquinoline Propanoic Acid Trifluoroacetate, a Compound Represented by the Formula (36g)

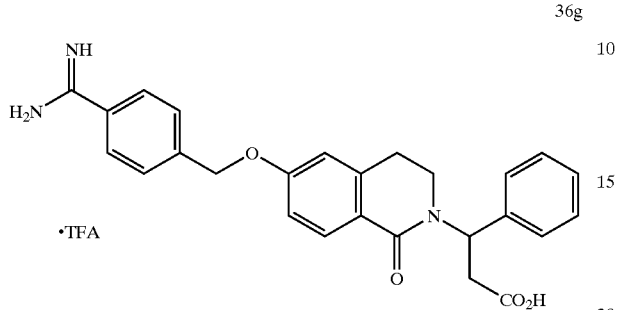

Part A:

The isoquinolone (2) (1.0 g, 3.95 mmol) and 60 wt. % NaH suspended in mineral oil (0.174 g, 4.35 mmol) were refluxed in THF (40 mL) for one hour. The mixture was cooled to room temperature and the alpha-methoxy benzyl chloride (0.683 g, 4.35 mmol) was added in one portion (ref., Liebigs *Ann. Chem.*, 191 (1932). The reaction mixture was stirred overnight at ambient temperature. The mixture was diluted with water (100 mL) and extracted with EtOAc (2×10 mL). The combined extracts were dried over anhydrous sodium sulfate and concentrated. The residue was chromatographed on silica gel eluting with 2:1 hexanes/EtOAc. Obtained 1.02 g of (31g) as a clear oil (68% of theory).

Part B:

Following the procedure employed for the preparation of (32a) (Example 10, part C), (32g) was prepared in 36% yield starting from 2.29 g of (31g).

Part C:

Following the procedure employed for the preparation of (4) (Example 1, part C), (33g) was prepared in 83% yield starting from 1.02 g of (32g).

Part D:

Following the procedure employed for the preparation of (25) (Example 5, part D), (34g) was prepared in 91% yield starting from 0.675 g of (33g).

Part E:

Following the procedure employed for the preparation of (6) (Example 1, part E), (35g) was prepared in 50% yield starting from 0.80 g of (34g).

Part F:

Following the procedure employed for the preparation of (7) (Example 1, part F), (36g) was prepared in 79% yield starting from 0.43 g of (35g).

$^1$H NMR (300 MHz, CD$_3$OD): 2.76–3.30 (m, 5H), 3.47–3.54 (m, 1H), 5.27 (s, 2H), 6.38 (t, J=7.4 Hz, 1H), 6.84 (d, J=2.3 Hz, 1H), 6.96 (dd, J=2.3, 8.7 Hz, 1H), 7.28–7.40 (m, 5H), 7.68 (d, J=8.2 Hz, 2H), 7.81 (d, J=8.2 Hz, 2H), 7.91 (d, J=8.7 Hz, 1H). IR (KBr) 3328, 3107, 1671, 1604, 1421, 1278, 1189, 1134, 1020 cm$^{-1}$; MS (FAB) m/e 444.1931 (444.1923 calc'd for C$_{26}$H$_{26}$N$_3$O$_4$).

Example 17

Preparation of 6-[[3-(Aminoiminomethyl)phenyl]ethynyl]-3,4-dihydro-1-oxo-2(1H)-isoquinoline Acetic Acid Trifluoroacetate, a Compound Represented by the Formula (12b)

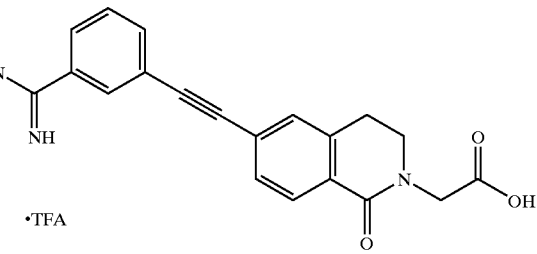

Part A:

Following the procedure employed for the preparation of (10a) (Example 2, part B), (10b) was prepared in 54% yield starting from 0.20 g of (8) (Example 2, part A) and 0.09 g of (9b).

Part B:

Following the procedure employed for the preparation of (6) (Example 1, part E), (11b) was prepared in 10% yield starting from 0.1 g of (9b).

Part C:

Following the procedure employed for the preparation of (7) (Example 1, part f), (12b) was prepared in 87% yield starting from 0.01 g of (11b).

$^1$H NMR (300 MHz, CD$_3$OD) 3.07 (t, J=6.5 Hz, 2H), 3.70 (t, J=6.6 Hz, 2H), 4.31 (s, 2H), 7.46 (s, 1H), 7.50 (d, J=8.2 Hz, 1H), 7.63 (t, J=7.8 Hz, 1H), 7.78 (d, J=7.6 Hz, 1H), 7.88 (d J=7.7 Hz, 1H), 7.92 (s, 1H), 7.96 (d, J=4.8 Hz, 1H); IR (CHCl$_3$) 3010, 1647, 1607, 1277, 1156 cm$^{-1}$; MS (FAB) m/e 348.1338 (348.1348 calc'd for C$_{20}$H$_{18}$N$_3$O$_3$).

Example 18

Preparation of 6-[2-[3-(Aminoiminomethyl)phenyl]ethyl]-3,4-dihydro-1-oxo-2(1H)-isoquinoline Acetic Acid Trifluoroacetate, a Compound Represented by the Formula (15b)

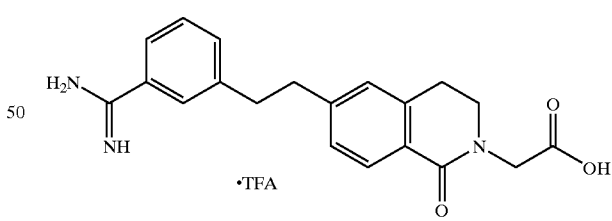

Part A:

Following the procedure employed for the preparation of (13a)-(Example 2, part A), (13b) was prepared in 98% yield starting from 0.13 g of (10b).

Part B:

Following the procedure employed for the preparation of (6) (Example 1, part E), (14b) was prepared in 64% yield starting from 0.09 g of (13b).

Part C:

Following the procedure employed for the preparation of (7) (Example 1, part F), (15b) was prepared in 86% yield starting from 0.09 g of (14b).

$^1$H NMR (300 MHz, CD$_3$OD) 3.00 (m, 6H), 3.65 (t, J=6.6 Hz, 2H), 4.28 (s, 2H), 7.09 (s, 1H), 7.13 (d, J=8.2 Hz, 1H), 7.49 (m, 2H), 7.59 (m, 2H), 7.79 (d, J=7.9 Hz, 1H); IR (KBr) 1716, 1679, 1639, 1195, 1134 cm$^{-1}$, S (FD) m/e 352. Anal. Calc'd for C$_{22}$H$_{22}$F$_3$N$_3$O$_5$: C, 56.77; H, 4.76; N, 9.03; Found: C, 56.65; H, 4.71; N, 8.73.

Example 19

Preparation of 6-[[(4-Aminoiminomethyl)phenyl]methylaminocarbonyl]-3,4-dihydro-1-oxo-2(1H)isoquinoline Acetic Acid Trifluoroacetate, a Compound Represented by the Formula 50

(50)

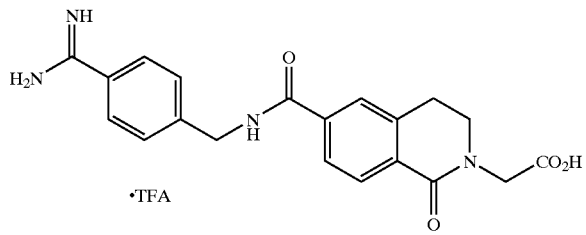

Part A:

A solution of (17) (6-carboxy-3,4-dihydro-1-oxo-2(1H)isoquinoline acetic acid-1,1-dimethylethyl ester) (0.20 g, 0.66 mmol), p-cyano benzylamine (0.10 g, 0.66 mmol), EDCI (0.15 g, 0.8 mmol), and DMAP (0.18 g, 1.4 mmol) in CH$_2$Cl$_2$ (7.0 mL) was maintained at room temperature for 18 hours and then concentrated. The residue was purified by chromatography (silica gel, 200–400 mesh, 25:1 CHCl$_3$-MeOH) giving 0.098 g (37%) of 6-[[(4-cyano phenyl)methylamino]carbonyl]-3,4-dihydro-1-oxo-2(1H)isoquinoline acetic acid-1,1-dimethylethyl ester, as a white solid.

Part B:

Following the procedure employed for the preparation of (6) (Example 1, part E), [[4-(1,1-dimethylethoxy carbonyl aminoiminomethyl) phenyl]methylamino carbonyl]-3,4-dihydro-1-oxo-2(1H)isoquinoline acetic acid-1,1-dimethyl ethyl ester was prepared in 38% yield starting from 0.09 g of 6-[[4-cyano phenyl)methylamino]carbonyl]-3,4-dihydro-1-oxo-2(1H)isoquinoline acetic acid-1,1-dimethylethyl ester.

Part C:

Following the procedure employed for the preparation of (7) (Example 1, part F), 6-[[(4-aminoimino methyl)phenyl]methylaminocarbonyl]-3,4-dihydro-1-oxo-2(1H)isoquinoline acetic acid Trifluoroacetate was prepared in 83% yield starting from 0.05 g of [[4-(1,1-dimethylethoxy carbonylaminoiminomethyl)phenyl]methyl amino carbonyl]-3,4-dihydro-1-oxo-2(1H)isoquinoline acetic acid-1,1-dimethyl ethyl ester.

$^1$H NMR (300 MHz, CD$_3$OD) 3.14 (t, J=6.4 Hz, 2H), 3.73 (t, J=6.7 Hz, 2H), 4.34 (br s, 2H), 4.68 (d, J=5.9 Hz, 2H), 7.6 (d, J=8.4 Hz, 2H), 7.79 (m, 4H), 8.03 (d, J=8.0 Hz, 1H); IR (KBr) 3327, 3109, 1670, 1639, 1190 cm$^{-1}$; MS (FD) m/e 381.

Example 20

Preparation of 40(+−)-6-[[(4-Aminoimidomethyl)phenyl]methoxy]-1,2,3,4-tetrahydronapthylene-2-acetic Acid Trifluoroacetate, a Compound Represented by the Formula (45)

(45)

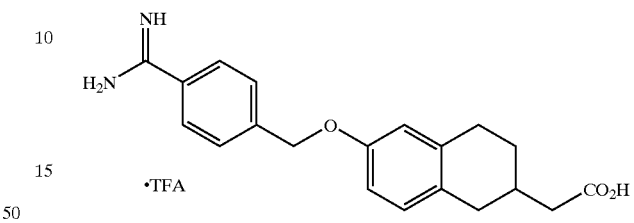

Part A:

A 0° C. slurry of 650 mg (16.3 mmol; 60% dispersion in mineral oil) of NaH in 50 mL THF was treated with 2.70 mL (3.0 g; 13.6 mmol) of triethyl-phosphonoacetate. After stirring at 0° C. for 0.25 hours, a solution of 2.0 g (11.3 mmol) of 6-methoxy-2-tetralone (38) (See, Scheme 6) in 10 mL THF was added dropwise. The cold bath was removed and the reaction stirred at RT for 16 hours. The reaction was quenched by the addition of 50 mL of brine. The two layers were separated and the organic phase dried over Na$_2$SO$_4$. Evaporation of the solvent gave 3.50 g of a brown oil. Purification by flash chromatography (SiO$_2$; 20% EtOAc in hexanes) afforded 2.10 g (8.52 mmol; 75%) of (39) as a light yellow oil.

Part B:

A solution of 1.00 g (4.06 mmol) of (39) in 20 mL of EtOH was charged with a slurry of 0.2 g of 10% Pd/C in 10 mL EtOH. The mixture was hydrogenated at 50 psi for 3.0 hours at room temperature. The catalyst was filtered off and the reaction evaporated in vacuo to give 1.10 g of an oil. Purification by radial chromatography (SiO$_2$; 5% EtOAc in hexanes) afforded 910 mg (3.66 mmol; 90%) of (40) as a clear oil.

Part C:

A −78° C. solution of 100 mg (0.40 mmol) of (40) in 4 mL CH$_2$Cl$_2$ was treated with BBr$_3$ (1.0 mL of a 1M solution in CH$_2$Cl$_2$). The reaction was allowed to reach ambient temperature over 4 hours and was stirred at room temperature for 18 hours. The reaction was cooled to −78° C. and was treated with 5 mL of EtOH. The mixture was allowed to warm and was stirred at room temperature for 3 hours. The volatiles were evaporated in vacuo and the residue dissolved in 5 mL of EtOH and the mixture stirred for 2 hours. Evaporation of the EtOH gave a brown oil which was reconstituted in 20 mL of EtOH and the solution was treated with a stream of HCl (g) for 10 minutes. The reaction was capped and was stirred at room temperature for 16 hours. Concentration in vacuo gave 61 mg of phenol (41). The material was taken up in 2 mL of DMF and was treated with 41 mg (0.30 mmol) of K$_2$CO$_3$, 8 mg (0.05 mmol) NaI and 57 mg (0.29 mmol) of alpha-bromo-p-tolunitrile. The reaction was stirred at room temperature for 16 hours and the DMF removed in vacuo. The residue was partitioned between 10 mL H$_2$O and 10 mL EtOAc. The organic layer was separated, was washed with 10 mL H$_2$O, and was dried over Na$_2$SO$_4$. Evaporation of the solvent in vacuo afforded 91 mg of a solid. Purification of the solid by radial chromatography (SiO$_2$; 25% EtOAc in hexanes) gave 82 mg (0.24 mmol; 60% from (40)) of (42) as a white solid.

Part D:
Following the procedure employed for the preparation of (6) (Example 1, part E), (43) was prepared in 50% yield starting from 0.429 g of (42).

Part E:
A solution of 250 mg (0.54 mmol) of (43) in 5 mL of EtOH was treated with 0.5 mL of 5 N aq NaOH (2.5 mmol). The reaction was stirred at room temperature for 6 hours at which time 3.0 mL of 1 N aq citric acid (3.0 mmol) was added. The EtOH was evaporated in vacuo. The white solid was filtered, was washed with $H_2O$, and was dried in vacuo to afford 130 mg of acid (44) as a white powder. The solid was slurried in 1 mL of anisole and the mixture treated with 10 mL of trifluoroacetic acid. The reaction was stirred at room temperature for 3 hours and was evaporated in vacuo. The residue was slurried in 10 mL $H_2O$ and the mixture extracted with hexanes (5×5 mL). The aqueous layer was lyopholized to afford 96 mg (0.26 mmol; 48% from (43)) of the trifluoroacetate salt of (45) as a white solid.

MS (FD), m/e 339 (M+1, 100). IR (KBr) 3301, 3145, 2915, 1711, 1664, 1503, 1437, 1196, 1143, 1057 $cm^{-1}$. Analytical Calculated for $C_{27}H_{34}N_2O_5 \cdot 1.5 H_2O$: C 55.11, H 5.47, N 5.84; Found C 55.46, H 5.15, N 5.45.

Example 21

Preparation of 6-[[4-(Guanidinomethyl)phenyl]methoxy]-3,4-dihydro-1-oxo-2(1H)-isoquinoline Acetic Acid Trifluoroacetate, a Compound Represented by the Formula

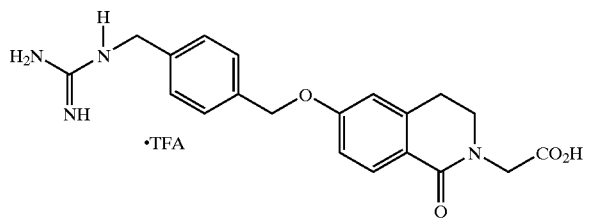

Part A:
A mixture of (4) and (51) (prepared from the dibromide and potassium pthalimide using standard protocols), $K_2CO_3$, and DMF was maintained at 80° C. for 4 hours and then allowed to cool to room temperature. The reaction mixture was diluted with EtOAc and washed with $H_2O$. The organic material was concentrated and the crude isolate was purified on silica giving (46) as a clear oil.

Part B:
A mixture of hydrazine hydrate (0.079 mL, of an 85% solution in $H_2O$, 1.4 mmol), (46) (0.075 g, 0.14 mmol), and EtOH (3 mL) was maintained at 60° C. for 1 hour and then allowed to cool to room temperature. The reaction mixture was diluted with EtOAc and washed with aqueous $NaHCO_3$. The organic material was concentrated giving 0.055 g (100%) of (47) as a clear oil.

Part C:
A mixture of (47) (0.049 g, 0.12 mmol), N,N'-bis(tert-butoxycarbonyl)-S-methylisothiourea (0.043 g, 0.15 mmol) and THF (1 mL) was maintained at room temperature for 60 hours and then concentrated. Chromatography (2:1 hexanes/EtOAc) gave 0.073 g (90%) of (49) as a clear oil.

Part D:
Following the procedure employed for the preparation of (7) (Example 1 part F), (50) was prepared in 78% yield starting from 0.07 g of (49).

$^1$H NMR (300 MHz, $CD_3OD$) 3.05 (bt, 2H), 3.65 (bt, 2H), 4.28 (s, 2H), 5.20 (s, 2H), 6.90 (m, 2H), 7.35 (d, 2H), 7.50 (d, 2H), 7.85 (d, 2H); IR (KBr) 3364, 3199, 1736, 1687, 1633, 1609, 1179 $cm^{-1}$; MS (FAB) m/e 383.1732 (383.1717 calcd for $C_{20}H_{23}N_4O_2$).

Example 22

Preparation of 6-[4-(Piperidn-4-yl)propyloxy]-3,4-dihydro-1-oxo-B-(3-ethoxypropyl)-1-oxo-2(1H)-isoquinoline Propanoic Acid Trifluoroacetate, a Compound Represented by the Formula

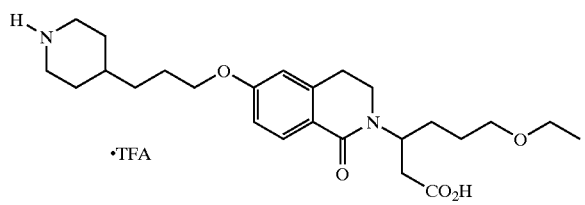

Part A:
A solution of (33a) (0.053 g, 0.14 mmol) and alcohol (51) (prepared from 3-(4-pyridyl)-propanol using standard protocols), triphenyl phosphine (0.046 g, 0.17 mmol), diethyl azodicarboxylate (0.028 mL, 0.17 mmol) in THF (1.3 mL) was maintained at room temperature for 1 hour and then concentrated. The crude residue was purified by chromatography (1:1 hexanes/EtOAC) giving 0.047 g (61%) of 52 as a clear oil.

Part B:
Following the procedure employed for the preparation of (7) (Example 1 part F), (53) was prepared in 95% yield starting from 0.042 g of (52).

$^1$H NMR (300 MHz, $CD_3OD$) 1.13 (t, J=7.0 Hz, 3H), 1.27–1.98 (m 15H), 2.58 (m, 2H), 2.96 (m, 4H), 3.28–3.51 (m, 6H), 4.02 (t, J=6.1 Hz, 2H), 5.05 (m, 1H), 6.75 (br s, 1H), 6.83 (d, J=8.7 Hz, 1H), 7.82 (d, J=8.6 Hz, 1H); MS (FAB) m/e 447. Anal. Calcd for $C_{27}H_{39}N_2O_7$: C, 57.85; H, 7.01; N, 5.00. Found: C, 58.13, H, 7.18; N, 5.28.

Example 23

Preparation of the Compound Represented by the Formula 66

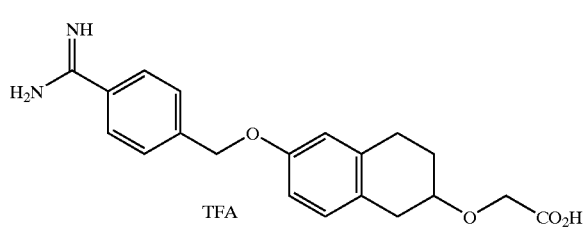

Part A:
A solution of DIBAH in toluene (100 mL of a 1.5 M solution, 150 mmol) and 6-methoxy-2-tetralone (60) (5.19 g, 28 mmol) was maintained at reflux for 17 hours and then cooled to 0° C. This mixture was quenched by slow addition of saturated aqueous $NH_4Cl$ (25 mL) followed by 1N HCl (25 mL) and allowed to slowly warm to room temperature with stirring. The resulting gelatinous mixture was filtered through Celite and the colorless aqueous filtrate extracted with EtOAc. The combined extracts were washed with 1N HCl, $H_2O$, and brine, dried ($MgSO_4$), and concentrated in vacuo. The crude material was purified by chromatography (silica gel 230–400 mesh, toluene:EtOAc gradient) to afford 1.75 g (38%) of 62 as a tan solid.

Part B:

To a solution of 62 (1.64 g, 10 mmol) in DMF (40 mL) at −5° C. was slowly added benzyltrimethylammonium hydroxide (Triton B, 4.5 mL, 10 mmol). After stirring 0.75 hours, α-bromo-p-tolunitrile (1.98 g, 10 mmol) was added as a solid and the solution was allowed to warm to room temperature gradually overnight. The mixture was diluted with EtOAc, washed with H$_2$O, 1N HCl, saturated NaHCO$_3$, and brine, dried (MgSO$_4$), and concentrated in vacuo. The crude material was purified by chromatography (silica gel 230–400 mesh, toluene:EtOAc gradient) to afford 2.05 g (73%) of 63 as a white solid.

Part C:

To a rapidly stirred mixture of 63 (2.0 g, 7.16 mmol), KOH (50% w/v aqueous, 20 mL), and tetrabutylammonium hydrogen sulfate (1.25 g, 3.58 mmol) in benzene (30 mL) was added neat tert-butyl bromoacetate (3.51 mL, 21.72 mmol) dropwise. The mixture was stirred at room temperature for 3 hours then diluted with EtOAc and washed with 1N HCl, saturated NaHCO$_3$, H$_2$O, and brine, dried (MgSO$_4$), and concentrated in vacuo. The crude material was purified by chromatography (silica gel 230–400 mesh, toluene:EtOAc gradient) to afford 2.38 g (85%) of 64 as a white solid.

Part D:

Following the general procedure outlined for the preparation of 6 (Example 1 part E), 65 was prepared in 63% yield starting from 2.33 g of 64.

Part E:

Following the general procedure outlined for the preparation of 7 (Example 1 part F), 66 was prepared in 98% yield starting from 1.78 g of 65. MS (FD) m/e 355

Example 24

Preparation of the Compound Represented by the Formula 69

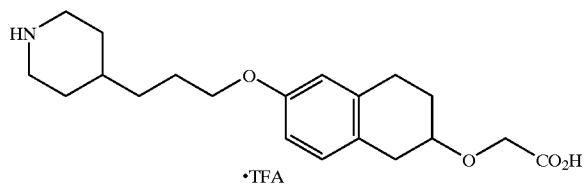

(69)

Part A:

To a solution of 62 (0.64, 3.9 mmol) in DMF (25 mL) at −5° C. was slowly added benzyltrimethylammonium hydroxide (Triton B, 1.77 mL, 3.9 mmol). After stirring 0.5 h, 1-tBOC-4-(3-bromopropyl)piperidine (1.19 g, 3.9 mmol) was added neat and the solution was allowed to warm to room temperature gradually overnight. Diluted the mixture with EtOAc, washed with H$_2$O, 1N HCl, saturated NaHCO$_3$, and brine, dried (MgSO$_4$), and concentrated in vacuo. The crude material was purified by chromatography (silica gel 230–400 mesh, toluene:EtOAc gradient) to afford 1.37 g (90%) of 67 as a colorless gum.

Part B:

To a rapidly stirred mixture of 67 (1.32 g, 3.4 mmol), KOH (50% w/v aqueous, 10 mL), and tetrabutylammonium hydrogen sulfate (0.6 g, 1.7 mmol) in benzene (15 mL) was added neat tert-butyl bromoacetate (0.61 mL, 3.74 mmol) dropwise. The mixture was stirred at room temperature for 3 hours then diluted with EtOAc and washed with 1N HCl, H$_2$O, and brine, dried (MgSO$_4$), and concentrated in vacuo. The crude material was purified by chromatography (silica gel 230–400 mesh, toluene:EtOAc gradient) to afford 1.56 g (91%) of 68 as a pale yellow oil.

Part C:

A mixture of 68 (1.51 g, 3 mmol) and TFA (15 mL) was stirred at room temperature for 2 hours and then concentrated in vacuo. To the resulting oil was added Et$_2$O/hexane and upon sonnication a solid was obtained. The material was filtered, washed with Et$_2$O and dried to afford 1 g (77%) of 69 as a tan solid. MS (FD) m/e 348

Example 25

Preparation of the Compound Represented by the Formula 72

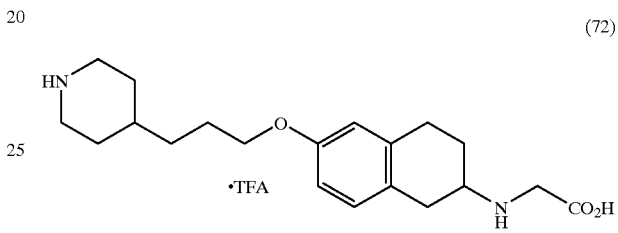

(72)

Part A:

To a solution of DMSO (0.26 mL, 3.6 mmol) in CH$_2$Cl$_2$ (13 mL) cooled to −70° C. was added neat trifluoroacetic anhydride (0.51 mL, 3.6 mmol) dropwise. The colorless solution was stirred for 0.25 hours at −78° C. then 67 (0.7 g, 1.8 mol) in CH$_2$Cl$_2$ (12 mL) was added dropwise over 5 min. The solution was stirred 1 hour at −78° C. then allowed to warm to room temperature and stirred another 1.5 hours. Diisopropylethylamine (0.72 mL, 4.14 mmol) was added neat and room temperature stirring continued for 1.5 hours. The solution was diluted with CH$_2$Cl$_2$ (50 mL) and washed with 1N HCl, saturated NaHCO$_3$, H$_2$O, and brine, dried (MgSO$_4$), and concentrated to afford ~0.7 g (>99%) of 70 as a colorless oil that was used immediately in the next step without further purification.

Part B:

A mixture of 70 (0.70 g, 1.8 mmol), NaBH$_3$CN (0.12 g, 1.8 mmol), glycine t-butyl ester (0.47 g, 3.6 mmol), glacial HOAc (0.1 mL, 1.8 mmol), and powdered 3 Å molecular sieves (0.4 g) in absolute EtOH (20 mL) was allowed to stir at room temperature for 17 hours. The mixture was filtered, the filtrate concentrated, and the resulting oil redissolved in EtOAc/H$_2$O and adjusted to pH 7.4 with 1N NaOH. The layers were separated, and the aqueous layer extracted with EtOAc. The EtOAc extracts were combined and washed with saturated NaHCO$_3$, H$_2$O, and brine, dried (Na$_2$SO$_4$), and concentrated. The crude isolate was purified by chromatography (silica gel 230–400 mesh, toluene:EtOAc gradient) to afford 0.17 g (19%) of 71 as a colorless gum.

Part C:

A mixture of 71 (0.2 g, 0.4 mmol) and TFA (10 mL) was stirred at room temperature for 3 hours and then concentrated in vacuo. To the resulting oil was added Et$_2$O slowly and upon sonication a solid was obtained. The material was filtered, washed with Et$_2$O and dried to afford 0.2 g (87%) of 72 as a tan solid. MS (FD) m/e 347.

Example 26

Preparation of the Compound Represented by the Formula 78

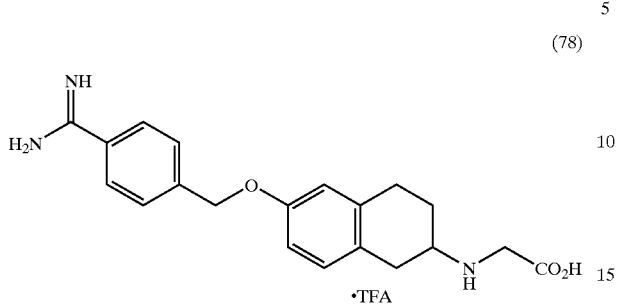

Part A:

To a solution of DMSO (0.28 mL, 4 mmol) in $CH_2Cl_2$ (13 mL) cooled to −78° C. was added neat trifluoroacetic anhydride (0.56 mL, 4 mmol) dropwise. The turbid white solution was stirred for 0.25 hours at −78° C. then 63 (0.558 g, 2 mmol) in $CH_2Cl_2$ (12 mL) was added dropwise over 5 min. The solution was stirred 1 hour at −78° C. then allowed to warm to room temperature and stirred another 1.5 hours. Diisopropylethylamine (0.8 mL, 4.6 mmol) was added neat and room temperature stirring continued for 1 hour. The solution was diluted with $CH_2Cl_2$ (50 mL) and washed with 1N HCl, saturated $NaHCO_3$, $H_2O$, and brine, dried ($MgSO_4$), and concentrated to afford 0.55 g (>99%) of 73 as a light yellow solid that was used immediately in the next step without further purification.

Part B:

A mixture of 73 (0.55 g, 2 mmol), $NaBH_3CN$ (0.13 g, 2 mmol), glycine t-butyl ester (0.52 g, 4 mmol), glacial HOAc (0.11 mL, 2 mmol), and powdered 3 Å molecular sieves (0.4 g) in absolute EtOH (25 mL) was allowed to stir at room temperature for 17 hours. The mixture was filtered, the filtrate concentrated, and the resulting gum redissolved in $EtOAc/H_2O$ and adjusted to pH 7.5 with 1N NaOH. The layers were separated, and the aqueous layer extracted with EtOAc. The combined EtOAc extracts were washed with saturated $NaHCO_3$, $H_2O$, and brine, dried ($Na_2SO_4$), and concentrated to afford ~0.8 g (99%) of 74 as a colorless gum without further purification.

Part C:

A mixture of 74 (0.784 g, 2 mmol), $K_2CO_3$ (0.829 g, 6 mmol), and $BOC_2O$ (0.873 g, 4 mmol) in $THF/H_2O$ (1:1, 20 mL) was stirred at room temperature for 5 hours. The THF was evaporated in vacuo and the aqueous residue diluted with brine (50 mL) and extracted with EtOAc. The combined extracts were washed with brine, dried ($MgSO_4$), and concentrated. The crude material was purified by chromatography (silica gel 230–400 mesh, toluene:EtOAc gradient) to afford 0.74 g (75%) of 76 as a pale yellow solid.

Part D:

Following the general procedure employed for the preparation of 6 (Example 1 part E), 77 was prepared in 31% yield starting from 0.66 g of 76.

Part E:

Following the general procedure employed for the preparation of 7 (Example 1 part F), 78 was prepared in 81% yield starting from 0.22 g of 77. MS (FD) m/e 354.

Example 27

Preparation of the Compound Represented by the Formula 80

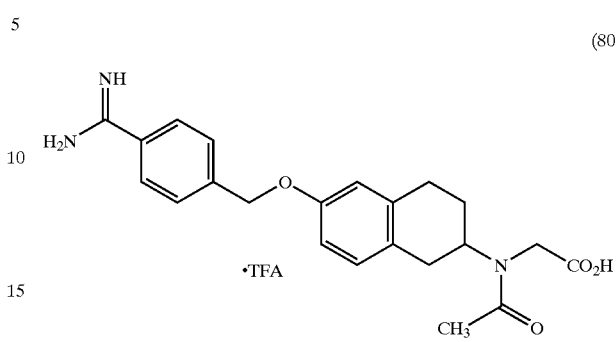

Part A:

Compound 74 was dissolved (1.96 g, 5 mmol) in $CH_2Cl_2$ (20 mL), pyridine was added (2 mL, 26 mmol), followed by dropwise addition of neat acetic anhydride (0.47 mL, 5 mmol). The gold solution was stirred at room temperature for 6 hours, then concentrated and the resulting oil redissolved in EtOAc, washed with 1N HCl, $H_2O$, and brine, dried ($MgSO_4$), and concentrated. The crude material was purified by chromatography (silica gel 230–400 mesh, toluene:EtOAc gradient) to afford 0.86 g (39%) of 75 as a white solid.

Part B:

Following the general procedure employed for the preparation of 6 (Example 1 part E), 79 was prepared in 81% yield starting from 1.19 g of 75.

Part C:

Following the general procedure employed for the preparation of 7 (Example 1 part F), 80 was prepared in 92% yield starting from 0.96 g of 79. MS (FD) m/e 396.

Example 28

Preparation of the Compound Represented by the Formula 88

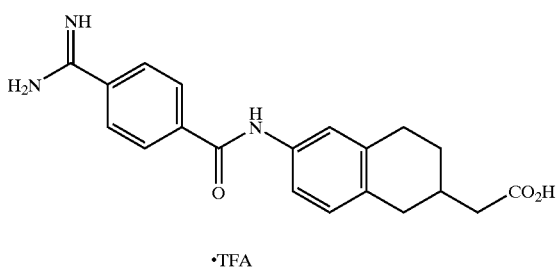

Part A:

A mixture of 81 (3.9 g, 13.3 mmol) and EtOH (20 mL) was treated with $NaBH_4$ (1.0 g, 26.6). The mixture was maintained at reflux for 1 hour and then allowed to cool. The reaction mixture was then diluted with EtOAc and washed with $H_2O$. The organic material was concentrated and the residue thus obtained was subjected to dehydration with TsOH (cat) in refluxing benzene. The crude dehydration mixture was diluted with EtOAc and washed with $H_2O$. The organic material was concentrated and the crude residue purified by chromatography (5:1 hexane/EtOAc) giving 2.6 g of 82.

Part B:

A mixture of 82 (2.6 g, 9.5 mmol), NMO (1.53 g, 11.3 mmol), tBuOH (8 mL), H$_2$O (8 mL), and acetone (8 mL) was treated with OsO$_4$ (0.1 mL of a 1 mg/mL solution in CCl$_4$) and the resulting mixture stirred at room temperature overnight. The mixture was then diluted with EtOAc and washed with H$_2$O and saturated aqueous NaHCO$_3$. The organic material was then concentrated. The crude residue was recrystallized from EtOAc/hexane giving 2.8 g of 83 as a white solid.

Part C:

Diol 83 (2.8 g) was suspended in benzene and TsOH (0.1 g) was added. This mixture was then maintained at reflux for 15 min. The solution was then diluted with EtOAc and washed 0.1N aqueous NaOH. The organic material was then concentrated. The crude residue was taken up in THF (25 mL) and the resulting solution was added to a mixture of NaH (0.5 g of a 60% dispersion in oil, 14.7 mmol), triethylphosphonoacetate (3.3 g, 14.7 mmol) and THF (25 mL) at 0° C. The resulting mixture was allowed to warm to room temperature and after three hours it was diluted with EtOAc and washed with H$_2$O. The organic material was concentrated and the crude isolate was purified on silica (3:1 hexane/EtOAc) giving 2.52 g of 84 as a clear oil.

Part D:

A mixture of 84 (2.51 g, 6.87 mmol), Pd/C (10% on carbon, 2.5 g) and EtOH (20 mL) was maintained under H$_2$ (balloon) for 2 hours and then filtered and concentrated. The residue was dissolved in CH$_2$Cl$_2$ (5 mL) and treated with p-cyanobenzoic acid (1.21 g, 8.3 mmol), EDCI (1.6 g, 8.3 mmol), and DMAP (cat). The resulting solution was allowed to stir for 4 hours and then it was diluted with EtOAc and washed with H$_2$O. The organic material was concentrated and the resulting solid material was crystallized from (EtOAc)/hexane) giving 1.35 g (54%) of 86 as a white solid.

Part E:

Following the general procedure outlined for the preparation of 6 (Example 1 part E), 87 was prepared in 80% yield starting from 1.35 g of 86.

Part F:

Following the general procedure outlined for the preparation of 7 (Example 1 part F), 88 was prepared in 70% yield starting from 0.2 g of 87. $^1$H NMR (300 MHz CD$_3$OD) 1.5 (m, 1H), 2.0 (m, 1H), 2.2 (m, 1H), 2.4 (m, 2H) 2.45 (dd, J=10.2, 16.2 Hz, 1H), 2.91 (m, 3H), 7.05 (d, J=8.2 Hz, 1H), 7.40 (m, 2H), 7.92 (d, J=8.4 Hz, 2H), 8.12 (d, J=8.4 Hz, 2H); IR (KBr) 3322, 3104, 1712, 1667, 1207 cm$^{-1}$; MS (FAB) m/e 352.1661 (352.1654 calcd for C$_{20}$H$_{22}$N$_3$O$_3$)

Example 29

Preparation of the Compound Represented by the Formula 95

(95)

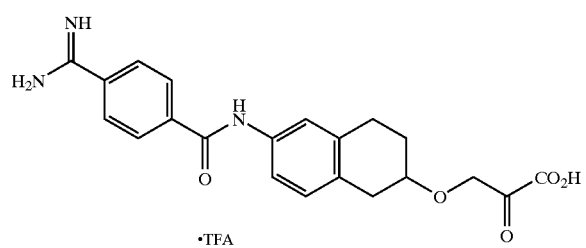

·TFA

Part A:

A mixture of 82 and NaH in THF was treated with benzylbromide and Bu$_4$NI (cat.) and the resulting solution was allowed to stand at room temperature for 2 hours. The solution was then diluted with EtOAc and washed with H$_2$O. The organic material was concentrated giving essentially pure 88 as a yellow oil.

Part B:

A mixture of 88 (1.0 g, 2.71 mmol), NMO (0.40 g, 3.0 mmol), t-BuOH (2.0 mL) acetone (2.0 mL), and H$_2$O (2 mL) were treated with OsO$_4$ (0.1 mL of a 1 mg/mL solution in CCl$_4$) and the resulting solution allowed to stand overnight. The mixture was then diluted with EtOAc and washed with saturated aquous NaHCO$_3$ and H$_2$O. The organic material was concentrated and the crude residue taken up in benzene (25 mL) and treated with TsOH (cat.). The resulting mixture was maintained at reflux for 15 minutes and then concentrated. The crude isolate was taken up in EtOH and treated with NaBH$_4$ (0.25 g) and allowed to stand for 1 hour. This mixture was diluted with EtOAc and washed with H$_2$O. The organic material was concentrated and the crude isolate was purified by chromatography (1:1 hexanes/EtOAc) giving 0.19 g of 90 as a clear oil.

Part C:

A mixture of 90 (0.18 g, 0.64 mmol), and t-butyl bromoacetate (0.18, 0.95 mmol) benzene (5 mL), 50% of NaOH (5 mL), and Bu$_4$NHSO$_4$ (cat.) was vigorously stirred at room temperature for 12 hours. This mixture was then diluted with EtOAc and washed with H$_2$O. The organic material was concentrated and the crude isolate purified by chromatography (5:1 hexanes/EtOAc) yielding 0.09 g (35%) of 91 as a clear oil.

Part D:

A mixture of 91 (0.31 g) and 10% Pd/C (0.3 g) in EtoAc was maintained in an atmosphere of H$_2$ (balloon) for 4 hours and then filtered and the filtrate concentrated. The crude residue was taken up in CH$_2$Cl$_2$ (5 mL) and was treated with p-cyanobenzoic acid (0.12 g, 0.70 mmol), EDCI (0.23 g, 0.79 mmol), and DMAP (cat). The resulting solution was maintained at room temperature for 2 hours and then diluted with EtOAc and washed with H$_2$O. The organic material was concentrated and the crude residue purified on silica (3:1 hexanes/EtOAc) giving 0.24 g of 93 as a clear oil.

Part E:

Following the general procedure employed for the preparation of 6 (Example 1 part E), 94 was prepared in 56t yield starting from 0.23 g of 93.

Part F:

Following the general procedure employed for the preparation of 7 (Example 1 part F), 95 was prepared in 63% yield starting from 0.16 g of 94.

$^1$H NMR (300 MHz CD$_3$OD) 1.90 (m, 1H), 2.05 (m, 1H), 2.7–3.3 (m, 4H) 3.90 (m 1H), 4.20 (s, 2H), 7.10 (d, J=8.0 Hz, 1H), 7.40 (m, 2H), 7.90 (d, J=8.3 Hz, 2H), 8.15 (d, J=8.3 Hz, 2H); IR (KBr) 3326, 2936, 1664, 1598 cm$^{-1}$; MS (FAB) m/e 368 Anal. Calcd. for C$_{22}$H$_{22}$N$_3$O$_6$F$_3$: C, 54.89; H, 4.61; N, 8.73. Found: C, 54.90; H, 4.67; N, 8.50.

Example 30

Preparation of the Compound Represented by the Formula 102

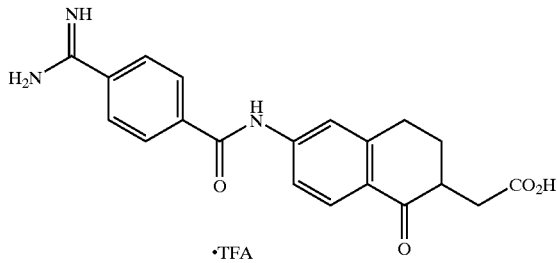
(102)

Part A:

A mixture of tetralone 96 (5.0 grams, 24.6 mmol), glyoxylic acid monohydrate (8.4 g, 93.6 mmol), NaOH (4.35 g. 108.9 mmol), methanol (50 mL) and H$_2$O (50 mL) was maintained at reflux for 1.25 hours and then chilled to 0° C. The reaction was then acidified (with stirring) with concentrated HCl. The formed ppt (97) (5.8 g) was collected by filtration.

Part B:

A mixture of 97 (20.0 g, 77.2 mmol) and Zn (14.1 g, 216 mmol) in HOAc (160 mL) and H$_2$O (60 mL) was maintained at reflux for 1.25 hours and then filtered. The filtrate was diluted when H$_2$O and the resulting mixture extracted with EtOAc. The combined extracts were concentrated. The crude isolate was taken up in concentrated HCl (100 mL) and maintained at reflux for 0.5 hours. The mixture was then diluted with H$_2$O (300 mL) and cooled to 5° C. The mixture was carefully neutralized to a pH 4 by the addition of solid Na$_2$CO$_3$. The formed ppt was collected by filtration and dried in vac. This material was then suspended in EtOH and the resulting solution was saturated with HCl(g). The mixture was then concentrated. The material thus formed was suspended in H$_2$O and the pH of the resulting solution was adjusted to pH 10 with solid NaOH. This material was extracted with EtOAc and the extracts concentrated. The crude product was recrystallized from EtOAc/Hexanes giving 12.1 grams of pure 98 as a tan solid.

Part C:

A mixture of 98 (6.8 g, 27.5 mmol), p-cyanobenzoic acid (4.4 g, 30.2 mmol), EDCI (7.86 g, 41.2 mmol), DMAP (0.1 g), and CH$_2$Cl$_2$ (10 mL) was stirred at room temperature for 4 hours. This mixture was then diluted with EtOAc and washed with H$_2$O. The organic material was then concentrated affording crude 99 as a tan solid. Recrystallization from EtOAc/hexanes gave 7.86 g of pure 99.

Part D:

Following the general procedure outlined for the preparation of 6 (Example 1 part E), 100 was obtained in 74% yield starting from 7.85 g of 99.

Part E:

Following the general procedure outlined for the preparation of 7 (Example 1 part F), 101 was obtained in 90% yield starting from 5.0 g of 100.

Part F:

A mixture of 100 (2.0 g, 4.1 mmol) and EtOH (5 mL) was treated with NaOH (0.49 g, 12.1 mmol) and the resulting solution was maintained at room temperature for 2 hours. The solution was then concentrated and the resulting residue taken up in H$_2$O. The aqueous material was washed once with EtOAc and then carefully acidified (pH 4) with KHSO$_4$. The formed precipitate was collected by filtration and dried in-vacuo. This material was then treated with TFA (10 mL) for one hour and then concentrated. The crude material was taken up in hot H$_2$O, filtered, and then lyophilized giving pure 102 as a white powder.

$^1$H NMR (300 MHz CD$_3$OD) 2.0 (m, 1H), 2.25 (m, 1H), 2.50 (dd, J=6.4, 16.4 Hz, 1H), 2.90 (dd, J=4.2, 16.5 Hz, 1H) 2.90–3.2 (m, 3H) 7.6 (dd J=1.9, 8.6 Hz, 1H), 7.80 (s, 1H), 7.95 (m, 3H), 8.14 (d, J=8.3 Hz, 2H); IR (KBr) 3330, 3108, 1712, 1669, 1538 cm$^{-1}$; MS (FAB) 366. Anal. Calcd. for C$_{22}$H$_{20}$N$_3$O$_6$F$_3$: C, 55.12; H, 4.20; N, 8.76. Found: C, 54.88; H, 4.31; N, 8.46.

Example 31

Preparation of the Compound Represented by the Formula 118

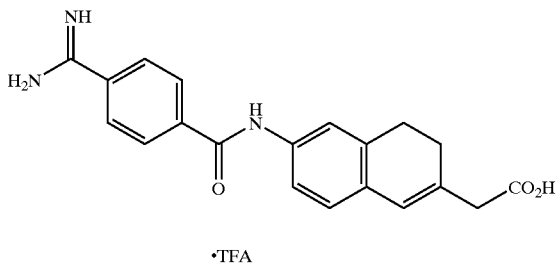
(118)

Part A:

A mixture of 100 (0.2 g, 0.4 mmol) and EtOH (10 mL) was treated with NaBH$_4$ (0.025 g, 0.4 mmol) and allowed to stand at room temperature for 1 hour. This mixture was then concentrated and the residue dissolved in EtOAc. This mixture was washed with H$_2$O and concentrated. The crude residue was taken up in THF (15 mL) and treated with TsOH (cat.). The resulting solution was maintained at reflux for 1.5 hours. This mixture was concentrated and the residue taken up in EtOAc and the resulting solution was washed with 0.1N NaOH and then concentrated. Chromatography (1:1 hexanes/EtOAc) gave 0.08 g of pure 116 as a white solid.

Part B:

Following the general procedure outlined for the preparation of 102 (Example 30 part F), 118 was obtained in 80% yield starting from 0.08 g of 116.

$^1$H NMR (300 MHz CD$_3$OD) 2.34 (br t, J=8.0 Hz, 2 H), 2.83 (br t, J=8.0 Hz, 2H), 3.28 (s, 2H), 6.40 (s, 1H), 7.0 (d, J=8.7 Hz, 1H), 7.5 (m, 2H), 7.92 (d, J=8.3 Hz, 2H), 8.10 (d, J=2H); IR (KBr) 3385, 3089, 1716, 1672, 1194 cm$^{-1}$; MS (FAB) m/e 350.1505 (350.1505 calcd. for C$_{20}$H$_{20}$N$_3$O$_3$)

Example 32

Preparation of the Compound Represented by the Formula 123

(123)

·TFA

Part A:

A mixture of 98 (0.14 g, 0.58 mmol) acid 119 (0.095 g, 0.58 mmol), EDCI (0.16 g, 0.86 mmol), DMAP (cat), and CH$_2$Cl$_2$ (3 mL) was maintained at room temperature overnight. The mixture was then diluted with EtOAc and washed with H$_2$O. The organic material was concentrated and the crude residue purified on silica (hexanes/EtOAc 2:1) giving 0.095 g (40%) of 120.

Part B:

Following the general procedure described for the preparation of 6 (Example 1 part E), 121 was prepared in 37% yield starting from 0.95 g of 120.

Part C:

A mixture of 121 (0.04 g, 0.08 mmol), NaOH (0.003 g, 0.08 mmol) and EtOH (5 mL) was maintained at room temperature for 6 hours and then concentrated. The residue was dissolved in H$_2$O and acidified to pH 4 with KHSO$_4$. The resulting mixture was extracted with EtOAc and the extracts were concentrated. Chromatography (EtOAc) gave 0.014 g of 122. Treatment of this material with TFA (5 mL) for 1 hour followed by concentration gave 0.014 g of 123.

$^1$H NMR (300 MHz CD$_3$OD) 2.0 (ddd, J=4.5, 13.0, 25.8 Hz, 1H), 2.30 (m, 1H), 2.45 (dd, J=6.4, 16.5 Hz, 1H), 2.90 (dd, J=5.7, 16.5 Hz, 1H), 2.9–3.2 (m, 3H), 7.6 (m, 1H), 7.75 (m, 3H), 7.95 (m, 2H); IR (KBr) 3341, 3118, 1664, 1205 cm$^{-1}$; MS (FAB) m/e 384.

Example 33

Preparation of the Compound Represented by the Formula 130

(130)

·TFA

Part A:

A mixture of 2-bromo,6-benzyloxynapthylene (124) (1.0 g, 3.2 S mmol) and THF (25 mL) was treated with t-BuLi (4.2 mL of a 1.7 M solution in pentane, 7.0 mmol) at –78° C. After 1 hour, diethyl oxalate (0.5 mL, 3.5 mmol) was added and the resulting mixture was allowed to warm to room temperature. The reaction mixture was then diluted with EtOAc and washed with H$_2$O. The organic layer was concentrated. The crude material was purified by chromatography (3:1 hexane/EtOAc) giving 0.52 g of pure 125.

Part B:

A mixture of 125 (7.0 g, 6.0 mmol) and EtOH (50 mL) was treated with NaBH$_4$ (0.12 g, 6.0 mmol) and allowed to stir for 1 hour. The mixture was then diluted with EtOAc and washed with 1N HCl. The organic material was then concentrated. The crude material was taken up in pyridine (10 mL) and treated with Ac$_2$O (10 mL). After 1 hour, the solution was concentrated to dryness and the residue was passed through a plug of silica (4:1 hexane/EtOAc). The material thus obtained was subjected to catalytic hydrogenation employing 10% Pd/C (balloon). After removal of the catalyst by filtration and concentration one obtains 0.48 g (35%) of the desired compound 126.

Part C:

A mixture of 126 (0.48 g, 2.1 mmol), α-bromo-p-tolunitrile (0.45 g, 2.3 mmol), K$_2$CO$_3$ (0.32 g, 2.3 mmol), Bu$_4$NI (cat), and DMF (5 mL) was maintained at 80° for 4 hours and then allowed to cool to room temperature. This solution was diluted with EtOAc and the resulting solution was washed with H$_2$O. The organic material was then concentrated. The crude residue was recrystallized from EtoAc/Hexanes giving 0.33 g (45%) of 127 as a tan solid.

Part D:

Following the general procedure outlined for the preparation of 6 (Example 1 part E), 128 was obtained in 50% yield starting from 0.33 g of 127.

Part E:

A mixture of 128 (0.10 g, 0.22 mmol), EtOH (5 mL), and aqueous NaOH (0.22 mL of a 2 N solution, 0.44 mmol) was stirred at room temperature for 5 hours and then concentrated. The residue was taken up in H$_2$O and the resulting solution was extracted with EtOAc. The pH of the aqueous material was then adjusted to pH 4 with HCl (1N) and the resulting mixture extracted with EtOAc. The extracts were concentrated and the crude material was treated with TFA (10 mL) for 1 hour at room temperature. The reaction mixture was then concentrated to dryness affording 0.07 g of 130 as a white solid.

$^1$H NMR (300 MHz CD$_3$OD) 3.85 (s, 2 H), 5.2 (s, 2H), 7.2–7.4 (m, 3H), 7.6–7.9 (m, 7H); IR (KBr) 3334, 3106, 1695, 1669, 1130 cm$^{-1}$; MS (FAB) m/e 335. Anal. Calcd. for C$_{22}$H$_{19}$N$_2$O$_5$F$_3$: C, 58.93; H, 4.27; N, 6.25. Found: C, 58.70, H, 4.46; N, 5.97.

Example 34

Preparation of the Compound Represented by the Formula (135)

·TFA

Part A:

A mixture of 2 (0.5 g, 2.0 mmol) and THF (10 mL) was treated with LiAlH$_4$ (0.15 g, 4.0 mmol) and then maintained at reflux for 2 hours. The mixture was allowed to cool to room temperature and then quenched with H₂O and 15% NaOH. The resulting mixture was filtered and concentrated. This procedure allowed the isolation of 0.45 g of material whose purity was sufficient for the next transformation. A portion of this material (0.25, g, 1.1 mmol), K₂ CO₃ (0.16 g, 1.17 mmol) tert-butyl bromoacetate (0.25 g, 1.17 mmol), and CH₃CN (5 mL) was stirred at room temperature for 15 hours. The mixture was then diluted with EtOAc and washed with H₂O. The organic material was concentrated and the crude residue purified on silica (2.5:1 hexanes/EtOAc) giving 0.34 g (90%) of 132.

Part C:
A mixture of 132 (0.1 g, 0.28 mmol), (Pd/C (10% on carbon 0.1 g), and EtOAc was maintained under an atmosphere of H₂ for 12 hours and then filtered and concentrated. Chromatography (1.5:1 hexanes/EtOAc) gave 0.039 g (521) of 133.

Part D:
A mixture of 133 (0.073 g, 0.28 mmol), NaH (0.012 g of a 60% dispersion in oil, 0.31 mmol) in THF (10 mL) was stirred at room temperature for 1/2 hour and then treated with a solution of 1-tBOC-4-(3-bromopropyl)piperidine (0.093, 0.31 mmol) in THF (1 mL). The resulting solution was maintained at reflux for 2 hours and then allowed to cool to room temperature. The reaction mixture was diluted with EtOAc and washed with H₂O. The organic material was concentrated and the resulting material was chromatographed on silica (3:1 hex/EtOAc) giving 0.086 g of alkylated product. This material (0.076 g) was dissolved in TFA (5 mL) and maintained at room temperature for 1 hour. This material was then concentrated. The crude residue was taken up in 10% HCl (5 mL) and lyophilized giving 0.51 g of 135 as a white powder.

¹H NMR (300 MHz CD₃OD) 1.30–1.58 (m, 4H), 1.60–1.75 (m, 1H), 1.85 (m, 2H), 1.95 (m, 2H), 3.0 (m, 2H), 3.2 (m, 2H), 3.4 (m, 2H), 3.65 (brs, 2H), 4.0 (t, J=6.2 Hz, 2H), 4.18 (s, 2H), 4/45 (s, 2H), 6.82 (m, 2H), 7.15 (d, J=8.4 Hz, 1H); IR (KBr) 3406, 2946, 1741, 1614 cm⁻¹; MS (FAB) m/e 333.2182 (333.2178 calcd. for C₁₉H₂₉N₂O₃)

Example 35

Preparation of the Compound Represented by the Formula 140

(140)

·TFA

Part A:
A mixture of 2 (0.5 g, 2.0 mmol) and THF (10 mL) was treated with LiAlH₄ (0.15 g, 4.0 mmol) and the resulting mixture was maintained at reflux for 16 hours. The mixture was allowed to cool to room temperature and then quenched with H₂O and 15% NaOH. The resulting mixture was filtered and concentrated. The crude product of reduction was taken up in THF/H₂O (1:1, 10 mL) and treated with Boc₂O (0.64 g, 2.9 mmol) and K₂CO₃ (0.41 g, 2.9 mmol). The resulting mixture was stirred at room temperature for 2 hours and then diluted with EtOAc. The organic material was washed with H₂O and concentrated. The crude isolate was chromatographed on silica (1:1 hexanes/EtOAc) giving 0.58 g of pure 131.

Part B:
A mixture of 131 (0.58 g), Pd/C (10% on carbon, 0.58 g), and ETOAC (30 mL) was maintained under an atmosphere at H₂ (balloon) for 1 hour and then filtered and concentrated. Recovered 0.46 g of essentially pure 136.

Part C:
A mixture of 136 (0.46 g, 1.95 mmol), K₂CO₃ (0.3 g, 2.1 mmol), a-bromo-p-tolunitrile (0.42 g, 2.1 mmol), Bu₄NI (cat), and acetone was maintained at reflux for 6 hours. The reaction mixture was then diluted with EtOAc and washed with H₂O. The organic material was concentrated and the crude residue was purified by chromatography (1:1 hex/EtOAc) giving 0.34 g of 137.

Part D:
A mixture of 137 (0.34 g, 0.94 mmol) and TFA (10 mL) was maintained at room temperature for 1 hour and then concentrated. The residue was taken up in saturated aqueous NaHCO₃ and the resulting mixture was extracted with EtOAc. The extracts were combined and concentrated. The crude residue taken up in CH₃CN (10 mL) and the resulting solution was treated with K₂CO₃ (0.14 g, 1.0 mmol) and tert-butyl bromoacetate (0.20 g, 1.0 mmol). The resulting mixture was stirred at 60° C. for 2.5 hours and then diluted with EtOAc. The organic material was washed with H₂O and concentrated. The crude residue was purified on silca (2.5:1 hexanes/EtOAc) giving 0.18 g of 138.

Part E:
Following the procedure outlined for the preparation of 6 (Example 1 part E), 139 was prepared in 33% yield starting from 0.18 g of 138.

Part F:
Following the procedure outlined for the preparation of 7 (Example 1 part F), 140 was prepared in 66% yield starting from 0.075 g of 139.

¹H NMR (300 MHz CD₃OD) 3.19 (m, 2H), 3.62 (m, 2H), 4.05 (s, 2H), 4.21 (s, 2H), 6.92 (m, 2H), 7.11 (d, J=8.3 Hz, 1H), 7.65 (d, J=8.4 Hz, 2H), 7.82 (d, J=8.4 Hz, 2H); IR (KBr) 3333, 3104, 1668, 1617, 1191 cm⁻¹; MS (FAB) m/e 340.1

Example 36

Preparation of the Compound Represented by the Formula 146

(146)

·TFA

Part A:
A mixture of 141 (12.3 g, 60.2 mmol) and 5N HCl (75 mL) was maintained at reflux for 12 hours and then concentrated to dryness. The residue was taken up in saturated aqueous NaHCO₃ and this mixture was extracted with EtOAc. The extracts were then dried over NaSO₄ and concentrated. The crude product was purified on silica (15:85 MeOH/CH₂Cl₂) giving 5.0 g of 142 as a tan solid.

Part B:

A mixture of 142 (2.6 g, 16.0 mmol), benzyl bromide (5.5 g, 32.0 mmol), K₂CO₃ (4.43 g, 32.0 mmol), CH₃CN (30 mL), and Bu₄NI (cat) was maintained at reflux for 3.5 hours and then diluted with EtOAc and washed with H₂O. The organic material was dried and concentrated. Chromatography (15:85 MeOH/CH₂Cl₂) allowed the isolation of a fraction containing both mono and dibenzylated material. This mixture was dissolved in THF and the resulting solution was treated with LiAlH₄ (1.52 g, 40 mmol). The mixture was refluxed for 4 hours and then quenched with water and 15% NaOH. The resulting mixture was filtered and concentrated. The crude product thus isolated was immediately taken up in THF/H₂O and treated with BOC₂O(3.84 g, 17.6 mmol) and K₂CO₃ (6.6 g, 48.0 mmol). After 1 hour, the mixture was diluted with EtOAc and washed with H₂O and brine. The organic material was concentrated and the crude isolate was purified on silica giving 6.25 g of a mixture of mono-benzyl and di-benzylated tetrahydroisoquinolines. This mixture was subjected to catalytic hydrogenation (Pd/C) in EtOH giving 1.92 g of pure 143 after chromatography (1:3 MeOH/CH₂Cl₂) on silica.

Part C:

A mixture of 143 (1.92 g, 8.2 mmol), p-cyanobenzoic acid (1.2 g, 8.2 mmol), EDCI (1.7 g, 9.0 mmol), and DMAP (cat) in CH₂Cl₂ (20 mL) was maintained at room temperature for 2 hours. The mixture was then diluted with EtOAc and washed with H₂O. The organic material was then concentrated giving crude 144 whose purity was sufficient for the next reaction. Crude 144 was dissolved in TFA and allowed to stand at room temperature for 1 hour and was then concentrated. The residue was taken up in saturated aqueous NaHCO₃ and the resulting mixture was extracted with EtOAc. The organic extracts were concentrated giving the desired amine. Chromatography (silica, 10% TEA in MeOH) gave 1.23 g of material whose purity was sufficient for the next step. A mixture of this material (1.2 g, 4.7 mmol), t-butyl bromoacetate (0.99 g, 5.1 mmol) K₂CO₃ (0.70 g, 5.1 mmol), Bu₄NI (cat) and CH₃CN was stirred at room temperature for 3 hours. The mixture was then diluted with EtOAc and washed with H₂O. The organic material was dried NaSO₄ and concentrated. Chromatography (1:9 MeOH/CHC13) gave 0.62 g of 145 as a yellow oil.

Part E:

Following the general procedure employed for the preparation of 6 (Example 1 part E), 146 was obtained in 26% yield starting from 0.1 g of 145.

Part F:

Following the general procedure employed for the preparation of 7 (Example 1 part F), 147 was obtained in 80% yield from 0.034 g of 146.

¹H NMR (300 MHz CD₃OD) 3.23 (m, 2H), 3.62 (m, 2H), 4.10 (s, 2H), 4.51 (m, 2H), 7.2 (d, J=8.2 Hz, 1H), 7.6 (m, 1H), 7.75 (s, 1H), 7.92 (d, J=8.4 Hz, 2H), 8.16 (d, J=8.4 Hz, 2H).

Example 37

Preparation of the Compound Represented by the Formula 155

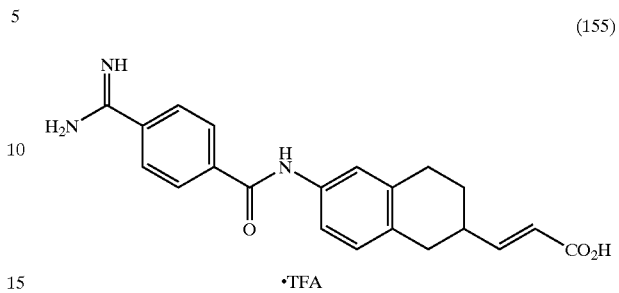

(155)

·TFA

Part A:

A solution of ester 148 (0.81 g, 3.23 mmol), and THF (7 mL) was treated with LiBH₄ (0.14 g, 6.5 mmol) and allowed to stand at room temperature for 6 hours. The mixture was then diluted with EtOAc and washed with H₂O. The organic material was concentrated giving 0.65 g of material whose purity was sufficient for the next step. A mixture of this material(0.65 g, 3.1 mmol), TBSCl (0.51 g, 3.5 mmol) imidazole (0.24 g, 3.47 mmol), and DMF (5 mL) was maintained at room temperature for 1 hour. The mixture was then diluted with EtOAc and washed with H₂O. The organic material was concentrated and the crude residue was purified on silica (5:1 hexanes/EtOAc) giving 0.96 g of pure 149.

Part B:

A mixture of 149 (0.96 g) and Pd/C (lot on carbon, 0.96 g) in EtOAc was maintained under an atmosphere of H₂ (balloon) for 1 hour and then filtered and concentrated. The crude isolate was taken up in CH₂Cl₂ (5 mL) and treated with p-cyanobenzoic acid (0.45 g, 3.1 mmol), EDCI (0.64 g, 3.34 mmol), and DMAP (cat). The resulting solution was maintained at room temperature for 2 hours and then diluted with EtOAc. The organic material was washed with H₂O and then concentrated. Chromatography (1:1 hexanes/EtOAc) gave 1.09 g of pure 150.

Part C:

A mixture of 150 (1.09 g, 2.59 mmol) and TBAF (5.2 mL at a 1M solution in THF, 5.2 mmol) was maintained at room temperature for 1 hour. This mixture was diluted with EtOAc, washed with H₂O, and then concentrated giving 0.71 g of essentially pure primary alcohol. This material (0.65 g, 2.11 mmol) was oxidized with DMSO, oxalyl chloride, and TEA (method of Swern). The crude isolate thus obtained was taken up in THF (5 mL) and added to a mixture of t-butyl diethylphosphonoacetate (0.71 g, 3.2 mmol), NaH (0.13 g at a 60% dispersion in oil, 3.2 mmol) and THF (10 mL). After 1 hour, the mixture was diluted with EtOAc and washed with H₂O. The organic material was then concentrated and the crude residue was fractionated on silica (5:1 hexanes/EtOAc) giving 0.27 g of 151, 0.197 g of 152, and 0.47 g of recovered starting alcohol.

Part D:

Following the procedure described for the preparation of 7, (Example 1 part E and F) 155 was prepared in 54% yield starting from 0.27 g of 152.

¹H NMR (300 MHz CD₃OD) 1.65 (m, 1H), 2.05 (m, 1H), 2.60–2.95 (m, 5H), 5.85 (d, J=15.5 Hz, 1H), 7.05 (dd, J=9.6, 15.8 Hz, 1H), 7.10 (d, J=8.3 Hz, 1H), 7.4 (m, 2H), 7.91 (d, J=8.4 Hz, 2H), 8.17 (d, J=8.4 Hz, 2H); IR (KBr) 3313, 3102, 1670, 1203 cm⁻¹; MS (FAB) m/e 364. Anal. Calcd. for C₂₃H₂₂N₃O₅F₃: C, 57.86; H, 4.65,; N, 8.80. Found: C, 57.59; H, 4.84; N, 8.78.

Example 38

Preparation of the Compound Represented by the Formula 154:

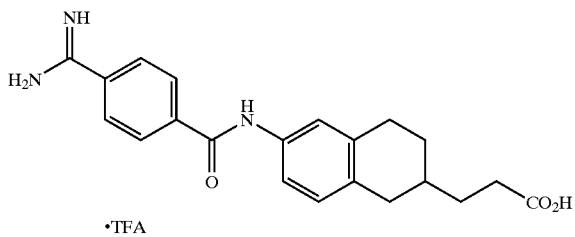

(154)

Part A:

A mixture of 151 (0.18 g, 0.43 mmol) and Pd/C (10% on carbon, 0.18 g) in EtOH was maintained under an atmosphere of $H_2$ (balloon) for 30 minutes and then was filtered and concentrated. Chromatography (3:1 hexanes/EtOAc) gave 0.09 g of 153 as a clear oil.

Part B:

Following the general procedure employed for the preparation of 7 (Example 1 part E and F), 154 was prepared in 51% yield starting from 0.09 g of 153.

$^1$H NMR (300 MHz $CD_3OD$) 1.4 (m, 1H), 1.7 (m, 3H), 1.97 (m, 1H), 2.4 (m, 3H), 2.85 (m, 3H), 7.08 (d, J=8.3 Hz, 1H), 7.40 (m, 2H), 7.90 (d, J=8.4 Hz, 2H), 8.17 (d, J=8.4 Hz, 2H); IR (KBr) 3317, 3102, 2926, 1708, 1666, 1142 cm$^{-1}$; MS (FAB) m/e 366.1815 (366.1818 calcd. for $C_{21}H_{24}N_3O_3$)

Example 39

Preparation of the Compound Represented by the Formula 161

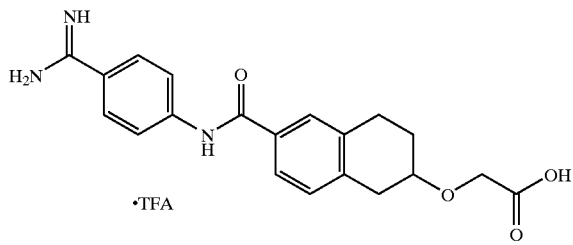

Part A:

A mixture of 6-bromotetralone 156 (1.0 g, 4.4 mmol) and EtOH (10 mL) was treated with $NaBH_4$ (1 g) at room temperature. After 1 hour, the mixture was diluted with EtOAc and washed with $H_2O$. The organic material was concentrated to dryness and the crude isolate was dissolved in dry DMF (10 mL) and treated with TBSCl (1.0 g, 6.6 mmol) and imidazole (0.45 g, 6.6 mmol). The resulting solution was allowed to stand at room temperature overnight. This mixture was then diluted with EtOAc and washed with $H_2O$ and concentrated. The crude isolate was purified on silica (hexanes) giving 0.8 g of 157 (52%) as a clear oil.

Part B:

A mixture of 157 (1.93 g, 5.7 mmol) and THF (25 mL) was treated with t-BuLi (8.4 mL of 1.7M solution in pentane) at −78° C. After 30 minutes, a stream of dry $CO_2$ was bubbled through the solution and the reaction was allowed to warm to room temperature. The resulting THF mixture was diluted with $H_2O$, acidified with 1N HCl, and extracted with EtOAc. The extracts were concentrated affording 1.50 grams of crude acid. A 0.5 g (1.63 mmol) portion of this material was dissolved in $CH_2Cl_2$ (2.0 mL) and the resulting solution was treated with benzyl alcohol (0.19 g, 1.8 mmol), EDCI (0.34 g, 1.8 mmol) and DMAP (cat). This mixture was allowed to stand for two hours and then was diluted with EtOAc and washed with $H_2O$. The organic material was concentrated and the crude residue treated with TBAF (1.8 mL of a 1M solution in THF, 1.8 mmol). After 25 minutes, the mixture was diluted with EtOAc and washed with $H_2O$. The organic material was concentrated affording 0.45 g of 158 as an essentially pure oil.

Part C:

A mixture of 158 (0.45 g, 1.59 mmol), t-butyl bromoacetate (0.96 g, 4.9 mmol) benzene (5 mL), 50% aqueous NaOH (5 mL), and $Bu_4NHSO_4$ (cat) was stirred rapidly at room temperature for 5 hours. The mixture was then diluted with EtOAc and washed with $H_2O$. The organic material was concentrated and the crude residue purified on silica (5:1 hexanes/EtoAc) giving 0.44 g (69%) of the desired alkylated product as a clear oil. A mixture of this material (0.44 g, 1.1 mmol), Pd/C (10% on carbon, 0.44 g) and EtOAc (10 mL) was stirred under an atmosphere of H2 (balloon) for 2 hours. The material was then filtered and concentrated giving a 0.29 g of essentially pure 159.

Part D:

A mixture of 159 (0.29 g, 0.94 mmol), EDCI (0.2 g, 1.0 mmol) 4-aminobenzonitrile (0.12 g, 1.0 mmol), DMAP (cat) and $CH_2Cl_2$ (5 mL) was maintained at room temperature for 4 hours. This mixture was then diluted with EtOAc and washed with $H_2O$. The organic material was then concentrated. Chromatography (2.5:1 hexanes/EtOAc) gave a fraction (0.28 g) containing the desired amide 160 and what is presumed to be the symmetrical anhydride of 159. This material was taken on to the next step.

Part E:

The material obtained in the previous step (0.28 g) was taken up in pyridine (20 mL) and TEA (2 mL) and the resulting solution was saturated with $H_2S$. This mixture was allowed to stand at room temperature for 12 hours and then diluted with EtOAc and washed with $H_2O$. The organic material was concentrated and the crude mixture was chromatographed on silica (EtOAc) giving 0.13 g of pure intermediate thioamide. This material was then processed in the same fashion as described in example 1 part E, ultimately giving 0.07 g of pure Boc protected material. This material was taken up in TFA and stirred at room temperature for 1 hour and then concentrated giving 0.056 g of 161.

$^1$H NMR (300 MHz $CD_3OD$) 1.92–2.17 (m, 2H), 2.80–3.22 (m, 4H), 4.05 (m, 1H), 4.22 (s, 2H), 7.27 (d, J=S. 3 Hz, 1H), 7.72 (m, 2H), 7.682 (d, J=8.4 Hz, 2H), 8.02 (d, J=8.4 Hz, 2H); IR (KBr) 3318, 3147, 1739, 1656, 1137 cm$^{-1}$; MS (FAB) m/e 368.

Example 40

Preparation of the Compound Represented by the Formula 168

(168)

*TFA

Part A:

A mixture of 156 (1.25 g, 5.5 mmol), ethylene glycol (3.4 g, 55 mmol), TsOH (cat), and benzene (25 mL) was maintained at reflux with $H_2O$ removal for 3 hours. The mixture was then diluted with EtOAc and the resulting solution was washed with 1N NaOH. The organic material was then concentrated and the crude residue purified by chromatography (5:1 hexanes/EtOAc) giving 1.15 g (77%) of 162 as a clear oil.

Part B:

A solution of 162 (1.15 g 4.3 mmol) and THF (15 mL) was treated with t-BuLi (6.3 mL of a 1.7M solution in pentane, 10.7 mmol) at −78° C. for 30 minutes and then quenched by the addition of $CO_2(g)$. The reaction mixture was allowed to warm to room temperature and then was diluted with $H_2O$. The resulting mixture was acidified with concentrated HCl and extracted with EtOAc. The organic extracts were concentrated and the crude isolate was taken up in $CH_2Cl_2$ (10 mL) and treated with benzyl alcohol (0.58 g, 5.4 mmol), EDCI (1.02 g, 5.4 mmol), and DMAP (cat). The resulting solution was maintained at room temperature overnight and then diluted with EtOAc and washed with $H_2O$. The organic material was concentrated and the crude residue chromatographed on silica giving one fraction (1.06 g) which contained the desired product 163 and benzyl alcohol in a 1:1 ratio. This material was suitable for use in the next reaction.

Part C:

The above mixture was dissolved in acetone (20 mL) and treated with 1N HCl (2 mL) and maintained at reflux for one hour. The mixture was then diluted with EtOAc and washed with saturated aqueous $NaHCO_3$. The organic material was then concentrated. The crude isolate was taken up in THF and added to a mixture of t-butyl diethylphosphonoacetate (1.1 g, 4.93 mmol), NaH (0.1 g of a 60% dispersion in oil, 4.93 mmol), and THF (25 mL) at −78° C. The resulting solution was allowed to warm to room temperature and then maintained at reflux for one hour. The mixture was then diluted with EtOAc and washed with $H_2O$. The organic material was concentrated and the crude isolate was purified on silica (2.5:1 hexanes/EtOAc) giving 0.47 g of 164 as a mixture of olefin isomers.

Part D:

A mixture of 164 (0.47 g) and Pd/C (10% on carbon, 0.47g) in EtOH was maintained under an atmosphere of $H_2$ (balloon) for 2 hours and then filtered and concentrated giving 0.29 g of essentially pure 165.

Part E:

A mixture of 165 (0.29 g, 1.0 mmol), EDCI (0.28 g, 1.5 mmol), p-cyanobenzoic acid (0.12 g, 1.0 mmol), DMAP (cat), and $CH_2Cl_2$ (5 mL) was maintained at 100° C. in a sealed tube for 2 h and then diluted with EtOAc and washed with $H_2O$. The organic material was concentrated and the residue chromatographed on silica (80:1 $CHCl_3$/THF) giving 0.28 g (69%) of 166.

Part F:

Following the procedure outlined for the preparation of 6 (Example 1 part E), 167 was prepared in 56% yield starting from 0.28 g of 166.

Part G:

Following the procedure outlined for the preparation of 7 Example 1 part F), 168 was prepared in 91% yield starting from 0.22 g of 167.

$^1$H NMR (300 MHz $CD_3OD$) 1.5 (m, 1H), 2.0 (m, 1H), 2.2 (m, 1H), 2.35–2.55 (m, 3H), 2.95 (m, 3H), 7.05 (d, J=8.25 Hz, 1H), 7.4 (m, 2H), 7.93 (d, J=8.4 Hz, 2H), 8.15 (d, J=8.4 Hz, 2H); IR (KBr) 3322, 3104, 1712, 1667, cm$^{-1}$; MS (FAB) m/e 352.1654 (352.1661 calcd. for $C_{20}H_{22}N_3O_3$)

Example 41

Preparation of the Compound Represented by the Formula (177)

(177)

*TFA

Part A:

A mixture of 169 (3.5 g) and Claisen's alkali (NaOH in EtOH) (75 mL) was maintained at reflux for 6 hours and then allowed to cool. The mixture was concentrated to ½ volume and the remaining aqueous material neutralized to pH 7 with concentrated HCl. The mixture was then extracted with EtOAc and the combined extracts concentrated. The residue was taken up in THF/$H_2O$ (1:1, 20 mL) and treated with $K_2CO_3$ (3.2 g, 23 mmol), and CBz chloride (3.92 g, 23 mmol). The mixture was rapidly stirred for 1 hour and then diluted with EtOAc and washed with $H_2O$. The organic material was concentrated and the crude residue was subjected to acylation with $Ac_2O$ (5 mL) in pyridine (10 mL). After 2 hours the mixture was concentrated to dryness and the residue chromatographed (3:1 hexanes/EtoAc) giving 6.42 g of pure 170.

Part B:

A mixture of 170 (6.42 g, 19.75 mmol), MCPBA (4.27 g, 24.69 mmol), and $CH_2Cl_2$ (40 mL) was maintained at room temperature for 15 hours. At this time, the mixture was diluted with EtOAc and washed with saturated aqueous $NaHCO_3$ and $H_2O$. The organic material was then concentrated. The crude material was taken up in acetone (450 mL) and treated with NaI (4 g). The resulting solution was maintained at reflux for 4 hours and then allowed to cool. The mixture was concentrated, dissolved in EtOAc, washed with $H_2O$, and reconcentrated. This material was then treated with 0.1N LiOH (290 mL) in THF (290 mL) for 12 hours. The mixture was diluted with EtOAc and washed with $H_2O$ and the remaining organic material was concentrated. Chromatography (2:1 hexanes/EtOAc) gave 3.58 g of 171.

Part C:

A mixture of 171 (6.8 g, 2.6 mmol), TBSCl (0.43 g, 2.9 mmol), imidazole (0.21 g, 3.2 mmol), and DMF (5 mL) was stirred at room temperature for 16 hours. This material was then diluted with EtOAc and washed with $H_2O$. The organic material was concentrated giving essentially pure TBS ether. A mixture of this material (0.98 g, 2.4 mmol), and THF (10 mL) was treated with NaH (0.07 g of a 60% dispersion in oil, 2.6 mmol) and allowed to stand for 1 hour. The mixture was then treated with benzylbromide (0.45 g, 2.6 mmol) and Bu₄NI (cat) and allowed to stand for 5 hours. The mixture was then diluted with EtOAc and washed with H₂O. The organic material was then concentrated. The crude residue was taken up in THF and treated with TBAF (2.9 mL of a 1M solution in THF, 2.9 mmol). After one hour at room temperature, the mixture was diluted with EtOAc and washed with H₂O. The organic material was concentrated and the crude material was chromatographed on silica (hexanes/EtOAc 1:1) giving 0.94 g (95%) of 172.

Part D:
Following the procedure employed for the preparation of 68 (Example 24 part B), 173 was prepared in 80% yield starting from 0.43 g of 172.

Part E:
A mixture of 173 (0.65 g, 1.16 mmol), and Pd/C (10% on carbon, 0.65 g) in EtOH (10 mL) was maintained under an atmosphere of H₂ (balloon) for 2.5 hours and then filtered and the filtrate concentrated. The crude material was then taken up in CH₂Cl₂ (5 mL) and treated with EDCI (0.23 g, 1.2 mmol), p-cyanobenzoic acid (0.18 g, 1.2 mmol) and DMAP (cat). The resulting solution was maintained at room temperature for 1 hour and then diluted with EtOAc. The resulting mixture was washed with H₂O and then concentrated. The crude residue was chromatographed on silica (1:2 hexanes/EtOAc) giving 0.32 g (71%) 175.

Part F:
Following the procedure employed for the preparation of 6 (Example 1 part E), 176 was prepared in 59% yield starting from 0.31 g of 175.

Part G:
Following the procedure employed for the preparation of 7 (Example 1 part F), 177 was prepared in 70% yield starting from 0.23 g of 176.
¹H NMR (300 MHz CD₃OD) 2.85 (dd, J=5.4, 16.4 Hz, 1H), 3.06 (dd, J=4.4, 16.5 Hz, 1H), 4.0–4.2 (m, 5H), 7.05 (d, J=8.25 Hz, 1H), 7.18 (m, 1H), 7.22 (s, 1H), 7.92 (d, J=8.4 Hz, 2H), 8.10 (d, J=8.4 Hz, 2H); IR (KBr) 3340, 1667, 1603, 1201, cm⁻¹; MS (FAB) m/e 370. Anal. Calcd. for C₂₁H₂₀N₃O₇F₃: C, 52.18; H, 4.17; N, 8.69. Found: C, 52.15; H, 4.02; N, 8.54.

Example 42

Preparation of the Compound Represented by the Formula 186

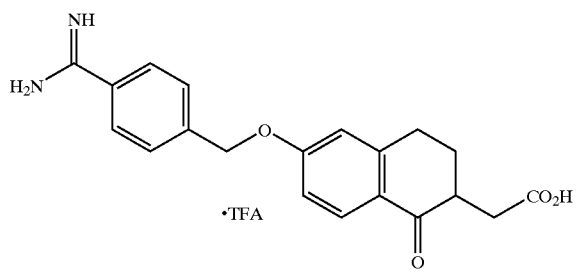

(186)

Part A:
To a mixture of 178 (2.17 g, 13.4 mmol) and sodium glyoxylate (4.25 g, 37.4 mmol) was added 1N NaOH (50 mL, 50 mmol). The solution was stirred 4 hours at room temperature, adjusted to pH 1 with conc. HCl, 5N HCl (200 mL) was added and reflux maintained for 24 hours. The mixture was allowed to cool and the resulting precipitate collected. The filtrate was extracted with EtOAc, the combined extracts washed with brine, dried (MgSO₄), and concentrated in vacuo to give a solid that was combined with the above precipitate to afford 3.02 g (99%) of 179 as a brown solid without further purification.

Part B:
To a stirred solution of 179 (0.95 g, 4.36 mmol) in glacial HOAc/H₂O (2:1, 15 mL) was added zinc dust (1.0 g, 15.3 mmol). The mixture was heated at reflux for 2 hours, cooled to room temperature, diluted with EtOAc, and washed with 1N HCl, H₂O, and brine. The organic material was dried (MgSO₄), and concentrated to afford 0.89 g (93%) of 180 as a brown solid without further purification.

Part C:
180 (0.88 g, 4.0 mmol) was dissolved in THF/EtOAc (1:4 25 mL), diphenyldiazomethane added (0.97 g, 5.0 mmol) as a solid and the red solution let stir 5 days at room temperature followed by 4 hours at reflux. The mixture was diluted with EtOAc, washed with 1N HCl, saturated NaHCO₃, H₂O, and brine, dried (MgSO₄), and concentrated in vacuo. The crude isolate was purified by chromatography (silica gel 230–400 mesh, toluene:EtOAc gradient) to afford 0.77 g (50%) of 181 as a tan solid.

Part D:
To a solution of 181 (0.77 g, 2 mmol) in DMF (20 mL) was added K₂CO₃ (0.276 g, 2 mmol) as a solid. After stirring 0.5 hours at room temperature, α-bromo-p-tolunitrile (0.40 g, 2.0 mmol) was added as a solid and the solution allowed to stir at room temperature for 4 hours. The mixture was diluted with EtOAc, washed with H₂O, 1N HCl, saturated NaHCO₃, and brine, dried (MgSO₄), and concentrated in vacuo. The crude material was purified by chromatography (silica gel prep plate, 8:2 toluene:EtOAc) to afford 0.83 g (83%) of 184 as a light yellow solid.

Part E:
Following the general procedure described for the preparation of 6 (Example 1 part E), 185 was prepared in 41% yield starting from 0.8 g of 184.

Part F:
Following the general procedure described for the preparation of 6 (Example 1 part F), 186 was prepared in 41% yield starting from 0.8 g of 185. MS (FD) m/e 355.

Example 43

Preparation of the Compound Represented by the Formula 190

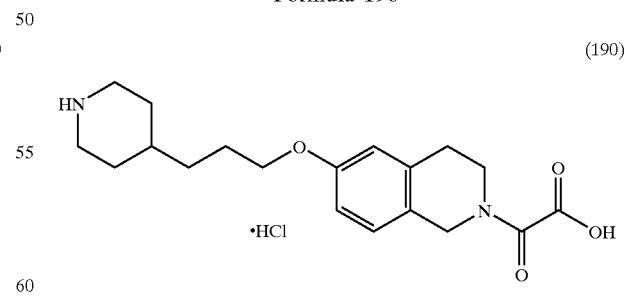

(190)

Part A:
A mixture of 2 (1.0 g, 3.95 mmol) and THF (20 mL) was treated with LiAlH₄ (0.30 g, 7.9 mmol) and maintained at reflux for 2 hours. The mixture was allowed to cool to room temperature and then quenched with water and 15% NaOH. The resulting mixture was filtered and concentrated. The crude material thus obtained was dissolved in pyridine (10 mL) and treated with methyl oxalylchloride (0.38 mL, 4.3 mmol). The resulting mixture was maintained at room temperature for 1 hour and then diluted with EtOAc and washed with H₂O. The organic material was concentrated and the crude residue purified on silica (3:1 hexanes/EtOAc) giving 0.65 g of 187.

Part B:

A mixture of 187 (0.65 g) and Pd/C (10% on carbon, 0.65 g) and EtOH (10 mL) was maintained under an atmosphere of H₂ (balloon) for 2 hours and then filtered and the filtrate concentrated. This process yielded 0.45 g of essentially pure 188.

Part C:

A mixture of 188 (0.098 g, 0.42 mmol), NaH (0.018 g of a 60% dispersion in oil, 0.46 mmol) and THF (2 mL) was stirred at reflux for 0.5 hour and then treated with 1-tBOC-4-(3-bromopropyl)piperidine (0.141 g, 0.42 mmol). The resulting mixture was maintained at reflux for 8 hours and then diluted with EtOAc and washed with H₂O and brine. The organic material was concentrated and the crude isolate was purified on silica (1.5:1 hexanes/EtOAc) giving 0.11 g of 189.

Part D:

A mixture of 189 (0.11 g, 0.25 mmol), NaOH (0.02 g, 0.5 mmol) and EtOH (5 mL) was maintained at room temperature for 1 hour and then concentrated. The residue was taken up in H₂O and the mixture acidified to pH 4 with KHSO₄. This mixture was extracted with EtOAc and the extracts concentrated. The crude residue was treated with TFA (5 mL) for 1 hour and then concentrated. The residue was taken up in 0.1 N HCl and lyophilized giving 0.051 g of 190.

$^1$H NMR (300 MHz CD₃OD) 1.2–1.7 (m, 6H), 1.8 (m, 2H), 1.95 (m, 2H), 2.9 (m, 4H), 3.35 (m, 2H), 3.75 (m, 2H), 3.95 (m, 2H), 4.6 (m, 2H), 6.25 (m, 2H), 7.1 (m, 1H); IR (KBr) 2940, 1735, 1653, 1187, cm$^{-1}$; MS (FAB) m/e 347.

Example 44

Preparation of the Compound Represented by the Formula 193

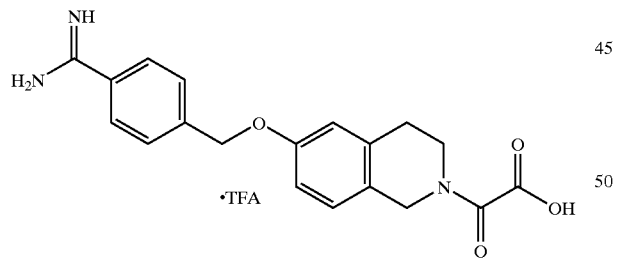

(193)

Part A:

A mixture of 188 (0.19 g, 0.81 mmol), NaH (0.021 g of a 60% dispersion in oil, 0.89 mmol) and THF (5 mL) was stirred at room temperature for 0.5 hour and then treated with α-bromo-p-tolunitrile (0.17 g, 0.89 mmol): The resulting mixture was maintained at reflux for 8 hours and then diluted with EtOAc and washed with H₂O. The organic material was concentrated and the crude residue purified on silica (1:1 hexanes/EtOAc) giving 0.22 g of 191.

Part B:

Following the procedure outlined for the preparation of 6 (Example 1 part F), 192 was prepared in 44% yield starting from 0.22 g of 191.

Part C:

A mixture of 192 (0.12 g, 0.27 mmol), NaOH (0.22 g, 0.55 mmol), EtOH (5 mL) was maintained at room temperature for 1 hour and then concentrated. The residue was dissolved in H₂O and the resulting solution was acidified to pH 4 with KHSO₄. This solution was then lyophilized. The crude residue thus produced was extracted with MeOH and the combined extracts were filtered and concentrated. The isolated material was treated with TFA (5 mL) for 1 hour and then concentrated. In this manner, one isolates 0.05 g of 193. $^1$H NMR (300 MHz CD₃OD) 2.91 (m, 2H), 3.72 (m, 2H), 4.6 (m, 2H), 5.25 (s, 2H), 6.8 (m, 2H), 7.0 (m, 1H), 7.6 (d, J=8.3 Hz, 2H), 7.8 (mn J=8.3 Hz, 2H); IR (KBr) 3336, 3114, 1668, 1506, cm$^{-1}$; MS (FAB) m/e 354.

Example 45

Preparation of Ethyl rac-(6-(4-(Aminoiminomethyl) phenylmethoxy)-3,4-dihydro-2H-1-benzopyran-2-yl) acetate Hydrochloride, a Compound Represented by the Formula (194)

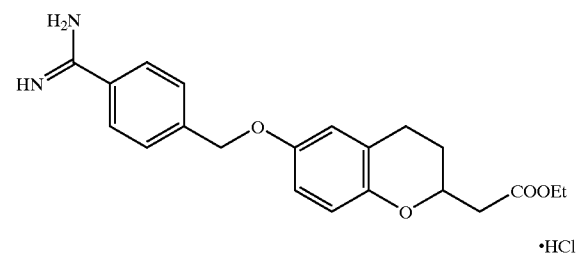

(194)

Step A: Preparation of Ethyl rac-(6-(4-Cyanophenyl) methoxy-3,4-dihydro-2H-1-benzopyran-2-yl)acetate, an Intermediate Represented by the Formula (195)

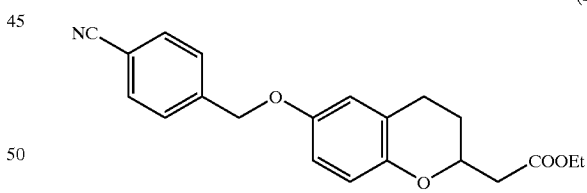

(195)

6.0 g (25.4 mmol) ethyl rac-(3,4-dihydro-6-hydroxy-2H-1-benzopyran-2-yl)acetate (prepared according to Eur. Pat. Appl. EP 129 906, the disclosure of which is incorporated herein by reference) and 4.9 g (25.0 mmol) 4-cyanobenzyl bromide were dissolved 36 ml in dry acetone, and 3.5 g (25.3 mmol) potassium carbonate were added. After stirring overnight at 50° C. another 0.3 g (1.3 mmol) of the benzopyran were added, and the reaction was continued for the same time. The inorganic solid was removed by filtration, the filtrate concentrated in vacuo, and the pure nitrile obtained from the residue by chromatography on silica gel with hexane/acetone 40:5.

Yield: 6.7 g (76%) of pale yellow solid, m.p. 75–76° C.

Step B: Preparation of Ethyl rac-(3,4-Dihydro-6-(4-(ethoxycarbonimidoyl)phenylmethoxy)-2H-1-benzopyran-2-yl)acetate Hydrochloride, an Intermediate Represented by the Formula (196):

(196)

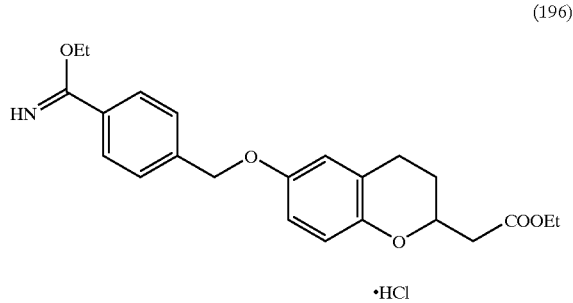

·HCl 7.45 g (21.2 mmol) of the nitrile from Step (A) were suspended in 340 ml dry ethanol. The suspension was cooled with an ice bath and saturated with gaseous hydrogen chloride (approximately 5 hours). After standing overnight a clear solution had been formed. The solution was evaporated to dryness in vacuo, and the compound (196) was stirred with hexane, filtered with suction, and dried in vacuo.

Yield: 6.43 g (70%) of a pale yellow powder, m.p. 118–119° C.

Step C: Preparation of Compound (194), Ethyl rac-(6-(4-(Aminoiminomethyl)phenylmethoxy)-3,4-dihydro-2H-1-benzopyran-2-yl)acetate Hydrochloride:

385 ml of a saturated solution of ammonia in ethanol were cooled with ice, and 6.43 g (14.8 mmol) of the intermediate from Step B were added. The Step B intermediate was stirred overnight at room temperature, and the solvent was removed in vacuo. The remaining solid title compound was stirred with hexane, filtered with suction, and dried in vacuo at 40° C. Yield: 5.32 g (89%) of white powder, m.p. 123–125° C.

Example 46

Preparation of rac-(6-(4-(Aminoiminomethyl)phenylmethoxy)-3,4-dihydro-2H-1-benzopyran-2-yl)acetic Acid Trifluoroacetate, a Compound Represented by the Formula (197)

(197)

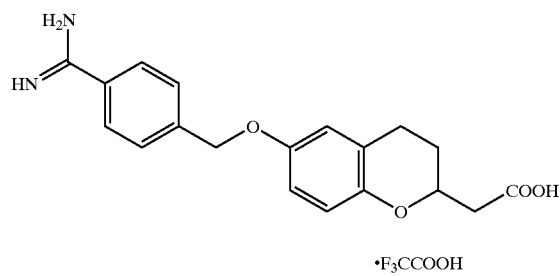

·F₃CCOOH

Step A: Preparation of Ethyl rac-(6-(4-(N-tert.-Butoxycarbonyl(aminoiminomethyl))phenylmethoxy)-3,4-dihydro-2H-1-benzopyran-2-yl)acetate, an Intermediate Represented by the Formula (198):

(198)

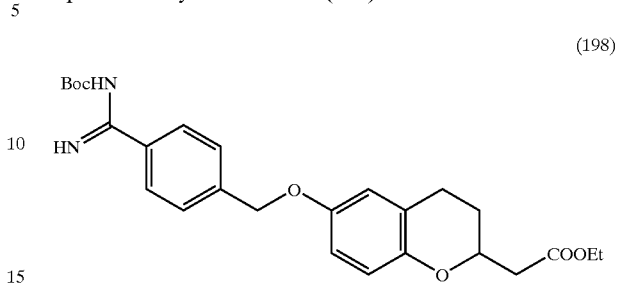

3.7 g (9.1 mmol) of the amidine of Example 45 was dissolved in 55 ml of a mixture of THF/H$_2$O 1:1. After addition of 1.65 g (11.9 mmol) potassium carbonate, 1.99 g (9.1 mmol) Boc$_2$O was added dropwise, and the mixture was stirred overnight at room temperature. The mixture was then diluted with 100 ml ethyl acetate. The organic layer was separated, washed with water, dried over sodium sulfate, and concentrated in vacuo to give the pure protected amidine.

Yield: 4.3 g (100%) of an oil.

Step B: Preparation of rac-(6-(4-(N-tert.-Butoxycarbonyl(aminoiminomethyl))phenylmethoxy)-3,4-dihydro-2H-1-benzopyran-2-yl)acetic Acid, an Intermediate Represented by the Formula (199):

(199)

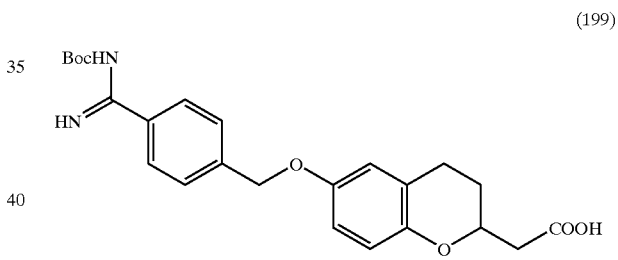

5.2 g (11.1 mmol) of the ester from Step A was dissolved in 75 ml of ethanol. After addition of 36 ml 2N aqueous sodium hydroxide the mixture was heated at 60° C. for some minutes. The mixture was then adjusted to pH 6 with acetic acid. The ethanol was removed in vacuo, and ethyl acetate was added. The organic layer was separated, dried over sodium sulfate, concentrated in vacuo, and the title carboxylic acid was obtained from the residue by chromatography on silica gel with dichloromethane/ethanol 40:5.

Yield: 2.0 g (41%) of a white powder, m.p. 220–222° C. (dec.).

Step C: Preparation of rac-(6-(4-(Aminoiminomethyl)phenylmethoxy)-3,4-dihydro-2H-1-benzopyran-2-yl)acetic Acid Trifluoroacetate 0.15 g (0.34 mmol) of the protected amidine from Step B and 2.8 ml trifluoroacetic acid were mixed and stirred at room temperature for 1.5 hours. The solvent was removed in vacuo, and the title amidine precipitated after addition of 10 ml water. The product was filtered with suction, stirred again with 10 ml water, filtered, and dried in vacuo.

Yield: 0.09 g (58%) of a white powder, m.p. 210–212° C.

Example 47

Preparation of Ethyl rac-(6-(N-(4-(Aminoiminomethyl)benzoyl)amino)-3,4-dihydro-2H-1-benzopyran-2-yl)acetate Hydrochloride, a Compound Represented by the Formula (200)

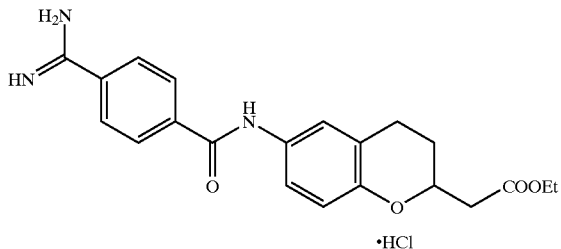

(200)

Step A: Preparation of tert.-Butyl (2-oxo-2H-1-Benzopyran-6-yl)carbamate, an Intermediate Represented by the Formula (201):

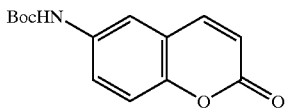

(201)

100 g (523 mmol) 6-Nitrocoumarin was dissolved in 600 ml dry ethanol, and the solution was kept under an atmosphere of argon. 86 g (1.364 mol) ammonium formate and 6 g 10% Pd-C were added with stirring, while the temperature rose to 45° C. and a gas evolution was observed. The reaction mixture was heated with reflux for 3 hours and diluted with another 200 ml ethanol. The hot mixture was filtered through Celite followed by washing with 200 ml hot ethanol. The unprotected amine precipitated upon cooling, filtered with suction, washed with hexane, and dried in vacuo. Another crop of the amine was obtained by concentration of the filtrate.

Total yield of the intermediate amine was 74 g.

The crude amine was dissolved in 300 ml of a mixture of THF/H$_2$O 1:1 and kept under an atmosphere of argon. 110 g (504 mmol) Boc$_2$O and 95 g (687 mmol) dried potassium carbonate were added. The reaction mixture was stirred overnight at room temperature, diluted with 750 ml water, and extracted with ethyl acetate (3×1 l). The combined organic layers were dried over sodium sulfate and concentrated in vacuo. The residue was dissolved in 2 L dichloromethane and stirred in the presence of 1 kg silica gel, which was filtered with suction and washed with dichloromethane. The filtrate was concentrated in vacuo to give the title compound. An analytical sample was purified by chromatography on silica gel with dichloromethane.

Yield: 112 g (82%) of pale yellow crystals, m.p. 142–143° C.

Step B: Preparation of tert.-Butyl (3,4-Dihydro-2-oxo-2H-1-benzopyran-6-yl)carbamate, an Intermediate Represented by the Formula (202):

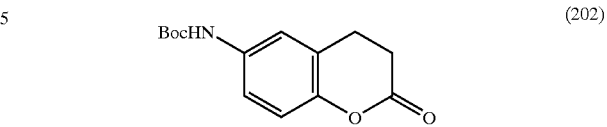

(202)

85 g (325 mmol) of the coumarin from Step A were dissolved in a mixture of 1150 ml ethanol and 115 ml acetic acid, and the solution was filled into a hydrogenation autoclave.

6 g 10% Pd—C were added, and it was hydrogenated at room temperature and a pressure of 20 atm hydrogen. After two days another 3 g Pd—C were added, and the reaction was continued for two days. The catalyst was removed by filtration, and the filtrate was concentrated in vacuo. The residue was dissolved in 1 L ethyl acetate, washed with 500 ml saturated aqueous sodium bicarbonate, dried over sodium sulfate, and the solvent was removed in vacuo. The title lactone was purified by chromatography on silica gel with dichloromethane containing 1% ethanol.

Yield: 21 g (25%) of colorless crystals, m.p. 158–159° C.

Step C: Preparation of tert.-Butyl rac-(3,4-Dihydro-2-hydroxy-2H-1-benzopyran-6-yl)carbamate, an Intermediate Represented by the Formula (203):

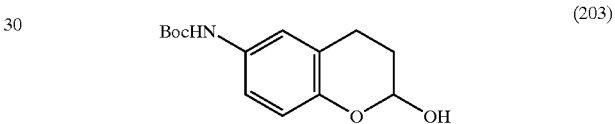

(203)

21 g (79.8 mmol) of the lactone from the previous Step was dissolved in 340 ml dry dichloromethane and kept under an atmosphere of argon. The solution was cooled to −70° C. and maintained at this temperature, while 67 ml of a 25% solution of diisobutylaluminum hydride (DIBAL-H) in toluene was added dropwise within 45 minutes. After an additional hour stirring at this temperature 20 ml methanol were added slowly, and the mixture was poured into 1 L saturated aqueous ammonium chloride solution. Solids were removed by filtration through Celite and washed with dichloromethane. The filtrate was dried over sodium sulfate, concentrated in vacuo to give the pure title compound as detected by its $^1$H-NMR.

Yield: 16.5 g (78%) of a yellow oil.

Step D: Preparation of Ethyl rac-(6-(N-tert.-Butoxycarbonylamino)-3,4-dihydro-2H-1-benzopyran-2-yl)acetate, an Intermediate Represented by the Formula (204):

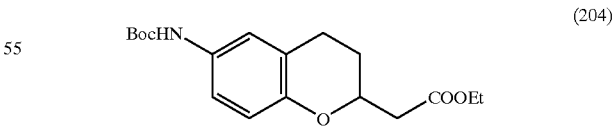

(204)

11.2 g (42.2 mmol) of the compound from Step C and 14.7 g (42.2 mmol) ethoxycarbonylmethylene triphenylphosphorane were dissolved in 130 ml dry toluene and heated with reflux for 22 hours. The reaction mixture was cooled to room temperature, and 300 mg sodium hydride were added. After additional 5 hours heating the mixture was poured into 1 L ice-cold water. It was extracted three times with ethyl acetate, and the combined organic layers were washed with 300 ml water, dried over sodium sulfate, and concentrated in vacuo. The benzopyran (204) was obtained from the residue by chromatography on silica gel with dichloromethane.

Yield: 5.5 g (39%) of a colorless amorphous solid, m.p. 67–69° C.

Step E: Preparation of Ethyl rac-(6-(N-(4-Cyanobenzoyl) amino)-3,4-dihydro-2H-1-benzopyran-2-yl)acetate, an Intermediate Represented by the Formula (205):

(205)

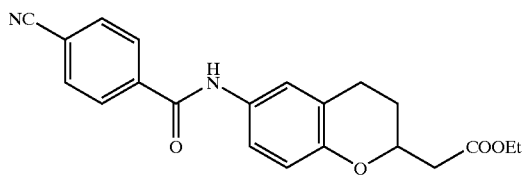

2.0 g (6.0 mmol) of the protected amine from the previous step was treated with 6 ml trifluoroacetic acid and stirred for 2 hours at room temperature. The mixture was neutralized with saturated aqueous sodium bicarbonate solution and extracted with ethyl acetate. The organic layer was dried over sodium sulfate and concentrated under reduced pressure to leave a dark oil of unprotected ethyl rac-(6-amino-3,4-dihydro-2H-1-benzopyran-2-yl)acetate. It was dissolved in 40 ml dry THF, treated with 4 ml dry pyridine and 1.0 g (6.0 mmol) 4-cyanobenzoyl chloride, and stirred overnight at room temperature. The mixture was poured into ice-cold aqueous sodium bicarbonate solution and extracted with ethyl acetate. The organic layer was washed successively with aqueous copper(II) sulfate solution and with brine, dried over sodium sulfate, and concentrated in vacuo. The nitrile (205) was obtained from the residue by chromatography on silica gel with dichloromethane/ethanol 96:4.

Yield: 1.4 g (64%) of pale yellow crystals, m.p.146–148° C.

Step F: Preparation of Ethyl rac-(6-(N-(4-(Aminoiminomethyl)benzoyl)amino)-3,4-dihydro-2H-1-benzopyran-2-yl)acetate Hydrochloride 1.4 g (3.8 mmol) of the nitrile from the previous Step was dissolved in 50 ml dry ethanol. The solution was cooled with ice and saturated with gaseous hydrogen chloride. After stirring overnight at room temperature the solvent was removed under reduced pressure, and the residue was treated with a saturated solution of ammonia in ethanol. The reaction mixture was stirred for three days, evaporated in vacuo, and the title compound was obtained as a yellow oil by chromatography on silica gel with dichloromethane/ethanol 65:35 containing 5% ammonia in ethanol. A crystalline sample for analytical and biological tests was obtained by stirring with a mixture of ethanol/etheral hydrogen chloride/ether.

Yield: 0.9 g (56%) of yellow crystals, m.p. 253° C. (dec.).

Example 48

Preparation of rac-(6-(N-(4-(Aminoiminomethyl)benzoyl)amino)-3,4-dihydro-2H-1-benzopyran-2-yl) acetic Acid, a Compound Represented by the Formula (206):

(206)

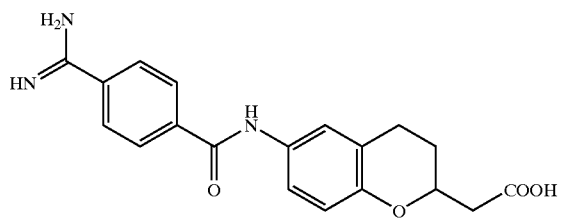

0.2 g (0.48 mmol) of the ester from Example 47 were added to a mixture of 4 ml ethanol and 0.5 ml 2 N aqueous sodium hydroxide. The mixture was diluted with water until it became a clear solution. After slight warming it was stirred at room temperature for 3 hours and acidified with 2 N acetic acid, while a precipitate was formed, which was filtered, washed with water, and dried in vacuo. The very unsoluble compound (206) was characterized by elemental analysis and mass spectrum.

Yield: 0.16 g (95%) of a colorless amorphous solid, m.p. 291–292° C. (dec.).

Example 49

Preparation of rac-(6-(N-(4-Carbamoylbenzoyl) amino)-3,4-dihydro-2H-1-benzopyran-2-yl)acetic Acid, a Compound Represented by the Formula (207)

(207)

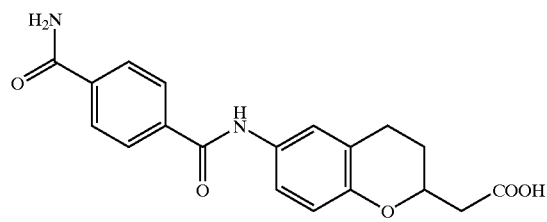

Method A:

0.47 g (1.12 mmol) of the ester from Example 47 were added to a mixture of 5 ml ethanol and 5 ml 2 N aqueous sodium hydroxide. The mixture was heated on a steam bath for 15 minutes, cooled to room temperature, and brought to pH 4 with 2 N aqueous hydrochloric acid, while a precipitate was formed. The precipitate was filtered with suction, and the amide (207) was purified by suspension in a small amount of hot ethanol.

Yield: 60 mg (15%) of a beige amorphous solid, m.p. 273–274° C.

Method B:

0.7 g (1.92 mmol) of the nitrile from Example 47, Step E were dissolved in 15 ml 98% formic acid, and a stream of gaseous hydrogen chloride was passed through the mixture for 4 hours. The reaction mixture was stirred overnight at room temperature, and the solvent was removed in vacuo.

The remaining solids were stirred with water, filtered with suction, and washed with ethanol and ether, successively. The amide was suspended in hot ethanol, filtered, and dried in vacuo.

Yield: 0.45 g (66%) of grey crystals, m.p. 264–265° C.

Example 50

Preparation of Ethyl rac-3-(6-(N-(4-(Aminoiminomethyl)benzoyl)amino)-3,4-dihydro-2-methyl-2H-1-benzopyran-2-yl)propanoate Hydrochloride, a Compound Represented by Formula (208)

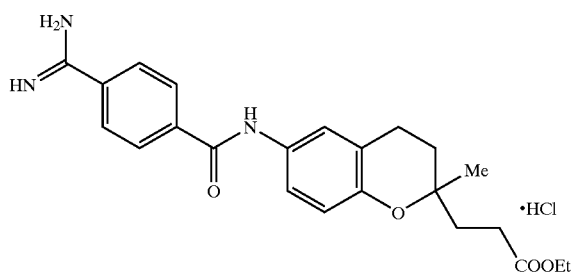
(208)

Step A: Preparation of Ethyl rac-3-(3,4-Dihydro-2-methyl-6-nitro-4-oxo-2H-1-benzopyran-2-yl)propanoate, an Intermediate Represented by the Formula (209):

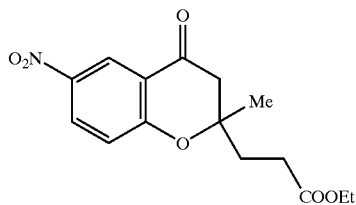
(209)

5.4 g (29.8 mmol) 2-hydroxy-5-nitroacetophenone (prepared by methods from J. Am. Chem. Soc. 1954, 76, 4993, the disclosure of which is incorporated herein by reference), 5.8 g (40.2 mmol) ethyl 4-oxopentanoate, and 1.7 ml pyrrolidine were dissolved in 50 ml toluene, and the mixture was heated for 6 hours with azeotropic removal of water. The mixture was concentrated in vacuo, and the remaining oil was 1:0 dissolved in ethyl acetate. The solution was washed with 1 N aqueous hydrochloric acid and with brine, successively, dried over sodium sulfate, and the solvent was removed under reduced pressure. The chromanone (209) crystallized from the residue.

Yield: 5.3 g (58%) of a pale yellow amorphous solid, m.p. 88–90° C.

Step B: Preparation of Ethyl 3-(3,4-Dihydro-4-hydroxy-2-methyl-6-nitro-2H-1-benzopyran-2-yl)propanoate, an Intermediate Represented by the Formula (210)

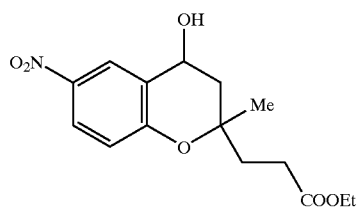
(210)

3.2 g (10.4 mmol) of the chromanone from Step A were dissolved in 100 ml ethanol. 0.76 g (20.0 mmol) sodium borohydride were added in small portions, and the mixture was stirred at room temperature for 5 hours.

The reaction mixture was concentrated in vacuo, acidified with 1 N aqueous hydrochloric acid, and extracted with ethyl acetate. The organic layer was dried over sodium sulfate, and the solvent removed under reduced pressure. The benzopyran (210) was obtained by chromatography on silica gel with dichloromethane containing 4% ethanol.

Yield: 2.0 g (62%) of an oil.

Step C: Preparation of Ethyl rac-3-(2-Methyl-6-nitro-2H-1-benzopyran-2-yl)propanoate, an Intermediate Represented by the Formula (211):

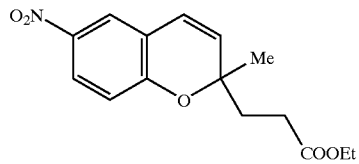
(211)

2.0 g (6.5 mmol) of the alcohol from the previous step were dissolved in 75 ml toluene, and a catalytic amount of 4-toluenesulfonic acid was added. The mixture was heated with reflux for 7 hours, while water was removed azeotropically. The reaction mixture was washed with aqueous sodium bicarbonate solution, the organic layer dried over sodium sulfate, and concentrated in vacuo. The title chromene was obtained from the residue by chromatography on silica gel with ethyl acetate/hexane 1:3.

Yield: 0.85 g (45%) of an oil.

Step D: Preparation of Ethyl rac-3-(6-Amino-3,4-dihydro-2-methyl-2H-1-benzopyran-2-yl)propanoate, an Intermediate Represented by the Formula (212):

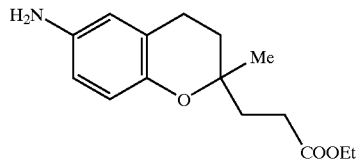
(212)

1.6 g (5.5 mmol) of the 6-nitrochromene from the previous Step was dissolved in a mixture of 20 ml ethanol and 10 ml acetic acid. 400 mg Pd-C were added and the mixture was filled into an autoclave. It was stirred overnight at room temperature under an atmosphere of 20 bar hydrogen until the reduction was complete. The catalyst was removed by filtration, and ethanol was distilled in vacuo. The reaction mixture was diluted with ethyl acetate, washed with concentrated aqueous sodium bicarbonate solution, dried over sodium sulfate, and concentrated under reduced pressure to give the crude title amine, which was pure as detected by $^1$H-NMR.

Yield: 1.6 g of an oil, which darkened upon standing.

Step E: Preparation of Ethyl rac-3-(6-(N-(4-Cyanobenzoyl)amino)-3,4-dihydro-2-methyl-2H-1-benzopyran-2-yl)propanoate, a Compound Represented by the Formula (213):

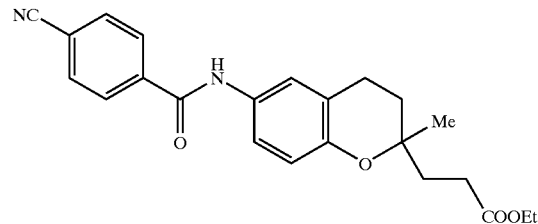

(213)

1.6 g (6.1 mmol) of the crude amine from Step D were dissolved in 40 ml dry THF. 5 ml dry pyridine and 1.0 g (6.0 mmol) 4-cyanobenzoyl chloride were added successively. The mixture was stirred overnight at room temperature and poured into an ice-cold solution of aqueous sodium bicarbonate. It was extracted with ethyl acetate, and the organic layer was washed with aqueous copper(II) sulfate and with brine, dried over sodium sulfate, and concentrated in vacuo. The pure nitrile was obtained by chromatography on silica gel with dichloromethane/ethanol 97:3.

Yield: 1.5 g (63%) of a dark viscous oil.

Step F: Preparation of Ethyl rac-3-(6-(N-(4-(Aminoiminomethyl)benzoyl)amino)-3,4-dihydro-2-methyl-2H-1-benzopyran-2-yl)propanoate Hydrochloride 1.5 g (3.8 mmol) of the nitrile from Step E were dissolved in 50 ml dry ethanol. The solution was cooled with an ice bath, saturated with gaseous hydrogen chloride, and stirred overnight at room temperature. The reaction mixture was concentrated under reduced pressure, and the residue was treated with a saturated solution of ammonia in ethanol. It was stirred for additional 24 hours at room temperature, concentrated in vacuo, and chromatographed on silica gel with dichloromethane/ethanol 65:35 containing 5% saturated ammonia in ethanol to give the title amidine as an oil. A crystalline sample for analytical and biological tests was obtained by stirring in a mixture of ethanol/etheral hydrogen chloride/ether.

Yield: 0.94 g (55%) of yellow crystals, m.p. 118–120° C.

Example 51

Preparation of rac-3-(6-(N-(4-Carbamoylbenzoyl)amino)-3,4-dihydro-2-methyl-2H-1-benzopyran-2-yl)propanoic Acid, a Compound Represented by the Formula (214)

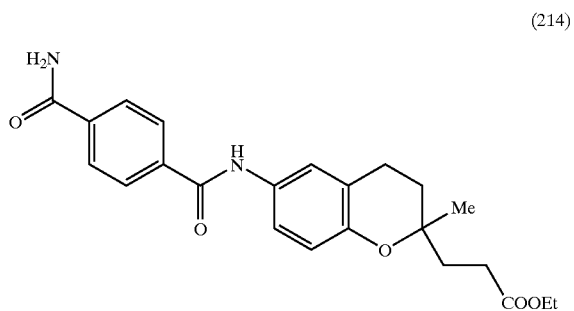

(214)

0.5 g (1.12 mmol) of the ester from Example 50 was added to a mixture of 5 ml 2N aqueous sodium hydroxide and 5 ml ethanol. The reaction mixture was stirred with heating on a steam bath for 20 minutes, while the mixture became a clear solution, and was then brought to pH 4 with 2N aqueous hydrochloric acid, and extracted with ethyl acetate. The organic layer was dried over sodium sulfate and concentrated in vacuo. The reaction mixture was purified by chromatography on silica gel with chloroform/ethanol 1:1. The remaining oil obtained from the pure fractions was treated with 2 ml trifluoroacetic acid and stirred for 2 hours at room temperature. The solvent was removed under reduced pressure, and the title amide crystallized from the residue by treating with ethanol.

Yield: 70 mg (16%) of a beige amorphous solid, m.p. 237–238° C.

Example 52

Preparation of Ethyl rac-3-(6-(4-(Aminoiminomethyl)phenylmethoxy)-2-methyl-2H-1-benzopyran-2-yl)propanoate Hydrochloride, a Compound Represented by the Formula (215)

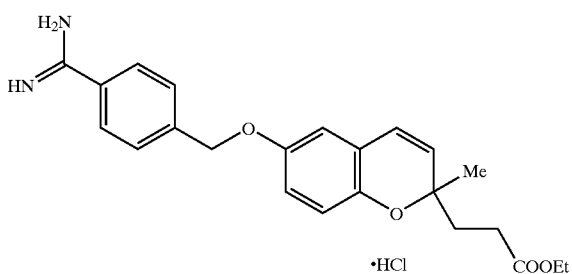

(215)

Step A: Preparation of 4-((3-Acetyl-4-hydroxyphenoxy)methyl)benzonitrile, an Intermediate Represented by the Formula (216):

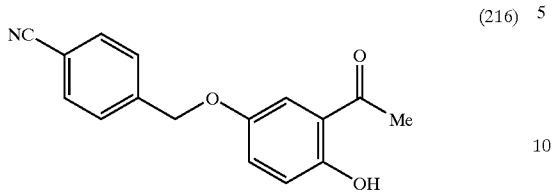
(216)

45 g (296 mmol) 2,5-dihydroxyacetophenone and 58.4 g (298 mmol) 4-cyanobenzyl bromide were dissolved in 650 ml dry acetone, and 45 g (326 mmol) potassium carbonate and 4.5 g potassium iodide were added. After heating with reflux for 6.5 hours the inorganic solids were removed by filtration and washed with acetone. The combined filtrates were concentrated in vacuo, and the residue was stirred with 600 ml hot methanol. The methanol solution was cooled to room temperature, and the compound (216) was filtered with suction, washed successively with methanol and hexane, and dried in vacuo at 40° C.

Yield: 69.5 g (88%) of beige crystals, m.p. 123–127° C.

Step B: Preparation of Ethyl rac-3-(6-(4-Cyanophenylmethoxy)-3,4-dihydro-2-methyl-4-oxo-2H-1-benzopyran-2-yl)propanoate, an Intermediate Represented by the Formula (217):

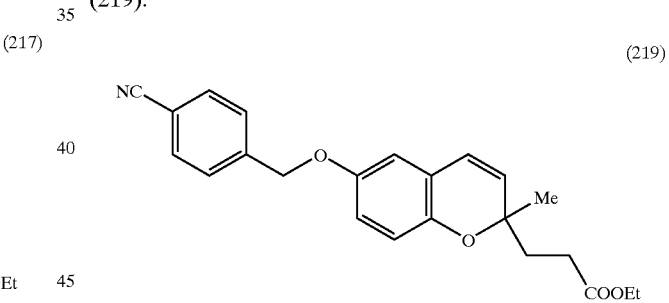
(217)

30 g (112.2 mmol) of the acetophenone from the previous Step, 20.4 g (141.5 mmol) ethyl 4-oxopentanoate, and 9.6 ml pyrrolidine were dissolved in 500 ml dry toluene. The mixture was stirred 20 hours at room temperature followed by 5.5 hours heating with azeotropic removal of water. The mixture was concentrated under reduced pressure, and the remaining oil was stirred for 30 minutes in 200 ml aqueous 2N hydrochloric acid. It was extracted with dichloromethane, and the organic layer was washed successively with 2N hydrochloric acid, water, and with brine. It was then dried over 0.4 nm mole sieve and concentrated in vacuo to leave a brown oil, which was chromatographed on silica gel with dichloromethane. The oily benzopyran (217) solidified by stirring with aqueous 2N hydrochloric acid. It was filtered with suction, washed successively with water and hexane, and dried in vacuo.

Yield: 12.27 g (28%) of yellow crystals, m.p. 88–92° C.

Step C: Preparation of ethyl 3-(6-(4-Cyanophenylmethoxy)-3,4-dihydro-4-hydroxy-2-methyl-2H-1-benzopyran-2-yl)propanoate, an Intermediate Represented by the Formula (218):

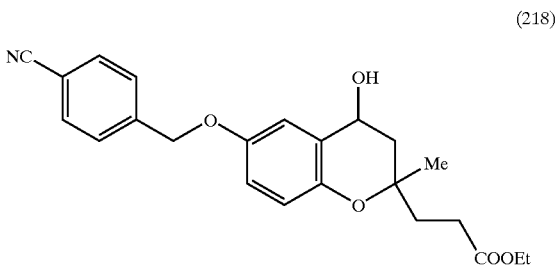
(218)

0.8 g (2.0 mmol) of the chromanone from Step B were dissolved in 10 ml dry ethanol, and 40 mg (1.06 mmol) sodium borohydride were added. After stirring overnight at room temperature another 40 mg of the hydride were added, and stirring was continued for 4 hours until the reduction was complete. The solvent was removed in vacuo, and the residue was treated with a mixture of water and dichloromethane. The aqueous layer was extracted with dichloromethane, and the combined organic layers were dried over 0.4 nm mole sieve. After concentration under reduced pressure the benzopyran was obtained by chromatography on silica gel with dichloromethane containing up to 2% ethanol.

Yield: 0.46 g (57%) of an oil.

Step D: Preparation of Ethyl rac-3-(6-(4-Cyanophenylmethoxy)-2-methyl-2H-1-benzopyran-2-yl)propanoate, an Intermediate Represented by the Formula (219):

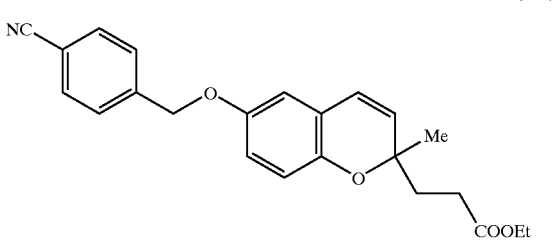
(219)

380 mg (0.96 mmol) of the compound from the previous step were dissolved in 25 ml toluene. After addition of a catalytic amount of 4-toluenesulfonic acid the mixture was heated for 1 hour with azeotropic removal of water until the reaction was complete. It was washed two times with saturated aqueous sodium bicarbonate, dried over 0.4 nm mole sieve, and concentrated in vacuo. The crude chromene was purified by chromatography on silica gel with dichloromethane.

Yield: 230 mg (63%) of an oil.

Step E: Preparation of Ethyl rac-3-(6-(4-(Aminoiminomethyl)phenylmethoxy)-2-methyl-2H-1-benzopyran-2-yl)propanoate Hydrochloride 1.5 g (4.0 mmol) of the nitrile from the previous Step were dissolved in 100 ml dry ethanol. The solution was cooled to 5–10° C., saturated with hydrogen chloride, stirred at room temperature overnight, and concentrated in vacuo. The remaining brown oil was treated with 100 ml saturated ethanolic solution of ammonia and stirred for two days. The solvent was removed in vacuo, and the title amidine was obtained from the residue by chromatography on silica gel with dichloromethane/ethanol 95:5 and ascending polarity up to 80:20.

Yield: 1.19 g (69%) of a yellow, amorphous solid; m.p.<50° C.

Example 53

Preparation of rac-3-(6-(4-(Aminoiminomethyl)phenylmethoxy)-2-methyl-2H-1-benzopyran-2-yl)propanoic Acid Hydrochloride, a Compound Represented by the Formula (220):

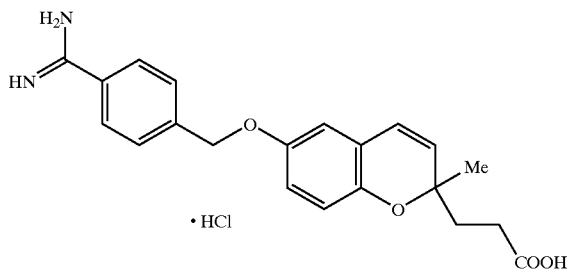

(220)

200 mg (0.464 mmol) of the ester from Example 52 were dissolved in 5 ml ethanol. Two drops of water and 0.64 ml of a 0.9 N ethanolic sodium ethoxide solution were added, and the mixture was stirred for 3 hours at 50° C. After addition of the same amount of sodium ethoxide, the reaction was continued for 2 hours at 50° C. and for three days at room temperature. A precipitate had been formed, which was filtered with suction, washed successively with ethanol and hexane. The crude solid was heated in a mixture of 4 ml water and 1 ml aqueous 2N hydrochloric acid for some minutes and stirred for 2 hours at room temperature. The mixture was evaporated to dryness, and the title hydrochloride was suspended three times in 3 ml hot isopropanol. The hot solutions were decanted, combined, and concentrated to dryness. It was washed two times with ether, and dried in vacuo.

Yield: 68 mg (36%) of a beige, amorphous solid, m.p. 56° C.

Example 54

Preparation of rac-(3,4-Dihydro-6-(4-(piperidin-4-yl)butoxy)-2H-1-benzopyran-2-yl)acetic Acid Trifluoroacetate, a Compound Represented by the Formula (225):

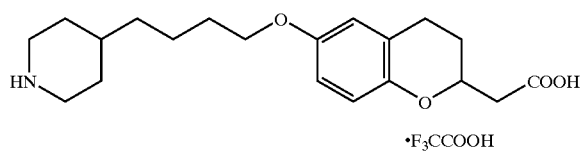

(225)

Step A: Preparation of Ethyl rac-(6-(4-(1-(tert.-Butoxycarbonyl)piperidin-4-yl)butoxy)-3,4-dihydro-2H-1-benzopyran-2-yl)acetate, an Intermediate Represented by the Formula (226):

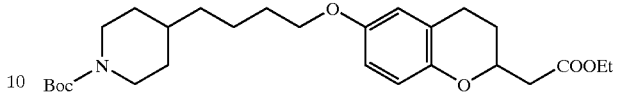

(226)

0.92 g (3.9 mmol) ethyl rac-(3,4-dihydro-6-hydroxy-2H-1-benzopyran-2-yl)acetate (prepared according to Eur. Pat. Appl. EP 129 906, the disclosure of which is incorporated herein by reference) were dissolved in 25 ml dry DMF. The solution was cooled to −5° C., and 1.8 ml 40% benzyltrimethylammonium hydroxide (Triton B) in methanol were added dropwise. After 40 minutes at this temperature 1.25 g (3.9 mmol) 4-(4-bromobutyl)-1-(tert.-butoxycarbonyl)piperidine (prepared according to Eur. Pat. Appl. EP 478 328, the disclosure of which is incorporated herein by reference) were added. The mixture was stirred at −5° C. for additional 3 hours, warmed to room temperature, stirred overnight, and poured into 150 ml ethyl acetate. It was then washed with water, 1 N aqueous hydrochloric acid, water, saturated aqueous sodium bicarbonate, water, and with brine, successively. The organic layer was dried over sodium sulfate and concentrated in vacuo. The title compound was obtained by chromatography on silica gel with hexane/ethyl acetate 4:1.

Yield: 0.64 g (35%) of a colorless oil.

Step B: Preparation of rac-(6-(4-(1-(tert.-Butoxycarbonyl)piperidin-4-yl)butoxy)-3,4-dihydro-2H-1-benzopyran-2-yl)acetic Acid, an Intermediate Represented by the Formula (227):

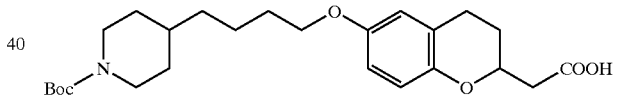

(227)

0.64 g (1.35 mmol) of the ester from Step A were dissolved in 10 ml ethanol, and 5.6 ml of a 1 N ethanolic solution of sodium ethoxide were added. The reaction mixture was stirred at room temperature for seven days and concentrated to dryness under reduced pressure. The residue was treated with water and neutralized with 10% aqueous KHSO$_4$ solution. It was extracted with ethyl acetate. The organic layer was dried over sodium sulfate, and the solvent was removed in vacuo to give the pure carboxylic acid.

Yield: 0.58 g (96%) of a pale yellow oil, which slowly solidified upon standing.

Step C: Preparation of rac-(3,4-Dihydro-6-(4-(piperidin-4-yl)butoxy)-2H-1-benzopyran-2-yl)acetic Acid Trifluoroacetate 0.4 g (0.9 mmol) of the protected piperidine from the previous Step were treated with 6 ml trifluoroacetic acid. The mixture was stirred for 2 hours at room temperature and evaporated in vacuo. After addition of water it was extracted with ether, and the organic layer was dried over sodium sulfate and concentrated under reduced pressure. The title compound was purified by chromatography on silica gel with dichloromethane/ethanol 96:4.

Yield: 120 mg (29%) of a beige oil, which solidified in part upon standing.

Example 55

Preparation of rac-(6-(5-(Aminoiminomethyl)pentoxy)-3,4-dihydro-2H-1-benzopyran-2-yl)acetic Acid Trifluoroacetate, a Compound Represented by the Formula (253):

(253)

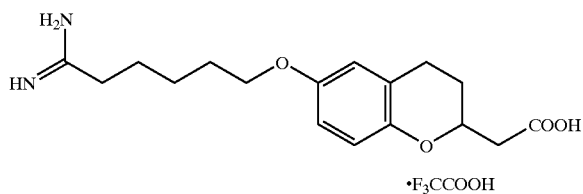

·F₃CCOOH

Step A: Preparation of Ethyl rac-(6-(5-Cyanopentoxy)-3,4-dihydro-2H-1-benzopyran-2-yl)acetate, an Intermediate Represented by the Formula (254):

(254)

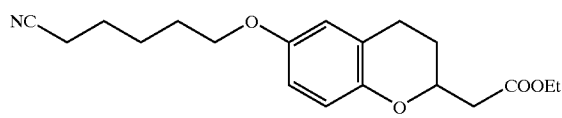

2.19 g (9.27 mmol) ethyl rac-(3,4-dihydro-6-hydroxy-2H-1-benzopyran-2-yl)acetate (prepared according to Eur. Pat. Appl. EP 129 906, the disclosure of which is incorporated herein by reference) and 2.0 g (11.4 mmol) 6-bromocapronitrile were dissolved in 30 ml dry acetone. 2.0 g (14.5 mmol) potassium carbonate, 250 mg potassium iodide, and 100 mg triethylbenzylammonium chloride were added, and the mixture was heated with reflux for 10 hours followed by stirring at room temperature for two days. The inorganic solid was removed by filtration and washed with acetone, and the combined filtrates were concentrated in vacuo. The nitrile (254) was obtained from the residue by chromatography on silica gel with dichloromethane containing up to 4% ethanol.

Yield: 1.32 g (43%) of an oil.

Step B: Preparation of Ethyl rac-(6-(5-(aminoiminomethyl)pentoxy)-3,4-dihydro-2H-1-benzopyran-2-yl)acetate Hydrochloride, an Intermediate Represented by the Formula (255):

(255)

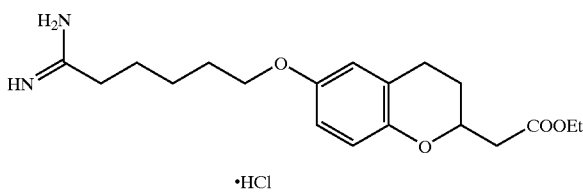

·HCl 1.25 g (3.77 mmol) of the nitrile from Step A were dissolved in 50 ml dry ethanol. The solution was cooled to 0° C. and saturated with hydrogen chloride. After stirring overnight it was concentrated in vacuo. The residue was treated with a mixture of 10 ml liquid ammonia and 50 ml dry ethanol and stirred overnight at room temperature. The solvent was removed under reduced pressure, and the remaining material was stirred with ethanol and dichloromethane, successively. Solids were removed by filtration after each procedure, and the filtrates were concentrated under reduced pressure. The crude title compound from the last filtrate was purified by chromatography on silica gel with dichloromethane/ethanol 9:1 followed by 8:2.

Yield: 0.97 g (67%) of a white powder, m.p. 82–84° C.

Step C: Preparation of Ethyl rac-(6-(5-(N-tert.-Butoxycarbonylaminoiminomethyl)pentoxy)-3,4-dihydro-2H-1-benzopyran-2-yl)acetate, an Intermediate Represented by the Formula (256):

(256)

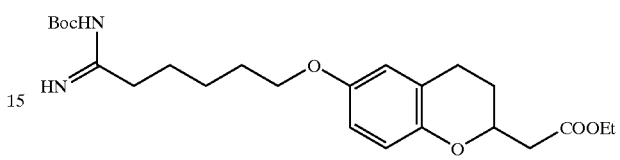

0.7 g (1.82 mmol) of the amidine from Step B were dissolved in 11 ml THF/H₂O 1:1. After addition of 335 mg (2.42 mmol) potassium carbonate and 0.4 g (1.83 mmol) Boc₂O the mixture was stirred overnight at room temperature. It was diluted with 25 ml ethyl acetate. The aqueous layer was separated and extracted with ethyl acetate. The combined organic layers were washed with water, dried over sodium sulfate, and concentrated to dryness in vacuo to give the crude protected amidine, which was used for the next Step.

Yield: 0.87 g of a yellow oil.

Step D: Preparation of rac-(6-(5-(N-tert.-Butoxycarbonylaminoiminomethyl)pentoxy)-3,4-dihydro-2H-1-benzopyran-2-yl)acetic acid, an Intermediate Represented by the Formula (257)

(257)

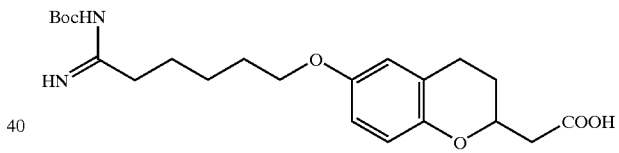

A mixture of 13 ml ethanol and 6 ml 2 N aqueous sodium hydroxide was added to 0.81 g (1.81 mmol) of the ester from the previous Step. The mixture was stirred at room temperature for 4 hours and neutralized with diluted acetic acid. After evaporation in vacuo the residue was stirred with a mixture of dichloromethane/methanol 1:1. Solids were removed by filtration and washed, and the combined filtrates were concentrated under reduced pressure. The carboxylic acid (257) was obtained by chromatography on silica gel with dichloromethane and enhancing the polarity by addition of 3% ethanol.

Yield: 215 mg (28%) of an oil.

Step E: Preparation of rac-(6-(5-(Aminoiminomethyl)pentoxy)-3,4-dihydro-2H-1-benzopyran-2-yl)acetic Acid Trifluoroacetate 112 mg (0.266 mmol) of the protected amidine from Step D were treated with 2.2 ml trifluoroacetic acid, and the mixture was stirred at room temperature for 1 hour. The solvent was removed in vacuo, and the residue was stirred with 10 ml water, while the title compound precipitated. The product was filtered with suction, washed with water and with ether, successively, and dried in vacuo. Another crop was obtained from the combined filtrates, which were washed two times with ether and concentrated under reduced pressure.

Total yield: 91 mg (79%) of a beige powder, m.p. 132–134° C.

Example 56

Preparation of rac-3-(6-(N-(4-(Aminoiminomethyl)benzoyl)amino)-3,4-dihydro-2-methyl-2H-1-benzopyran-2-yl)propanoic Acid, a Compound Represented by the Formula (258)

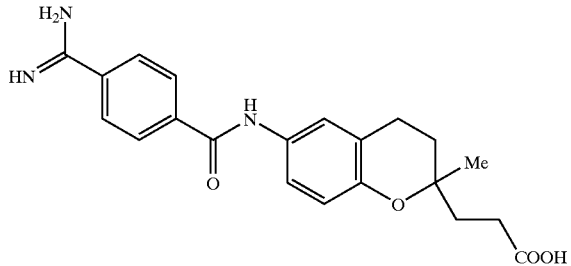

(258)

0.4 g (0.9 mmol) of the ester from Example 50 were added to a mixture of 8 ml ethanol and 0.5 ml 2 N aqueous sodium hydroxide. It was stirred overnight at room temperature, diluted with 10 ml water, and brought to pH 4 with acetic acid. The title compound precipitated from the solution. It was filtered, washed with water, and dried in vacuo.

Yield: 280 mg (82%) of a colorless amorphous powder, m.p. 278–280° C. (dec.).

Example 57

Preparation of Ethyl rac-(3, 4-Dihydro-6-(N-(4-((methylamino)iminomethyl)benzoyl)amino)-2H-1-benzopyran-2-yl)acetate Hydrochloride, a Compound Represented by the Formula (260)

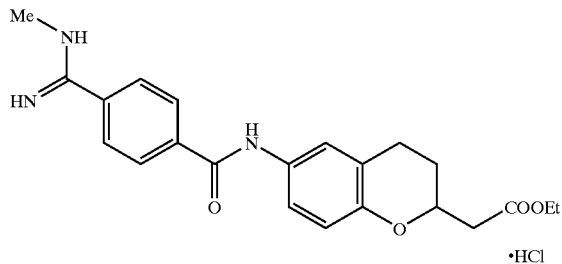

(260)

Step A: Preparation of Ethyl rac-(3,4-Dihydro-6-(N-(4-(ethoxycarbonimidoyl)benzoyl)amino)-2H-1-benzopyran-2-yl)acetate Hydrochloride, an Intermediate Represented by the Formula (261):

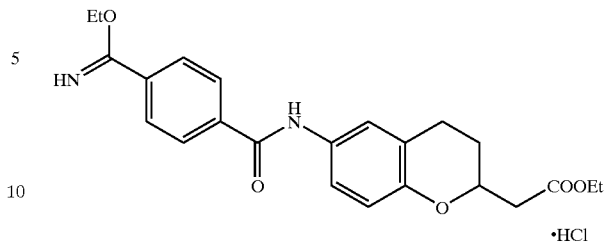

(261)

2.0 g (5.5 mmol) of the nitrile from Example 47, Step E were dissolved in 65 ml dry ethanol. The solution was cooled with ice and saturated with gaseous hydrogen chloride. It was stirred overnight at room temperature and concentrated under reduced pressure to give the intermediate as a crystalline solid, which was used for the next step.

Yield: 2.4 g (98%).

Step B: Preparation of ethyl rac-(3,4-dihydro-6-(N-(4-((methylamino)iminomethyl)benzoyl)amino)-2H-1-benzopyran-2-yl)acetate Hydrochloride 1.35 g (3.0 mmol) of the crude intermediate from the previous Step in 50 ml dry ethanol were cooled with ice. It was neutralized with a 30% ethanolic solution of methylamine followed by 2 hours stirring. Another 5 ml of the methylamine solution were added, and stirring was continued for 6 hours, while the temperature was maintained below 5° C. A clear solution was obtained, which was concentrated under reduced pressure. The title compound crystallized upon treating of the residue with ethanol, and was purified by heating of an ethanolic suspension.

Yield: 0.9 g (69%) of a yellow amorphous solid, m.p. 278–279° C.

Example 58

Preparation of rac-(3,4-Dihydro-6-(N-(4-((methylamino)iminomethyl)benzoyl)amino)-2H-1-benzopyran-2-yl)acetic Acid, a Compound Represented by the Formula (262)

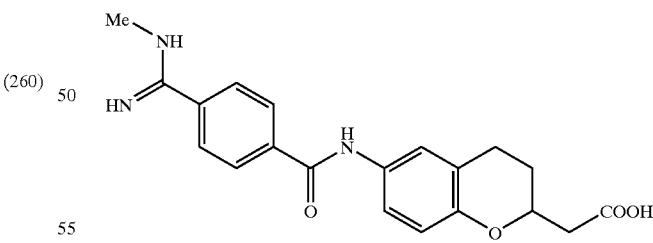

(262)

To 207 mg (0.48 mmol) of the ester from Example 57 were given 4 ml ethanol, 0.5 ml 2 N aqueous sodium hydroxide, and three drops of water, and the mixture was stirred overnight at room temperature. A precipitate was formed. It was brought to pH 5 with 2 N acetic acid, and the title compound was filtered with suction, washed with water and with ethanol, successively, and dried in vacuo.

Yield: 0.12 g (68%) of a pale yellow powder, m.p. 275–276° C. (dec.).

Example 59

Preparation of Ethyl rac-(6-(N-(4-((Benzoylamino)iminomethyl)benzoyl)amino)-3,4-dihydro-2H-1-benzopyran-2-yl)acetate, a Compound Represented by the Formula (263)

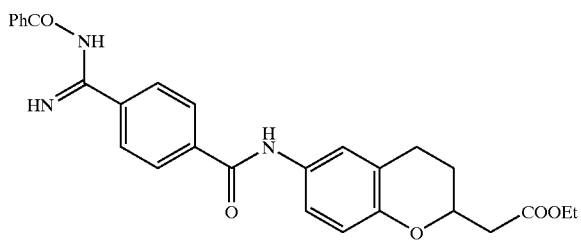

(263)

A solution of 0.42 g (1.0 mmol) of the ester from Example 47, 0.22 g triethylamine, and 20 mg 4-dimethylaminopyridine in 20 ml dry dichloromethane was cooled to −20° C., and a solution of 0.15 g (1.1 mmol) benzoyl chloride in 2 ml dichloromethane was added dropwise at this temperature. The mixture became clear by slow warming to room temperature, and stirring was continued for 3 hours. After addition of water it was extracted with ethyl acetate. The organic layer was dried over sodium sulfate and concentrated under reduced pressure. The title benzoate was obtained by chromatography on silica gel with dichloromethane/ethanol 96:4 as an oil. A crystalline sample for analytical and biological tests was obtained by stirring with ether.

Yield: 0.21 g (43%) of a beige powder, m.p. 149–150° C. (dec.).

Example 60

Preparation of rac-9-(6-Aminoiminomethyl-2-methyl-2H-1-benzopyran-2-yl)nonanoic Acid, a Compound Represented by the Formula (264)

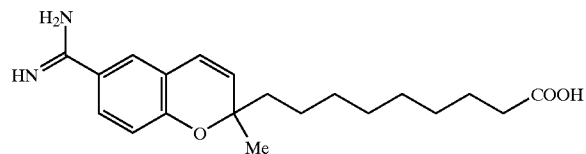

(264)

Step A: Preparation of Ethyl rac-9-(6-Cyano-3,4-dihydro-2-methyl-4-oxo-2H-1-benzopyran-2-yl)nonanoate, an Intermediate Represented by the Formula (265):

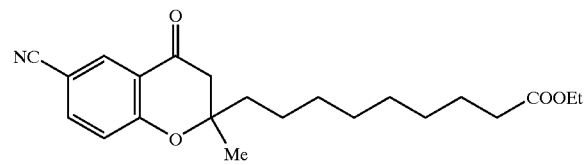

(265)

5-Cyano-2-hydroxyacetophenone was prepared by rearrangement of 4-acetoxybenzonitrile (Arch. Pharm. 1977, 310, 119, the disclosure of which is incorporated herein by reference) and ethyl 10-oxoundecanoate by PdCl$_2$-catalyzed oxidation of ethyl 10-undecenoate (J. Organomet. Chem. 1987, 334, C 5, the disclosure of which is incorporated herein by reference). 32.4 g (201 mmol) of the acetophenone, 35.0 g (153.3 mmol) of the ester, and 7 ml pyrrolidine were dissolved in 160 ml toluene. After standing at room temperature for 1 hour it was heated with azeotropic removal of water for 8 hours. The solvent was removed in vacuo, and the residue was dissolved in dichloromethane. It was washed with water, and the aqueous layer was extracted with dichloromethane. The combined organic layers were dried over sodium sulfate and concentrated under reduced pressure. The title chromanone was obtained by chromatography on silica gel with dichloromethane.

Yield: 12.6 g (22%) of an oil.

Step B: Preparation of Ethyl 9-(6-Cyano-3,4-dihydro-4-hydroxy-2-methyl-2H-1-benzopyran-2-yl)nonanoate, an Intermediate Represented by the Formula (266):

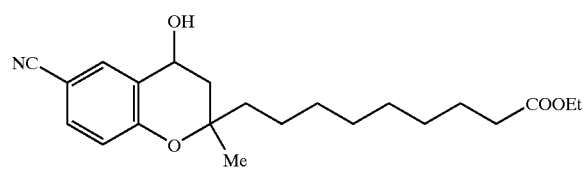

(266)

12.6 g (33.9 mmol) of the chromanone from Step A were dissolved in 300 ml dry ethanol. 2.6 g (68.7 mmol) sodium borohydride were added in small portions, while the temperature was kept below 25° C. It was stirred overnight, concentrated in vacuo, hydrolyzed with a mixture of ice and aqueous hydrogen chloride, and extracted with dichloromethane for three times. The combined organic layers were dried over sodium sulfate and concentrated under reduced pressure. The title benzopyran was obtained by chromatography on silica gel with dichloromethane.

Yield: 11.2 g (88%) of an oil.

Step C: Preparation of Ethyl rac-9-(6-Cyano-2-methyl-2H-1-benzopyran-2-yl)nonanoate, an Intermediate Represented by the Formula (267)

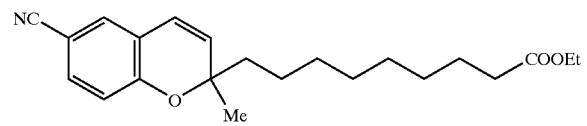

(267)

11.2 g (30.0 mmol) of the compound from Step B were dissolved in 200 ml toluene. A catalytic amount of p-toluenesulfonic acid was added, and it was heated with azeotropic removal of water for 7 hours. The mixture was washed with saturated aqueous sodium bicarbonate solution, dried over sodium sulfate, and concentrated under reduced pressure. The title benzopyran was purified by chromatography on silica gel with dichloromethane.

Yield: 3.0 g (28%) of an oil.

Step D: Preparation of Ethyl rac-9-(6-aminoiminomethyl-2-methyl-2H-1-benzopyran-2-yl)nonanoate hydrochloride, an Intermediate Represented by the Formula (268):

(268)

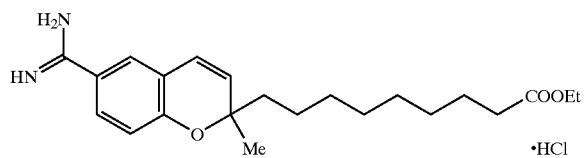

1.5 g (4.2 mmol) of the chromene from the previous Step were dissolved in 50 ml dry ethanol. The solution was saturated with hydrogen chloride and stirred overnight at room temperature. The solvent was removed in vacuo, and the residue was treated with a saturated solution of ammonia in ethanol. It was stirred overnight and concentrated to dryness under reduced pressure to give the pure title amidine.

Yield: 1.4 g (81%) of an oil.

Step E: Preparation of rac-9-(6-Aminoiminomethyl-2-methyl-2H-1-benzopyran-2-yl)nonanoic Acid 7 ml 2 N aqueous sodium hydroxide and 5 ml acetonitrile were added to 0.6 g (1.47 mmol) of the ester from the previous Step, and the mixture was heated for 30 minutes on a steam bath. It was brought to pH 7 with 2 N acetic acid, while a precipitate formed. It was filtered with suction, washed successively with ice-water and acetone, and dried in vacuo.

Yield: 0.4 g (79%) of a white powder, m.p. 223–225° C. (dec.).

Example 61

Preparation of rac-(3,4-Dihydro-6-(2-(piperidin-4-yl)ethoxy)-2H-1-benzopyran-2-yl)acetic Acid Trifluoroacetate, a Compound Represented by the Formula (269)

(269)

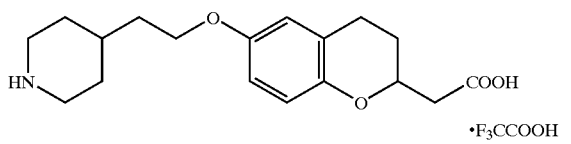

·F₃CCOOH

Step A: Preparation of Ethyl rac-(6-(2-(1-(tert.-Butoxycarbonyl)piperidin-4-yl)ethoxy)-3,4-dihydro-2H-1-benzopyran-2-yl)acetate, an Intermediate Represented by the Formula (270):

(270)

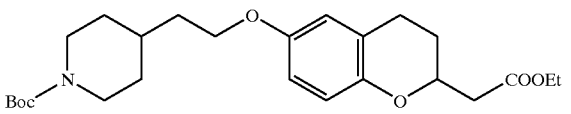

To a solution of 2.2 g (7.5 mmol) 4-(2-bromoethyl)-1-(tert.-butoxycarbonyl)piperidine (prepared by bromination of 2-(1-(tert.-butoxycarbonyl)piperidin-4-yl)ethanol according to Eur. Pat. Appl. EP 478 328) in 50 ml dry acetonitrile were added 2.84 g (8.72 mmol) dry cesium carbonate. After dropwise addition of a solution of 3.05 g (12.9 mmol) ethyl rac-(3,4-dihydro-6-hydroxy-2H-1-benzopyran-2-yl)acetate (prepared according to Eur. Pat. Appl. EP 129 906) in 20 ml dry acetonitrile it was stirred over night at room temperature. Another 1 g cesium carbonate was added and stirring was continued for 2 hours at 70° C. and overnight at room temperature. The mixture was filtered through Celite, which was washed with acetonitrile and acetone. The filtrate was concentrated under reduced pressure, and the residue was stirred with hexane/ethyl acetate 4:1 and two times with ethyl acetate, successively. The combined solutions, which had been separated from insoluble material, were concentrated in vacuo, and the compound (270) was obtained by chromatography on silica gel with hexane followed by hexane/ethyl acetate 4:1.

Yield: 2.9 g (86%) of a yellow oil, which solidified upon standing.

Step B: Preparation of rac-(6-(2-(1-(tert.-Butoxycarbonyl)piperidin-4-yl)ethoxy)-3,4-dihydro-2H-1-benzopyran-2-yl)acetic Acid, an Intermediate Represented by the Formula (271)

(271)

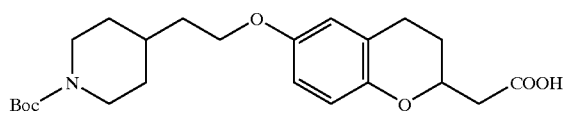

To a solution of 1.5 g (3.35 mmol) of the ester from the previous step in 100 ml ethanol were added 6.8 ml 2 N aqueous sodium hydroxide, and the mixture was stirred overnight at room temperature. It was adjusted to pH 5 with diluted acetic acid and concentrated under reduced pressure. The title acid was obtained by chromatography on silica gel with dichloromethane followed by addition of up to 3% ethanol.

Yield: 0.54 g (38%) of a beige oil.

Step C: Preparation of rac-(3,4-Dihydro-6-(2-(piperidin-4-yl)ethoxy)-2H-1-benzopyran-2-yl)acetic Acid Trifluoroacetate 117 mg (0.28 mmol) of the protected piperidine from Step B were stirred in 2.3 ml trifluoroacetic acid at room temperature for 30 minutes, and it was concentrated to dryness in vacuo to leave the pure title compound.

Yield: 115 mg (95%) of a brown resin.

Example 62

Preparation of Ethyl rac-(6-(N-(4-Aminoiminomethyl-2-chlorobenzoyl)amino)-1-oxo-1,2,3,4-tetrahydronaphthalen-2-yl)acetate Hydrochloride, a Compound Represented by Formula (278)

(278)

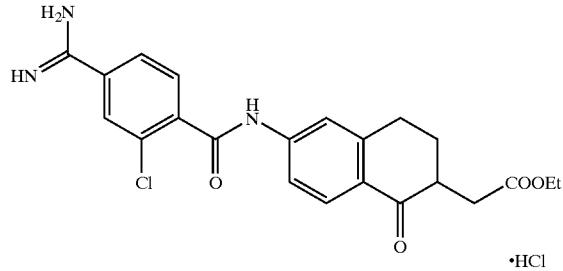

·HCl

Step A: Preparation of Ethyl rac-(6-(N-(2-chloro-4-cyanobenzoyl)amino)-1-oxo-1,2,3,4-tetrahydronaphthalen-2-yl)acetate, an Intermediate Represented by the Formula (280):

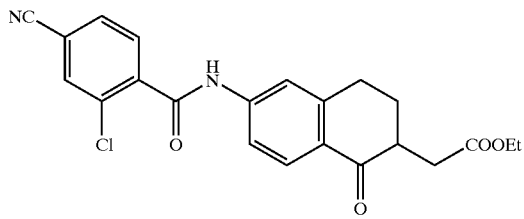

(280)

5.7 g (31.4 mmol) of 2-chloro-4-cyano-benzoic acid, which was prepared by oxidation of 3-chloro-4-methyl-benzonitrile (according to Chem. Ber. 1936, 69, 537, the disclosure of which is incorporated herein by reference), were dissolved in 300 ml toluene, and 10.25 g (86.2 mmol) thionyl chloride were added. After 4 hours heating with reflux the same amount of thionyl chloride was added and heating was continued overnight. The solvent was removed under reduced pressure, the residue dissolved in 100 ml toluene, and again it was concentrated in vacuo to leave the crude acid chloride as a yellow oil.

Yield: 4.1 g (65%).

A solution of 0.98 g (3.96 mmol) of the tetralone 98 and 3.3 ml dry pyridine in 33 ml dry THF was cooled with ice, and a solution of 1.0 g (5.0 mmol) of the crude 2-chloro-4-cyano-benzoyl chloride in 33 ml dry THF was added dropwise. The mixture was warmed slowly to room temperature, stirred over night, and poured into ice-cold water. The mixture was extracted with ethyl acetate, and the organic layer was washed with saturated aqueous sodium bicarbonate and with brine, successively, and dried over sodium sulfate. The product was concentrated under reduced pressure, and the residue was stirred with hexane to give the crystalline nitrile (280), which was filtered and dried in vacuo at 50° C.

Yield: 1.5 g (92%) of beige crystalline solid, m.p. 173–175° C.

Step B: Preparation of Ethyl rac-(6-(N-(2-Chloro-4-(ethoxycarbonimidoyl)benzoyl)amino)-1-oxo-1,2,3,4-tetrahydronaphthalen-2-yl)acetate Hydrochloride, an Intermediate Represented by the Formula (281):

(281)

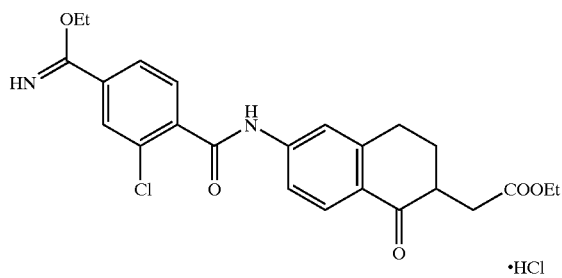

·HCl 1.35 g (3.3 mmol) of the nitrile from Step A were suspended in 50 ml dry ethanol, and the temperature of the mixture was kept below 5° C., while it was stirred and saturated with hydrogen chloride (approx. 6 hours). After standing overnight a stream of hydrogen was passed for additional 3 hours. It was concentrated to dryness under reduced pressure, and the residue was stirred with hexane to give the crystalline title compound, which was filtered and dried in vacuo.

Yield: 1.3 g (80%) of beige crystalline solid, m.p. 234–235° C.

Step C: Preparation of ethyl rac-(6-(N-(4-aminoiminomethyl-2-chlorobenzoyl)amino)-1-oxo-1,2,3,4-tetrahydronaphthalen-2-yl)acetate hydrochloride 1.2 g (2.43 mmol) of the compound from the previous Step were given to 50 ml of a cooled saturated solution of ammonia in ethanol. After stirring overnight at room temperature another 20 ml of the ethanolic solution were added and stirring was continued for the same period. Solids were removed by filtration, and the filtrate was concentrated under reduced pressure. The residue was stirred with hexane to give the crude crystalline title compound, which was purified by chromatography on silica gel with chloroform/methanol 8:1.

Yield: 0.2 g (18%) of a beige crystalline powder, m.p. 225–226° C.

Example 63

Preparation of rac-(6-(N-(4-Aminoiminomethyl-2-chlorobenzoyl)amino)-1-oxo-1,2,3,4-tetrahydronaphthalen-2-yl)acetic Acid, a Compound Represented by the Formula (282)

(282)

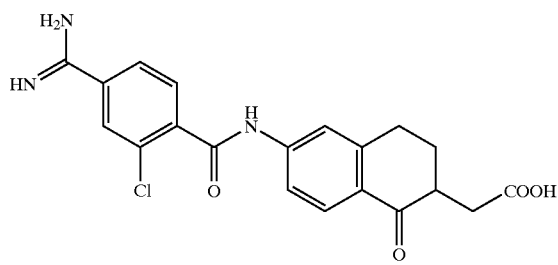

0.2 g (0.43 mmol) of the ester from Example 62 in a mixture of 5 ml ethanol and 0.7 ml 2 N aqueous sodium hydroxide were stirred at room temperature overnight. The reaction mixture was brought to pH 4 with 2 N acetic acid, and the precipitate was filtered with suction, washed with water and acetone, successively, and dried in vacuo.

Yield: 0.13 g (75%) of a white powder, m.p. 240–242° C. (dec.).

Example 64

Preparation of Ethyl rac-(6-(N-(4-((Aminoiminomethyl)amino)benzoyl)amino)-3,4-dihydro-2H-1-benzopyran-2-yl)acetate, an Compound Represented by the Formula (283)

(283)

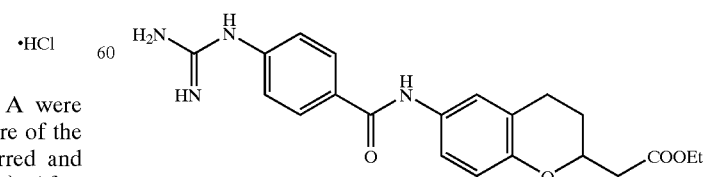

4-Guanidinobenzoic acid hydrochloride was prepared from 4-aminobenzoic acid according to a literature procedure (Recl. Trav. Chim. Pays-Bas 1953, 72, 643, the disclosure of which is incorporated herein by reference). It was heated in thionyl chloride for one hour followed by concentration to dryness to give the crude benzoyl chloride hydrochloride. 0.62 g (1.85 mmol) of the compound from Example 47, Step D were stirred for 1 hour at room temperature in 2 ml trifluoroacetic acid, and the mixture was concentrated to dryness in vacuo. The mixture was treated with saturated aqueous sodium bicarbonate solution and extracted with ethyl acetate. The organic layer was dried over sodium sulfate and concentrated under reduced pressure, and the oily residue was dissolved in 20 ml dry pyridine followed by addition of 0.44 g (1.88 mmol) crude 4-guanidinobenzoyl chloride hydrochloride. After stirring overnight at room temperature the mixture was poured into 100 ml water, while a precipitate was formed, which was collected by filtration, washed with water, and dried in vacuo. The title compound was purified by chromatography on silica gel with ethanol/concentrated aqueous ammonia 85:15.

Yield: 0.15 g (20%) of a brown amorphous solid

Example 65

Preparation of rac-(6-(N-(4-((Aminoiminomethyl)amino)benzoyl)amino)-3,4-dihydro-2H-1-benzopyran-2-yl)acetic Acid, a Compound Represented by the Formula (284)

(284)

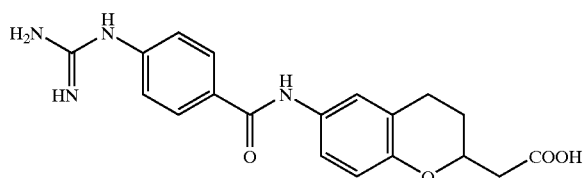

0.08 g (0.2 mmol) of the ester from Example 64 were dissolved in 30 ml ethanol followed by addition of 0.4 ml aqueous 2 N sodium hydroxide solution. The mixture was stirred at room temperature for two days, and the mixture was concentrated to dryness under reduced pressure. The residue was dissolved in water, and the solution was neutralized with acetic acid, while the title acid precipitated. It was filtered with suction, washed with water, and dried in vacuo.

Yield: 0.045 g (61%) of a beige crystalline solid, m.p. 258–260° C.

Example 66

Ethyl rac-3-(6-(4-(Aminoiminomethyl)phenylmethoxy)-3,4-dihydro-2-methyl-4-oxo-2H-1-benzopyran-2-yl)propanoate Hydrochloride, a Compound Represented by the Formula (299)

(299)

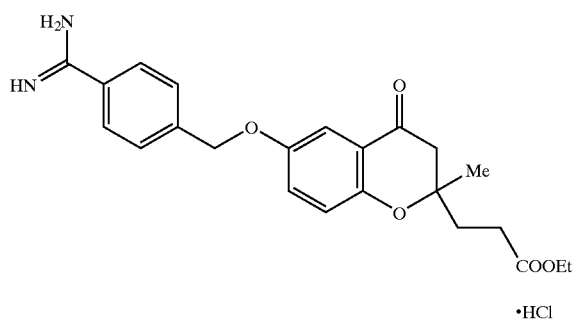

Example 67 rac-3-(6-(4-(Aminoiminomethyl)phenylmethoxy)-3,4-dihydro-2-methyl-4-oxo-2H-1-benzopyran-2-yl)propanoic Acid Hydrochloride, a Compound Represented by the Formula (300)

(300)

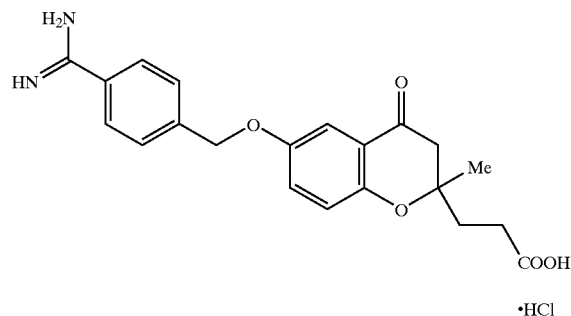

Example 68

Preparation of Ethyl rac-(3,4-Dihydro-6-(N-(4-((ethoxycarbonylamino)iminomethyl)benzoyl)amino)-2H-1-benzopyran-2-yl)acetate, a Compound Represented by the Formula (303)

(303)

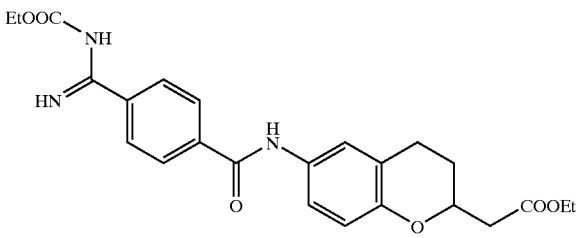

418 mg (1 mmol) of the benzopyran from Example 47, 0.3 ml triethylamine, and 20 mg 4-dimethylaminopyridine were dissolved in 20 ml dry dichloromethane, and the solution was cooled to −20° C. 119 mg (1.1 mmol). Ethyl chloroformate in 2 ml dry dichloromethane was added dropwise at this temperature, and after 30 min it was warmed to room temperature and stirred for additional 2 hours. The mixture was poured into ice-cold water, and the organic layer was dried over sodium sulfate and concentrated under reduced pressure. The remaining crystalline title compound was stirred with ether, filtered, and dried in vacuo.

Yield: 360 mg (79%) of a pale yellow solid, m.p. 163–165° C.

Example 69

Preparation of Ethyl rac-(6-(N-(4-(Aminoiminomethyl)-2-fluorobenzoyl)amino)-3,4-dihydro-2H-1-benzopyran-2-yl)acetate Hydrochloride, a Compound Represented by the Formula (304)

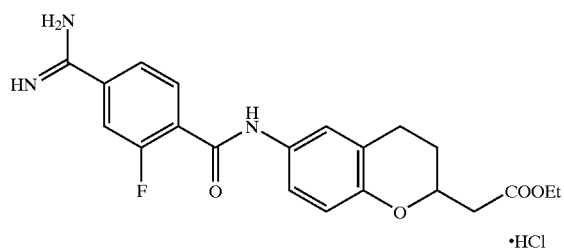

Step A: Preparation of Ethyl rac-(6-(N-(4-cyano-2-fluorobenzoyl)amino)-3,4-dihydro-2H-1-benzopyran-2-yl)acetate, an Intermediate Represented by the Formula (307):

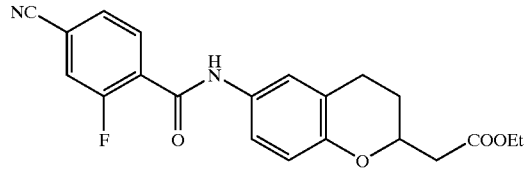

5.0 g (30.3 mmol) of the acid 119 were heated for 1 hour with reflux in 50 ml thionyl chloride containing one drop of DMF. The reaction mixture was concentrated under reduced pressure, and the crude acid chloride was dissolved in 130 ml dry THF. This solution was added dropwise at 0° C. to crude ethyl (6-amino-3,4-dihydro-2H-1-benzopyran-2-yl)acetate in 200 ml dry THF and 20 ml dry pyridine, which had been obtained according to Example 47, Step E from 10.0 g (29.8 mmol) of the protected derivative with 20 ml trifluoroacetic acid. After stirring overnight at room temperature the mixture was poured into ice-cold water containing sodium bicarbonate. The precipitate of the title nitrile was filtered with suction, heated for some minutes in ethanol, filtered again after cooling, and the crystals were washed with hexane and dried in vacuo.

Yield: 8.6 g (75%) of a beige amorphous solid, m.p. 154–155° C.

Step B: Preparation of Ethyl rac-(6-(N-(4-(Aminoiminomethyl)-2-fluorobenzoyl)amino)-3,4-dihydro-2H-1-benzopyran-2-yl)acetate Hydrochloride 4.5 g (11.8 mmol) of the nitrile from the previous Step in 150 ml dry ethanol were cooled to 0° C. and saturated with gaseous hydrogen chloride. After stirring overnight at room temperature it was concentrated under reduced pressure. The crystalline residue was treated with 150 ml of a saturated ethanolic solution of ammonia and stirred again overnight. The crude title compound was obtained after concentration in vacuo, recrystallized from ethanol followed by crystallization from a mixture of ethanol/water/ether.

Yield: 3.0 g (58%) of a pale yellow powder, m.p. 198–200° C.

Example 70

Preparation of rac-(6-(N-(4-(Aminoiminomethyl)-2-fluorobenzoyl)amino)-3,4-dihydro-2H-1-benzopyran-2-yl)acetic Acid, a Compound Represented by the Formula (308)

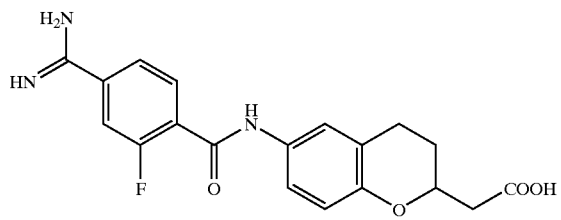

1.2 g (2.75 mmol) of the ester from Example 69 were stirred overnight at room temperature in a mixture of 20 ml ethanol and 5 ml 2 N aqueous sodium hydroxide solution. It was brought to pH 4 with 2 N acetic acid, and the precipitate of the title compound was filtered with suction, washed successively with water and with acetone, and dried in vacuo at 50° C.

Yield: 0.84 g (82%) of a pale yellow powder, m.p. 250° C.

Example 71

Preparation of Ethyl rac-(3,4-Dihydro-6-(N-(4-((Ethylamino)iminomethyl)benzoyl)amino)-2H-1-benzopyran-2-yl)acetate Hydrochloride, a Compound Represented by the Formula (309)

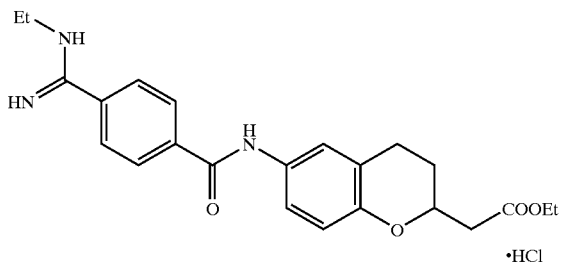

1.8 g (4.0 mmol) of the crude intermediate of Example 57, Step A were dissolved in 50 ml ethanol. The solution was cooled with ice, and 2 ml of a 50% ethanolic solution of ethylamine were added. It was stirred overnight at room temperature, and the solvent was removed under reduced pressure. The residue was stirred with a small amount of ethanol to give the pure crystalline title compound, which was filtered and dried in vacuo.

Yield: 1.6 g (89%) of a pale yellow powder, m.p. 290–291° C.

Example 72

Preparation of rac-(3,4-Dihydro-6-(N-(4-((ethylamino)iminomethyl)benzoyl)amino)-2H-1-benzopyran-2-yl)acetic Acid, a Compound Represented by the Formula (310)

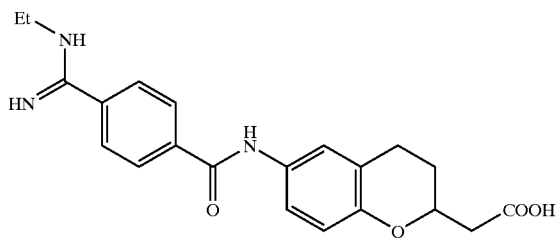

(310)

0.8 g (1.8 mmol) of the ester from Example 71 were suspended in a mixture of 16 ml ethanol, 2 ml 2 N aqueous sodium hydroxide, and some drops of water. It was stirred overnight at room temperature, while the suspension became a solution, which was brought to pH 5 with 2 N acetic acid. The precipitate of the pure title compound was collected by filtration, washed successively with water and acetone, and dried in vacuo.

Yield: 0.65 g (95%) of a yellow powder, m.p. 260–262° C. (dec.).

Example 73

Preparation of Ethyl rac-(3,4-Dihydro-6-(N-(4-((dimethylamino)iminomethyl)benzoyl)amino)-2H-1-benzopyran-2-yl)acetate Hydrochloride, a Compound Represented by the Formula (311)

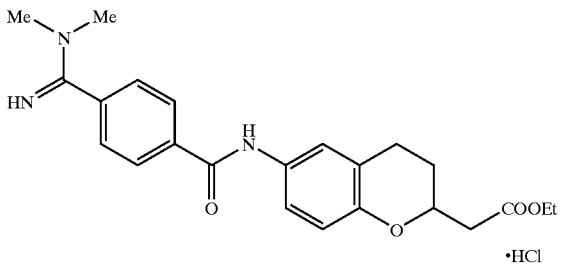

(311)

1.8 g (4.0 mmol) of the crude intermediate of Example 57, Step A were dissolved in 50 ml ethanol. The solution was cooled with ice, and 2 ml of a 50% ethanolic solution of dimethylamine were added. It was stirred overnight at room temperature, and the solvent was removed under reduced pressure. The residue was stirred with a small amount of ethanol to give the pure crystalline title compound, which was filtered and dried in vacuo.

Yield: 1.35 g (75%) of a white powder, m.p. 248° C.

Example 74

Preparation of Ethyl rac-(3,4-Dihydro-6-(N-(4-((methoxycarbonylamino)iminomethyl)benzoyl)amino)-2H-1-benzopyran-2-yl)acetate, a Compound Represented by the Formula (312)

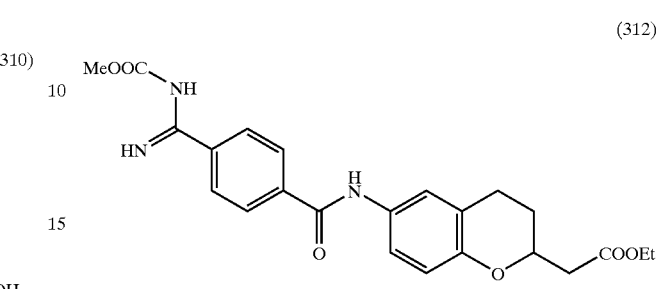

(312)

To 417 mg (1.0 mmol) of the amidine from Example 47, 0.3 ml triethylamine, and 20 mg 4-dimethylaminopyridine in 40 ml dichloromethane were added at 0° C. 104 mg (1.1 mmol) methyl chloroformate, and the mixture was stirred overnight at room temperature. A white precipitate was formed, which was collected by filtration and chromatographed on silica gel with dichloromethane/ethanol 9:1 to give the pure title carbamate.

Yield: 0.21 g (48%) of a white powder, m.p. 204–206° C.

Example 75

Preparation of Ethyl rac-(6-(N-(4-(Aminoiminomethyl)-2-chlorobenzoyl) amino) -3,4-dihydro-2H-1-benzopyran-2-yl) acetate Hydrochloride, a Compound Represented by the Formula (313)

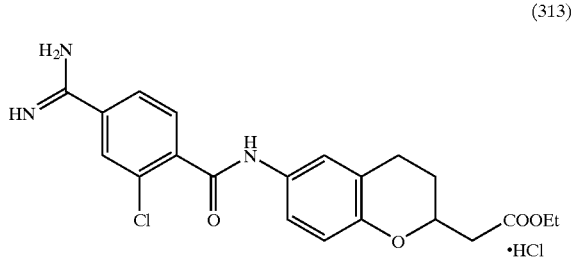

(313)

Step A: Preparation of Ethyl rac-(6-(N-(2-chloro-4-cyanobenzoyl)amino)-3,4-dihydro-2H-1-benzopyran-2-yl) acetate, an Intermediate Represented by the Formula (314)

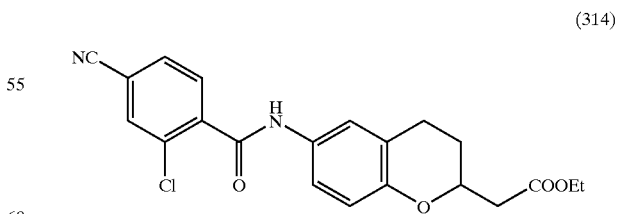

(314)

3.0 g (8.94 mmol) of the benzopyran from Example 47, Step D were stirred with 6 ml trifluoroacetic acid for 2 hours at room temperature. The mixture was treated with saturated aqueous sodium bicarbonate solution and extracted with ethyl acetate. The organic layer was dried over sodium sulfate, and the solvent was removed in vacuo to give the crude unprotected aminobenzopyran, which was dissolved in a mixture of 50 ml dry THF and 8 ml dry pyridine. 50 ml of a solution of crude 2-chloro-4-cyanobenzoyl chloride in dry THF, which had been prepared from 1.1 g (6.1 mmol) 2-chloro-4-cyanobenzoic acid (Chem. Ber. 1936, 69, 537, the disclosure of which is incorporated herein by reference) according to Example 62, Step A, was added dropwise at 0° C. After stirring overnight at room temperature the mixture was poured into ice-cold water containing sodium bicarbonate. It was extracted with ethyl acetate, and the organic layer was washed successively with aqueous Cu(II) sulfate solution and with brine, dried over sodium sulfate, and concentrated under reduced pressure. The nitrile (314) was obtained from the residue by chromatography on silica gel with chloroform/methanol 96:4. It crystallized from the pure fractions after stirring with a small amount of ethanol.

Yield: 1.1 g (46%) of beige crystals, m.p. 152–154° C.

Step B: Preparation of Ethyl rac-(6-(N-(4-(Aminoiminomethyl)-2-chlorobenzoyl)amino)-3,4-dihydro-2H-1-benzopyran-2-yl)acetate Hydrochloride:

1.1 g (2.76 mmol) of the nitrile from the previous Step were dissolved in 25 ml ethanol, and the solution was cooled to 0° C. and saturated with gaseous hydrogen chloride. It was stirred overnight at room temperature followed by concentration under reduced pressure. The residue was treated with 20 ml of a saturated solution of ammonia in ethanol, and again it was stirred overnight. After removal of the solvent in vacuo the remaining title compound was recrystallized from ethanol/water/ether.

Yield: 0.9 g (72%) of a pale yellow powder, m.p. 225–226° C.

Example 76

Preparation of rac-(6-(N-(4-(Aminoiminomethyl)-2-chlorobenzoyl)amino)-3,4-dihydro-2H-1-benzopyran-2-yl)acetic Acid, a Compound Represented by the Formula (314)

(314)

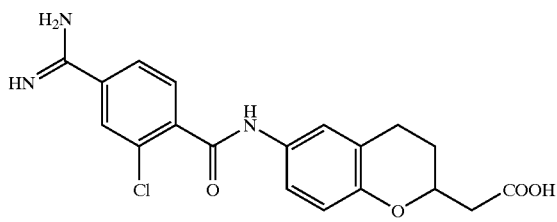

0.3 g (0.66 mmol) of the ester from Example 75 were stirred overnight at room temperature with a mixture of 5 ml ethanol and 0.5 ml 2 N aqueous sodium hydroxide solution. It was brought to pH 5 with 2 N acetic acid. The precipitate of the title compound was filtered with suction, washed successively with water and with acetone, and dried in vacuo.

Yield: 0.19 g (74%) of a white powder, m.p. 269–270° C.(dec.).

Example 77

Preparation of Ethyl rac-(3,4-Dihydro-6-(N-(3-(piperidine-4-yl)propenoyl)amino)-2H-1-benzopyran-2-yl)acetate Trifluoroacetate, a Compound Represented by the Formula (327)

(327)

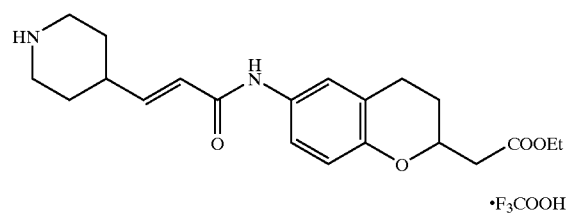

•F₃COOH

Step A: Preparation of Ethyl rac-(6-(N-(3-(1-(tert.-butoxycarbonyl)piperidine-4-yl)propenoyl)amino)-3,4-dihydro-2H-1-benzopyran-2-yl)acetate, an Intermediate Represented by the Formula (329):

(329)

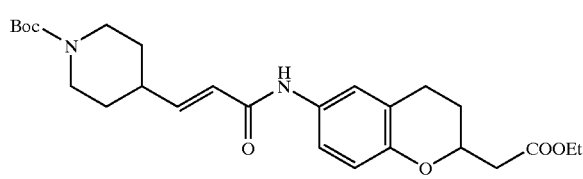

0.85 g (3.33 mmol) of the acid 386 were dissolved in a mixture of 23 ml dry dichloromethane and 0.26 ml dry DMF. The solution was kept at a temperature between –10° C. and 0° C., while 0.46 g (3.6 mmol) oxalyl chloride were added slowly. After stirring for 40 minutes at this temperature the mixture was added dropwise to a solution of 0.5 ml triethylamine and crude ethyl (6-amino-3,4-dihydro-2H-1-benzopyran-2-yl)acetate (prepared with trifluoroacetic acid from 1.5 g (4.5 mmol) of the Boc-protected amine as described in Example 47) in 35 ml dry dichloromethane. After stirring for 90 minutes at this temperature the mixture was poured into ice-cold water, and the aqueous layer was extracted with dichloromethane. The combined organic layers were washed with water, dried over sodium sulfate, and concentrated under reduced pressure. The title compound was purified by chromatography on silica gel with dichloromethane/ethanol 80:1.

Yield: 0.81 g (51%) of an oil.

Step B: Preparation of Ethyl rac-(3,4-Dihydro-6-(N-(3-(piperidine-4-yl)propenoyl)amino)-2H-1-benzopyran-2-yl)acetate Trifluoroacetate 0.81 g (1.71 mmol) of the protected piperidine from the previous Step were stirred for 2 hours at room temperature in 6 ml trifluoroacetic acid. It was poured into ice-cold water, adjusted to pH 7 with sodium bicarbonate, and extracted with dichloromethane. The organic layer was dried over sodium sulfate and concentrated under reduced pressure, and the residue was stirred with a mixture of hexane and ether to give the crystalline title compound, which was collected by filtration, and dried at 50° C. in vacuo.

Yield: 0.18 g (22%) of reddish crystals, m.p. 72–73° C.

Example 78

Preparation of rac-(3,4-Dihydro-6-(N-(3-(piperidine-4-yl)propenoyl)amino)-2H-1-benzopyran-2-yl)acetic Acid, a Compound Represented by the Formula (330)

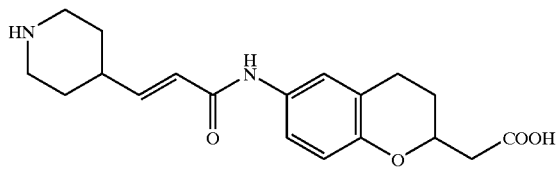

(330)

0.1 g (0.2 mmol) of the ester from Example 77 were stirred overnight at room temperature in a mixture 2.5 ml ethanol and 0.35 ml 2 N aqueous sodium hydroxide solution. The reaction mixture was cooled with ice and brought to pH 5.5 with 2 N acetic acid. The precipitate of the title acid was filtered with suction, washed with a small amount of cold water, and dried at 50° C. in vacuo.

Yield: 42 mg (59%) of beige crystals, m.p. 175–178° C.

Example 79

Preparation of Ethyl rac-(6-(N-(4-(Aminoiminomethyl)benzoyl)amino)-3,4-dihydro-4,4-dimethyl-2H-1-benzopyran-2-yl)acetate Hydrochloride, a Compound Represented by the Formula (331)

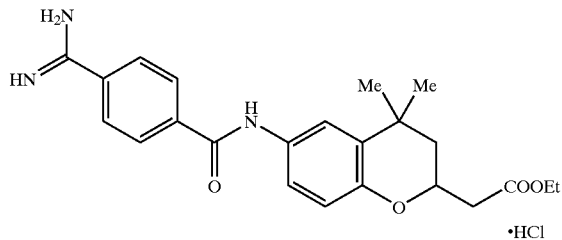

(331)

Step A: Preparation of tert.-butyl (3,4-dihydro-4,4-dimethyl-2-oxo-2H-1-benzopyran-6-yl)carbamate, an Intermediate Represented by the Formula (332):

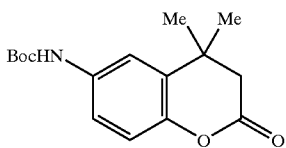

(332)

To a suspension of 1.5 g 10% Pd-C in 300 ml ethanol were added under an atmosphere of argon 29.2 g (132.0 mmol) 3,4-dihydro-4,4-dimethyl-6-nitro-2-oxo-2H-1-benzopyran (prepared by nitration of 3,4-dihydro-4,4-dimethyl-2-oxo-2H-1-benzopyran according to J. Am. Chem. Soc. 1970, 92, 4377, the disclosure of which is incorporated herein by reference) and 21.4 g (339.4 mmol) ammonium formate. The temperature raised for approximately 1 hour to 50° C. accompanied by a gas evolution, and it was heated for additional 3 hours at 80° C. The catalyst was filtered through Celite, which was washed with 500 ml hot ethanol. The combined filtrates were concentrated under reduced pressure to a volume of 100 ml, and the formed precipitate was filtered with suction. A second crop of the crude 6-amino-3,4-dihydro-4,4-dimethyl-2-oxo-2H-1-benzopyran was obtained after further concentration. Both crops were combined and dissolved in 80 ml THF followed by addition of 80 ml water, 25.3 g (183 mmol) potassium carbonate, and 29.2 g (133.8 mmol) Boc$_2$O. After 8 hours stirring at room temperature another 2.9 g Boc$_2$O and 2.5 g potassium carbonate were added, and stirring was continued overnight. The mixture was poured into 300 ml water and extracted with ethyl acetate, and the organic layer was dried over sodium sulfate and concentrated under reduced pressure. A first crop of the title compound crystallized from the oily residue with diisopropylether. An additional amount was obtained from the concentrated mother liquid by chromatography on silica gel with toluene crystallizing from the oily pure fractions with diisopropylether.

Total yield: 31.6 g (82%) of colorless crystals, m.p. 106–108° C.

Step B: Preparation of tert.-Butyl rac-(3,4-Dihydro-4,4-dimethyl-2-hydroxy-2H-1-benzopyran-6-yl)carbamate, an Intermediate Represented by the Formula (333):

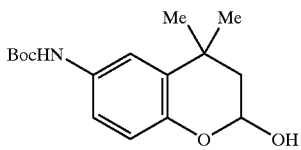

(333)

31.6 g (108.5 mmol) of the benzopyran from the previous Step were dissolved in 450 ml dry THF and cooled to –70° C. under an atmosphere of argon. At this temperature 133 ml of a 25% solution of DIBAH in toluene was added dropwise within 1 hour, and the mixture was stirred for additional 2 hours. It was quenched carefully with 35 ml methanol and warmed to room temperature, and the mixture was poured into 1000 ml saturated aqueous ammonium chloride solution. After vigorous stirring the upper organic layer solidified to a gel, which was separated and stirred with 1000 ml ethyl acetate. It was then filtered through Celite and washed with 500 ml ethyl acetate. The combined filtrates were dried over sodium sulfate and concentrated in vacuo to give a brown resin, from which the pure title acetal was obtained by chromatography on silica gel with toluene/acetone 95:5.

Yield: 25.9 g (81%) of a yellow resin

Step C: Preparation of Ethyl rac-(6-(N-tert.-Butoxycarbonylamino)-3,4-dihydro-4,4-dimethyl-2H-1-benzopyran-2-yl)acetate, an Intermediate Represented by the Formula (334):

(334)

To a solution of 25.9 g (88.3 mmol) of the compound from Step B in 150 ml toluene were added 32.4 g (93.0 mmol) of ethoxycarbonylmethylene triphenylphosphorane followed by 0.6 g (15 mmol) 60% sodium hydride in small portions. The mixture was heated at 120° C. for 3 hours, cooled to room temperature, and solids were removed by filtration. The filtrate was concentrated under reduced pressure, and the compound (334) was obtained by chromatography on silica gel with hexane/ethyl acetate 4:1 to 1:1.

Yield: 6.9 g (22%) of colorless crystals, m.p. 116–119° C.

Step D: Preparation of Ethyl rac-(6-(N-(4-Cyanobenzoyl) amino)-3,4-dihydro-4,4-dimethyl-2H-1-benzopyran-2-yl) acetate, an Intermediate Represented by the Formula (335):

(335)

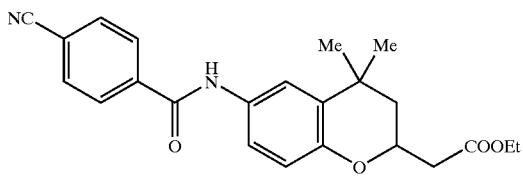

2.18 g (6.0 mmol) of the compound from the previous Step were deprotected by stirring in 10 ml trifluoroacetic acid as described in Example 47, Step E, and the brown oil of the crude 6-aminobenzopyran was dissolved in 40 ml dry pyridine. After addition of 0.99 g (6.0 mmol) 4-cyanobenzoyl chloride the mixture was stirred at room temperature overnight. It was concentrated to dryness in vacuo and dissolved three times in toluene followed by concentration under reduced pressure, in order to remove remaining pyridine. The title nitrile crystallized from the brown residue upon stirring with a small amount of ethanol. It was filtered with suction, washed with cold ethanol, and dried in vacuo.

Yield: 1.7 g (72%) of a white powder, m.p. 163–165° C.

Step E: Preparation of Ethyl rac-(6-(N-(4-(Aminoiminomethyl)benzoyl)amino)-3,4-dihydro-4,4-dimethyl-2H-1-benzopyran-2-yl)acetate Hydrochloride A suspension of 1.7 g (4.33 mmol) of the nitrile from Step D in 100 ml dry ethanol was cooled with ice and saturated with gaseous hydrogen chloride. After standing overnight at room temperature it was concentrated to dryness under reduced pressure, and the residue was dissolved in 50 ml 10% ethanolic solution of ammonia. The mixture was stirred at room temperature for three days until the reaction was complete. The solvent was removed in vacuo, and the resinous residue was dissolved in toluene/acetone 7:3. A first crop of the title amidine crystallized from the solution, and another crop was obtained by chromatography on silica gel using the same mixture of solvents.

Total yield: 1.6 g (83%) of a yellow crystalline solid, m.p. 122–124° C.

Example 80

Preparation of rac-(6-(N-(4-(Aminoiminomethyl) benzoyl)amino)-3,4-dihydro-4,4-dimethyl-2H-1-benzopyran-2-yl)acetic Acid, a Compound Represented by the Formula (336)

(336)

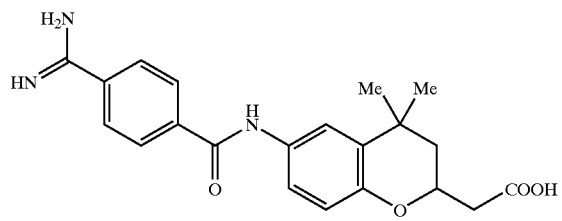

0.3 g (0.67 mmol) of the ester from Example 79 were suspended in 10 ml ethanol followed by addition of 1 ml aqueous 2 N sodium hydroxide. It was stirred at room temperature for 4 hours. The mixture was filtered, the filtrate concentrated to dryness under reduced pressure, and the residue was dissolved in water. It was then neutralized with diluted acetic acid, and the precipitate of the compound (336) was filtered with suction, washed thoroughly with water, and dried in vacuo at 50° C.

Yield: 0.2 g (78%) of a yellow crystalline solid, m.p. 248–250° C.

Example 81

Preparation of Ethyl rac-(3,4-Dihydro-6-(N-(4-((propylamino) iminomethyl)benzoyl) amino) -2H-1-benzopyran-2-yl)acetate Hydrochloride, a Compound Represented by the Formula (337)

(337)

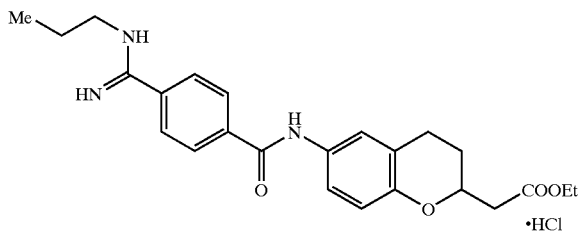

To a solution of 0.8 g (1.8 mmol) of the crude intermediate of Example 57, Step A in 20 ml ethanol were added at 0° C. 0.3 ml n-propylamine. The mixture was stirred overnight at room temperature and concentrated under reduced pressure. The residue was treated with ethanol and ether to give the pure crystalline title compound, which was collected by filtration and dried in vacuo.

Yield: 0.63 g (76%) of a white powder, m.p. 271–273° C.

Example 82

Preparation of rac-(3,4-Dihydro-6-(N-(4-((propylamino)iminomethyl)benzoyl)amino)-2H-1-benzopyran-2-yl)acetic Acid, a Compound Represented by the Formula (338)

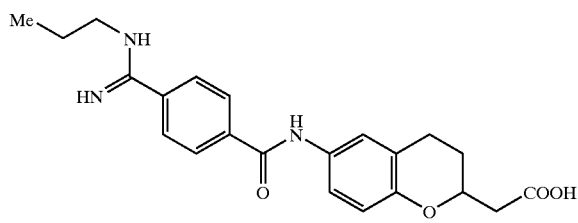

(338)

0.25 g (0.54 mmol) of the ester from Example 81 were stirred at room temperature overnight with 5 ml ethanol and 0.7 ml 2 N aqueous sodium hydroxide. The mixture was brought to pH 4 with 2 N acetic acid, and the precipitate of the acid (338) was filtered with suction, washed successively with water and with acetone, and dried in vacuo.

Yield: 0.16 g (74%) of a pale yellow powder, m.p. 241–242° C. (dec.).

Example 83

Preparation of Ethyl rac-(6-(N-(4-((Butylamino)iminomethyl)benzoyl)amino)-3,4-dihydro-2H-1-benzopyran-2-yl)acetate Hydrochloride, a Compound Represented by the Formula (339)

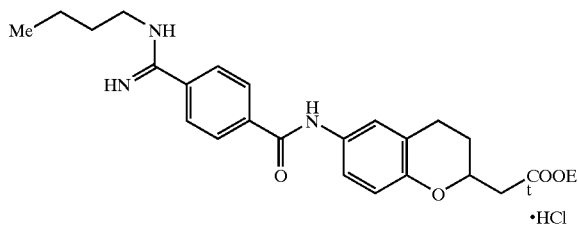

(339)

The compound was prepared from 0.8 g (1.8 mmol) of the crude intermediate of Example 57, Step A and 0.3 ml n-butylamine as described in Example 81.

Yield: 0.6 g (71%) of a pale yellow powder, m.p. 265–267° C.

Example 84

Preparation of rac-(6-(N-(4-((Butylamino)iminomethyl)benzoyl)amino)-3,4-dihydro-2H-1-benzopyran-2-yl)acetic Acid, a Compound Represented by the Formula (340)

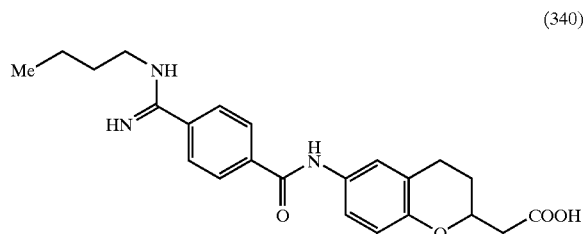

(340)

0.25 g (0.53 mmol) of the ester from Example 83 were hydrolyzed to the title acid as described in Example 82.

Yield: 0.13 g (60%) of a white powder, m.p. 240–241° C. (dec.).

Example 85

Preparation of Ethyl rac-(3,4-Dihydro-6-(N-(4-((propoxycarbonylamino)iminomethyl)benzoyl)amino)-2H-1-benzopyran-2-yl)acetate, a Compound Represented by the Formula (341)

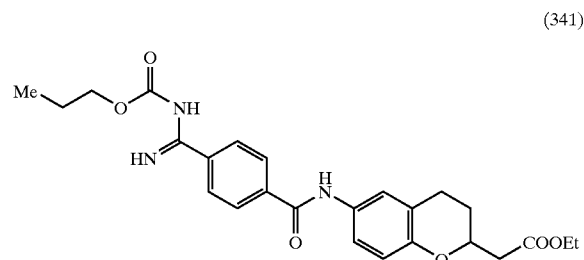

(341)

417 mg (1.0 mmol) of the compound from Example 47, 0.3 ml triethylamine, 20 mg 4-dimethylaminopyridine, and 135 mg (1.1 mmol) propyl chloroformate were dissolved in 20 ml dichloromethane at 0° C. followed by stirring overnight at room temperature. After addition of the same volume of water it was extracted with ethyl acetate. The organic layer was dried over sodium sulfate and concentrated under reduced pressure to give the crude title compound, which was recrystallized from dichloromethane/hexane.

Yield: 0.27 g (58%) of a pale yellow amorphous solid, m.p. 183–184° C.

Example 86

Preparation of Propyl rac-(6-(N-(4-(Aminoiminomethyl)benzoyl)amino)-3,4-dihydro-2H-1-benzopyran-2-yl)acetate hydrochloride, a Compound Represented by the Formula (342)

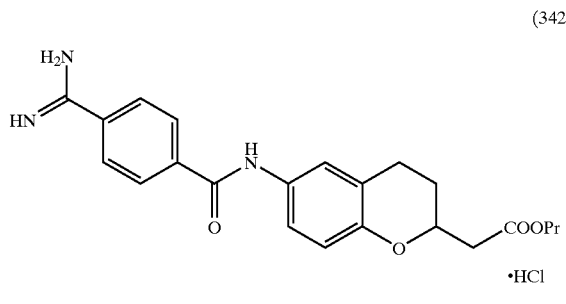

(342)

·HCl

A solution of 0.5 g (1.37 mmol) of the nitrile from Example 47, Step E in 50 ml n-propanol was cooled with ice and saturated with gaseous hydrogen chloride. After stirring overnight at room temperature the mixture was concentrated under reduced pressure, and the residue was treated with 50 ml of a saturated solution of ammonia in n-propanol. Again the mixture was stirred overnight at room temperature, the solvent removed in vacuo, and the remaining title amidine was recrystallized from n-propanol.

Yield: 0.36 g (61%) of a yellow powder, m.p. 238–240° C. (dec.).

Example 87

Preparation of Methyl rac-(6-(N-(4-(Aminoiminomethyl)benzoyl)amino)-3,4-dihydro-2H-1-benzopyran-2-yl)acetate Hydrochloride, a Compound Represented by the Formula (343)

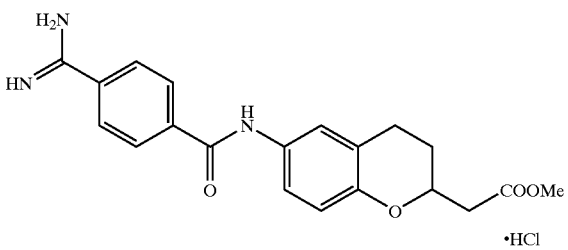

(343)

·HCl

A suspension of 0.35 g (1.0 mmol) of the acid from Example 48 in 20 ml methanol was cooled to 0° C. and saturated with gaseous hydrogen chloride. After 2 hours stirring it was concentrated under reduced pressure, and the remaining compound (343) was recrystallized from methanol/ether.

Yield: 0.29 g (72%) of yellow crystals, m.p 235–237° C.

Example 88

Preparation of Ethyl rac-(3,4-Dihydro-6-(N-(2-fluoro-4-((methoxycarbonylamino)iminomethyl)benzoyl)amino)-2H-1-benzopyran-2-yl)acetate, a Compound Represented by the Formula (349)

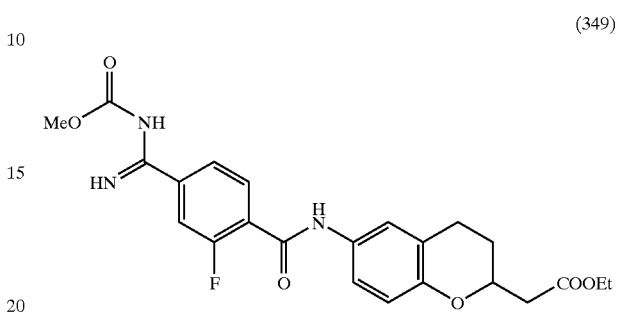

(349)

436 mg (1.0 mmol) of the amidine from Example 69, 0.3 ml triethylamine, and 20 mg 4-dimethylaminopyridine were dissolved in 29 ml dichloromethane followed by addition of 104 mg (1.1 mmol) methyl chloroformate at 0° C. After stirring overnight at room temperature a white precipitate of the title compound had been formed. It was filtered with suction and washed successively with water and with ether.

Yield: 0.35 g (77%) of a pale yellow powder, m.p. 202–204° C.

Example 89

Preparation of Ethyl rac-(3,4-Dihydro-6-(N-(4-((ethoxycarbonylamino)iminomethyl)-2-fluorobenzoyl) amino)-2H-1-benzopyran-2-yl) acetate, a Compound Represented by the Formula (350)

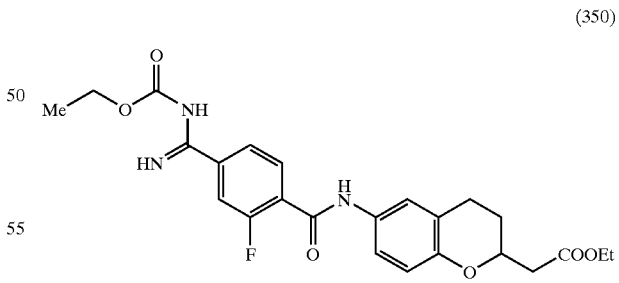

(350)

The title carbamate was prepared as described in Example 88 from 436 mg (1.0 mmol) of the amidine from Example 69 and 119 mg (1.1 mmol) ethyl chloroformate. It was recrystallized from dichloromethane/hexane.

Yield: 0.35 g (74%) of a white powder, m.p. 168–169° C.

Example 90

Preparation of Ethyl rac-(3,4-Dihydro-6-(N-(2-fluoro-4-((propoxycarbonylamino)iminomethyl)benzoyl)amino)-2H-1-benzopyran-2-yl)acetate, a Compound Represented by the Formula (351)

(351)

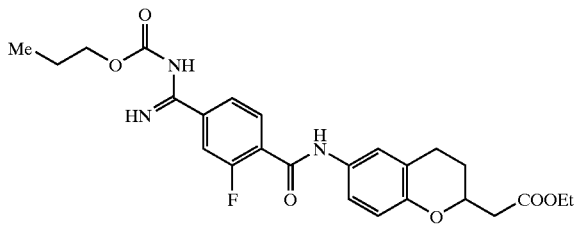

The title compound was prepared as described in Example 85 from 436 mg (1.0 mmol) of the amidine from Example 69 and 135 mg (1.1 mmol) propyl chloroformate.

Yield: 0.29 g (60%) of a white crystalline solid, m.p. 157–159° C.

Example 91

Proposed Method for Preparation of rac-4-Aminoiminomethyl-N-(3,4-dihydro-2-(1H-tetrazol-5-yl)methyl-2H-1-benzopyran-6-yl)benzamide, a Compound Represented by the Formula (352)

(352)

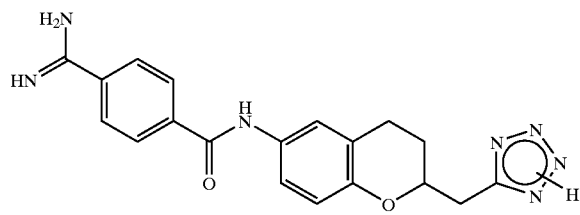

Step A: Preparation of tert.-Butyl rac-(2-Cyanomethyl-3,4-dihydro-2H-1-benzopyran-6-yl)carbamate, an Intermediate Represented by the Formula (353):

(353)

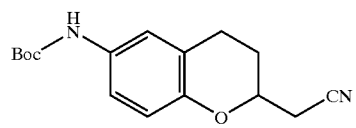

Step B: Preparation of tert.-Butyl rac-(3,4-Dihydro-2-(1H-tetrazol-5-yl)methyl-2H-1-benzopyran-6-yl)carbamate, an Intermediate Represented by the Formula (354):

(354)

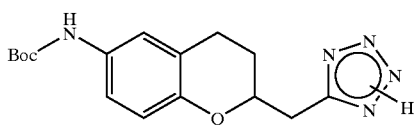

Step C: Preparation of rac-4-Cyano-N-(3,4-dihydro-2-(1H-tetrazol-5-yl)methyl-2H-1-benzopyran-6-yl)benzamide, a Compound Represented by the Formula (355):

(355)

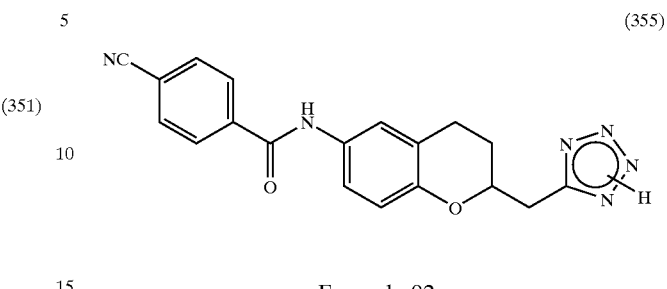

Example 92

Preparation of Ethyl rac-(3,4-Dihydro-6-(N-(4-(N'-(phenylmethylamino)iminomethyl)benzoyl)amino)-2H-1-benzopyran-2-yl)acetate Hydrochloride, a Compound Represented by the Formula (356)

(356)

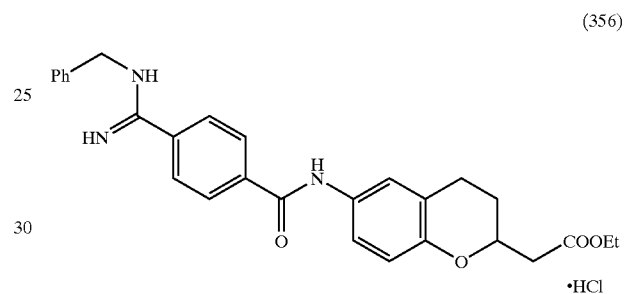

A mixture of 0.49 g (1.1 mmol) of the intermediate from Example 57 Step A and 0.5 ml benzylamine in 15 ml dry ethanol was stirred for 5 hours at room temperature. The solvent was removed under reduced pressure, and the remaining title compound crystallized from ethanol/ether. The crystals were collected by filtration, washed with ether, and dried in vacuo.

Yield: 0.49 g (88%) of pale yellow crystals, m.p. 254–256° C.

Example 93

Preparation of rac-(3,4-Dihydro-6-(N-(4-(N'-(phenylmethylamino)iminomethyl)benzoyl)amino)-2H-1-benzopyran-2-yl)acetic Acid, a Compound Represented by the Formula (357)

(357)

0.2 g (0.39 mmol) of the ester from Example 92 were added to a mixture of 10 ml ethanol and 0.5 ml 2 N aqueous sodium hydroxide solution. After gentle warming it was stirred overnight at room temperature. The mixture was brought to pH 4 with 2 N acetic acid, and the precipitate of the title acid was filtered with suction, washed successively with water and with acetone, and dried in vacuo.

Yield: 0.12 g (69%) of a pale yellow powder, m.p. 220° C. (dec.)

Example 94

Preparation of Ethyl rac-(3,4-Dihydro-6-(N-(4-((pentylamino)iminomethyl)benzoyl)amino)-2H-1-benzopyran-2-yl)acetate Hydrochloride, a Compound Represented by the Formula (363)

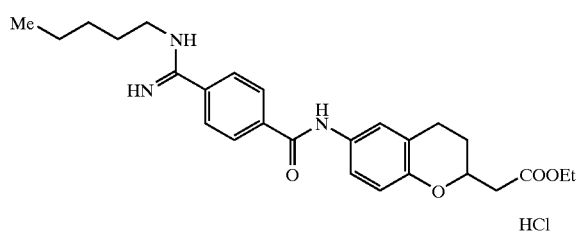

(363)

HCl

To a suspension of 447 mg (1.0 mmol) of the intermediate from Example 57, Step A in 15 ml dry ethanol were added at 0° C. 0.5 ml n-pentylamine. The mixture became a clear solution upon stirring overnight at room temperature. It was concentrated under reduced pressure, and the crystalline residue of the title compound was recrystallized from ethanol/ether.

Yield: 0.33 g (68%) of pale yellow crystals, m.p. 267–269° C.

Example 95

Preparation of rac-(3,4-Dihydro-6-(N-(4-((pentylamino)iminomethyl)benzoyl)amino)-2H-1-benzopyran-2-yl)acetic Acid, a Compound Represented by the Formula (364)

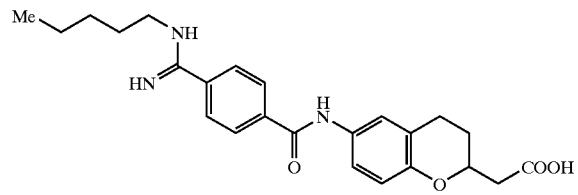

(364)

0.15 g (0.31 mmol) of the ester from Example 94 were stirred overnight at room temperature in a mixture of 10 ml ethanol and 0.7 ml 2 N aqueous sodium hydroxide solution. It was brought to pH 4 with 2 N acetic acid, and the precipitate of the title acid was filtered, washed successively with water and with acetone, and dried in vacuo.

Yield: 98 mg (75%) of colorless crystals, m.p. 223–225° C. (dec.).

Reference numbers in the following Examples are found in Reaction Schemes 27 to 33, supra.

Example 96

Preparation of Compound 368

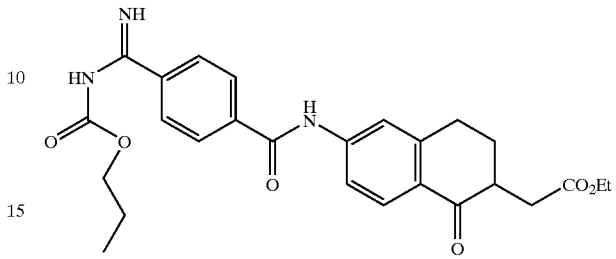

(368)

A mixture of 365 (1.25 g, 2.0 mmol), $H_2O$ (5 mL), and THF (5 mL) was treated with propyl chloroformate (0.34 g, 2.7 mmol) and $K_2CO_3$ (0.19 g, 13.5 mmol) at room temperature. After 1 hour the mixture was diluted with EtOAc and washed with $H_2O$. The organic material was concentrated and the crude residue was recrystallized from EtOAc/Hexane giving 0.8 g of 368 as a white solid.

$^1$H NMR (300 MHz, DMSO) 10.63 (s, 1H), 9.17 (br s, 2H), 8.05 (dd, J=8.3, 19.6 Hz, 4H), 7.85 (m, 2H), 7.73 (d, J=8.5 Hz, 1H), 4.06 (q, J=7.0 Hz, 2H), 3.99 (t, J=6.5 Hz, 2H), 3.1 (m, 1H), 2.93 (m, 2H), 2.73 (dd, J=6.2, 16.3 Hz, 1H), 2.42 (m, 1H), 2.11 (m, 1H), 1.98 (m, 1H), 1.60 (m, 2H), 1.16 (t, J=7.0 Hz, 3H), 0.91 (t, J=7.3 Hz, 3H); IR (KBr) 1737, 1661, 1603, 1525, 1256 cm$^{-1}$; MS (FAB) m/e 480.

Example 97

Preparation of Compound 367

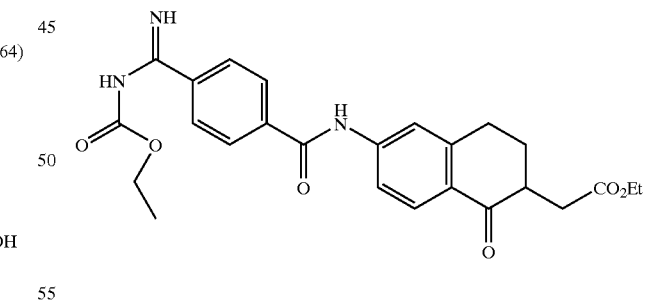

(367)

Following the procedure used for the preparation of 368, 367 was prepared in 91% yield starting from 0.50 g of 365 and 0.10 g of ethyl chloroformate.

$^1$H NMR (300 MHz, CDCl$_3$) 8.55 (s, 1H), 7.80 (m, 5H), 7.48 (d, J=8.8 Hz, 1H), 4.26 (m, 4H), 3.05 (m, 4H), 2.52 (m, 1H), 2.28 (m, 1H), 2.0 (m, 1H), 1.39 (t, J=7.1 Hz, 3H), 1.32 (t, J=7.2 Hz, 3H); IR (KBr) 1727, 1686, 1661, 1602, 1256 cm$^{-1}$; MS (FAB) m/e 466. Analysis for $C_{22}H_{27}N_3O_6$: Calc.: C, 64.51 H, 5.85; N, 9.03. Found: C, 64.77; H, 5.87; N, 8.82.

Example 98

Preparation of Compound 369

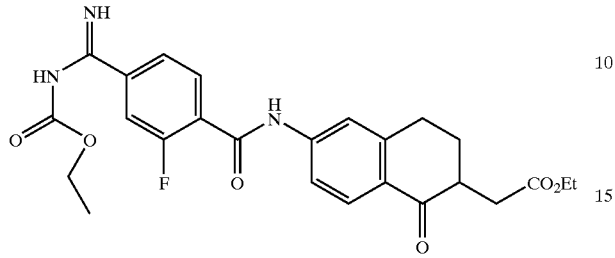

(369)

Following the procedure used for the preparation of 368, 370 was prepared in 87% yield starting from 0.26 g of 366 and 0.07 g of ethyl chloroformate.

$^1$H NMR (300 MHz, CDCl$_3$) 8.64 (app d, J=15.0 Hz, 1H), 8.20 (t, J=7.9 Hz, 1H), 8.01 (d, J=8.5 Hz, 1H), 7.84 (d, J=12.7 Hz, 1H), 7.79 (s, 1H), 7.72 (s, J=8.3 Hz, 1H), 7.42 (d, J=8.7 Hz, 1H), 4.24 (m, 4H), 3.13 (m, 4H), 2.44 (m, 1H), 2.26 (m, 1H), 1.99 (m, 1H), 1.37 (t, J=7.0 Hz, 3H), 1.28 (t, J=7.3 Hz, 3H); IR (KBr) 1731, 1673, 1520, 1256 cm$^{-1}$.

Example 99

Preparation of Compound 370

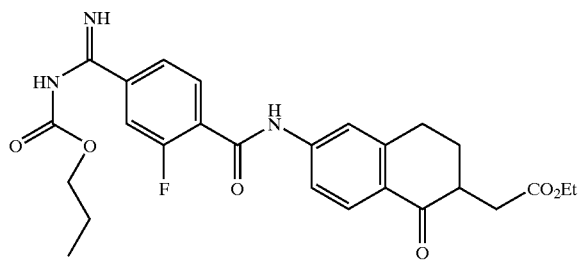

(370)

Following the procedure used for the preparation of 368, 370 was prepared in 86% yield starting from 0.26 g of 366 and 0.08 g of propyl chloroformate.

$^1$H NMR (300 MHz, CDCl$_3$) 8.65 (app d, J=15.1 Hz, 1H), 8.20 (t, J=8.1 Hz, 1H), 8.0 (d, J=8.5 Hz, 1H), 7.84 (d, J=12.8 Hz, 1H), 7.78 (s, 1H), 7.72 (d, J=8.2 Hz, 1H), 7.41 (d, J=8.4 Hz, 1H), 4.17 (m, 4H), 3.0 (m, 4H), 2.42 (m, 1H), 2.25 (m, 1H), 2.0 (m, 1H), 1.78 (m, 2H), 1.28 (t, J=7.3 Hz, 3H), 1.00 (t, J=7.5 Hz, 3H); IR (KBr) 1733, 1662, 1520, 1251 cm$^{-1}$; MS (FAB) m/e 498.

Example 100

Preparation of Compound 371

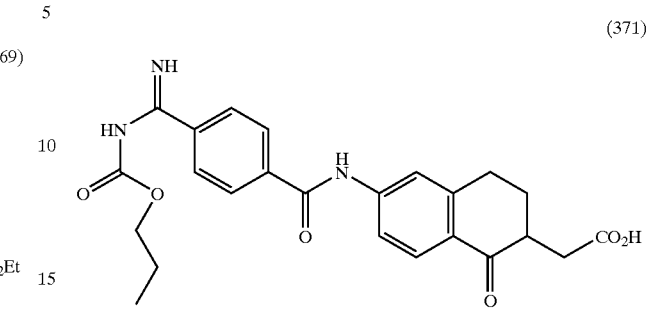

(371)

A mixture of 368 (0.11 g, 0.23 mmol) and EtOH (5 mL) was treated with NaOH (1.1 mL of a 2 N solution, 2.3 mmol) and the resluting solution was allowed to stir for 5 hours at room temperature. The reaction mixture was then concentrated and the residue taken up in H$_2$O. This material was extracted with EtOAc and the extracts discarded. The remaining aqueous material was acidified to pH 5 with 1N HCl and the resulting material extracted with EtOAc. The extracts were dried (MgSO$_4$) and concentrated affording 0.06 g (57%) of the desired acid 371 as a white solid.

$^1$H NMR (300 MHz, CD$_3$OD) 8.0–7.9 (m, 5H), 7.79 (br s, 1H), 7.64 (dd, J=2.1, 8.6 Hz, 1H), 4.11 (t, J=6.7 Hz, 2H), 3.15–2.95 (m, 3H), 2.89 (dd, J=5.6, 16.4 Hz, 1H), 2.48 (dd, J=6.6, 16.5 Hz, 1H), 2.27 (m, 1H), 2.06 (m, 1H), 1.71 (m, 2H), 1.00 (t, J=7.4 Hz, 3H); MS (FD) m/e 452.

Example 101

Preparation of Compound 381

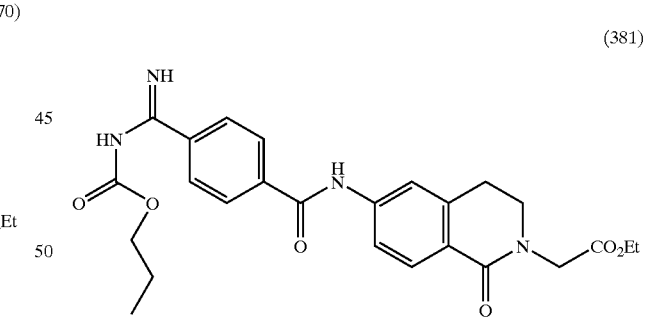

(381)

Following the procedure used for the preparation of 368, 381 was prepared in 47% yield starting from 0.082 g of 374 and 0.13 g of propyl chloroformate.

$^1$H NMR (300 MHz, CDCl$_3$) 8.60 (br s, 1H), 7.89 (d, J=8.5 Hz, 1H), 7.85 (s, 5H), 7.40 (d, J=10 Hz, 1H), 4.31 (s, 2H), 4.21 (q, J=7.1 Hz, 2H), 4.15 (t, J=6.9 Hz, 2H), 3.64 (t, J=6.6 Hz, 2H), 3.0 (t, J=6.5 Hz, 2H), 1.8 (m, 2H), 1.28 (t, J=7.1 Hz, 3H), 0.99 (t, J=7.4 Hz, 3H); IR (KBr) 3390, 3286, 1732, 1655, 1617, 1274 cm$^{-1}$. MS (FAB) m/e 481. Analysis for C$_{25}$H$_{28}$N$_4$O$_6$: Calc.: C, 62.49; H, 5.82; N, 11.66. Found: C, 62.65; H, 5.87; N, 11.43.

Example 102

Preparation of Compound 391

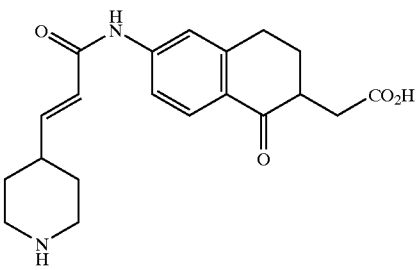

(391)

Step A:

A solution of alcohol 384 (5.0 g, 23.5 mmol—prepared from 4-pyridylcarbinol via hydrogenation and protection) and $CH_2Cl_2$ (25 mL) was added to a solution of oxalyl chloride (2.8 mL, 32.5 mmol), DMSO (2.5 mL, 34.9 mmol) and $CH_2Cl_2$ (25 mL) at −78° C. After 1 hour the reaction was treated with $Et_3N$ (6.5 mL, 46.5 mmol) and allowed to warm to room temperature. This mixture was diluted with EtOAc and washed with $H_2O$. The organic material was dried ($MgSO_4$) and concentrated. The crude residue was taken up in THF (25 mL) and added to a −78° C. mixture of triethyl phosphonoacetate (6.23 g, 28.2 mmol), NaH (1.12 g of a 60% dispersion in oil, 28.2 mmol), and THF (25 mL). This mixture was allowed to warm to room temperature. After 1 hour the mixture was diluted with EtOAc and washed with $H_2O$. The organic phase was concentrated and the crude material was purified by chromatography (3:1 Hexanes/EtOAc) giving 4.7 g (71%) of 1016 as a clear oil.

Step B:

A mixture of 385 (1.0 g, 3.53 mmol), LiOH (71 mL of a 0.1 N solution in $H_2O$, 7.1 mmol), and THF (70 mL) was stirred at room temperature overnight. The mixture was then concentrated to one half volume and acidified to pH 5 with 1N HCl. The resulting mixture was extracted with EtOAc and the extracts were concentrated giving 0.72 g (80%) of the desired acid 386 as an essentially pure white solid.

Step C:

Oxalyl chloride (0.08 mL, 1.0 mmol) was added to a mixture of 386 and benzene (5 mL). One drop of DMF was added and the mixture was stirred at room temperature for 1 h. The resulting solution was concentrated affording the crude acid chloride 387 as an oil. This material was dissolved in $CH_2Cl_2$ (5 mL) and added to a solution of aniline 98 (0.17 g, 0.69 mmol), pyridine (5 mL), and $CH_2Cl_2$ (5 mL). The resulting mixture was stirred at room temperature for 1 hour and then diluted with EtOAc and washed with $H_2O$. The organic material was concentrated and the crude material was purified by chromatography on silica (1.5:1 hexane/EtOAc) giving 0.25 g (90%) of 388 as a white solid.

Step D:

A solution of 388 (0.24 g, 0.49 mmol) and THF (10 mL) was treated with LiOH (10 mL of a 0.1N solution in $H_2O$, 1.0 mmol) and allowed to stir at room temperature overnignt. This mixture was then concentrated to one-half volume and carefully acidified with 1N HCl (pH 5). The aqueous mixture was then extracted with EtOAc and the extracts concentrated. The crude acid 390 was dissolved in TFA (10 mL), allowed to stand at room temperature for 1 hour and then concentrated. The crude material thus formed was dissolved in 1N HCl and the resulting solution lyophilized giving 0.15 g (80%) of 391 as a white powder.

$^1H$ NMR (300 MHz, $CDCl_3$) 7.89 (d, J=8.5 Hz, 1H), 7.68 (s, 1H), 7.51 (d, J=8.5 Hz, 1H), 6.87 (dd, J=6.5, 15.4 Hz, 1H), 6.20 (d, J=15.4 Hz, 1H), 3.44 (br d, J=12.8 Hz, 2H), 3.0 (m, 6H), 2.6 (m, 1H), 2.4 (m, 1H), 2.25 (m, 1H), 2.05 (m, 3H), 1.70 (m, 2H); IR (KBr) 3384, 2953, 1726, 1672, 1533 $cm^{-1}$. MS (FAB) m/e 357. Analysis for $C_{20}H_{25}N_2O_4Cl$: Calc.: C, 61.14; H, 6.41; N, 7.13. Found: C, 61.40; H, 6.60; N, 7.18.

Example 103

Preparation of Compound 389

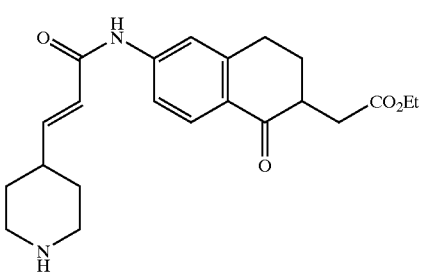

(389)

A solution of 388 (0.60 g, 1.2 mmol) and TFA (10 mL) was maintained at room temperature for 1 hour and then concentrated. The residue was dissolved in $H_2O$ (10 mL), treated with HCl (2.5 mL of a 1N solution, 2.5 mmol) and the resulting solution was lyophilized giving 0.49 g (95%) of 389 as a white powder.

$^1H$ NMR (300 MHz, $CDCl_3$) 7.92 (d, J=8.6 Hz, 1H), 7.72 (s, 1H), 7.54 (d, J=8.7 Hz, 1H), 6.93 (dd, J=6.5, 15.6 Hz, 1H), 6.24 (d, J=15. 5 Hz, 1H), 4.18 (q, J=7.1 Hz, 2H), 3.49 (m, 2H), 3.10 (m, 5H), 2.82 (dd, J=6.3, 16.4 Hz, 1H), 2.65 (m, 1H), 2.51 (dd, J=6.2, 16.4 Hz, 1H), 2.3 (m, 1H), 2.1 (m, 3H), 1.68 (m, 2H), 1.22 (t, J=7.0 Hz, 3H); IR (KBr) 3346, 3286, 2935, 1734, 1676, 1584 $cm^{-1}$. MS (FAB) m/e 385. Analysis for $C_{22}H_{29}N_2O_4$: Calc.: C, 62.78; H, 6.94; N, 6.66. Found: C, 63.01; H, 6.90; N, 6.75.

Example 104

Preparation of Compound 400

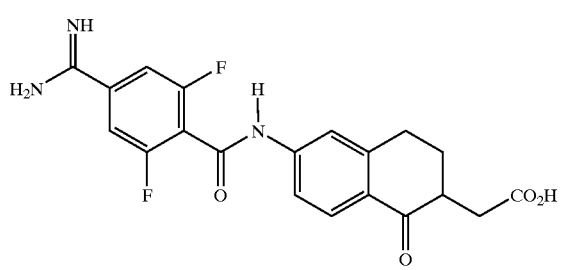

(400)

Step A:

A mixture of 3,5-difluoro benzonitrile 394 (0.5 g, 3.59 mmol), TMEDA (0.77 g, 7.3 mmol), and THF (15 mL) was treated with n-BuLi (2.6 mL of a 1.4 M solution in hexane, 3.6 mmol) at −78° C. The reaction mixture was stirred at −78° C. for 15 minutes and then quenched with $CO_2$ (g). The mixture was allowed to warm to room temperatrue where it was concentrated. The residue was taken up in $H_2O$ and washed with $Et_2O$. The remaining aqueous material was acidified to pH 2 with 1N HCl and then extracted with EtOAc. The extracts were then concentrated giving 0.53 g of 395 as a white solid.

Step B:

A mixture of 395 (0.28 g, 1.51 mmol), DMF (1 drop), and benzene (10 mL) was treated with oxalyl chloride at room temperature. This mixture was allowed to stir for 30 min and then was concentrated. The crude residue was taken up in $CH_2Cl_2$ (5 ml) and added to a solution of 98 (0.38 g, 1.51 mmol), pyridine (3 mL) and $CH_2Cl_2$ (3 mL). This mixture was stirred at room temperature for 0.5 hour and then diluted with EtOAc and washed with $H_2O$. The organic material was concentrated and the residue was chromatographed on silica (1:1 hexane/EtOAc) giving 0.56 g of 397.

Step C:

The nitrile was converted to the Boc protected amidine 398 using the general procedure outlined for the preparation of 6 (example 1 part E).

Step D:

Amidine 398 was converted to the fully deprotected compound 400 using the general procedure outlined for the preparation of 130 (example 33 part E).

$^1$H NMR (300 MHz, $CD_3OD$) 7.98 (d, J=8.6 Hz, 1H), 7.74 (s, 1H), 7.68 (m, 2H) 7.64 (d, J=8.6 Hz, 1H), 3.0 (m, 3H), 2.88 (dd, J=6.4, 16.6 Hz, 1H), 2.46 (dd, J=6.4, 16.6 Hz, 1H), 2.25 (m, 1H), 2.0 (m, 1H); IR (KBr) 3306, 1660, 1603, 1426, 1039 $cm^{-1}$. MS (FAB) m/e 402.

Example 105

Preparation of Compound 405

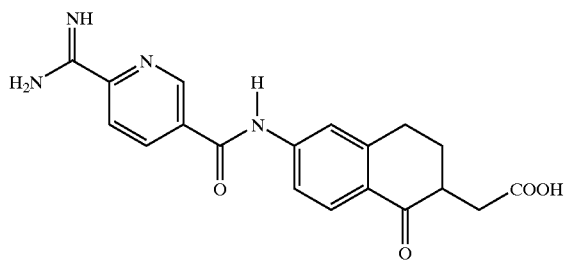

(405)

Step A: Preparation of the Intermediate (402):

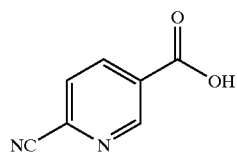

(402)

To a mixture of nicotinic acid-N-oxide (8.8 g, 63 mmol) in 100 mL anhydrous DMF was added $Et_3N$ (32 g, 316 mmol) resulting in a homogenous solution. The mixture was treated with TMSCl (34 g, 316 mmol) and was stirred for 30 minutes at ambient temperature before adding NaCN (12.4 g, 253 mmol). The reaction was warmed to 100° C. for 16 hours, then cooled to room temperature and filtered. The filtrate was concentrated to dryness under vacuum, was treated with 2 N aq HCl (150 ml) and extracted several times with $CH_2Cl_2$. The extracts were dried over $MgSO_4$, concentrated to dryness and purified by chromatrography ($SiO_2$, 1% v/v MeOH—$CHCl_3$) to recover 4.01 g of a solid.

Step B: Preparation of the Intermediate (403):

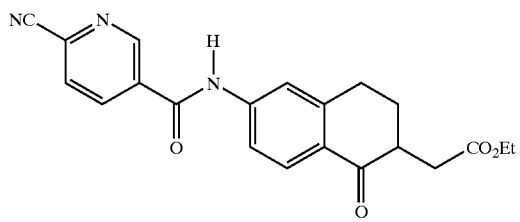

(408)

A mixture of 6-cyano-3-pyridine carboxylic acid (1.2 g, 8.1 mmol), 4-dimethylaminopyridine (1.0 g, 8.1 mmol), diisopropylethylamine (1.1 g, 8.1 mmol), compound 98 (2.0 g, 8.1 mmol) in 25 mL of $CH_2Cl_2$ was treated with 1(3-dimethlyaminopropyl)-3-ethylcarbodiimide hydrochloride (2.4 g, 12.2 mmol). The reaction was stirred at ambient temperature for 60 hours. The mixture was applied to a bed of silica gel and was eluted with 0.5% v/v MeOH—$CHCl_3$ to yield 2.76 g (90%) of 408 a white solid.

Step C: Preparation of the Intermediate (409):

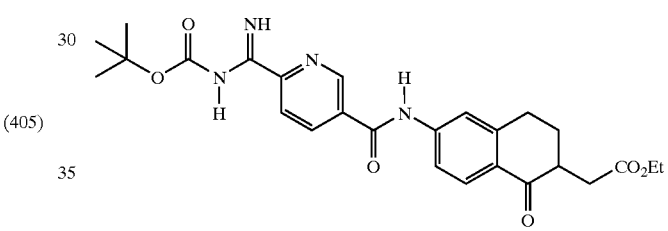

(409)

A solution of the nitrile 403 (0.214 g, 0.57 mmol) in 50 mL of a 1 M solution of $CH_3SH$ in EtOH was treated with 75 mg (1.1 mmol) of $CH_3SNa$ and the mixture stirred at ambient temperature for 2 hours. Solid $NH_4I$ (0.7 g) was added and the mixture was heated to reflux until the reaction as over as indicated by TLC. The solution was concentrated to dryness and the residue taken up in 5 mL THF. The solution was treated with $K_2CO_3$ (0.75 g, 5.4 mmol), $BOC_2O$ (1.2 g, 5.4 mmol), THF (5 ml) and $H_2O$ (5 ml) and the mixture was stirred overnight. The reaction mixture was diluted with EtOAc and washed with $H_2O$. The organic layer was dried over $MgSO_4$, concentrated to dryness, and purified by chromatography ($SiO_2$, 40% v/v EtOAc/Hexanes) to yield 183 mg of 409 as a solid.

Step D:

The protected amidine (70 mg, 0.14 mmol) 404 was mixed with EtOH (2 mL) and 1N aq. NaOH (0.57 mL). The reaction was stirred at ambient temperature overnight (16 hours) then acidified with HOAc (1 ml). This product was concentrated to dryness then purified by chromatography ($SiO_2$, 5:1:94 v/v MeOH/HOAc/$CHCl_3$). The resulting foam was treated with trifluoroacetic acid (5 ml) and anisol (5 ml) for 60 hours. The reaction was concentrated to dryness to recover 25 mg of 405 as a solid.

Example 106

Preparation of Compound 410

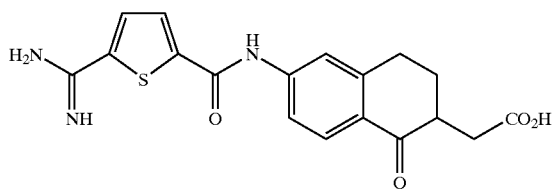

Step A:

To a flame dried flask was added diisopropylamine (3.85 mL, 27.45 mmol) and dry THF (20 mL, distilled from CaH). The mixture was stirred under a nitrogen atmosphere and cooled to −78° C. To this solution was added n-BuLi such that the solution temperature did not rise above −70° C. In a separate, flame dried flask was added 2-thiophenecarbonitrile (2.0 g, 18.3 mmol) to dry THF (20 mL). The solution was cooled to −78° C. and stirred under a nitrogen atmosphere for 15 minutes. The 2-thiophenecarbonitrile solution was then transferred, via a cannula needle, to the LDA solution and the reaction mixture stirred an additional 1 hour at −78° C. Carbon dioxide gas was then added over a 20 minute period as the solution reached room temperature. After concentrating, in vacuo, the resulting residue was taken up in KOH (100 mL, 0.01 M) and washed with EtOAc (2×75 mL). The aqueous layer was then acidified to pH 2 with concentrated HCl and saturated with NaCl. Product was extracted with EtOAc (4×100 mL) and the combined organic extracts concentrated, in vacuo. The resulting residue was purified by column chromatography on silica gel 60 (230–400 mesh) with product eluted by 20% MeOH in $CHCl_3$ (2% v/v acetic acid). The appropriate fractions were combined and concentrated, in vacuo, giving 760 mg (27%) of 407 as a tan solid.

Step B:

To 407 (260 mg, 1.7 mmol) was added 98 (420 mg, 1.7 mmol), EDCI (520 mg, 2.72 mmol), 4-DMAP (catalytic), and $CH_2Cl_2$ (6 mL). The mixture was stirred at room temperature for 12 hours and then diluted with EtOAc (40 mL) and the organics washed with HCl (40 ml, 0.1 M), NaOH (40 mL, 0.1 M) and $H_2O$ (40 mL). The organic layer was then concentrated, in vacuo, and the resulting residue purified by column chromatography on silica gel 60 (230–400 mesh) with product elution by 10% THF in $CHCl_3$. The appropriate fractions were combined and concentrated, in vacuo, giving 200 mg (31%) of 408 as a tan solid.

Step C:

Nitrile 408 was converted to 409 using the general procedure outlined for the preparation of 6 (Example 1 part E).

Step D:

Amidine 409 was converted to the fully de-protected compound 410 using the general procedure outlined for the preparation of 130 (example 33 part E).

$^1$H NMR (300 MHz, $CD_3OD$) 2.02 (m, 1H), 2.26 (m, 1H), 2.48 (dd, J=6.4, 10.1 Hz, 1H), 2.86 (dd, J=5.7, 10.7 Hz, 1H), 3.11 (m, 3H), 7.63 (dd, J=2, 6.6 Hz, 1H), 7.76 (bs, 1H), 7.95 (m, 2H), 8.03 (d, J=4.1 Hz, 1H); IR (KBr) 3322, 3096, 1667, 1585, 1537, 1502, 1425, 1384, 1342, 1284, 1267 $cm^{-1}$; MS (FAB) m/e 372.2; melting point 205–208 dec. Analysis for $C_{20}H_{18}N_3O_6F_3S$: Calc.: C, 49.48; H, 3.74; N, 8.66. Found: C, 49.45; H, 3.76; N, 8.44.

Assay Methods

The identification of compounds which are active platelet aggregation inhibitors (PAI) is made possible by the observation that compounds which block the binding of fibrinogen to the GPIIb-IIIa complex in vitro also are capable of inhibiting thrombin or ADP-induced aggregation of human platelets and the formation of platelet-thrombi in vivo. This observation provides the basis for obtaining potent PAI's by evaluating the ability of test materials to disrupt fibrinogen-GPIIb-IIIa interactions.

The following assay methods were used to evaluate the compounds of the invention, inclusive of the compounds represented by formulae (I), (II), (Ix), (Xd) and (Xe) as previously described.

No. 1—The ELISA IIb-IIIa Assay

In the following assay, GPIIb-IIIa is prepared in purified form, by a method such as described by Fitzgerald, L. A., et al., Anal Biochem (1985) 151:169–177, (the disclosure of which is incorporated herein by reference). GPIIb-IIIa is coated onto microtiter plates. The coated support is then contacted with fibrinogen and with the test material (e.g., compounds of Formula I) and incubated for a sufficient time to permit maximal binding of fibrinogen to the immobilized GPIIb-IIIa. Fibrinogen is typically provided at a concentration of about 5–50 nM and the test material can, if desired, be added at a series of dilution. Typical incubations are 2 to 4 hours at 25° C., the time and temperature being interdependent.

After incubation, the solution containing the fibrinogen and test material is removed and the level of binding of fibrinogen measured by quantitating bound fibrinogen to GPIIb-IIIa. Any suitable means of detection may be used, but it is convenient to employ labeled fibrinogen, for example using biotinylated labels. Such methods are well known in the art.

A. Description of Assays—Plate Assays

Purified platelet GPIIb-IIIa receptor was prepared as described by Fitzgerald, L. A., et al., Anal Biochem (1985) 151:169–177 (1985). Vitronectin receptor was prepared as described by Smith, J. W., J. Biol Chem (1988) 263:18726–18731. After purification, the receptors were stored in 0.1% Triton X-100 at 0.1–1.0 mg/ml.

The receptors were coated to the wells of 96-well flat-bottom ELISA plates (Linbro EIA-Plus microtiter plate, Flow Laboratories) after diluting 1:200 with a solution of 20 mM Tris-HCl, 150 mM NaCl, 1 mM $CaCl_2$, pH 7.4, to reduce the Triton X-100 concentration to below its critical micellar concentration and adding an aliquot of 100 ul to each well. The wells were all allowed to incubate overnight at 4° C., and then aspirated to dryness. Additional sites were blocked by the addition of bovine serum albumin (BSA) at 35 mg/ml in the above buffer for 2 hours at 30° C. to prevent nonspecific binding. The wells were then washed once with binding buffer (50 nM Tris-HCl, 100 mM NaCl 2 mM $CaCl_{2, 1}$ mg/ml BSA).

The corresponding ligands (fibrinogen, von Willebrand Factor, or vitronectin) were conjugated to biotin using commercially available reagents and standard protocols. The labeled ligands were added to the receptor-coated wells at final concentration of 10 nM (100 ul/well) and incubated for 3 hours at 25° C. in the presence or absence of the test samples. After incubation, the wells are aspirated to dryness and bound ligand is quantitated.

The bound protein is detected by the addition of antibiotin antibody conjugated to alkaline phosphatase followed by addition of substrate (p-nitrophenyl phosphate), and determination of the optical density of each well at 405 nM. Decreased color development is observed in wells incubated with test samples which inhibit binding of ligand to receptor.

No. 2—The Platelet Aggregation Assay

In addition to the ELISA IIb-IIIa assay previously described the Aggregation-Human PRP/ADP Assay is useful for evaluating therapeutic compounds.

Platelet-rich plasma was prepared from healthy human volunteers for use in determining inhibition of platelet aggregation by the compounds. Blood was collected via a 21 gauge butterfly cannula, using a two-syringe technique into 1/10 volume of 3.8% trisodium citrate.

Platelet-rich plasma was prepared at room temperature by centrifugation of the citrated whole blood at 100×g for 12 minutes. The platelet rich plasma contained approximately 200–400,000 platelets/$\mu$l.

Platelet-poor plasma was prepared by centrifugation of citrated whole blood at 12,000×g for 2 minutes.

Platelet aggregation was assayed in a 4-channel platelet aggregation profiler (PAP-4, Biodata, Hatboro, Pa.) according to the manufacturers directions. Inhibition of platelet aggregation was studied by adding varying amounts of adenosine diphosphate (ADP) to stirred human platelet-rich plasma. Specifically, the human platelet-rich plasma was incubated with the compound being tested for 1 minute at 37° C. prior to the addition of a variety of aggregating agents most often ADP 5 $\mu$M, but also 1 $\mu$g/ml collagen, 1 $\mu$M U46619 and 0.3 $\mu$M platelet activating factor.

TABLE OF ASSAY TEST RESULTS

| Example No. | ELISA IIb/IIIa $IC_{50}$ uM | Agg: Human PRP/ADP $IC_{50}$uM |
| --- | --- | --- |
| 01 | 0.6 | 20 |
| 02 | 0.030 | 0.52 |
| 03 | 0.110 | 1.0 |
| 04 | 0.0033 | 0.1 |
| 05 | 0.033 | 7 |
| 06 | 0.05 | 0.7 |
| 07 | 0.015 | 2 |
| 08 | 0.08 | 0.55 |
| 09 | 0.085 | 0.85 |
| 10 | 0.061 | 0.47 |
| 11 | 0.040 | 0.60 |
| 12 | 0.024 | 0.57 |
| 13 | 0.1 | 0.68 |
| 14 | 0.045 | 0.4 |
| 15 | 0.5 | 0.23 |
| 16 | 0.007 | 0.2 |
| 17 | 45.0 | >100.0 |
| 18 | 11.0 | >100.0 |
| 19 | 13 | >100.0 |
| 20 | 0.3 | 20 |
| 21 | 10 | >100.0 |
| 22 | 0.2 | 2 |
| 23 | 0.19 | 25 |
| 24 | 0.76 | 6.5 |
| 25 | 0.22 | NT |
| 26 | 0.52 | NT |
| 27 | 0.11 | NT |
| 28 | 0.005 | 0.19 |
| 29 | 0.015 | 0.28 |
| 30 | 0.002 | 0.06 |
| 31 | 0.016 | 15 |
| 32 | 0.004 | 0.10 |
| 33 | 0.005 | NT |
| 34 | 0.22 | 2.3 |

-continued

TABLE OF ASSAY TEST RESULTS

| Example No. | ELISA IIb/IIIa $IC_{50}$ uM | Agg: Human PRP/ADP $IC_{50}$uM |
| --- | --- | --- |
| 35 | 0.03 | 0.33 |
| 36 | 0.005 | 0.17 |
| 37 | 0.1 | 4.4 |
| 38 | 0.24 | 2.8 |
| 39 | 0.031 | 0.36 |
| 40 | 0.053 | 1.6 |
| 41 | 0.046 | 0.3 |
| 42 | 0.027 | 0.45 |
| 43 | 1.0 | NT |
| 44 | 0.16 | NT |
| 45 | NT | 11 |
| 46 | 0.0033 | 2.5 |
| 47 | 0.77 | 0.24 |
| 48 | 0.004 | 0.066 |
| 49 | NT | 100 |
| 50 | 3.93 | 100 |
| 51 | 1.16 | 40 |
| 52 | NT | 100 |
| 53 | 0.72 | 21 |
| 54 | NT | 12 |
| 55 | 3.46 | >100 |
| 56 | 0.14 | 0.9 |
| 57 | >10 | 0.66 |
| 58 | 0.0334 | 0.28 |
| 59 | >10 | 21 |
| 60 | 1.8 | >10 |
| 61 | >1 | 100 |
| 62 | NT | 6.8 |
| 63 | 0.0094 | 0.092 |
| 64 | 0.80 | 11 |
| 65 | 0.18 | 4.8 |
| 66 | NT | >100 |
| 67 | NT | 29 |
| 68 | >1 | NT |
| 69 | 0.009 | 0.16 |
| 70 | 0.0013 | 0.082 |
| 71 | >10 | 1.5 |
| 72 | 0.0185 | 0.28 |
| 73 | >10 | 1.2 |
| 74 | NT | NT |
| 75 | NT | 1.8 |
| 76 | 0.014 | 0.56 |
| 77 | NT | 1.3 |
| 78 | 0.02 | 0.18 |
| 79 | NT | >100 |
| 80 | 1 | >100 |
| 81 | NT | 0.39 |
| 82 | 0.019 | 0.12 |
| 83 | NT | 0.14 |
| 84 | 0.0055 | 0.084 |
| 85 | NT | >100 |
| 86 | NT | 0.078 |
| 87 | NT | 0.084 |
| 88 | 0.099 | 0.084 |
| 89 | NT | NT |
| 90 | NT | NT |
| 91 | NT | NT |
| 92 | NT | 0.24 |
| 93 | 0.0094 | 0.086 |
| 94 | NT | NT |
| 95 | NT | NT |

Note: NT = not tested

Pharmaceutical Compositions

Pharmaceutical formulations containing compounds of the invention can be administered orally in the form of tablets, capsules, solutions, emulsions or suspensions, inhaled liquid or solid particles, as a spray, through the skin by an appliance such a transdermal patch (such as described in U.S. Pat. Nos. 5,296,222 and 5,271,940, the disclosures of which are incorporated herein by reference) or rectally, for example, in the form of suppositories. The lipophilic prodrug derivatives of the invention (e.g., formula Xd, Xe) are particularly well suited for transdermal absorption administration and delivery systems. Administration can also take place parenterally, for example in the form of injectable solutions.

Tablets are prepared by mixing the Active Ingredient ("Active Ingredient" is one or more compounds of the invention inclusive of those corresponding to formulae I, II, Xd, or Xe) with pharmaceutically inert, inorganic or organic carriers, diluents, and/or excipients. Examples of such excipients which can be used for tablets, are lactose, maize starch or derivatives thereof, talc, stearic acid or salts thereof. Examples of suitable excipients for soft gelatin capsules are vegetable oils, waxes, fats, semisolid and liquid polyols.

Suitable excipients for the preparation of solutions and syrups are water, polyols, sucrose, invert sugar and glucose.

Suitable excipients for injectable solutions are water, alcohols, polyols, glycerol and vegetable oils.

These pharmaceutical products can additionally contain preservatives, solubilizers, stabilizers, wetting agents, emulsifiers, sweeteners, colorants, flavorings, buffers, coating agents and antioxidants.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use.

The Active Ingredient can also be made in microencapsulated form.

Exemplary formulations using the Active Ingredient are described below:

FORMULATION 1

Hard gelatin capsules are prepared using the following ingredients:

|  | (mg/capsule) |
|---|---|
| Active Ingredient | 250.0 |
| Starch | 305.0 |
| Magnesium stearate | 5.0 |

The above ingredients are mixed and filled into hard gelatin capsules in 560 mg quantities.

FORMULATION 2

A tablet formula is prepared using the ingredients below:

|  | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

FORMULATION 3

A dry powder inhaler formulation is prepared containing the following components:

|  | Weight % |
|---|---|
| Active ingredient | 5 |
| Lactose | 95 |

The active mixture is mixed with the lactose and the mixture is added to a dry powder inhaling appliance.

FORMULATION 4

Tablets, each containing 60 mg of active ingredient, are prepared as follows:

|  | (milligrams) |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules as produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION 5

Capsules, each containing 80 mg of medicament are made as follows:

|  | (milligrams) |
|---|---|
| Active ingredient | 80.0 |
| Starch | 109.0 |
| Magnesium stearate | 1.0 |
| Total | 190.0 |

The active ingredient, cellulose, starch, and magnesium stearate are blended passed through a No. 20 mesh U.S. sieve, and filled into hard gelatin capsules in 190 mg quantities.

FORMULATION 6

Suppositories, each containing 225 mg of active ingredient are made as follows:

| Active Ingredient | 225 mg |
|---|---|
| Saturated fatty acid glycerides to | 2000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION 7

Suspensions, each containing 50 mg of medicament per 5.0 mL dose are made as follows:

| Active ingredient | 50.0 mg |
|---|---|
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION 8

Capsules, each containing 150 mg of medicament, are made as follows:

|  | (milligrams) |
|---|---|
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

Method of Treatment

This invention provides a method of preventing or treating thrombosis in mammals, especially humans, which method comprises administering to the human or mammal a therapeutically effective amount of the compounds of this invention. The platelet aggregation inhibitors of the invention are useful therapeutically to prevent thrombus formation. Indications appropriate to such treatment include, without limitation, atherosclerosis and arteriosclerosis, acute myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic cardiovascular devices (e.g., in-dwelling catheters or shunts "extracorporeal circulating devices"). These syndromes represent a variety of stenotic and occlusive vascular disorders thought to be initiated by platelet activation on vessel walls.

The PAIs may be used for prevention or abortion of arterial thrombus formation, in unstable angina and arterial emboli or thrombosis, as well as treatment or prevention of myocardial infarction (MI) and mural thrombus formation post MI. For brain-related disorders, treatment or prevention of transient ischemic attack and treatment of thrombotic stroke or stroke-in-evolution are included.

The PAIs may also be used for prevention of platelet aggregation, embolization, or consumption in extracorporeal circulations, including improving renal dialysis, cardiopulmonary bypasses, hemoperfusions, and plasmapheresis.

PAIs prevent platelet aggregation, embolization, or consumption associated with intravascular devices, and administration results in improved utility of intraaortic balloon pumps, ventricular assist devices, and arterial catheters.

The PAIs will also be useful in treatment or prevention of venous thrombosis as in deep venous thrombosis, IVC, renal vein or portal vein thrombosis, and pulmonary venous thrombosis.

Various disorders involving platelet consumption, such as thrombotic thrombocytopenic purpura are also treatable.

In addition, the PAIs of the present invention may be used in numerous nontherapeutic applications where inhibiting platelet aggregation is desired. For example, improved platelet and whole blood storage can be obtained by adding sufficient quantities of the compounds, the amount of which will vary depending upon the length of proposed storage time, the conditions of storage, the ultimate use of the stored material, etc.

Preferably, the compounds of this invention are administered in the form of a pharmaceutical formulation. Thus, the compounds of this invention may be administered orally, parenterally, topically, rectally and etc., in, appropriate dosage units, as desired.

The term parenteral as used herein includes subcutaneous, intravenous, intraarterial, injection or infusion techniques, without limitation. The term, "topically" encompasses administration rectally and by inhalation spray, as well as the more common routes of the skin and the mucous membranes of the mouth and nose.

Actual dosage levels of active ingredients in the pharmaceutical compositions of this invention may be varied so as to administer an amount of the active compound(s) that is effective to achieve the desired therapeutic response for a particular patient.

The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including the body weight, general health, diet, time and route of administration, combination with other drugs and the severity of the particular disease being treated.

The range of therapeutic dosages is from about 0.01 to about 10,000 milligrams per day, with from 1 to 300 milligrams being preferred.

Many modifications and variations of this invention may be made without departing from its scope, as is apparent to those skilled in the art. The specific embodiments described herein are offered by way of example only, and the invention is to be limited only by the terms of the appended claims.

What is claimed is:

1. A bicyclic compound having a nucleus formed from two fused six-membered rings, A and B, represented by the formula (I), or a pharmaceutically acceptable salt, solvate or prodrug derivative thereof:

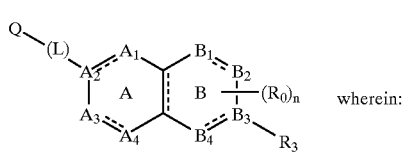

(I)

wherein:

the bicyclic nucleus of rings A and B is formula (17) below:

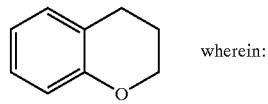

(17)

wherein:

$R_3$ is an acidic group comprising a carboxylic acid radical;
n is a number from 0 to 5;
$R_0$ is the same or different and is independently selected from the group consisting of hydrogen, alkyl, hydroxy, alkoxy, amino, substituted amino, halo, and =O;
the linking group —(L)— is selected from a group of from 1 to 4 chain atoms having the general formulae:

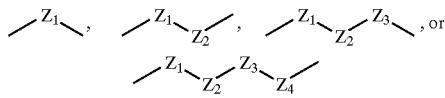

where $Z_1$, $Z_2$, $Z_3$, and $Z_4$ are atoms independently selected from the group consisting of carbon, substituted carbon, nitrogen, substituted nitrogen, and oxygen; and
Q is a basic group selected from the group consisting of piperidyl, amidinophenyl, amidophenyl, guanidinophenyl, and groups of the formula:

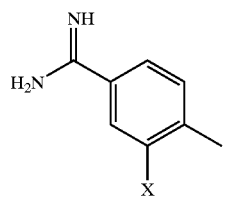

wherein X is a halogen.

2. A compound of claim 1, wherein the carboxylic acid of the acidic group $R_3$ is selected from the following formulae:

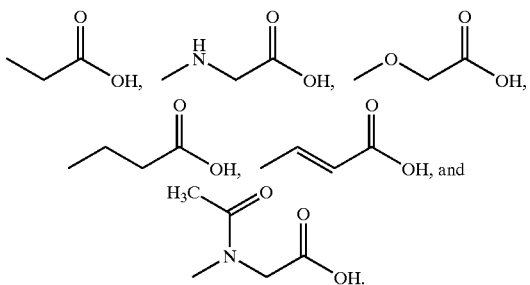

3. A compound of claim 1, wherein the carboxylic acid of the acidic group $R_3$ is selected from the following formulae:

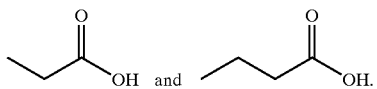

4. The compound of claim 1, wherein the basic group is amidinophenyl or guanidinophenyl.

5. The compound of claim 1, wherein the halo substituent of the basic group is fluoro.

6. The compound of claim 1, wherein the linking group is selected from the formulae:

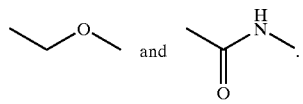

7. A prodrug bicyclic compound having a nucleus formed from two fused six-membered rings, A and B, represented by the formula (I), or a pharmaceutically acceptable salt or solvate thereof:

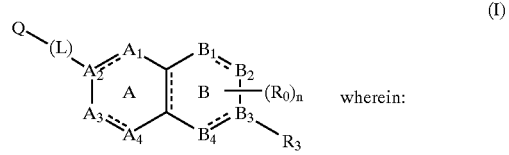

(I)

wherein:

the bicyclic nucleus of rings A and B is formula (17) below:

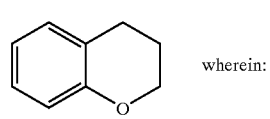

(17)

wherein:

$R_3$ is an acidic group comprising an ester derivative of a carboxylic acid radical;
n is a number from 0 to 5;
$R_0$ is the same or different and is independently selected from the group consisting of hydrogen, alkyl, hydroxy, alkoxy, amino, substituted amino, halo, and =O;
the linking group —(L)— is selected from a group of from 1 to 4 chain atoms having the general formulae:

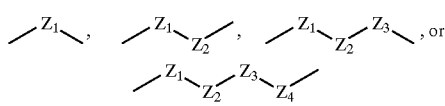

where $Z_1$, $Z_2$, $Z_3$, and $Z_4$ are atoms independently selected from the group consisting of carbon, substituted carbon, nitrogen, substituted nitrogen, and oxygen; and Q is an acylated basic group wherein the basic group is selected from the group consisting of piperidyl, amidinophenyl, amidophenyl, guanidinophenyl, and groups of the formula:

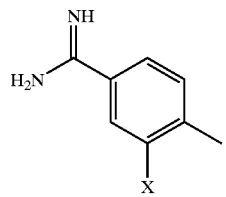

wherein X is a halogen.

8. The compound of claim 7, wherein the ester derivative of the carboxylic acid radical is an ester selected from the group consisting of methyl, ethyl, and propyl.

9. The compound of claim 7, wherein the acylated portion of the acylated basic radical has the formula:

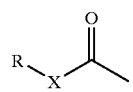

where R is $C_1$–$C_8$ alkyl, aryl, and $C_7$–$C_{12}$ substituted aryl; and X is a bond, C, O, or N.

10. The compound of claim 9, wherein the acylated portion is selected from the group consisting of

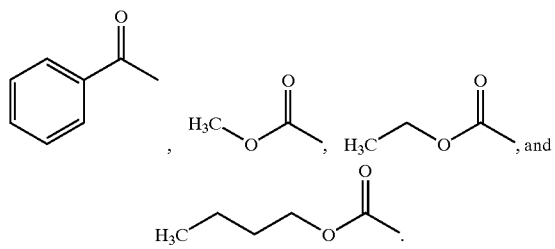

11. A compound selected from the group consisting of compounds represented by the following formulae or a pharmaceutically acceptable salt, solvate, or prodrug derivative thereof:

(VIII)

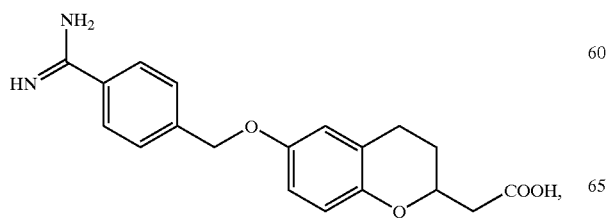

(VIIIa)

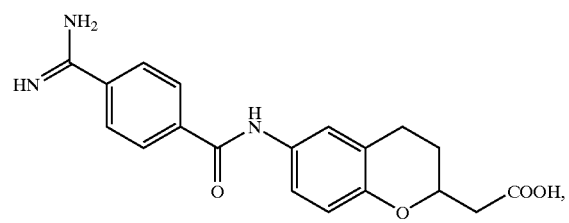

(VIIIb)

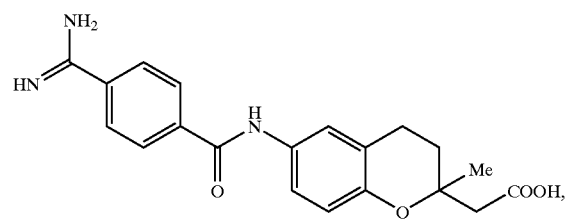

(VIIId)

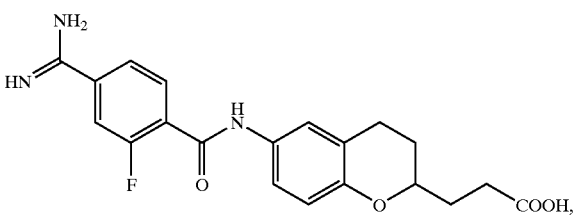

(VIIIf)

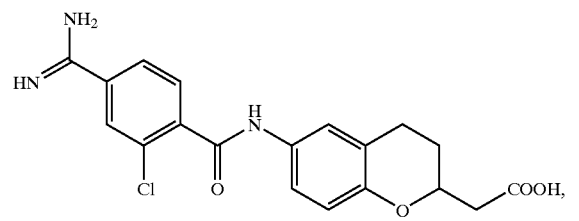

(300)

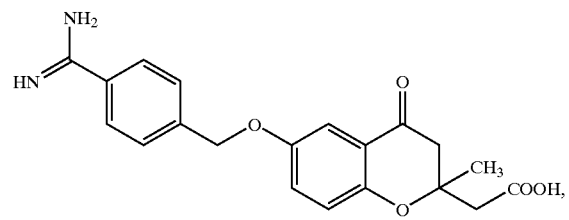

(336)

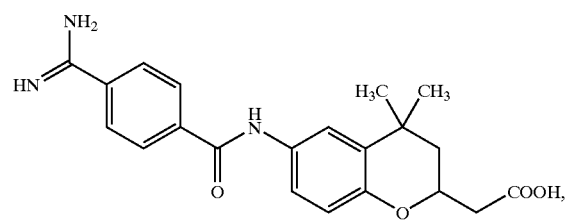

-continued (284)

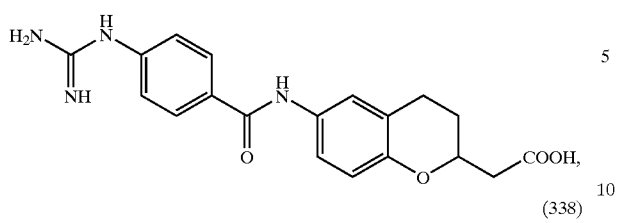

(338)

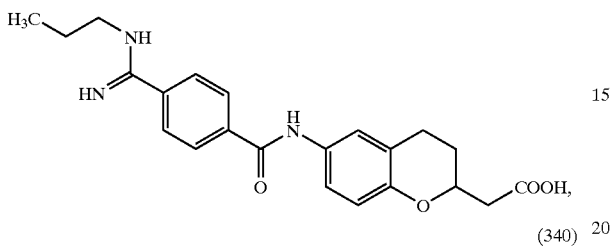

(340)

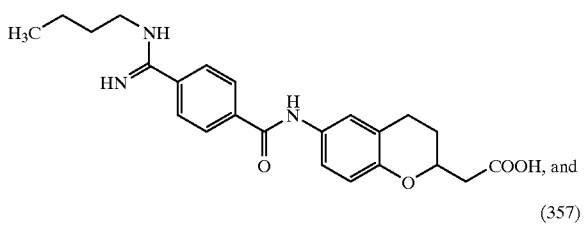

(357)

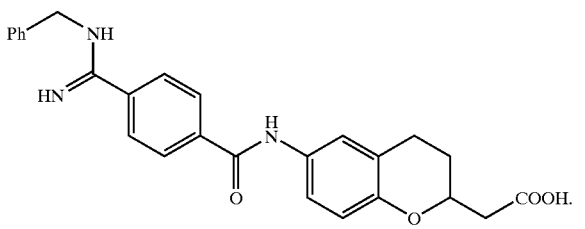

12. A compound selected from the group consisting of compounds represented by the following formulae or a pharmaceutically acceptable salt, solvate, or prodrug derivative thereof:

(VIIIa)

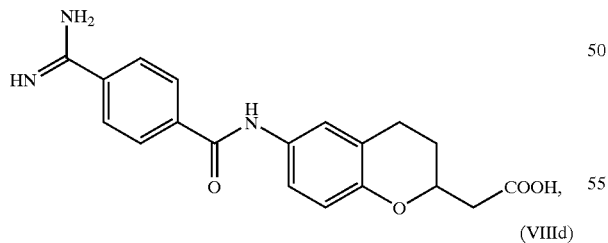

(VIIId)

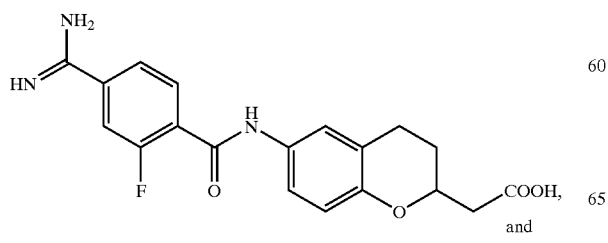
and

-continued (VIIIf)

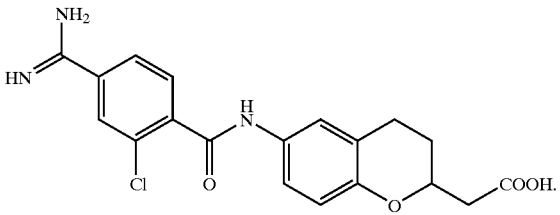

13. A platelet aggregation inhibiting pharmaceutically formulation comprising:

(i) a therapeutically effective platelet aggregation inhibiting amount of a bicyclic compound of claim 1; and (ii) a pharmaceutically acceptable carrier or diluent therefor.

14. A method for effecting inhibition of platelet aggregation which comprises administering to a mammal in need thereof a therapeutically effective platelet aggregation inhibiting amount of the bicyclic compound of claim 1.

15. A method of inhibiting fibrinogen binding by contacting glycoprotein IIb-IIIa sites with the compound of claim 1.

16. A method of treating a mammal to alleviate the pathological effects of atherosclerosis and arteriosclerosis, acute myocardial infraction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts; wherein the method comprises administering to said mammal at least one bicyclic compound of claim 1; wherein, said bicyclic compound is administered to said mammal in an amount sufficient to inhibit binding of fibrinogen on glycoprotein IIb-IIIa sites in said mammal to thereby inhibit said effects.

17. The method of claim 6, wherein said mammal is a human.

18. A bicyclic compound having a nucleus formed from two fused six-membered rings, A and B, represented by the formula (I), or a pharmaceutically acceptable salt, solvate or prodrug derivative thereof:

(I)

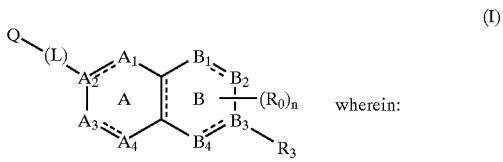
wherein:

the bicyclic nucleus of rings A and B is formula (17) below:

(17)

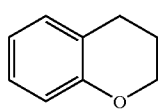
wherein:

$R_3$ is an acidic group comprising a carboxylic acid radical selected from the following formulae:

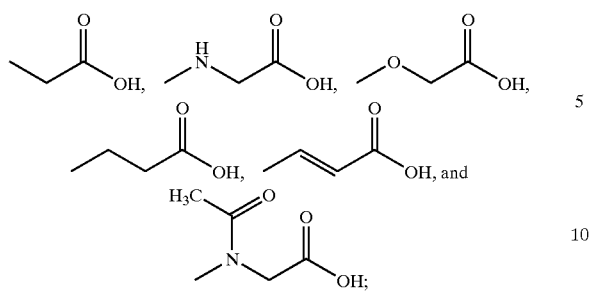

n is a number from 0 to 5;

$R_0$ is the same or different and is independently selected from the group consisting of hydrogen, alkyl, hydroxy, alkoxy, amino, substituted amino, halo, and =O;

linking group —(L)— is a divalent substituted or unsubstituted chain of from 1 to 2 atoms selected from the group consisting of carbon, nitrogen, and oxygen; and Q is a basic group selected from the group consisting of amidinophenyl, guanidinophenyl, and groups of the formula:

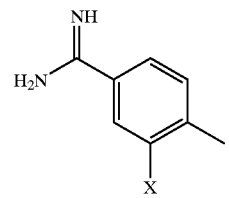

wherein X is a halogen.

* * * * *